United States Patent
Fotin-Mleczek et al.

(10) Patent No.: US 11,559,570 B2
(45) Date of Patent: Jan. 24, 2023

(54) PRIME-BOOST REGIMENS INVOLVING ADMINISTRATION OF AT LEAST ONE MRNA CONSTRUCT

(71) Applicant: CureVac SE, Tübingen (DE)

(72) Inventors: Mariola Fotin-Mleczek, Sindelfingen (DE); Jochen Probst, Wolfschlugen (DE)

(73) Assignee: CureVac SE, Tübingen (DE)

( * ) Notice: Subject to any disclaimer, the term of this patent is extended or adjusted under 35 U.S.C. 154(b) by 0 days.

(21) Appl. No.: 15/574,146

(22) PCT Filed: May 13, 2016

(86) PCT No.: PCT/EP2016/060928
§ 371 (c)(1),
(2) Date: Nov. 14, 2017

(87) PCT Pub. No.: WO2016/184822
PCT Pub. Date: Nov. 24, 2016

(65) Prior Publication Data
US 2018/0125952 A1  May 10, 2018

(30) Foreign Application Priority Data
May 15, 2015 (WO) ............... PCT/EP2015/000999

(51) Int. Cl.
*A61K 39/00* (2006.01)
*A61K 39/12* (2006.01)

(52) U.S. Cl.
CPC .......... *A61K 39/00* (2013.01); *A61K 39/0011* (2013.01); *A61K 39/12* (2013.01); *A61K 2039/5256* (2013.01); *A61K 2039/53* (2013.01); *A61K 2039/54* (2013.01); *A61K 2039/545* (2013.01); *A61K 2039/55561* (2013.01); *A61K 2039/55566* (2013.01); *A61K 2039/55583* (2013.01); *A61K 2039/57* (2013.01); *C12N 2710/10043* (2013.01); *C12N 2760/00034* (2013.01)

(58) Field of Classification Search
None
See application file for complete search history.

(56) References Cited

U.S. PATENT DOCUMENTS

| | | |
|---|---|---|
| 2005/0032730 A1 | 2/2005 | Von der Mulbe et al. |
| 2005/0059624 A1 | 3/2005 | Hoerr et al. |
| 2005/0250723 A1 | 11/2005 | Hoerr et al. |
| 2006/0188490 A1 | 8/2006 | Hoerr et al. |
| 2008/0025944 A1 | 1/2008 | Hoerr et al. |
| 2008/0267873 A1 | 10/2008 | Hoerr et al. |
| 2009/0324584 A1 | 12/2009 | Hoerr et al. |
| 2010/0048883 A1 | 2/2010 | Ketterer et al. |
| 2010/0189729 A1 | 7/2010 | Hoerr et al. |
| 2010/0203076 A1 | 8/2010 | Fotin-Mleczek et al. |
| 2010/0291156 A1 | 11/2010 | Barner et al. |
| 2010/0305196 A1 | 12/2010 | Probst et al. |
| 2011/0053829 A1 | 3/2011 | Baumhof et al. |
| 2011/0250225 A1 | 10/2011 | Fotin-Mleczek et al. |
| 2012/0021043 A1 | 1/2012 | Kramps et al. |
| 2012/0258046 A1 | 10/2012 | Mutzke |
| 2012/0328655 A1* | 12/2012 | Dubensky, Jr. .... A61K 39/0011 424/231.1 |
| 2013/0129754 A1 | 5/2013 | Thess et al. |
| 2013/0142818 A1 | 6/2013 | Baumhof et al. |
| 2013/0259879 A1 | 10/2013 | Baumhof et al. |
| 2013/0280283 A1 | 10/2013 | Lorenz et al. |
| 2013/0295043 A1 | 11/2013 | Kallen et al. |
| 2013/0336998 A1 | 12/2013 | Kallen et al. |
| 2014/0200261 A1* | 7/2014 | Hoge ................. A61K 31/7105 514/44 R |
| 2015/0037326 A1 | 2/2015 | Butler-Ransohoff et al. |
| 2015/0050302 A1 | 2/2015 | Thess |
| 2015/0057340 A1 | 2/2015 | Thess et al. |
| 2015/0093413 A1 | 4/2015 | Thess et al. |
| 2015/0118183 A1 | 4/2015 | Baumhof |

(Continued)

FOREIGN PATENT DOCUMENTS

| | | |
|---|---|---|
| WO | WO 2006-002079 | 1/2006 |
| WO | WO 2006/133497 | 12/2006 |

(Continued)

OTHER PUBLICATIONS

Greenspan et al (Nature Biotechnology. 1999; 7: 936-937).*
Frankiw et al. (Nature Reviews Immunology. Jul. 30, 2019: 1).*
Peters et al. (Annual Review of Immunology. 2020; 38: 123-145).*
International Preliminary Report on Patentability issued in corresponding PCT Application No. PCT/EP2016/060928, dated Nov. 21, 2017.
International Search Report and Written Opinion issued in corresponding PCT Application No. PCT/EP2016/060928, dated Sep. 9, 2016.
Lin, "Boosting with recombinant vaccinia increase HPV-16 E7-Specific T cell precursor frequencies and antitumor effects of HPV-16 E7-Expressing sindbis virus replicon particles,"*Mol. Ther.*, 8(4):559-566, 2003.

(Continued)

*Primary Examiner* — Shanon A. Foley
(74) *Attorney, Agent, or Firm* — Parker Highlander PLLC

(57) ABSTRACT

The present invention relates to prime-boost regimens that involve the administration of at least one mRNA construct, such as the use of such constructs in "boost" administration subsequently to "prime" administration of certain other antigenic composition(s). Such inventive regimens may, in particular, be useful for the induction of an immune response in a subject, and/or the vaccination of such subject against infection from one or more pathogens, and/or the treatment or prevention of one or more diseases or conditions, including a tumour or cancer, allergy or autoimmune conditions, and/or a disease or condition associated with infection from a pathogen. The present invention further describes methods, uses, vaccination compositions, kits and packaged vaccine components related to or useful for one or more of such regimens.

Figure 1:
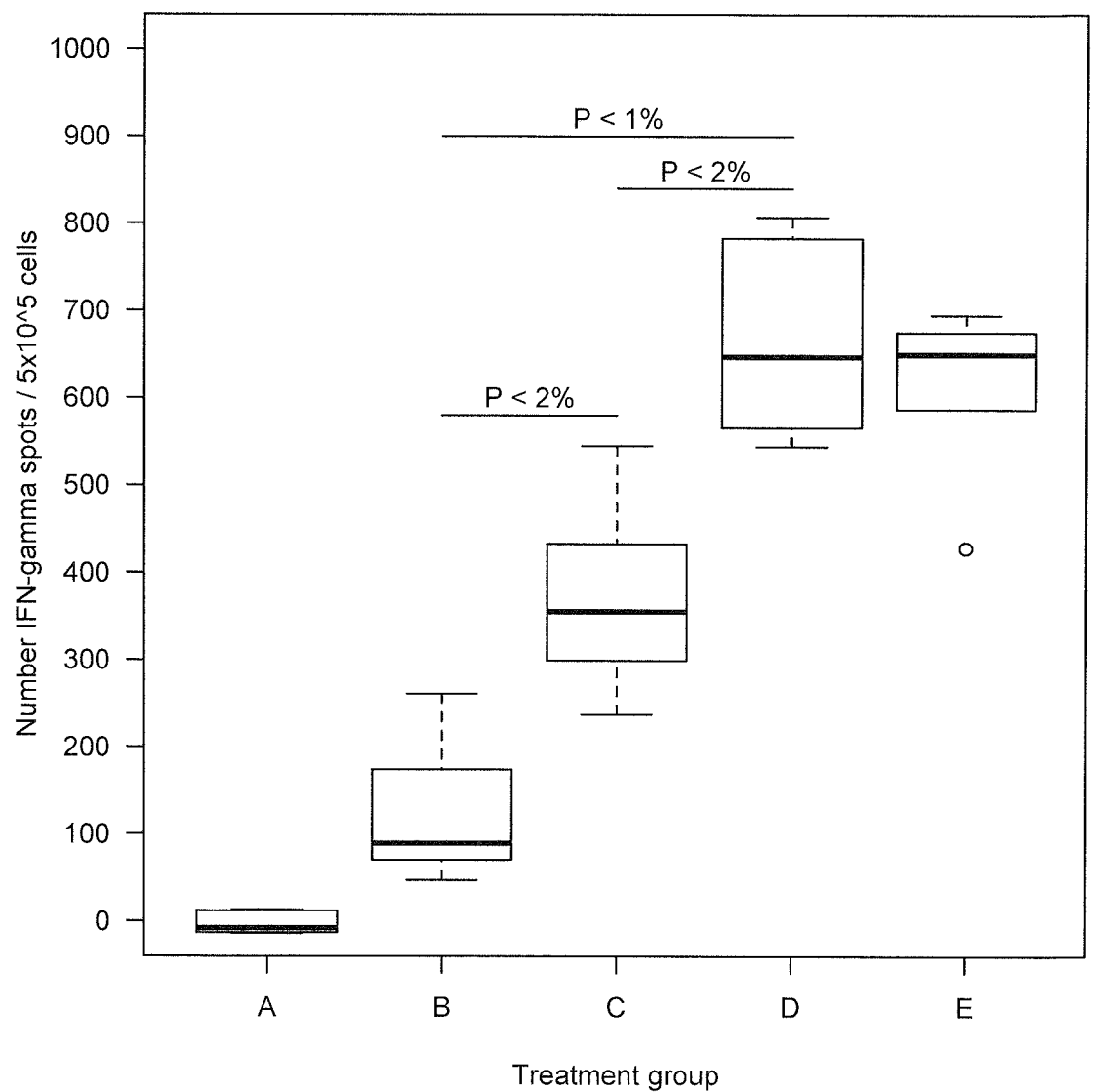

22 Claims, 3 Drawing Sheets
Specification includes a Sequence Listing.

(56) References Cited

U.S. PATENT DOCUMENTS

| | | |
|---|---|---|
| 2015/0118264 A1 | 4/2015 | Baumhof et al. |
| 2015/0165006 A1 | 6/2015 | Thess et al. |
| 2015/0184195 A1 | 7/2015 | Thess et al. |
| 2015/0218554 A1 | 8/2015 | Thess |
| 2015/0306249 A1 | 10/2015 | Baumhof et al. |
| 2015/0320847 A1 | 11/2015 | Thess et al. |
| 2016/0130345 A1 | 5/2016 | Fotin-Mleczek et al. |
| 2016/0166668 A1 | 6/2016 | Kallen et al. |
| 2016/0166678 A1 | 6/2016 | Kallen et al. |
| 2016/0166710 A1 | 6/2016 | Baumhof |
| 2016/0166711 A1 | 6/2016 | Schnee et al. |
| 2016/0168207 A1 | 6/2016 | Kramps et al. |
| 2016/0168227 A1 | 6/2016 | Kallen et al. |
| 2016/0235864 A1 | 8/2016 | Schlake et al. |
| 2016/0304883 A1 | 10/2016 | Grund et al. |
| 2016/0304938 A1 | 10/2016 | Wochner |
| 2016/0326575 A1 | 11/2016 | Von Der Mulbe et al. |
| 2016/0331844 A1 | 11/2016 | Fotin-Mleczek et al. |
| 2017/0014496 A1 | 1/2017 | Fotin-Mleczek et al. |
| 2017/0029847 A1 | 2/2017 | Thess |
| 2017/0114378 A1 | 4/2017 | Wochner et al. |
| 2017/0252430 A1 | 9/2017 | Fotin-Mleczek et al. |
| 2017/0326225 A1 | 11/2017 | Rauch et al. |
| 2018/0044687 A1 | 2/2018 | Thess et al. |
| 2018/0125952 A1* | 5/2018 | Fotin-Mleczek ...... A61K 39/00 |

FOREIGN PATENT DOCUMENTS

| | | |
|---|---|---|
| WO | WO 2008/011609 | 1/2008 |
| WO | WO 2010-037539 | 4/2010 |
| WO | WO 2014-005958 | 1/2014 |
| WO | WO 2014/108515 | 7/2014 |
| WO | WO 2015/142963 | 9/2015 |
| WO | WO 2015/143193 | 9/2015 |
| WO | WO 2016-107877 | 7/2016 |
| WO | WO 2016-165825 | 10/2016 |
| WO | WO 2016-165831 | 10/2016 |
| WO | WO 2016-174227 | 11/2016 |
| WO | WO 2016-174271 | 11/2016 |
| WO | WO 2016-184575 | 11/2016 |
| WO | WO 2016-184576 | 11/2016 |
| WO | WO 2016-193206 | 12/2016 |
| WO | WO 2016-193226 | 12/2016 |
| WO | WO 2016-203025 | 12/2016 |
| WO | WO 2017-001058 | 1/2017 |
| WO | WO 2017-009376 | 1/2017 |
| WO | WO 2017-021546 | 2/2017 |
| WO | WO 2017-025120 | 2/2017 |
| WO | WO 2017-025447 | 2/2017 |
| WO | WO 2017-036580 | 3/2017 |

OTHER PUBLICATIONS

Zhang et al., "Toward more accurate pan-specific MHC-peptide binding prediction: a review of current methods and tools," *Briefings in Bioinformatics*, 13(3):350-364, 2012.

Baldwin et al., "Protection against Tuberculosis with Homologous or Heterologous Protein/Vector Vaccine Approaches Is Not Dependent on CD8 + T Cells," *The Journal of Immunology*, 191:2514-2525, 2013.

Bogers et al., "Macaques primed with self-amplifying RNA vaccines expressing HIV-1 envelope and boosted with recombinant protein show potent T- and B-cell responses," *Retrovirology* 9(Suppl 2):P24, 2012.

Bot et al., "Programmed cell death-1 (PD-1) at the heart of heterologous prime-boost vaccines and regulation of CD8 + T cell immunity," *Journal of Translational Medicine* 8:132, 1-11, 2010.

Dai et al., "Early Treg suppression by a listeriolysin-O-expressing *E. coli* vaccine in heterologous prime-boost vaccination against cancer," *Vaccine* 30:6903-6911, 2012.

Duthie et al., "Heterologous Immunization With Defined RNA and Subunit Vaccines Enhances T Cell Responses That Protect Against Leishmania donovani," *Frontiers in Immunology*, 9:Article 2420, 1-9, 2018.

Fiorino et al., "Prime-boost strategies in mucosal immunization affect local IgA production and the type of Th response," *Frontiers in Immunology* 4:Article 128,1-8, 2013.

Fotin-Mleczek et al., "Highly potent mRNA based cancer vaccines represent an attractive platform for combination therapies supporting an improved therapeutic effect," *The Journal of Gene Medicine* 14:428-439, 2012.

Hamilton et al., "TOPs and their regulation," *Biochemical Society Transactions* 34:12-16, 2006.

Kardani et al., "Prime-boost vaccine strategy against viral infections: Mechanisms and benefits," *Vaccine* 34:413-423, 2016.

Lu, "Heterologous prime-boost vaccination," *Current Opinion in Immunology*, 21:346-351, 2009.

McShane, "Prime-Boost immunization strategies for infectious diseases," *Current Opinion in Molecular Therapeutics* 4:23-27, 2002.

Nascimento and Leite, "Recombinant vaccines and the development of new vaccine strategies," *Brazilian Journal of Medical and Biological Research* 45:1102-1111, 2012.

Noe et al., "A Full-Length Plasmodium falciparum Recombinant Circumsporozoite Protein Expressed by Pseudomonas fluorescens Platform as a Malaria Vaccine Candidate," *PLOS One* 9:e107764, 2014.

Opposition against EP 3 294 326 submission of BioNTech dated Jan. 21, 2022.

Pardi et al., "Generating an Anti-HIV Vaccine Using Nucleoside-modified mRNA Encoding Envelope," *AIDS Research and Human Retroviruses* 30(S1):A249, 2014.

Pardi et al., "mRNA vaccines—a new era in vaccinology," *Nat. Rev. Drug Des.*, 17:261-279, 2018.

Radosevic et al., "Heterologous prime-boost vaccinations for poverty-related diseases: advantages and future prospects," *Expert Review Vaccines* 8:577-592, 2009.

Ramshaw and Ramsay, "The prime-boost strategy: exciting prospects for improved vaccination," *Trends Immunology Today* 21:163-165, 2000.

Sahin et al., "mRNA-based therapeutics—developing a new class of drugs," *Nature Reviews Drug Discovery* 13:759-780, 2014.

Schlake et al., "Developing mRNA-vaccine technologies," *RNA Biology* 9:1319-1330, 2012.

Tritel et al., "Prime-Boost Vaccination with HIV-1 Gag Protein and Cytosine Phosphate Guanosine Oligodeoxynucleotide, Followed by Adenovirus, Induces Sustained and Robust Humoral and Cellular Immune Responses," *The Journal of Immunology* 171:2538-2547, 2003.

Ulmer et al., "RNA-based vaccines," *Vaccine* 30:4414-4418, 2012.

Van Lint et al., "mRNA From a chemical blueprint for protein production to an off-the-shelf therapeutic," *Human Vaccines & Immunotherapeutics* 9:265-274, 2013.

Zhang et al., "Advances in mRNA vaccines for infectious diseases," *Front. Immunol.*, 10:594, 2019.

Zhang et al., "Targeting the Genital Tract Mucosa with a Lipopeptide/Recombinant Adenovirus Prime/Boost Vaccine Induces Potent and Long-Lasting CD8 + T Cell Immunity against Herpes: Importance of MyD88," *The Journal of Immunology* 189:4496-4509, 2012.

\* cited by examiner

SEQUENCE LISTING

```
<160> NUMBER OF SEQ ID NOS: 10

<210> SEQ ID NO 1
<211> LENGTH: 24
<212> TYPE: DNA
<213> ORGANISM: Artificial Sequence
<220> FEATURE:
<223> OTHER INFORMATION: Histone stem-loop nucleotide sequence
```

```
<400> SEQUENCE: 1
caaaggctct tttcagagcc acca                                            24

<210> SEQ ID NO 2
<211> LENGTH: 24
<212> TYPE: RNA
<213> ORGANISM: Artificial Sequence
<220> FEATURE:
<223> OTHER INFORMATION: Histone stem-loop RNA sequence

<400> SEQUENCE: 2
caaaggcucu uuucagagcc acca                                            24

<210> SEQ ID NO 3
<211> LENGTH: 186
<212> TYPE: DNA
<213> ORGANISM: Artificial Sequence
<220> FEATURE:
<223> OTHER INFORMATION: Nucleotide sequence of 3'-UTR element of human
      albumin gene

<400> SEQUENCE: 3
catcacattt aaaagcatct cagcctacca tgagaataag agaaagaaaa tgaagatcaa      60
tagcttattc atctcttttt cttttcgtt ggtgtaaagc caacaccctg tctaaaaaac     120
ataaatttct ttaatcattt tgcctctttt ctctgtgctt caattaataa aaatggaaa     180 gaacct                                                               186

<210> SEQ ID NO 4
<211> LENGTH: 44
<212> TYPE: DNA
<213> ORGANISM: Artificial Sequence
<220> FEATURE:
<223> OTHER INFORMATION: Nucleotide sequence of 3' UTR element of an
      alpha-globin gene

<400> SEQUENCE: 4
gcccgatggg cctcccaacg ggccctcctc ccctccttgc accg                       44

<210> SEQ ID NO 5
<211> LENGTH: 42
<212> TYPE: DNA
<213> ORGANISM: Artificial Sequence
<220> FEATURE:
<223> OTHER INFORMATION: Nucleotide sequence for 5'-UTR element

<400> SEQUENCE: 5
ggcgctgcct acggaggtgg cagccatctc cttctcggca tc                         42

<210> SEQ ID NO 6
<211> LENGTH: 671
<212> TYPE: DNA
<213> ORGANISM: Artificial Sequence
<220> FEATURE:
<223> OTHER INFORMATION: Nucleotide sequence of IRES of EMCV

<400> SEQUENCE: 6
ttgaaagccg ggggtgggag atccggattg ccagtctgct cgatatcgca ggctgggtcc      60
gtgactaccc actcccccctt taattccgcc cctctccctc cccccccccct aacgttactg   120 gccgaagccg cttggaataa ggccggtgtg cgtttgtcta tatgttattt tccaccatat    180
tgccgtcttt tggcaatgtg agggcccgga aacctggccc tgtcttcttg acgagcattc    240
ctaggggtct ttcccctctc gccaaaggaa tgcaaggtct gttgaatgtc gtgaaggaag    300
```

```
cagttcctct ggaagcttct tgaagacaaa caacgtctgt agcgacccct tgcaggcagc    360 ggaaccccc  acctggcgac aggtgcctct gcggccaaaa gccacgtgta taagatacac    420
ctgcaaaggc ggcacaaccc cagtgccacg ttgtgagttg atagttgtg  gaaagagtca    480 aatggctctc ctcaagcgta ttcaacaagg ggctgaagga tgcccagaag gtaccccatt    540
gtatgggatc tgatctgggg cctcggtgca catgctttac gtgtgtttag tcgaggttaa    600
aaaacgtcta ggcccccga  accacgggga cgtggttttc ctttgaaaaa cacgatgata    660
atagatctac c                                                        671

<210> SEQ ID NO 7
<211> LENGTH: 461
<212> TYPE: DNA
<213> ORGANISM: Artificial Sequence
<220> FEATURE:
<223> OTHER INFORMATION: Nucleotide sequence of IRES of EMCV

<400> SEQUENCE: 7
agcaggtttc cccaactgac acaaaacgtg caacttgaaa ctccgcctgg tctttccagg     60
tctagagggg taacactttg tactgcgttt ggctccacgc tcgatccact ggcgagtgtt    120
agtaacagca ctgttgcttc gtagcggagc atgacggccg tgggaactcc tccttggtaa    180
caaggaccca cggggccaaa agccacgccc acacgggccc gtcatgtgtg caaccccagc    240
acggcgactt tactgcgaaa cccactttaa agtgacattg aaactggtac ccacacactg    300
gtgacaggct aaggatgccc ttcaggtacc ccgaggtaac acgcgacact cgggatctga    360 gaagggact  ggggcttcta taaaagcgct cggtttaaaa agcttctatg cctgaatagg    420
tgaccggagg tcggcacctt tcctttacaa ttaaagaccc t                       461

<210> SEQ ID NO 8
<211> LENGTH: 66
<212> TYPE: DNA
<213> ORGANISM: Artificial Sequence
<220> FEATURE:
<223> OTHER INFORMATION: Nucleotide sequence of F2A peptide, version 1,
      of FMDV

<400> SEQUENCE: 8
gtgaagcaga cactcaattt cgaccttctg aagttggctg agatgttga gtctaaccca     60 ggcccc                                                               66

<210> SEQ ID NO 9
<211> LENGTH: 66
<212> TYPE: DNA
<213> ORGANISM: Artificial Sequence
<220> FEATURE:
<223> OTHER INFORMATION: Nucleotide sequence of F2A peptide, version 2,
      of FMDV

<400> SEQUENCE: 9
gtcaaacaga ccttgaactt cgacttgctc aaactggccg gggatgtgga gtccaatcct     60
ggacct                                                               66

<210> SEQ ID NO 10
<211> LENGTH: 7
<212> TYPE: PRT
<213> ORGANISM: Artificial Sequence
<220> FEATURE:
<223> OTHER INFORMATION: linker sequence
```

```
<400> SEQUENCE: 10

Gly Gly Gly Ser Gly Gly Gly
1               5
```

PRIME-BOOST REGIMENS INVOLVING ADMINISTRATION OF AT LEAST ONE MRNA CONSTRUCT

This application is a national phase application under 35 U.S.C. § 371 of International Application No. PCT/EP2016/060928, filed May 13, 2016, which claims benefit of International Application No. PCT/EP2015/000999, filed May 15, 2015, the entire contents of each of which are hereby incorporated by reference.

The present invention relates to novel prime-boost regimens that involve the administration of at least one mRNA construct, such as the use of such constructs in "boost" administration subsequently to "prime" administration of certain other antigenic composition(s). Such inventive regimens may, in particular, be useful for the induction of an immune response in a subject, and/or the vaccination of such subject against infection from one or more pathogens, and/or the treatment or prevention of one or more diseases or conditions, including a tumour or cancer, allergy or autoimmune conditions, and/or a disease or condition associated with infection from a pathogen. The present invention further describes methods, uses, vaccination compositions, kits and packaged vaccine components related to or useful for one or more of such regimens.

A significant bottleneck in developing vaccines against infection from pathogens or for the treatment or prevention of certain diseases or conditions, such as a tumour or cancer, allergy or autoimmune conditions, is the ability to induce a strong and effective immune response. When administered as a sole immunogenic component, many vaccines candidates in research and development induce some, but not a sufficiently strong or effective, immune response. Accordingly, such candidate vaccines—including those seeking to address socially, medically or economically important infections such as influenza or rabies, or prostate or lung cancer—are not sufficiently effective to warrant further research or clinical development despite them perhaps showing low toxicity or side effects compared to alternative vaccines or therapies. Yet more problematic is the situation with vaccine candidates seeking to address infections such as Ebola or HIV for which there is currently no effective vaccination approved and commercially available. Indeed, an average vaccine, taken from the preclinical phase, requires a subsequent development timeline of 10.71 years and has a market entry probability of only 6% (Pronker et al, 2013; PLoS One 8(3):e57755). Even some approved vaccine products may have suffered such problem(s) during development, and their ultimate—and approvable—efficiency was brought about only by using conventional and non-optimal approaches to induce an immune response that is sufficiently strong, efficacious and/or long lasting.

One conventional approach to improve the immune response of a vaccine candidate or product is by the use of an adjuvant in the vaccine composition; that is an additional component added to the vaccine formulation that increases the immunogenicity of the antigens in the vaccine. Approved adjuvants include alum, aluminium phosphate and aluminium hydroxide (Lindblad, 2004; Immunol Cell Biol 82:497) and particularly for use in the vaccination of animals, certain oil in water-based adjuvants such as squalene in water (Brito et al, 2011; Vaccine 29:6262). However, conventional adjuvants such as alum have a number of disadvantages including that of the potential for allergic reactions and/or not working with all antigens such as malaria and tuberculosis (Leslie, 2013; Science 341:26)

Another conventional approach to provide a vaccination that produces a sufficiently strong, effective and/or long-lasting immune response and/or protection is to either: (i) administer the vaccine composition in increased dosages; or (ii) additionally administer one or more subsequent vaccinations (so called "boost" vaccinations) after the initial (so called "prime") vaccination, where the subsequent vaccinations may be with the same vaccine product—for example, RABIPUR® rabies vaccine, innactivated (Vodopija, 1999; Vaccine 17:13)—or in combination with other vaccine products addressing the same infection, disease or condition—for example, influenza vaccines containing different antigens (Stephenson et al, 2008; N Engl J Med 359:1631). However, such conventional approaches are disadvantageous for a number of reasons, including where increased amounts of the vaccine composition are needed. For example, the typical time to generate a conventional seasonal flu vaccine is 3 to 6 months, and requires a very specific production method and facilities involving the culturing and isolation of antigen from chicken eggs (Matthews, 2006; The Bridge 36(3):17).

The per-person costs associated with such typical production times and very specialised production process for conventional vaccines are often substantial. Indeed, one course of pre-exposure vaccinations against rabies with the RABIPUR® vaccine (produced by virus propagation in purified chick embryo cell culture) costs in the order of hundreds of Euros per person. If the same vaccination efficiency were possible by using half the dose of administered vaccine, then not only would substantial cost savings be possible, but the same specialised production process (with, consequential, a limited number of specialised facilities able to produce such vaccine) could be used to produce—in the same time—sufficient vaccine for twice the number of subjects; such factors having significant social and public health advantages especially for third-world, epidemic or pandemic vaccination campaigns.

One particular issue arises when the vaccine composition (or an alternative one) is needed to be administered subsequently and perhaps repeatedly to the "prime" composition. Such subsequent boost administrations may be needed to be given some time after the prime administration, such as days, weeks or months thereafter, but under subsequent conditions that may not be optimal for any vaccination. For example, in an emergency situation such as an infection epidemic or cases of biological warfare/terrorism, an emergency worker may receive a first (prime) administration within a sophisticated medical environment but such prime administration may provide only temporary or limited protection. Only if a subsequent boost administration is received by the emergency worker will sufficient and/or long lasting protection be provided. However, by which time the emergency worker may already be in "field conditions" that are not suitable for storage, transport or administration of conventional vaccines; for example there may be a lack of cold-chain storage and transport needed for conventional protein-based vaccines. Furthermore, and with reference to the previous paragraph, in such emergency situations it would be advantageous if existing stocks of conventional (eg protein) vaccines were used for as many subjects as possible—providing an initial but not long-lasting protection—by using such stocks of conventional vaccines for prime vaccination, and then using new methods to boost or prolong such initial protection, such as by using a regimen with a second composition that can be rapidly and flexibly produced for different infection/pathogen risk without extensive stockpiling or reservation of specialist vaccine production facilities for each and every possible infection/pathogen risk.

Another particular issue may be the development of anti-vector immunity limiting the immunogenicity of viral vector vaccines. For example, when a viral vector (e.g. an adenoviral vector) is used as the "prime" composition the vaccinated individual can develop neutralising antibodies directed against the viral vector (Zaiss et al. 2009; J Cell Biochem 108(4): 778-790), and hence the use of the same (or similar) viral vector for subsequent "boost" vaccinations may become less efficacious or even generate side effects.

WO2003/011332 (Isis Innovation Ltd) describes methods relating to improved polypeptide vaccination strategies; including to boost an immune response in an individual previously primed against or exposed to at least one of a plurality of epitopes, by the administration of a plurality of individual nucleic acid constructs, each encoding one of said plurality of epitopes.

WO2005/035779 (Powderject Vaccines Inc) relates to a method of eliciting a T cell response against a T cell epitope in a host mammalian subject; including a method that uses a first administration of a nucleotide of interest (NOI) and a second administration with a NOI, wherein the time between these administrations is from 21 to 365 days.

WO2009/056535 (Genimmune NV) describes methods and kits for inducing a CTL response using a prime boost regimen; wherein a polypeptide construct comprising at least two CTL epitopes is used as a first priming composition, and then a second boosting composition comprising a vector encoding one or more CTL epitopes.

WO2013/006842 (Novartis AG) generally relates to immunogenic compositions that comprise an mRNA component and a polypeptide component, and in other aspects describes kits and methods for treating or preventing an infectious disease that include: (i) a priming composition comprising a self-replicating RNA molecule that encodes an epitope from a pathogen; and (ii) a boosting composition comprising a second epitope from the same pathogen in polypeptide form. WO2015/189425 (Glaxosmithkline Biologicals SA) describes immunogenic combinations including a polypeptide antigen and a nucleic acid component for concurrent administration.

WO2014/005643 and WO2014/006191 (Okairos AG) describe novel prime-boost regimens involving immunogenic polypeptides encoded by polynucleotides; in particular, vaccine compositions comprising: (i) a priming composition comprising a first vector comprising a nucleic acid encoding an immunogenic polypeptide; and (ii) at least one boosting composition comprising a second vector comprising a nucleic acid encoding an immunogenic polypeptide, wherein at least one epitope in each polypeptide is immunologically identical, and each of the compositions is administered intranasally or intramuscularly.

WO2014/139587 and WO2014/141176 (Okairos AG) describe improved poxviral vaccines; including the use of poxviral vectors for priming of the immune response, and for boosting the immune response using a vector comprising a nucleic acid encoding an antigenic protein, a second antigenic protein or viral like particles.

Accordingly there is a need, from one or more of the above perspectives, for improved methods and/or compositions for inducing an immune response in a subject, such as for the vaccination of the subject against infection from one or more pathogens and/or the treatment or prevention of a disease or condition in such subject.

It is therefore an object of the present invention to provide alternative, improved, simpler, faster, more flexible, cheaper and/or integrated means, methods and/or compositions that address one or more of these or other problems. Such an object underlying the present invention is solved by the subject matter as disclosed or defined anywhere herein, for example by the subject matter of the attached claims.

Generally, and by way of brief description: (x) described herein is; and/or (y) a main aspect of the present invention can be described as follows:

A method for inducing an immune response in a subject; the method comprising the steps:

(a) administering to a subject in need thereof at least once an effective amount of a first antigenic composition that comprises at least one immunogenic peptide or polypeptide and/or that comprises at least one nucleic acid construct that encodes at least one immunogenic peptide or polypeptide; and (b) subsequently administering to the subject at least once an effective amount of a second antigenic composition that comprises at least one mRNA construct that encodes at least one immunogenic peptide or polypeptide, wherein:

the nucleic acid construct, if comprised in the first antigenic composition, is not an mRNA construct; and at least one epitope of the immunogenic peptide or polypeptide comprised in, or encoded by the nucleic acid construct comprised in, the first antigenic composition is immunologically equivalent to at least one epitope of the immunogenic peptide or polypeptide encoded by the mRNA construct of the second antigenic composition.

In particular, an object underlying the present invention is solved according to one main aspect by:

A second antigenic composition that comprises at least one mRNA construct that encodes at least one immunogenic peptide or polypeptide, for use in administering to a subject in need thereof at least once an effective amount of the second antigenic composition subsequently to administration to the subject at least once of an effective amount of a first antigenic composition that comprises at least one immunogenic peptide or polypeptide and/or that comprises at least one nucleic acid construct that encodes at least one immunogenic peptide or polypeptide, wherein:

the nucleic acid construct, if comprised in the first antigenic composition, is not an mRNA construct; and at least one epitope of the immunogenic peptide or polypeptide comprised in, or encoded by the nucleic acid construct comprised in, the first antigenic composition is immunologically equivalent to at least one epitope of the immunogenic peptide or polypeptide encoded by the mRNA construct of the second antigenic composition.

In one aspect, the present invention preferably concerns:

A second antigenic composition that comprises at least one mRNA construct that encodes at least one immunogenic peptide or polypeptide, for use as a vaccine, in administering to a subject in need thereof wherein at least once an effective amount of the second antigenic composition is administered to a subject in need thereof subsequently to administration to the subject at least once of an effective amount of a first antigenic composition that comprises at least one immunogenic peptide or polypeptide and/or that comprises at least one nucleic acid construct that encodes at least one immunogenic peptide or polypeptide, wherein:
the nucleic acid construct, if comprised in the first antigenic composition, is not an mRNA construct; and
at least one epitope of the immunogenic peptide or polypeptide comprised in, or encoded by the nucleic acid construct comprised in, the first antigenic composition is immunologically equivalent identical to or at least 70%, 75%, 80%, 85%, 90%, 95% or at least 98% identical to at least one epitope of the immunogenic peptide or polypeptide encoded by the mRNA construct of the second antigenic composition.

In particularly, an object underlying the present invention is also solved according to a related main aspect by:

A first antigenic composition that comprises at least one immunogenic peptide or polypeptide and/or that comprises at least one nucleic acid construct that encodes at least one immunogenic peptide or polypeptide, for use in administering to a subject in need thereof at least once an effective amount of the first antigenic composition and prior to administration to the subject at least once an effective amount of a second antigenic composition that comprises at least one mRNA construct that encodes at least one immunogenic peptide or polypeptide,
wherein:
the nucleic acid construct, if comprised in the first antigenic composition, is not an mRNA construct; and
at least one epitope of the immunogenic peptide or polypeptide comprised in, or encoded by the nucleic acid construct comprised in, the first antigenic composition is immunologically equivalent to at least one epitope of the immunogenic peptide or polypeptide encoded by the mRNA construct of the second antigenic composition.

In a further aspect, the invention preferably relates to:

A first antigenic composition that comprises
at least one immunogenic peptide or polypeptide and/or that comprises
at least one nucleic acid construct that encodes at least one immunogenic peptide or polypeptide,
for use as a vaccine, in administering to a subject in need thereof wherein at least once an effective amount of the first antigenic composition is administered to a subject in need thereof and prior to administration to the subject at least once an effective amount of a second antigenic composition that comprises at least one mRNA construct that encodes at least one immunogenic peptide or polypeptide,
wherein:
the nucleic acid construct, if comprised in the first antigenic composition, is not an mRNA construct; and
at least one epitope of the immunogenic peptide or polypeptide comprised in, or encoded by the nucleic acid construct comprised in, the first antigenic composition is immunologically equivalent identical to or at least 70%, 75%, 80%, 85%, 90%, 95% or at least 98% identical to at least one epitope of the immunogenic peptide or polypeptide encoded by the mRNA construct of the second antigenic composition.

In another aspect, the invention provides:

A first antigenic composition that comprises
at least one immunogenic peptide or polypeptide and/or that comprises
at least one nucleic acid construct that encodes at least one immunogenic peptide or polypeptide,
and
a second antigenic composition that comprises
at least one mRNA construct that encodes at least one immunogenic peptide or polypeptide,
wherein
the nucleic acid construct, if comprised in the first antigenic composition, is not an mRNA construct; and
at least one epitope of the immunogenic peptide or polypeptide comprised in, or encoded by the nucleic acid construct comprised in, the first antigenic composition is immunologically equivalent to at least one epitope of the immunogenic peptide or polypeptide encoded by the mRNA construct of the second antigenic composition,
for use as a vaccine, wherein an effective amount of the second antigenic composition is administered at least once to a subject in need thereof
subsequently to administration to the subject at least once of an effective amount of a first antigenic composition.

More preferably, that aspect of the invention concerns:

A first antigenic composition that comprises
at least one immunogenic peptide or polypeptide and/or that comprises
at least one nucleic acid construct that encodes at least one immunogenic peptide or polypeptide,
and
a second antigenic composition that comprises
at least one mRNA construct that encodes at least one immunogenic peptide or polypeptide,
wherein
the nucleic acid construct, if comprised in the first antigenic composition, is not an mRNA construct; and
at least one epitope of the immunogenic peptide or polypeptide comprised in, or encoded by the nucleic acid construct comprised in, the first antigenic composition is identical to or at least 70%, 75%, 80%, 85%, 90%, 95%, 98% or at least 99% identical to at least one epitope of the immunogenic peptide or polypeptide encoded by the mRNA construct of the second antigenic composition,
for use as a vaccine, wherein an effective amount of the second antigenic composition is administered at least once to a subject in need thereof
subsequently to administration to the subject at least once of an effective amount of a first antigenic composition.

In another main aspect, the invention also relates to:

A vaccine combination comprising:
a first antigenic composition or a first vaccine composition as described, defined or claimed herein; and
a second antigenic composition or a second vaccine composition as described, defined or claimed herein.

In a further main aspect, the invention also relates to:

A kit, preferably for inducing an immune response in a subject; the kit comprising a plurality of separate containers, the contents of at least two containers differing from each other in whole or in part,
the first of such containers containing:
a first antigenic composition or a first vaccine composition as described, defined or claimed herein; and
the second of such containers containing:
a second antigenic composition or a second vaccine composition as described, defined or claimed herein.

In a yet further main aspect, the invention also relates to:

A packaged vaccine comprising:
a first antigenic composition or a first vaccine composition as described, defined or claimed herein; and/or
a second antigenic composition or a second vaccine composition as described, defined or claimed herein,
the package comprising additionally instructions to:
(a) administer to a subject, preferably one in need thereof, at least once an effective amount of the first antigenic composition; and (b) subsequently administer to the subject at least once an effective amount of the second antigenic composition.

In other aspects, the invention also relates to a first vaccine composition comprising a first antigenic composition as described, defined or claimed herein, and to a second vaccine composition comprising a second antigenic composition as described, defined or claimed herein.

The present invention, and particular non-limiting aspects and/or embodiments thereof, can be described in more detail below. Although the present invention is further described in more detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention which will be limited only by the appended claims and other disclosures herein.

In the following, the elements of the present invention will be described in more detail. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

The practice of the present invention will employ, unless otherwise indicated, conventional methods of chemistry, biochemistry, and recombinant DNA techniques which are explained in the literature in the field (cf, eg, Molecular Cloning: A Laboratory Manual, 2nd Edition, Sambrook et al, eds, Cold Spring Harbor Laboratory Press, Cold Spring Harbor; 1989).

Unless defined otherwise, all technical and scientific terms used herein have the same meanings as commonly understood by one of ordinary skill in the art. For example, the terms used herein are defined as described in "A multilingual glossary of biotechnological terms: (IUPAC Recommendations)", Leuenberger et al, Eds, Helvetica Chimica Acta, CH-4010 Basel, Switzerland (1995).

Where the term "comprising" or "comprising of" is used herein, it does not exclude other elements. For the purposes of the present invention, the term "consisting of" is considered to be a particular embodiment of the term "comprising of". If hereinafter a group is defined to comprise at least a certain number of embodiments, this is also to be understood to disclose a group that consists of all and/or only of these embodiments.

Where used herein, "and/or" is to be taken as specific disclosure of each of the two specified features or components with or without the other. For example "A and/or B" is to be taken as specific disclosure of each of (i) A, (ii) B and (iii) A and B, just as if each is set out individually herein. The term "comprising" encompasses the term "consisting essentially of" which, in turn, encompasses the term "consisting of". Thus, at each occurrence in the present application, the term "comprising" may be replaced with the term "consisting essentially of" or "consisting of". Likewise, at each occurrence in the present application, the term "consisting essentially of" may be replaced with the term "consisting of".

The term "optional" or "optionally" as used herein means that the subsequently described event, circumstance or condition may or may not occur, and that the description includes instances where said event, circumstance, or condition occurs and instances in which it does not occur.

In the context of the present invention, the terms "about" and "approximately" denote an interval of accuracy that the person skilled in the art will understand to still ensure the technical effect of the feature in question. The term typically indicates deviation from the indicated numerical value by ±20%, ±15%, ±10%, and for example ±5%. As will be appreciated by the person of ordinary skill, the specific such deviation for a numerical value for a given technical effect will depend on the nature of the technical effect. For example, a natural or biological technical effect may generally have a larger such deviation than one for a man-made or engineering technical effect. Where an indefinite or definite article is used when referring to a singular noun, e.g. "a", "an" or "the", this includes a plural of that noun unless something else is specifically stated.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

In a main aspect, the invention relates to a method for inducing an immune response in a subject; the method comprising the steps:

(a) administering to a subject in need thereof at least once an effective amount of a first antigenic composition that comprises at least one immunogenic peptide or polypeptide and/or that comprises at least one nucleic acid construct that encodes at least one immunogenic peptide or polypeptide; and (b) subsequently administering to the subject at least once an effective amount of a second antigenic composition that comprises at least one mRNA construct that encodes at least one immunogenic peptide or polypeptide, wherein:

the nucleic acid construct, if comprised in the first antigenic composition, is not an mRNA construct; and at least one epitope of the immunogenic peptide or polypeptide comprised in, or encoded by the nucleic acid construct comprised in, the first antigenic composition is immunologically equivalent to at least one epitope of the immunogenic peptide or polypeptide encoded by the mRNA construct of the second antigenic composition.

Certain embodiments of the invention (for example, methods of the invention such as the aspect above) may be used for vaccinating a subject and/or treating or preventing a condition, disorder or disease in a subject.

In another (related) main aspect, the invention relates to a second antigenic composition that comprises at least one mRNA construct that encodes at least one immunogenic peptide or polypeptide, for use in administering to a subject in need thereof at least once an effective amount of the second antigenic composition subsequently to administration to the subject at least once of an effective amount of a first antigenic composition that comprises at least one immunogenic peptide or polypeptide and/or that comprises at least one nucleic acid construct that encodes at least one immunogenic peptide or polypeptide, wherein:

the nucleic acid construct, if comprised in the first antigenic composition, is not an mRNA construct; and at least one epitope of the immunogenic peptide or polypeptide comprised in, or encoded by the nucleic acid construct comprised in, the first antigenic composition is immunologically equivalent to at least one epitope of the immunogenic peptide or polypeptide encoded by the mRNA construct of the second antigenic composition.

In another aspect, the present invention concerns:

A second antigenic composition that comprises at least one mRNA construct that encodes at least one immunogenic peptide or polypeptide, for use as a vaccine, in administering to a subject in need thereof wherein at least once an effective amount of the second antigenic composition is administered to a subject in need thereof subsequently to administration to the subject at least once of an effective amount of a first antigenic composition that comprises at least one immunogenic peptide or polypeptide and/or that comprises at least one nucleic acid construct that encodes at least one immunogenic peptide or polypeptide, wherein:

the nucleic acid construct, if comprised in the first antigenic composition, is not an mRNA construct; and at least one epitope of the immunogenic peptide or polypeptide comprised in, or encoded by the nucleic acid construct comprised in, the first antigenic composition is immunologically equivalent identical to or at least 70%, 75%, 80%, 85%, 90%, 95% or at least 98% identical to at least one epitope of the immunogenic peptide or polypeptide encoded by the mRNA construct of the second antigenic composition.

In a (corresponding) main aspect, the invention relates to a first antigenic composition that comprises at least one immunogenic peptide or polypeptide and/or that comprises at least one nucleic acid construct that encodes at least one immunogenic peptide or polypeptide, for use in administering to a subject in need thereof at least once an effective amount of the first antigenic composition and prior to administration to the subject at least once an effective amount of a second antigenic composition that comprises at least one mRNA construct that encodes at least one immunogenic peptide or polypeptide, wherein:

the nucleic acid construct, if comprised in the first antigenic composition, is not an mRNA construct; and at least one epitope of the immunogenic peptide or polypeptide comprised in, or encoded by the nucleic acid construct comprised in, the first antigenic composition is immunologically equivalent to at least one epitope of the immunogenic peptide or polypeptide encoded by the mRNA construct of the second antigenic composition.

In a further aspect, the invention preferably relates to: A first antigenic composition that comprises at least one immunogenic peptide or polypeptide and/or that comprises at least one nucleic acid construct that encodes at least one immunogenic peptide or polypeptide, for use as a vaccine, in administering to a subject in need thereof wherein at least once an effective amount of the first antigenic composition is administered to a subject in need thereof and prior to administration to the subject at least once an effective amount of a second antigenic composition that comprises at least one mRNA construct that encodes at least one immunogenic peptide or polypeptide, wherein:

the nucleic acid construct, if comprised in the first antigenic composition, is not an mRNA construct; and at least one epitope of the immunogenic peptide or polypeptide comprised in, or encoded by the nucleic acid construct comprised in, the first antigenic composition is immunologically equivalent identical to or at least 70%, 75%, 80%, 85%, 90%, 95% or at least 98% identical to at least one epitope of the immunogenic peptide or polypeptide encoded by the mRNA construct of the second antigenic composition.

In a further aspect, the invention concerns:

A first antigenic composition that comprises at least one immunogenic peptide or polypeptide and/or that comprises at least one nucleic acid construct that encodes at least one immunogenic peptide or polypeptide, and a second antigenic composition that comprises at least one mRNA construct that encodes at least one immunogenic peptide or polypeptide, wherein the nucleic acid construct, if comprised in the first antigenic composition, is not an mRNA construct; and at least one epitope of the immunogenic peptide or polypeptide comprised in, or encoded by the nucleic acid construct comprised in, the first antigenic composition is identical to or at least 70%, 75%, 80%, 85%, 90%, 95%, 98% or at least 99% identical to at least one epitope of the immunogenic peptide or polypeptide encoded by the mRNA construct of the second antigenic composition, for use as a vaccine, wherein an effective amount of the second antigenic composition is administered at least once to a subject in need thereof subsequently to administration to the subject at least once of an effective amount of a first antigenic composition.

In particular, the present invention comprises medical uses, preferably as described herein, of the first antigenic composition as described herein, of the second antigenic composition as described herein, or of a combination of the first antigenic composition as described herein and the second antigenic composition as described herein. The medical uses as described herein preferably comprise the administration of the first antigenic composition and the second antigenic composition according in the order as described herein. More preferably, the medical uses described herein comprise administration of the second antigenic composition as defined herein subsequently to the administration (at least once) of the first antigenic composition as defined herein. More preferably, the first antigenic composition and the second antigenic composition are administered as 'prime' and 'boost', wherein the first antigenic composition is preferably the 'prime' dosage and the second antigenic composition is preferably the 'boost' dosage.

In preferred embodiments, the present invention provides the first antigenic composition as described herein, the second antigenic composition as described herein, or a combination of the first antigenic composition as described herein and the second antigenic composition as described herein for use as a medicament, preferably for use as a medicament for inducing an immune response.

In further preferred embodiments, the present invention provides the first antigenic composition as described herein, the second antigenic composition as described herein, or a combination of the first antigenic composition as described herein and the second antigenic composition as described herein for use as a vaccine. More preferably, the present invention provides the first antigenic composition as described herein, the second antigenic composition as described herein, or a combination of the first antigenic composition as described herein and the second antigenic composition as described herein for use as a vaccine, wherein the vaccine is used as a medicament for inducing an immune response.

According to another preferred embodiment, the invention concerns the first antigenic composition as described herein, the second antigenic composition as described herein, or a combination of the first antigenic composition as described herein and the second antigenic composition as described herein for use in the treatment or prophylaxis of a condition, disorder or disease, preferably as defined herein. Preferably, the first antigenic composition as described herein, the second antigenic composition as described herein, or a combination of the first antigenic composition as described herein and the second antigenic composition as described herein is provided for use as a vaccine in the treatment or prophylaxis of a condition, disorder or disease, preferably as defined herein.

According to a particularly preferred embodiment, the invention provides the first antigenic composition as described herein, the second antigenic composition as described herein, or a combination of the first antigenic composition as described herein and the second antigenic composition as described herein for use, preferably as a vaccine, in the treatment or prophylaxis of a condition, disorder or disease, wherein the condition, disorder or disease is preferably selected from the group consisting of:

infection with one or more pathogens (infectious diseases), preferably as defined herein;

cancer or tumour diseases, preferably as defined herein;

allergies or allergic diseases, preferably as defined herein; and autoimmune diseases, preferably as defined herein.

For the sake of clarity and readability, the certain scientific background information and definitions are provided herein, including those set out as follows. Any technical features disclosed thereby can be part of each and every embodiment of the invention, as can any technical features disclosed within any additional background information, definitions or explanations as may be provided elsewhere in the context of this disclosure.

Immunologic Equivalence of Epitopes/Antigens/Polypeptides:

Two or more epitopes, antigens and/or immunogenic polypeptides are "immunologically equivalent" if they are recognised by the same antibody, T-cell or B-cell. The recognition of two or more epitopes, antigens and/or immunogenic polypeptides by the same antibody, T-cell or B-cell is also known as "cross reactivity" of said antibody, T-cell or B-cell. Preferably, the recognition of two or more immunologically equivalent epitopes, antigens and/or immunogenic polypeptides by the same antibody, T-cell or B-cell is due to the presence of identical, substantially identical or similar epitopes in the respective antigen or polypeptides. Similar epitopes share enough structural and/or charge characteristics to be bound by the Fab region of the same antibody or B-cell receptor or by the V region of the same T-cell receptor. The binding characteristics of an antibody, T-cell receptor or B-cell receptor are, preferably, defined by the binding affinity of the receptor to the epitope in question.

Two epitopes, antigens and/or immunogenic polypeptides are typically "immunologically equivalent" as understood in the context of the present application if the affinity constant of the epitope, antigen or polypeptide with the lower affinity constant is at least 30%, at least 40%, at least 50%, at least 60%, at least 70%, at least 80%, at least 90%, at least 95% or at least 98% of the affinity constant of the epitopes, antigens and/or immunogenic polypeptide with the higher affinity constant. Methods for determining the binding affinity of an epitope, antigen and/or immunogenic polypeptide to an antibody or a receptor such as equilibrium dialysis or enzyme linked immunosorbent assay (ELISA) are well known in the art. More preferably, the expression 'immunologically equivalent' is used herein with respect to a peptide or a protein, such as an antigen or an epitope, which is identical to or at least 70%, 75%, 80%, 85%, 90%, 95% or at least 98% identical to a reference peptide or protein. The identity is typically determined by comparison of the amino acid sequence of the peptide or protein. Most preferably, the expression 'immunologically equivalent' as used herein with respect to a peptide or a protein, refers to a peptide or protein having an amino acid sequence, which is identical to or at least 70%, 75%, 80%, 85%, 90%, 95% or at least 98% identical to the amino acid sequence of a reference peptide or protein.

Immune System:

The immune system may protect organisms from infection. If a pathogen breaks through a physical barrier of an organism and enters this organism, the innate immune system provides an immediate, but non-specific response. If pathogens evade this innate response, vertebrates possess a second layer of protection, the adaptive immune system. Here, the immune system adapts its response during an infection to improve its recognition of the pathogen. This improved response is then retained after the pathogen has been eliminated, in the form of an immunological memory, and allows the adaptive immune system to mount faster and stronger attacks each time this pathogen is encountered. According to this, the immune system comprises the innate and the adaptive immune system. Each of these two parts contains so called humoral and cellular components.

Immune Response:

An immune response may typically either be a specific reaction of the adaptive immune system to a particular antigen (so called specific or adaptive immune response) or an unspecific reaction of the innate immune system (so called unspecific or innate immune response). One basis of the present invention relates to specific reactions (adaptive immune responses) of the adaptive immune system; particularly adaptive immune responses following the exposure to antigens (such as immunogenic polypeptides). However, this specific response can be supported by an additional unspecific reaction (innate immune response). Therefore, one basis of the present invention also relates to a compound for simultaneous stimulation of the innate and the adaptive immune system to evoke an efficient adaptive immune response. In the context of the present invention, an "antigenic composition" refers to a compound or admixture of compounds (such as in solution or pharmaceutical formulation) that is able to, is used to or useful for, has the capability to or in practice does evoke, raise, generate or elicit an immune response (preferably, an efficient adaptive immune response) when administered to or otherwise exposed to a subject.

Adaptive Immune System:

The adaptive immune system is composed of highly specialized, systemic cells and processes that eliminate or prevent pathogenic or tumour growth. The adaptive immune response provides the vertebrate immune system with the ability to recognize and remember specific pathogens (to generate immunity), and to mount stronger attacks each time the pathogen is encountered. The system is highly adaptable because of somatic hypermutation (a process of increased frequency of somatic mutations), and V(D)J recombination (an irreversible genetic recombination of antigen receptor gene segments). This mechanism allows a small number of genes to generate a vast number of different antigen receptors, which are then uniquely expressed on each individual lymphocyte. Because the gene rearrangement leads to an irreversible change in the DNA of each cell, all of the progeny (offspring) of that cell will then inherit genes encoding the same receptor specificity, including the Memory B cells and Memory T cells that are the keys to long-lived specific immunity. Immune network theory is a theory of how the adaptive immune system works, that is based on interactions between the variable regions of the receptors of T cells, B cells and of molecules made by T cells and B cells that have variable regions.

Adaptive Immune Response:

The adaptive immune response is typically understood to be antigen-specific. Antigen specificity allows for the generation of responses that are tailored to specific antigens, pathogens, tumours or pathogen-infected or cancer cells. The ability to mount these tailored responses is maintained in the body by "memory cells". Should a pathogen infect, or an antigen be presented to, the body more than once, these specific memory cells are used to quickly eliminate it. In this context, the first step of an adaptive immune response is the activation of naïve antigen-specific T cells or different immune cells able to induce an antigen-specific immune response by antigen-presenting cells. This occurs in the lymphoid tissues and organs through which naïve T cells are constantly passing. Cell types that can serve as antigen-presenting cells are inter alia dendritic cells, macrophages, and B cells. Each of these cells has a distinct function in eliciting immune responses. Dendritic cells take up antigens by phagocytosis and macropinocytosis and are stimulated by contact with e.g. a foreign antigen to migrate to the local lymphoid tissue, where they differentiate into mature dendritic cells. Macrophages ingest particulate antigens such as bacteria and are induced by infectious agents or other appropriate stimuli to express MHC molecules. The unique ability of B cells to bind and internalize soluble protein antigens via their receptors may also be important to induce T cells. Presenting the antigen on MHC molecules leads to activation of T cells which induces their proliferation and differentiation into armed effector T cells. The most important function of effector T cells is the killing of infected or antigen displaying cells by CD8+ cytotoxic T cells and the activation of macrophages by Th1 cells which together make up cell-mediated immunity, and the activation of B cells by both Th2 and Th1 cells to produce different classes of antibody, thus driving the humoral immune response. T cells recognize an antigen by their T cell receptors which do not recognize and bind antigen directly, but instead recognize short peptide fragments e.g. of pathogen-derived protein antigens, which are bound to MHC molecules on the surfaces of other cells.

Cellular Immunity/Cellular Immune Response:

Cellular immunity relates typically to the activation of macrophages, natural killer cells (NK), antigen-specific cytotoxic T-lymphocytes, and the release of various cytokines in response to an antigen. In a more general way, cellular immunity is not related to antibodies but to the activation of cells of the immune system. A cellular immune response is characterized e.g. by activating antigen-specific cytotoxic T-lymphocytes that are able to induce apoptosis in body cells displaying epitopes of an antigen on their surface, such as virus-infected cells, cells with intracellular bacteria, and cancer cells displaying tumor antigens; activating macrophages and natural killer cells, enabling them to destroy pathogens; and stimulating cells to secrete a variety of cytokines that influence the function of other cells involved in adaptive immune responses and innate immune responses.

Humoral Immunity/Humoral Immune Response:

Humoral immunity refers typically to antibody production and the accessory processes that may accompany it. A humoral immune response may be typically characterized, e.g., by Th2 activation and cytokine production, germinal center formation and isotype switching, affinity maturation and memory cell generation. Humoral immunity also typically may refer to the effector functions of antibodies, which include pathogen and toxin neutralization, classical complement activation, and opsonin promotion of phagocytosis and pathogen elimination.

Innate Immune System:

The innate immune system, also known as non-specific immune system, comprises the cells and mechanisms that defend the host from infection by other organisms in a non-specific manner. This means that the cells of the innate system recognize and respond to pathogens and other antigens in a generic way, but unlike the adaptive immune system, it does not confer long-lasting or protective immunity to the host. The innate immune system may be e.g. activated by ligands of pathogen-associated molecular patterns (PAMP) receptors, e.g. Toll-like receptors (TLRs) or other auxiliary substances such as lipopolysaccharides, TNF-alpha, CD40 ligand, or cytokines, monokines, lymphokines, interleukins or chemokines, IL-1, IL-2, IL-3, IL-4, IL-5, IL-6, IL-7, IL-8, IL-9, IL-10, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IFN-alpha, IFN-beta, IFN-gamma, GM-CSF, G-CSF, M-CSF, LT-beta, TNF-alpha, growth factors, and hGH, a ligand of human Toll-like receptor TLR1, TLR2, TLR3, TLR4, TLR5, TLR6, TLR7, TLR8, TLR9, TLR10, a ligand of murine Toll-like receptor TLR1, TLR2, TLR3, TLR4, TLR5, TLR6, TLR7, TLR8, TLR9, TLR10, TLR11, TLR12 or TLR13, a ligand of a NOD-like receptor, a ligand of a RIG-I like receptor, an immunostimulatory nucleic acid, an immunostimulatory RNA (isRNA), a CpG-DNA, an antibacterial agent, or an anti-viral agent. Typically a response of the innate immune system includes recruiting immune cells to sites of infection, through the production of chemical factors, including specialized chemical mediators, called cytokines; activation of the complement cascade; identification and removal of foreign substances present in organs, tissues, the blood and lymph, by specialized white blood cells; activation of the adaptive immune system through a process known as antigen presentation; and/or acting as a physical and chemical barrier to infectious agents.

Adjuvant/Adjuvant Component:

An adjuvant or an adjuvant component in the broadest sense is typically a (e.g. pharmacological or immunological) agent or composition that may modify, e.g. enhance, the efficacy of other agents, such as a drug or vaccine. Conventionally the term refers in the context of the invention to a compound or composition that serves as a carrier or auxiliary substance for immunogens and/or other pharmaceutically active compounds. It is to be interpreted in a broad sense and refers to a broad spectrum of substances that are able to increase the immunogenicity of antigens incorporated into or co-administered with an adjuvant in question. In the context of the present invention an adjuvant will preferably enhance the specific immunogenic effect of the active agents of the present invention. Typically, "adjuvant" or "adjuvant component" has the same meaning and can be used mutually. Adjuvants may be divided, e.g., into immuno potentiators, antigenic delivery systems or even combinations thereof.

The term "adjuvant" is typically understood not to comprise agents which confer immunity by themselves. An adjuvant assists the immune system unspecifically to enhance the antigen-specific immune response by e.g. promoting presentation of an antigen to the immune system or induction of an unspecific innate immune response. Furthermore, an adjuvant may preferably e.g. modulate the antigen-specific immune response by e.g. shifting the dominating Th2-based antigen specific response to a more Th1-based antigen specific response or vice versa. Accordingly, an adjuvant may favourably modulate cytokine expression/secretion, antigen presentation, type of immune response etc.

Immunostimulatory RNA:

An immunostimulatory RNA (isRNA) in the context of the invention may typically be an RNA that is able to induce an innate immune response itself. It usually does not have an open reading frame and thus does not provide a peptide-antigen or immunogen but elicits an innate immune response e.g. by binding to a specific kind of Toll-like-receptor (TLR) or other suitable receptors. However, of course also mRNAs having an open reading frame and coding for a peptide/protein (e.g. an antigenic function) may induce an innate immune response.

Antigen:

According to the present invention, the term "antigen" refers typically to a substance which may be recognized by the immune system and may be capable of triggering an antigen-specific immune response, e.g. by formation of antibodies or antigen-specific T-cells as part of an adaptive immune response. An antigen may be a protein or peptide. In this context, the first step of an adaptive immune response is the activation of naïve antigen-specific T cells by antigen-presenting cells. This occurs in the lymphoid tissues and organs through which naïve T cells are constantly passing. The three cell types that can serve as antigen-presenting cells are dendritic cells, macrophages, and B cells. Each of these cells has a distinct function in eliciting immune responses. Tissue dendritic cells take up antigens by phagocytosis and macropinocytosis and are stimulated by infection to migrate to the local lymphoid tissue, where they differentiate into mature dendritic cells. Macrophages ingest particulate antigens such as bacteria and are induced by infectious agents to express MHC class II molecules. The unique ability of B cells to bind and internalize soluble protein antigens via their receptors may be important to induce T cells. By presenting the antigen on MHC molecules leads to activation of T cells which induces their proliferation and differentiation into armed effector T cells. The most important function of effector T cells is the killing of infected cells by CD8+ cytotoxic T cells and the activation of macrophages by Th1 cells which together make up cell-mediated immunity, and the activation of B cells by both Th2 and Th1 cells to produce different classes of antibody, thus driving the humoral immune response. T cells recognize an antigen by their T cell receptors which does not recognize and bind antigen directly, but instead recognize short peptide fragments e.g. of pathogens' protein antigens, which are bound to MHC molecules on the surfaces of other cells.

T cells fall into two major classes that have different effector functions. The two classes are distinguished by the expression of the cell-surface proteins CD4 and CD8. These two types of T cells differ in the class of MHC molecule that they recognize. There are two classes of MHC molecules—MHC class I and MHC class II molecules—which differ in their structure and expression pattern on tissues of the body. CD4+ T cells bind to a MHC class II molecule and CD8+ T cells to a MHC class I molecule. MHC class I and MHC class II molecules have distinct distributions among cells that reflect the different effector functions of the T cells that recognize them. MHC class I molecules present peptides of cytosolic and nuclear origin e.g. from pathogens, commonly viruses, to CD8+ T cells, which differentiate into cytotoxic T cells that are specialized to kill any cell that they specifically recognize. Almost all cells express MHC class I molecules, although the level of constitutive expression varies from one cell type to the next. But not only pathogenic peptides from viruses are presented by MHC class I molecules, also self-antigens like tumour antigens are presented by them. MHC class I molecules bind peptides from proteins degraded in the cytosol and transported in the endoplasmic reticulum. The CD8+ T cells that recognize MHC class I:peptide complexes at the surface of infected cells are specialized to kill any cells displaying foreign peptides and so rid the body of cells infected with viruses and other cytosolic pathogens. The main function of CD4+ T cells (CD4+ helper T cells) that recognize MHC class II molecules is to activate other effector cells of the immune system. Thus MHC class II molecules are normally found on B lymphocytes, dendritic cells, and macrophages, cells that participate in immune responses, but not on other tissue cells. Macrophages, for example, are activated to kill the intravesicular pathogens they harbour, and B cells to secrete immunoglobulins against foreign molecules. MHC class II molecules are prevented from binding to peptides in the endoplasmic reticulum and thus MHC class II molecules bind peptides from proteins which are degraded in endosomes. They can capture peptides from pathogens that have entered the vesicular system of macrophages, or from antigens internalized by immature dendritic cells or the immunoglobulin receptors of B cells. Pathogens that accumulate in large numbers inside macrophage and dendritic cell vesicles tend to stimulate the differentiation of Th1 cells, whereas extracellular antigens tend to stimulate the production of Th2 cells. Th1 cells activate the microbicidal properties of macrophages and induce B cells to make IgG antibodies that are very effective of opsonising extracellular pathogens for ingestion by phagocytic cells, whereas Th2 cells initiate the humoral response by activating naïve B cells to secrete IgM, and induce the production of weakly opsonising antibodies such as IgG1 and IgG3 (mouse) and IgG2 and IgG4 (human) as well as IgA and IgE (mouse and human).

Epitope (Also Called "Antigen Determinant"):

T cell epitopes or parts of the proteins in the context of the present invention may comprise fragments preferably having a length of about 6 to about 20 or even more amino acids, e.g. fragments as processed and presented by MHC class I molecules, preferably having a length of about 8 to about 10 amino acids, e.g. 8, 9, or 10, (or even 11, or 12 amino acids), or fragments as processed and presented by MHC class II molecules, preferably having a length of about 13 or more amino acids, e.g. 13, 14, 15, 16, 17, 18, 19, 20 or even more amino acids, wherein these fragments may be selected from any part of the amino acid sequence. These parts of the proteins or fragments, in the context of the present invention, are recognised by the immune system, typically recognised by T cells in form of a complex consisting of the peptide fragment and an MHC molecule. Preferably, this recognition is mediated by the binding of antibodies, B cells, or T cells to the epitope in question. In this context, the term "binding" preferably relates to a specific binding. Preferably, the specific binding of antibodies to an epitope is mediated by the Fab (fragment, antigen binding) region of the antibody, specific binding of a B-cell is mediated by the Fab region of the antibody comprised by the B-cell receptor and specific binding of a T-cell is mediated by the variable (V) region of the T-cell receptor.

B cell epitopes are typically fragments located on the outer surface of (native) protein or peptide antigens as defined herein, preferably having 5 to 15 amino acids, more preferably having 5 to 12 amino acids, even more preferably having 6 to 9 amino acids, which may be recognized by antibodies, i.e. in their native form.

Such epitopes of proteins or peptides may furthermore be selected from any of the herein mentioned variants of such proteins or peptides. In this context antigenic determinants can be conformational or discontinuous epitopes which are composed of segments of the proteins or peptides as defined herein that are discontinuous in the amino acid sequence of the proteins or peptides as defined herein but are brought together in the three-dimensional structure or continuous or linear epitopes which are composed of a single polypeptide chain.

Epitopes usually consist of surface groupings of molecules such as amino acids or sugar side chains and usually have specific three-dimensional structural characteristics, as well as specific charge characteristics. The term "epitope" refers to conformational as well as non-conformational epitopes. Conformational and non-conformational epitopes are distinguished in that the binding to the former but not the latter is lost in the presence of denaturing solvents.

Immunogenic Polypeptide/Peptide:

An "immunogenic polypeptide" (or "immunogenic peptide", as applicable) as referred to in the present application is a polypeptide (or peptide, as applicable) which contains at least one epitope. Accordingly, such an "immunogenic polypeptide" (or "immunogenic peptide", as applicable) can elicit an immune response in a subject. Preferred immunogenic polypeptides induce a B-cell response or a T-cell response or a B-cell response and a T-cell response. An immunogenic polypeptide in the context of the present invention may be derived from a pathogen selected from the group consisting of viruses, bacteria and protozoa. In particular embodiments, it is derived from a virus. However, in an alternative particular embodiment of the present invention the immunogenic polypeptide is a polypeptide or fragment of a polypeptide expressed by a tumour or a cancer, or is associated with an allergy or an autoimmune disease.

Vaccine:

A vaccine is typically understood to be a prophylactic or therapeutic material providing at least one antigen or antigenic function. The antigen or antigenic function may stimulate the body's adaptive immune system to provide an adaptive immune response.

Antigen-Providing mRNA:

An antigen-providing mRNA in the context of the invention may typically be an mRNA, having at least one open reading frame that can be translated by a cell or an organism provided with that mRNA. The product of this translation is a peptide or protein that may act as an antigen, preferably as an immunogen. The product may also be a fusion protein composed of more than one immunogen, e.g. a fusion protein that consist of two or more epitopes, peptides or proteins derived from the same or different virus-proteins, wherein the epitopes, peptides or proteins may be linked by linker sequences.

Bi-/Multicistronic mRNA:

mRNA, that typically may have two (bicistronic) or more (multicistronic) open reading frames (ORF). An open reading frame in this context is a sequence of several nucleotide triplets (codons) that can be translated into a peptide or protein. Translation of such an mRNA yields two (bicistronic) or more (multicistronic) distinct translation products (provided the ORFs are not identical). For expression in eukaryotes such mRNAs may for example comprise an internal ribosomal entry site (IRES) sequence.

5'-CAP-Structure:

A 5'-CAP is typically a modified nucleotide, particularly a guanine nucleotide, added to the 5' end of an mRNA-molecule. Preferably, the 5'-CAP is added using a 5'-5'-triphosphate linkage (also named m7GpppN). Further examples of 5'-CAP structures include glyceryl, inverted deoxy abasic residue (moiety), 4',5' methylene nucleotide, 1-(beta-D-erythrofuranosyl) nucleotide, 4'-thio nucleotide, carbocyclic nucleotide, 1,5-anhydrohexitol nucleotide, L-nucleotides, alpha-nucleotide, modified base nucleotide, threo-pentofuranosyl nucleotide, acyclic 3',4'-seco nucleotide, acyclic 3,4-dihydroxybutyl nucleotide, acyclic 3,5 dihydroxypentyl nucleotide, 3'-3'-inverted nucleotide moiety, 3'-3'-inverted abasic moiety, 3'-2'-inverted nucleotide moiety, 3'-2'-inverted abasic moiety, 1,4-butanediol phosphate, 3'-phosphoramidate, hexylphosphate, aminohexyl phosphate, 3'-phosphate, 3'phosphorothioate, phosphorodithioate, or bridging or non-bridging methylphosphonate moiety. These modified 5'-CAP structures may be used in the context of the present invention to modify the inventive mRNA sequence. Further modified 5'-CAP structures which may be used in the context of the present invention are CAP1 (methylation of the ribose of the adjacent nucleotide of m7GpppN), CAP2 (methylation of the ribose of the $2^{nd}$ nucleotide downstream of the m7GpppN), CAP3 (methylation of the ribose of the 3rd nucleotide downstream of the m7GpppN), CAP4 (methylation of the ribose of the $4^{th}$ nucleotide downstream of the m7GpppN), ARCA (anti-reverse CAP analogue, modified ARCA (e.g. phosphothioate modified ARCA), inosine, N1-methyl-guanosine, 2'-fluoro-guanosine, 7-deaza-guanosine, 8-oxo-guanosine, 2-amino-guanosine, LNA-guanosine, and 2-azido-guanosine.

Fragments of Proteins:

"Fragments" of proteins or peptides in the context of the present invention may, typically, comprise a sequence of a protein or peptide as defined herein, which is, with regard to its amino acid sequence (or its encoded nucleic acid molecule), N-terminally and/or C-terminally truncated compared to the amino acid sequence of the original (native) protein (or its encoded nucleic acid molecule). Such truncation may thus occur either on the amino acid level or correspondingly on the nucleic acid level. A sequence identity with respect to such a fragment as defined herein may therefore preferably refer to the entire protein or peptide as defined herein or to the entire (coding) nucleic acid molecule of such a protein or peptide. Fragments of proteins or peptides in the context of the present invention may comprise a sequence of a protein or peptide as defined herein which represents at least 20%, preferably at least 30%, more preferably at least 40%, more preferably at least 50%, even more preferably at least 60%, even more preferably at least 70%, even more preferably at least 80%, and most preferably at least 90% of the full-length amino acid sequence.

Fragments of proteins or peptides in the context of the present invention may furthermore comprise a sequence of a protein or peptide as defined herein, which has a length of for example at least 5 amino acids, preferably a length of at least 6 amino acids, preferably at least 7 amino acids, more preferably at least 8 amino acids, even more preferably at least 9 amino acids; even more preferably at least 10 amino acids; even more preferably at least 11 amino acids; even more preferably at least 12 amino acids; even more preferably at least 13 amino acids; even more preferably at least 14 amino acids; even more preferably at least 15 amino acids; even more preferably at least 16 amino acids; even more preferably at least 17 amino acids; even more preferably at least 18 amino acids; even more preferably at least 19 amino acids; even more preferably at least 20 amino acids; even more preferably at least 25 amino acids; even more preferably at least 30 amino acids; even more preferably at least 35 amino acids; even more preferably at least 50 amino acids; or most preferably at least 100 amino acids. For example such fragment may have a length of about 6 to about 20 or even more amino acids, e.g. fragments as processed and presented by MHC class I molecules, preferably having a length of about 8 to about 10 amino acids, e.g. 8, 9, or 10, (or even 6, 7, 11, or 12 amino acids), or fragments as processed and presented by MHC class II molecules, preferably having a length of about 13 or more amino acids, e.g. 13, 14, 15, 16, 17, 18, 19, 20 or even more amino acids, wherein these fragments may be selected from any part of the amino acid sequence. These fragments are typically recognized by T-cells in form of a complex consisting of the peptide fragment and an MHC molecule, i.e. the fragments are typically not recognized in their native form. Fragments of proteins or peptides may comprise at least one epitope of those proteins or peptides. Furthermore also domains of a protein, like the extracellular domain, the intracellular domain or the transmembrane domain and shortened or truncated versions of a protein may be understood to comprise a fragment of a protein.

Variants of Proteins:

"Variants" of proteins or peptides as defined in the context of the present invention may be generated, having an amino acid sequence which differs from the original sequence in one or more mutation(s), such as one or more substituted, inserted and/or deleted amino acid(s). Preferably, these fragments and/or variants have the same biological function or specific activity compared to the full-length native protein, e.g. its specific antigenic property. "Variants" of proteins or peptides as defined in the context of the present invention may comprise conservative amino acid substitution(s) compared to their native, i.e. non-mutated physiological, sequence. Those amino acid sequences as well as their encoding nucleotide sequences in particular fall under the term variants as defined herein. Substitutions in which amino acids, which originate from the same class, are exchanged for one another are called conservative substitutions. In particular, these are amino acids having aliphatic side chains, positively or negatively charged side chains, aromatic groups in the side chains or amino acids, the side chains of which can enter into hydrogen bridges, e.g. side chains which have a hydroxyl function. This means that e.g. an amino acid having a polar side chain is replaced by another amino acid having a likewise polar side chain, or, for example, an amino acid characterized by a hydrophobic side chain is substituted by another amino acid having a likewise hydrophobic side chain (e.g. serine (threonine) by threonine (serine) or leucine (isoleucine) by isoleucine (leucine)). Insertions and substitutions are possible, in particular, at those sequence positions which cause no modification to the three-dimensional structure or do not affect the binding region. Modifications to a three-dimensional structure by insertion(s) or deletion(s) can easily be determined e.g. using CD spectra (circular dichroism spectra) (Urry, 1985, Absorption, Circular Dichroism and ORD of Polypeptides, in: Modern Physical Methods in Biochemistry, Neuberger et al. (ed.), Elsevier, Amsterdam).

A "variant" of a protein or peptide may have at least 70%, 75%, 80%, 85%, 90%, 95%, 98% or 99% amino acid identity over a stretch of 10, 20, 30, 50, 75 or 100 amino acids of such protein or peptide.

Furthermore, variants of proteins or peptides as defined herein, which may be encoded by a nucleic acid molecule, may also comprise those sequences, wherein nucleotides of the encoding nucleic acid sequence are exchanged according to the degeneration of the genetic code, without leading to an alteration of the respective amino acid sequence of the protein or peptide, i.e. the amino acid sequence or at least part thereof may not differ from the original sequence in one or more mutation(s) within the above meaning.

Identity of a Sequence:

In order to determine the percentage to which two sequences are identical, e.g. nucleic acid sequences or amino acid sequences as defined herein, preferably the amino acid sequences encoded by a nucleic acid sequence of the polymeric carrier as defined herein or the amino acid sequences themselves, the sequences can be aligned in order to be subsequently compared to one another. Therefore, e.g. a position of a first sequence may be compared with the corresponding position of the second sequence. If a position in the first sequence is occupied by the same component (residue) as is the case at a position in the second sequence, the two sequences are identical at this position. If this is not the case, the sequences differ at this position. If insertions occur in the second sequence in comparison to the first sequence, gaps can be inserted into the first sequence to allow a further alignment. If deletions occur in the second sequence in comparison to the first sequence, gaps can be inserted into the second sequence to allow a further alignment. The percentage to which two sequences are identical is then a function of the number of identical positions divided by the total number of positions including those positions which are only occupied in one sequence. The percentage to which two sequences are identical can be determined using a mathematical algorithm. A preferred, but not limiting, example of a mathematical algorithm which can be used is the algorithm of Karlin et al. (1993), PNAS USA, 90:5873-5877 or Altschul et al. (1997), Nucleic Acids Res., 25:3389-3402. Such an algorithm is integrated in the BLAST program. Sequences which are identical to the sequences of the present invention to a certain extent can be identified by this program.

Derivative of a Protein or Peptide:

A derivative of a peptide or protein is typically understood to be a molecule that is derived from another molecule, such as said peptide or protein. A "derivative" of a peptide or protein also encompasses fusions comprising a peptide or protein used in the present invention. For example, the fusion comprises a label, such as, for example, an epitope, e.g., a FLAG epitope or a V5 epitope. For example, the epitope is a FLAG epitope. Such a tag is useful for, for example, purifying the fusion protein.

Monocistronic mRNA:

A monocistronic mRNA may typically be an mRNA, that encodes only one open reading frame. An open reading frame in this context is a sequence of several nucleotide triplets (codons) that can be translated into a peptide or protein.

Nucleic Acid:

The term "nucleic acid" means any polymeric macromolecules made from nucleotide monomers, and is used synonymous with "polynucleotide". Nucleotide monomers are composed of a nucleobase, a five-carbon sugar (such as but not limited to ribose or 2'-deoxyribose), and one to three phosphate groups. Typically, a polynucleotide is formed through phosphodiester bonds between the individual nucleotide monomers. In the context of the present invention preferred nucleic acid molecules include but are not limited DNA- or RNA-molecule, and in particular messenger RNA (mRNA). Moreover, the term "nucleic acid" also includes artificial analogues of DNA or RNA, such as peptide nucleic acid (PNA), and also polynucleotides, such as RNA, that include non-natural nucleotides or nucleotide analogues such as those disclosed in WO2013/052523. Wherever herein reference is made to a nucleic acid or nucleic acid sequence encoding a particular protein and/or peptide, said nucleic acid or nucleic acid sequence, respectively, preferably also comprises regulatory and/or other sequences allowing in a suitable host, e.g. a human being, its expression and/or stability, i.e. transcription and/or translation of the nucleic acid sequence encoding the particular protein or peptide, and such nucleic acid or nucleic acid sequence (comprising the sequence encoding the protein and/or peptide and one or more such regulatory and/or other sequences) may be described as a "nucleic acid construct".

Pharmaceutically Effective Amount:

A pharmaceutically effective amount in the context of the invention is typically understood to be an amount that is sufficient to induce an immune response.

Poly (C) Sequence:

A poly-(C)-sequence is typically a long sequence of cytosine nucleotides, typically about 10 to about 200 cytosine nucleotides, preferably about 10 to about 100 cytosine nucleotides, more preferably about 10 to about 70 cytosine nucleotides or even more preferably about 20 to about 50 or even about 20 to about 30 cytosine nucleotides. A poly(C) sequence may preferably be located 3' of the coding region comprised by a nucleic acid.

Poly-A-Tail/Poly(A) Sequence:

A poly-A-tail also called "3'-poly(A) tail" or "poly(A) sequence" is typically a (long) sequence of adenosine nucleotides of up to about 400 adenosine nucleotides, e.g. from about 25 to about 400, preferably from about 50 to about 400, more preferably from about 50 to about 300, even more preferably from about 50 to about 250, most preferably from about 60 to about 250 adenosine nucleotides, added to the 3' end of a RNA.

Stabilized Nucleic Acid:

A stabilized nucleic acid, typically, exhibits a modification increasing resistance to in vivo degradation (e.g. degradation by an exo- or endo-nuclease) and/or ex vivo degradation (e.g. by the manufacturing process prior to vaccine administration, e.g. in the course of the preparation of the vaccine solution to be administered). Stabilization of RNA can, e.g., be achieved by providing a 5'-CAP-Structure, a Poly-A-Tail, or any other UTR-modification. It can also be achieved by backbone-modification or modification of the G/C-content of the nucleic acid. Various other methods are known in the art and conceivable in the context of the invention.

Carrier/Polymeric Carrier:

A carrier in the context of the invention may typically be a compound that facilitates transport and/or complexation of another compound. Said carrier may form a complex with said other compound. A polymeric carrier is a carrier that is formed of a polymer.

Cationic Component: The Term "Cationic Component" Typically Refers to a Charged molecule, which is positively charged (cation) at a pH value of typically about 1 to 9, preferably of a pH value of or below 9 (e.g. 5 to 9), of or below 8 (e.g. 5 to 8), of or below 7 (e.g. 5 to 7), most preferably at physiological pH values, e.g. about 7.3 to 7.4. Accordingly, a cationic peptide, protein or polymer according to the present invention is positively charged under physiological conditions, particularly under physiological salt conditions of the cell in vivo. A cationic peptide or protein preferably contains a larger number of cationic amino acids, e.g. a larger number of Arg, His, Lys or Orn than other amino acid residues (in particular more cationic amino acids than anionic amino acid residues like Asp or Glu) or contains blocks predominantly formed by cationic amino acid residues. The definition "cationic" may also refer to "polycationic" components.

Vehicle:

An agent, e.g. a carrier, that may typically be used within a pharmaceutical composition or vaccine for facilitating administering of the components of the pharmaceutical composition or vaccine to an individual.

3'-Untranslated Region (3'-UTR):

A 3'-UTR is typically the part of an mRNA which is located between the protein coding region (i.e. the open reading frame) and the poly(A) sequence of the mRNA. A 3'-UTR of the mRNA is not translated into an amino acid sequence. The 3'-UTR sequence is generally encoded by the gene which is transcribed into the respective mRNA during the gene expression process. The genomic sequence is first transcribed into pre-mature mRNA, which comprises optional introns. The pre-mature mRNA is then further processed into mature mRNA in a maturation process. This maturation process comprises the steps of 5'-Capping, splicing the pre-mature mRNA to excise optional introns and modifications of the 3'-end, such as polyadenylation of the 3'-end of the pre-mature mRNA and optional endo- or exonuclease cleavages etc. In the context of the present invention, a 3'-UTR corresponds to the sequence of a mature mRNA which is located 3' to the stop codon of the protein coding region, preferably immediately 3' to the stop codon of the protein coding region, and which extends to the 5'-side of the poly(A) sequence, preferably to the nucleotide immediately 5' to the poly(A) sequence. The term "corresponds to" means that the 3'-UTR sequence may be an RNA sequence, such as in the mRNA sequence used for defining the 3'-UTR sequence, or a DNA sequence which corresponds to such RNA sequence. In the context of the present invention, the term "a 3'-UTR of a gene", such as "a 3'-UTR of an albumin gene", is the sequence which corresponds to the 3'-UTR of the mature mRNA derived from this gene, i.e. the mRNA obtained by transcription of the gene and maturation of the pre-mature mRNA. The term "3'-UTR of a gene" encompasses the DNA sequence and the RNA sequence of the 3'-UTR.

5'-Untranslated Region (5'-UTR):

A 5'-UTR is typically understood to be a particular section of messenger RNA (mRNA). It is located 5' of the open reading frame of the mRNA. Typically, the 5'-UTR starts with the transcriptional start site and ends one nucleotide before the start codon of the open reading frame. The 5'-UTR may comprise elements for controlling gene expression, also called regulatory elements. Such regulatory elements may be, for example, ribosomal binding sites or a 5'-Terminal Oligopyrimidine Tract. The 5'-UTR may be posttranscriptionally modified, for example by addition of a 5'-CAP. In the context of the present invention, a 5'-UTR corresponds to the sequence of a mature mRNA which is located between the 5'-CAP and the start codon. Preferably, the 5'-UTR corresponds to the sequence which extends from a nucleotide located 3' to the 5'-CAP, preferably from the nucleotide located immediately 3' to the 5'-CAP, to a nucleotide located 5' to the start codon of the protein coding region, preferably to the nucleotide located immediately 5' to the start codon of the protein coding region. The nucleotide located immediately 3' to the 5'-CAP of a mature mRNA typically corresponds to the transcriptional start site. The term "corresponds to" means that the 5'-UTR sequence may be an RNA sequence, such as in the mRNA sequence used for defining the 5'-UTR sequence, or a DNA sequence which corresponds to such RNA sequence. In the context of the present invention, the term "a 5'-UTR of a gene", such as "a 5'-UTR of a TOP gene", is the sequence which corresponds to the 5'-UTR of the mature mRNA derived from this gene, i.e. the mRNA obtained by transcription of the gene and maturation of the pre-mature mRNA. The term "5'-UTR of a gene" encompasses the DNA sequence and the RNA sequence of the 5'-UTR.

5'Terminal Oligopyrimidine Tract (TOP):

The 5'terminal oligopyrimidine tract (TOP) is typically a stretch of pyrimidine nucleotides located at the 5' terminal region of a nucleic acid molecule, such as the 5' terminal region of certain mRNA molecules or the 5' terminal region of a functional entity, e.g. the transcribed region, of certain genes. The sequence starts with a cytidine, which usually corresponds to the transcriptional start site, and is followed by a stretch of usually about 3 to 30 pyrimidine nucleotides. For example, the TOP may comprise 3, 4, 5, 6, 7, 8, 9, 10, 11, 12, 13, 14, 15, 16, 17, 18, 19, 20, 21, 22, 23, 24, 25, 26, 27, 28, 29, 30 or even more nucleotides. The pyrimidine stretch and thus the 5' TOP ends one nucleotide 5' to the first purine nucleotide located downstream of the TOP. Messenger RNA that contains a 5'terminal oligopyrimidine tract is often referred to as TOP mRNA. Accordingly, genes that provide such messenger RNAs are referred to as TOP genes. TOP sequences have, for example, been found in genes and mRNAs encoding peptide elongation factors and ribosomal proteins.

Top Motif:

In the context of the present invention, a TOP motif is a nucleic acid sequence which corresponds to a 5'TOP as defined above. Thus, a TOP motif in the context of the present invention is preferably a stretch of pyrimidine nucleotides having a length of 3-30 nucleotides. Preferably, the TOP-motif consists of at least 3 pyrimidine nucleotides, preferably at least 4 pyrimidine nucleotides, preferably at least 5 pyrimidine nucleotides, more preferably at least 6 nucleotides, more preferably at least 7 nucleotides, most preferably at least 8 pyrimidine nucleotides, wherein the stretch of pyrimidine nucleotides preferably starts at its 5'end with a cytosine nucleotide. In TOP genes and TOP mRNAs, the TOP-motif preferably starts at its 5'end with the transcriptional start site and ends one nucleotide 5' to the first purin residue in said gene or mRNA. A TOP motif in the sense of the present invention is preferably located at the 5'end of a sequence which represents a 5'-UTR or at the 5'end of a sequence which codes for a 5'-UTR. Thus, preferably, a stretch of 3 or more pyrimidine nucleotides is called "TOP motif" in the sense of the present invention if this stretch is located at the 5'end of a respective sequence, such as the inventive mRNA, the 5'-UTR element of the inventive mRNA, or the nucleic acid sequence which is derived from the 5'-UTR of a TOP gene as described herein. In other words, a stretch of 3 or more pyrimidine nucleotides which is not located at the 5'-end of a 5'-UTR or a 5'-UTR element but anywhere within a 5'-UTR or a 5'-UTR element is preferably not referred to as "TOP motif".

TOP Gene:

TOP genes are typically characterised by the presence of a 5' terminal oligopyrimidine tract. Furthermore, most TOP genes are characterized by a growth-associated translational regulation. However, also TOP genes with a tissue specific translational regulation are known. As defined above, the 5'-UTR of a TOP gene corresponds to the sequence of a 5'-UTR of a mature mRNA derived from a TOP gene, which preferably extends from the nucleotide located 3' to the 5'-CAP to the nucleotide located 5' to the start codon. A 5'-UTR of a TOP gene typically does not comprise any start codons, preferably no upstream AUGs (uAUGs) or upstream open reading frames (uORFs). Therein, upstream AUGs and upstream open reading frames are typically understood to be AUGs and open reading frames that occur 5' of the start codon (AUG) of the open reading frame that should be translated. The 5'-UTRs of TOP genes are generally rather short. The lengths of 5'-UTRs of TOP genes may vary between 20 nucleotides up to 500 nucleotides, and are typically less than about 200 nucleotides, preferably less than about 150 nucleotides, more preferably less than about 100 nucleotides. Exemplary 5'-UTRs of TOP genes in the sense of the present invention are the nucleic acid sequences extending from the nucleotide at position 5 to the nucleotide located immediately 5' to the start codon (e.g. the ATG) in the sequences according to SEQ ID Nos. 1-1363, SEQ ID NO. 1395, SEQ ID NO. 1421 and SEQ ID NO. 1422 of the international patent application WO2013/143700 or homologs or variants thereof, whose disclosure is incorporated herewith by reference. In this context a particularly preferred fragment of a 5'-UTR of a TOP gene is a 5'-UTR of a TOP gene lacking the 5'TOP motif. The term '5'-UTR of a TOP gene' preferably refers to the 5'-UTR of a naturally occurring TOP gene.

Fragment of a Nucleic Acid Sequence, Particularly an mRNA:

A fragment of a nucleic acid sequence consists of a continuous stretch of nucleotides corresponding to a continuous stretch of nucleotides in the full-length nucleic acid sequence which is the basis for the nucleic acid sequence of the fragment, which represents at least 20%, preferably at least 30%, more preferably at least 40%, more preferably at least 50%, even more preferably at least 60%, even more preferably at least 70%, even more preferably at least 80%, and most preferably at least 90% of the full-length nucleic acid sequence. Such a fragment, in the sense of the present invention, is preferably a functional fragment of the full-length nucleic acid sequence. Fragments of a nucleic acid sequence in the context of the present invention may furthermore comprise a sequence of nucleotides as defined herein, which has a length of for example at least 15 nucleotides, preferably a length of at least 18 nucleotides, preferably at least 21 nucleotides, more preferably at least 24 nucleotides, even more preferably at least 27 nucleotides; even more preferably at least 30 nucleotides; even more preferably at least 33 nucleotides acids; even more preferably at least 36 nucleotides; even more preferably at least 39 nucleotides; even more preferably at least 42 nucleotides; even more preferably at least 45 nucleotides; even more preferably at least 48 nucleotides; even more preferably at least 51 nucleotides; even more preferably at least 54 nucleotides; even more preferably at least 57 nucleotides; even more preferably at least 60 nucleotides; even more preferably at least 75 nucleotides; even more preferably at least 90 nucleotides; even more preferably at least 105 nucleotides; even more preferably at least 150 nucleotides; or most preferably at least 300 nucleotides, or more nucleotides such as between about 300 and 500 nucleotides or between about 500 and 1,000 nucleotides.

Variant of a Nucleic Acid Sequence, Particularly an mRNA:

A variant of a nucleic acid sequence refers to a variant of nucleic acid sequences which forms the basis of a nucleic acid sequence. For example, a variant nucleic acid sequence may exhibit one or more nucleotide deletions, insertions, additions and/or substitutions compared to the nucleic acid sequence from which the variant is derived. Preferably, a variant of a nucleic acid sequence is at least 40%, preferably at least 50%, more preferably at least 60%, more preferably at least 70%, even more preferably at least 80%, even more preferably at least 90%, most preferably at least 95% identical to the nucleic acid sequence the variant is derived from. Preferably, the variant is a functional variant. A "variant" of a nucleic acid sequence may have at least 70%, 75%, 80%, 85%, 90%, 95%, 98% or 99% nucleotide identity over a stretch of 10, 20, 30, 50, 75 or 100 nucleotide of such nucleic acid sequence.

Homolog of a Nucleic Acid Sequence:

The term "homolog" of a nucleic acid sequence refers to sequences of other species than the particular sequence. It is particular preferred that the nucleic acid sequence is of human origin and therefore it is preferred that the homolog is a homolog of a human nucleic acid sequence. Preferably, a homolog of a nucleic acid sequence is at least 40%, preferably at least 50%, more preferably at least 60%, more preferably at least 70%, even more preferably at least 80%, even more preferably at least 90%, most preferably at least 95% identical to a reference nucleic acid. A "homolog" of a nucleic acid sequence may have at least 70%, 75%, 80%, 85%, 90%, 95%, 98% or 99% nucleotide identity over a stretch of 10, 20, 30, 50, 75 or 100 nucleotides of such nucleic acid sequence.

Jet Injection:

The term "jet injection", as used herein, refers to a needle-free injection method, wherein a fluid containing at least one inventive mRNA sequence and, optionally, further suitable excipients is forced through an orifice, thus generating an ultra-fine liquid stream of high pressure that is capable of penetrating mammalian skin and, depending on the injection settings, subcutaneous tissue or muscle tissue. In principle, the liquid stream forms a hole in the skin, through which the liquid stream is pushed into the target tissue. Preferably, jet injection is used for intradermal, subcutaneous or intramuscular injection of the mRNA sequence according to the invention. In a preferred embodiment, jet injection is used for intramuscular injection of the mRNA sequence according to the invention. In a further preferred embodiment, jet injection is used for intradermal injection of the mRNA sequence according to the invention.

Proteins, Polypeptides and Peptides:

The terms "protein", "polypeptide" and "peptide" are used interchangeably herein and refer to any peptide-linked chain of amino acids, regardless of length or co-translational or post-translational modification. Specially and additionally included in such definition for a protein polypeptide or protein that is not encoded on a nucleic acid construct are such chains that include one or more non-natural amino acids or amino-acids-like building blocks. In particular, such non-encoded peptides can encompass includes peptoids, N-methylated peptides, peptidomimetics and peptide-like molecules that incorporate non-natural amino acids or those having alterative chirality. In certain embodiments, a protein or polypeptide may consist of over about 20, 30, 50, 60, 80, 100, 150, 200, 250, 300 amino acids (or the equivalent including amino-acids-like building blocks), and a peptide may consist of less than about 100, 80, 60, 30, 20, or 15 amino acids (or the equivalent including amino-acids-like building blocks) such as between about 14 and 10, 12 and 8 or 11 and 6, and in certain embodiments less than 5 amino acids (or the equivalent including amino-acids-like building blocks). The term "co-translational" used herein refers to events that occur during the translation process of a nucleotide triplet into an amino acid chain. Those events typically alter or modify the chemical or structural properties of the resultant amino acid chain. Examples of co-translational events include but are not limited to events that may stop the translation process entirely or interrupt the peptide bond formation resulting in two discreet translation products. The term "post-translational" used herein refers to events that occur after the translation of a nucleotide triplet into an amino acid and the formation of a peptide bond to the preceding amino acid in the sequence. Such post-translational events may occur after the entire polypeptide was formed or already during the translation process on those parts of the polypeptide that have already been translated. Post-translational events typically alter or modify the chemical or structural properties of the resultant polypeptide. Examples of post-translational events include but are not limited to events such as glycosylation or phosphorylation of amino acids, or cleavage of the peptide chain, e.g. by an endopeptidase. Proteins, polyproteins or peptides usable in the present invention, in particular those not encoded by a nucleic acid construct, (including protein derivatives, protein variants, protein fragments, protein segments, protein epitopes and protein domains) can be further modified by chemical modification. Hence, in such embodiments a chemically modified polypeptide may comprise chemical groups other than the residues found in the 20 naturally occurring amino acids. Examples of such other chemical groups include without limitation glycosylated amino acids and phosphorylated amino acids. Chemical modifications of a polypeptide may provide advantageous properties as compared to the parent polypeptide, e.g. one or more of enhanced stability, increased biological half-life, or increased water solubility. Chemical modifications applicable to the variants usable in the present invention include without limitation: PEGylation, glycosylation of non-glycosylated parent polypeptides, or the modification of the glycosylation pattern present in the parent polypeptide. Such chemical modifications applicable to the variants usable in the present invention may occur co- or post-translational. In certain embodiments, a peptide can include the meaning of a polymer of amino acid monomers, where usually the monomers are linked by peptide bonds, and where such term "peptide" does not limit the length of the polymer chain of amino acids. However, in certain of such embodiments a peptide may for example contain less than 50 monomer units. Longer of such peptides can, in certain embodiments, called polypeptides, typically having 50 to 600 monomeric units, more specifically 50 to 300 monomeric units, or can be proteins. In alternative embodiments, a protein can have a meaning that includes a molecule that consists of one or more peptides and/or polypeptides, typically folded into 3-dimensional form, such as for facilitating a biological function.

The present invention, in particular the methods, compositions, (packaged) vaccine (compositions) or kits of the present invention may be used with, in, administered to or otherwise in connection with a subject; in particular wherein the term "subject" comprises the terms such as "patient", "individual", or "animal" as they relate to multicellular animals, such as vertebrates. For example, vertebrates in the context of the present invention are mammals, birds (e.g., poultry), reptiles, amphibians, bony fishes, and cartilaginous fishes, in particular domesticated animals of any of the foregoing as well as animals (in particular vertebrates) in captivity such as animals (in particular vertebrates) of zoos. Mammals in the context of the present invention include, but are not limited to, humans, non-human primates, domesticated mammals, such as dogs, cats, sheep, cattle, goats, pigs, horses etc., laboratory mammals such as mice, rats, rabbits, guinea pigs, etc. as well as mammals in captivity such as mammals of zoos. The term "animal" as used herein also includes humans. Particular non-limiting examples of birds include domesticated poultry, and include birds such as chickens, turkeys, ducks, geese, guinea fowl, pigeons, pheasants etc; while particular non-limiting examples of bony or cartilaginous fish include those suitable for cultivation by aquiculture, and include bony fish such as salmon, trout, perch, carp, cat-fish, etc. In particular embodiments of all applicable aspects of the invention, the subject may be a human subject, such as a human individual in need of treatment or prophylaxis of a condition, disorder or disease; and/or of the induction of an immune response; and/or administration with a (vaccine) composition or component of a kit or packaged vaccine of the present invention; and/or subjected to or used in one or more of treatment regimen disclosed herein, such as a method of the present invention.

The various aspects of the invention, in general, relate to various embodiments of methods, compositions, vaccines, kits, packages and components thereof for so-called "prime-boost" immunisation and/or vaccine regimens.

The present invention is based on the inventors' surprising finding that prime-boost administration regimens described herein, such as those generally described in the main aspects above, result in enhanced or improved immune response compared to alterative or prior art immunisation or vaccination regimens.

Prime-Boost:

In many cases, a single administration of a vaccine is not sufficient to generate the immune response (eg a sufficient number or type of long-lasting immune cells) which is required for effective treatment and/or prophylaxis such as protection in case of future infection of a pathogen in question, protect against conditions, disorders or diseases including tumour, cancer allergy or autoimmune conditions, disorders or diseases or for therapeutically treating a condition, disorder or disease, like a cancer, tumour, or autoimmune condition, disorder or disease. Consequently, repeated challenge with an antigenic composition in respect of a specific pathogen or condition, disorder or disease is required in order to establish lasting and protective immune response and/or immunity against said pathogen or condition, disorder or disease or to treat or cure a given condition, disorder or disease. An administration regimen comprising the repeated administration of one or more antigenic compositions (eg a vaccine) directed against or in respect of the same pathogen or condition, disorder or disease is referred to in the present application as "prime-boost" immunisation or vaccination regimen. Preferably, such a prime-boost immunisation or vaccination regimen involves at least two administrations of one or more antigenic compositions (such as a vaccine or vaccine composition) directed against or in respect of a specific pathogen, group of pathogens or specific or group of conditions, disorders or diseases. The first administration of such an antigenic composition is referred to as "priming", or as "prime administration" and such first antigenic composition can be referred to as the "priming" or "prime" composition. Correspondingly any subsequent administration of the same (or different) antigenic composition directed against the same specific or group of pathogen, conditions, disorders or diseases as the first antigenic composition can be referred to as "boosting", or as "boost administration" and such subsequently administered antigenic composition can be referred to as the "boosting" or "boost" composition.

Accordingly, certain embodiments of the various aspects of the present invention include where the first antigenic composition and the second antigenic composition are administered to the subject, respectively, in a prime-boost immunisation regime and/or a prime-boost vaccination regime. In certain of such embodiments, the second antigenic composition is subsequently administered (ie, administered after) within about 48 weeks, 24 weeks, 12 weeks, 8 weeks, 6 weeks, 5 weeks, 4 week, 3 weeks, or within about 28, 14 or 7 days of administration of the first antigenic composition. In particular of such embodiments, the second antigenic composition is subsequently administered within about 27, 24, 21, 18, 15, 12, 10, 9, 8, 7, 6, 5, 4, 3, 2 or 1 day(s) after administration of the first antigenic composition.

Certain embodiments of the present invention include those where the first (prime/priming) antigenic composition and/or the second (boost/boosting) antigenic composition is administered once. However, alternative embodiments of the present invention are also envisioned in which the first (prime/priming) antigenic composition and/or the second (boost/boosting) antigenic composition is (or is to be) administered to the subject more than once, such as in two of more administrations or doses.

Accordingly, the present invention also includes embodiments wherein: the first antigenic composition is administered in two or more doses prior to the administration of the second antigenic composition, and/or the second antigenic composition is administered in two or more doses subsequently to the administration of the first antigenic composition, such as from 2 to 7 doses, from 2 to 5 or from 3 to 5 doses (such as about 4 doses). In a particularly such embodiments, 3 consecutive doses of the first and/or second antigenic composition are administered to the subject. In another of such embodiments 2 consecutive doses of the first and/or second antigenic composition are administered to the subject. In particular embodiments, the first antigenic composition and/or the second antigenic composition is administered in a number of doses selected from the list of consisting of: 2, 3, 4, 5, 6, 7, 8, 9 and 10 times, or in certain other embodiments in a number of doses of more than 10 such as between 10 and 20.

In particular, when used in the present invention, the mRNA comprising second antigenic composition may alternatively be provided such that it is administered for preventing or treating a condition, disorder or diseases disclosed herein by two or more doses, each dose containing the same mRNA sequence (or one a different mRNA construct—such as a fragment, variant or derivative thereof—that encodes at least an epitope or antigen that is immunologically equivalent to that encoded by the earlier mRNA construct or that encodes that a different epitope or antigen but that is still directed against or in respect of the same condition, disorder or diseases). Certain of such embodiments, the two or more doses are administered consecutively, for example in one of such embodiments subsequently and shortly one after the other, e.g. within less than 10 minutes, preferably less than 2 minutes, and/or at the same (or different) site of the body to achieve the same or similar immunological effect as for administration of one single dose (such as a composition containing both mRNA constructs). In other of such embodiments, the two or more doses are administered within about 15 minutes, 30 minutes, 1 hour, 3 hours, 6 hours, 12, hours of each other.

In other embodiments of the present invention, the interval between the administration of one or more pairs of consecutive doses of the first antigenic composition (and/or consecutive doses of the second antigenic composition) is from about 1 to 180 days, such as about 5 to 120 days, and includes such embodiments from about 7 to 15 days or 15 to 30 days, and from about 7 to 14 days, 14 to 21 days, 21 to 28 days, 28 to 35 days, 35 to 45 days, 45 to 60 days, 60 to 75 days, 75 to 90 days, or 90 to 120 days. The present invention also includes embodiments where the interval between the administration of two or more doses of the first antigenic composition (and/or doses of the second antigenic composition) occurs over at least about 7 days, such as about 28 days. For example, for boost administration of at least 5 doses of the (mRNA comprising) second antigenic composition can be administered within about 20-30 days.

The various aspects of the present invention also include embodiments where a single dose of the mRNA comprising second antigenic (or vaccine composition) comprises an effective amount of the mRNA construct that encodes the at least one immunogenic peptide or polypeptide, and/or a specific amount of such RNA construct. Preferably, such mRNA construct is provided in an amount of at least 40 µg per dose, preferably in an amount of from 40 to 700 µg per dose, more preferably in an amount of from 80 to 400 µg per dose. More specifically, in the case of intradermal injection, which is preferably carried out by using a conventional needle, the amount of such mRNA construct comprised in a single dose is typically at least 200 µg, preferably from 200 µg to 1.000 µg, more preferably from 300 µg to 850 µg, even more preferably from 300 µg to 700 µg. In the case of intradermal injection, which is preferably carried out via jet injection (e.g. using a Tropis device; PharmaJet Inc, Boulder Colo., US), the amount of the such mRNA construct comprised in a single dose is typically at least 80 µg, preferably from 80 µg to 700 µg, more preferably from 80 µg to 400 µg. Moreover, in the case of intramuscular injection, which is preferably carried out by using a conventional needle or via jet injection, the amount of the such mRNA construct comprised in a single dose is typically at least 80 µg, preferably from 80 µg to 1.000 µg, more preferably from 80 µg to 850 µg, even more preferably from 80 µg to 700 µg.

According to a preferred embodiment, the first antigenic composition as described herein and the second antigenic composition are typically not administered concurrently. In this context, the term 'concurrently' preferably refers to events that occur within 30 minutes, more preferably one hour, or even more preferably within 2, 3, 4, 5, 6, 7, 8, 9, 10, 11, 12 or 24 hours. it is furthermore preferred that the second antigenic composition is administered within about 27, 24, 21, 18, 15, 12, 10, 9, 8, 7, 6, 5, 4, 3, 2 or 1 day(s) after administration of the first antigenic composition.

The first and/or second antigenic composition, in the context of any aspects of the present invention may be administered orally, parenterally, by inhalation spray, topically, rectally, nasally, buccally, vaginally or via an implanted reservoir. The term parenteral as used herein includes subcutaneous, intravenous, intramuscular, intra-articular, intra-synovial, intrasternal, intrathecal, intrahepatic, intralesional, intracranial, transdermal, intradermal, intrapulmonal, intraperitoneal, intracardial, intraarterial and sublingual injection or infusion techniques. Also envisioned are embodiments where the first and/or second antigenic composition is administered intra-nodally or intra-tumor-ally.

In particular embodiments the first antigenic composition and/or the second antigenic composition is administered by subcutaneous, intramuscular and/or intradermal injection. Sterile injectable forms of the inventive pharmaceutical compositions may be aqueous or oleaginous suspension. These suspensions may be formulated according to techniques known in the art using suitable dispersing or wetting agents and suspending agents.

Particularly preferred is intradermal and intramuscular injection. Sterile injectable forms of compositions or vaccines of the present invention may be aqueous or oleaginous suspension. These suspensions may be formulated according to techniques known in the art using suitable dispersing or wetting agents and suspending agents.

In more particular of such embodiments, the first antigenic composition and/or the second antigenic composition (preferably, at least one dose of the mRNA containing second antigenic composition) may be administered by conventional needle injection and/or needle-free jet injection; especially those embodiments where an antigenic composition in the context of any of the aspects of the present invention is administered by jet injection as defined herein, preferably intramuscularly or intradermally, more preferably intradermally. Particular approaches, methods and features of the administration of an mRNA comprising composition which may be incorporated as certain further embodiments of the present invention are disclosed in WO2015/024667, the description of which is incorporated herein by reference.

Furthermore, the inventors surprisingly found that the administration of an mRNA construct included in an antigenic composition as set out herein, in particular mRNA having one or more certain features set out herein, provides enhanced or improved immune response when such mRNA containing antigenic composition is used as a "boost" in a prime-boost administration regimen.

One such feature of the mRNA construct that encodes at least one epitope of the immunogenic peptide or polypeptide, is that it is modified, for example chemically and/or sequence modified, compared to the wild-type mRNA that encodes said epitope.

Chemical Modifications:

The term "RNA modification" as used herein may refer to chemical modifications comprising backbone modifications as well as sugar modifications or base modifications.

In this context, a modified RNA molecule as defined herein may contain nucleotide analogues/modifications, e.g. backbone modifications, sugar modifications or base modifications. A backbone modification in connection with the present invention is a modification, in which phosphates of the backbone of the nucleotides contained in an RNA molecule as defined herein are chemically modified. A sugar modification in connection with the present invention is a chemical modification of the sugar of the nucleotides of the RNA molecule as defined herein. Furthermore, a base modification in connection with the present invention is a chemical modification of the base moiety of the nucleotides of the RNA molecule. In this context, nucleotide analogues or modifications are preferably selected from nucleotide analogues, which are applicable for transcription and/or translation.

Sugar Modifications:

The modified nucleosides and nucleotides, which may be incorporated into a modified RNA molecule as described herein, can be modified in the sugar moiety. For example, the 2' hydroxyl group (OH) can be modified or replaced with a number of different "oxy" or "deoxy" substituents. Examples of "oxy"-2' hydroxyl group modifications include, but are not limited to, alkoxy or aryloxy (—OR, e.g., R=H, alkyl, cycloalkyl, aryl, aralkyl, heteroaryl or sugar); polyethyleneglycols (PEG), —O(CH$_2$CH$_2$O)$_n$CH$_2$CH$_2$OR; "locked" nucleic acids (LNA) in which the 2' hydroxyl is connected, e.g., by a methylene bridge, to the 4' carbon of the same ribose sugar; and amino groups (—O-amino, wherein the amino group, e.g., NRR, can be alkylamino, dialkylamino, heterocyclyl, arylamino, diarylamino, heteroarylamino, or diheteroaryl amino, ethylene diamine, polyamino) or aminoalkoxy.

"Deoxy" modifications include hydrogen, amino (e.g. NH$_2^-$; alkylamino, dialkylamino, heterocyclyl, arylamino, diaryl amino, heteroaryl amino, diheteroaryl amino, or amino acid); or the amino group can be attached to the sugar through a linker, wherein the linker comprises one or more of the atoms C, N, and O.

The sugar group can also contain one or more carbons that possess the opposite stereochemical configuration than that of the corresponding carbon in ribose. Thus, a modified RNA molecule can include nucleotides containing, for instance, arabinose as the sugar.

Backbone Modifications:

The phosphate backbone may further be modified in the modified nucleosides and nucleotides, which may be incorporated into a modified RNA molecule as described herein. The phosphate groups of the backbone can be modified by replacing one or more of the oxygen atoms with a different substituent. Further, the modified nucleosides and nucleotides can include the full replacement of an unmodified phosphate moiety with a modified phosphate as described herein. Examples of modified phosphate groups include, but are not limited to, phosphorothioate, phosphoroselenates, borano phosphates, borano phosphate esters, hydrogen phosphonates, phosphoroamidates, alkyl or aryl phosphonates and phosphotriesters. Phosphorodithioates have both non-linking oxygens replaced by sulfur. The phosphate linker can also be modified by the replacement of a linking oxygen with nitrogen (bridged phosphoroamidates), sulfur (bridged phosphorothioates) and carbon (bridged methylene-phosphonates).

Base Modifications:

The modified nucleosides and nucleotides, which may be incorporated into a modified RNA molecule as described herein can further be modified in the nucleobase moiety. Examples of nucleobases found in RNA include, but are not limited to, adenine, guanine, cytosine and uracil. For example, the nucleosides and nucleotides described herein can be chemically modified on the major groove face. In some embodiments, the major groove chemical modifications can include an amino group, a thiol group, an alkyl group, or a halo group.

In particularly preferred embodiments of the present invention, the nucleotide analogues/modifications are selected from base modifications, which are preferably selected from 2-amino-6-chloropurineriboside-5'-triphosphate, 2-Aminopurine-riboside-5'-triphosphate; 2-aminoadenosine-5'-triphosphate, 2'-Amino-2'-deoxycytidine-triphosphate, 2-thiocytidine-5'-triphosphate, 2-thiouridine-5'-triphosphate, 2'-Fluorothymidine-5'-triphosphate, 2'-O-Methyl inosine-5'-triphosphate 4-thiouridine-5'-triphosphate, 5-aminoallylcytidine-5'-triphosphate, 5-aminoallyluridine-5'-triphosphate, 5-bromocytidine-5'-triphosphate, 5-bromouridine-5'-triphosphate, 5-Bromo-2'-deoxycytidine-5'-triphosphate, 5-Bromo-2'-deoxyuridine-5'-triphosphate, 5-iodocytidine-5'-triphosphate, 5-Iodo-2'-deoxycytidine-5'-triphosphate, 5-iodouridine-5'-triphosphate, 5-Iodo-2'-deoxyuridine-5'-triphosphate, 5-methylcytidine-5'-triphosphate, 5-methyluridine-5'-triphosphate, 5-Propynyl-2'-deoxycytidine-5'-triphosphate, 5-Propynyl-2'-deoxyuridine-5'-triphosphate, 6-azacytidine-5'-triphosphate, 6-azauridine-5'-triphosphate, 6-chloropurineriboside-5'-triphosphate, 7-deazaadenosine-5'-triphosphate, 7-deazaguanosine-5'-triphosphate, 8-azaadenosine-5'-triphosphate, 8-azidoadenosine-5'-triphosphate, benzimidazole-riboside-5'-triphosphate, N1-methyladenosine-5'-triphosphate, N1-methylguanosine-5'-triphosphate, N6-methyladenosine-5'-triphosphate, O6-methylguanosine-5'-triphosphate, pseudouridine-5'-triphosphate, or puromycin-5'-triphosphate, xanthosine-5'-triphosphate. Particular preference is given to nucleotides for base modifications selected from the group of base-modified nucleotides consisting of 5-methylcytidine-5'-triphosphate, 7-deazaguanosine-5'-triphosphate, 5-bromocytidine-5'-triphosphate, and pseudouridine-5'-triphosphate.

In some embodiments, modified nucleosides include pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, and 4-methoxy-2-thio-pseudouridine.

In some embodiments, modified nucleosides include 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, and 4-methoxy-1-methyl-pseudoisocytidine.

In other embodiments, modified nucleosides include 2-aminopurine, 2, 6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, and 2-methoxy-adenine.

In other embodiments, modified nucleosides include inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methyl-inosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine.

In some embodiments, the nucleotide can be modified on the major groove face and can include replacing hydrogen on C-5 of uracil with a methyl group or a halo group. In specific embodiments, a modified nucleoside is 5'-O-(1-Thiophosphate)-Adenosine, 5'-O-(1-Thiophosphate)-Cytidine, 5'-O-(1-Thiophosphate)-Guanosine, 5'-O-(1-Thiophosphate)-Uridine or 5'-O-(1-Thiophosphate)-Pseudouridine.

In further specific embodiments, a modified RNA may comprise nucleoside modifications selected from 6-aza-cytidine, 2-thio-cytidine, α-thio-cytidine, Pseudo-iso-cytidine, 5-aminoallyl-uridine, 5-iodo-uridine, N1-methyl-pseudouridine, 5,6-dihydrouridine, α-thio-uridine, 4-thio-uridine, 6-aza-uridine, 5-hydroxy-uridine, deoxy-thymidine, 5-methyl-uridine, Pyrrolo-cytidine, inosine, α-thio-guanosine, 6-methyl-guanosine, 5-methyl-cytdine, 8-oxo-guanosine, 7-deaza-guanosine, N1-methyl-adenosine, 2-amino-6-Chloro-purine, N6-methyl-2-amino-purine, Pseudo-iso-cytidine, 6-Chloro-purine, N6-methyl-adenosine, α-thio-adenosine, 8-azido-adenosine, 7-deaza-adenosine.

Lipid Modification:

According to a further embodiment, a modified RNA molecule as defined herein can contain a lipid modification. Such a lipid-modified RNA molecule typically comprises an RNA as defined herein. Such a lipid-modified RNA molecule as defined herein typically further comprises at least one linker covalently linked with that RNA molecule, and at least one lipid covalently linked with the respective linker. Alternatively, the lipid-modified RNA molecule comprises at least one RNA molecule as defined herein and at least one (bifunctional) lipid covalently linked (without a linker) with that RNA molecule. According to a third alternative, the lipid-modified RNA molecule comprises an RNA molecule as defined herein, at least one linker covalently linked with that RNA molecule, and at least one lipid covalently linked with the respective linker, and also at least one (bifunctional) lipid covalently linked (without a linker) with that RNA molecule. In this context, it is particularly preferred that the lipid modification is present at the terminal ends of a linear RNA sequence.

Modification of the 5'-End of a Modified RNA Molecule:

According to another preferred embodiment of the invention, a modified RNA molecule as defined herein, can be modified by the addition of a so-called "5' CAP" structure. A 5'-cap is an entity, typically a modified nucleotide entity, which generally "caps" the 5'-end of a mature mRNA. A 5'-cap may typically be formed by a modified nucleotide, particularly by a derivative of a guanine nucleotide. Preferably, the 5'-cap is linked to the 5'-terminus via a 5'-5'-triphosphate linkage. A 5'-cap may be methylated, e.g. m7GpppN, wherein N is the terminal 5' nucleotide of the nucleic acid carrying the 5'-cap, typically the 5'-end of an RNA. m7GpppN is the 5'-CAP structure which naturally occurs in mRNA transcribed by polymerase II and is therefore not considered as modification comprised in a modified RNA in this context. Accordingly, a modified RNA of the present invention may comprise a m7GpppN as 5'-CAP, but additionally the modified RNA comprises at least one further modification as defined herein.

Further examples of 5'cap structures include glyceryl, inverted deoxy abasic residue (moiety), 4',5' methylene nucleotide, 1-(beta-D-erythrofuranosyl) nucleotide, 4'-thio nucleotide, carbocyclic nucleotide, 1,5-anhydrohexitol nucleotide, L-nucleotides, alpha-nucleotide, modified base nucleotide, threo-pentofuranosyl nucleotide, acyclic 3',4'-seco nucleotide, acyclic 3,4-dihydroxybutyl nucleotide, acyclic 3,5 dihydroxypentyl nucleotide, 3'-3'-inverted nucleotide moiety, 3'-3'-inverted abasic moiety, 3'-2'-inverted nucleotide moiety, 3'-2'-inverted abasic moiety, 1,4-butanediol phosphate, 3'-phosphoramidate, hexylphosphate, aminohexyl phosphate, 3'-phosphate, 3'phosphorothioate, phosphorodithioate, or bridging or non-bridging methylphosphonate moiety. These modified 5'-CAP structures are regarded as at least one modification in this context.

Particularly preferred modified 5'-CAP structures are CAP1 (methylation of the ribose of the adjacent nucleotide of m7G), CAP2 (methylation of the ribose of the 2nd nucleotide downstream of the m7G), CAP3 (methylation of the ribose of the 3rd nucleotide downstream of the m7G), CAP4 (methylation of the ribose of the 4th nucleotide downstream of the m7G), ARCA (anti-reverse CAP analogue, modified ARCA (e.g. phosphothioate modified ARCA), inosine, N1-methyl-guanosine, 2'-fluoro-guanosine, 7-deaza-guanosine, 8-oxo-guanosine, 2-amino-guanosine, LNA-guanosine, and 2-azido-guanosine.

In other embodiments, of the present invention, that region of the mRNA construct encoding the epitope is modified (for example, to increase stability of the mRNA construct) by increasing the G (guanosine)/C (cytosine) content of the mRNA of at least that region of the coding region thereof. In certain of such embodiments, the coding region of the mRNA has an increased G/C content. Therein, the G/C content of such (coding) region of mRNA of the coding region is increased compared to the G/C content of the (coding) region of its particular wild type (coding) sequence, ie the unmodified mRNA. However, the encoded amino acid sequence of such region of the mRNA is preferably not modified compared to the corresponding amino acid sequence of the particular wild type/unmodified mRNA.

Accordingly, in the various aspects of the present invention, the G/C content of the region of the mRNA construct encoding at least one epitope of the immunogenic peptide or polypeptide is increased compared with the G/C content of the region of the wild type mRNA that encodes the epitope of the immunogenic peptide or polypeptide. In certain of such embodiments, the amino acid sequence of the immunogenic peptide or polypeptide encoded by the G/C-enriched mRNA is not modified compared with the amino acid sequence of the epitope of the immunogenic peptide or polypeptide encoded by the wild type mRNA. In other particular embodiments, the G/C content of the region of the mRNA construct encoding the immunogenic peptide or polypeptide is increased compared with the G/C content of the region of the wild type mRNA that encodes the immunogenic peptide or polypeptide.

Without being bound by theory, modification of the G/C-content of the such (coding) region of the mRNA results in RNA constructs having an increased G (guanosine)/C (cytosine) content which are more stable than RNA sequences having an increased A (adenosine)/U (uracil) content. The codons of a coding sequence or a whole RNA might therefore be varied compared to the wild type coding sequence or mRNA, such that they include an increased amount of G/C nucleotide while the translated amino acid sequence is retained. In respect to the fact that several codons code for one and the same amino acid (so-called degeneration of the genetic code), the most favourable codons for the stability can be determined (so-called alternative codon usage). Preferably, the G/C content of the (coding) region of the mRNA construct as set forth in all aspects of the present the invention is increased by at least 7%, more preferably by at least 15%, particularly preferably by at least 20%, compared to the G/C content of the (coding) region of the wild type RNA. According to a specific embodiment at least 5%, 10%, 20%, 30%, 40%, 50%, 60%, more preferably at least 70%, even more preferably at least 80% and most preferably at least 90%, 95% or even 100% of the substitutable codons in the region coding for a protein or peptide as defined herein or its fragment or variant thereof or the whole sequence of the wild type mRNA sequence or coding sequence are substituted, thereby increasing the G/C content of said sequence. In this context, it is particularly preferable to increase the G/C content of the (coding) region of the mRNA construct to the maximum (i.e. 100% of the substitutable codons), in particular in the (coding) region, compared to the wild type sequence.

G/C Content Modification:

According to another embodiment, the mRNA as described herein may be modified, and thus stabilized, by modifying the guanosine/cytosine (G/C) content of the mRNA, preferably of a coding sequence of the mRNA.

In a particularly preferred embodiment of the present invention, the G/C content of a coding region of the mRNA as described herein is modified, particularly increased, compared to the G/C content of the coding region of the respective wild-type RNA, i.e. the unmodified mRNA. The amino acid sequence encoded by the mRNA is preferably not modified as compared to the amino acid sequence encoded by the respective wild-type mRNA. This modification of the mRNA is based on the fact that the sequence of any mRNA region to be translated is important for efficient translation of that mRNA. Thus, the composition of the mRNA and the sequence of various nucleotides are important. In particular, sequences having an increased G (guanosine)/C (cytosine) content are more stable than sequences having an increased A (adenosine)/U (uracil) content. According to the invention, the codons of the mRNA are therefore varied compared to the respective wild-type mRNA, while retaining the translated amino acid sequence, such that they include an increased amount of G/C nucleotides. In respect to the fact that several codons code for one and the same amino acid (so-called degeneration of the genetic code), the most favourable codons for the stability can be determined (so-called alternative codon usage). Depending on the amino acid to be encoded by the mRNA, there are various possibilities for modification of the mRNA sequence, compared to its wild-type sequence. In the case of amino acids, which are encoded by codons, which contain exclusively G or C nucleotides, no modification of the codon is necessary. Thus, the codons for Pro (CCC or CCG), Arg (CGC or CGG), Ala (GCC or GCG) and Gly (GGC or GGG) require no modification, since no A or U is present. In contrast, codons which contain A and/or U nucleotides can be modified by substitution of other codons, which code for the same amino acids but contain no A and/or U. Examples of these are: the codons for Pro can be modified from CCU or CCA to CCC or CCG; the codons for Arg can be modified from CGU or CGA or AGA or AGG to CGC or CGG; the codons for Ala can be modified from GCU or GCA to GCC or GCG; the codons for Gly can be modified from GGU or GGA to GGC or GGG. In other cases, although A or U nucleotides cannot be eliminated from the codons, it is however possible to decrease the A and U content by using codons which contain a lower content of A and/or U nucleotides. Examples of these are: the codons for Phe can be modified from UUU to UUC; the codons for Leu can be modified from UUA, UUG, CUU or CUA to CUC or CUG; the codons for Ser can be modified from UCU or UCA or AGU to UCC, UCG or AGC; the codon for Tyr can be modified from UAU to UAC; the codon for Cys can be modified from UGU to UGC; the codon for His can be modified from CAU to CAC; the codon for Gln can be modified from CAA to CAG; the codons for Ile can be modified from AUU or AUA to AUC; the codons for Thr can be modified from ACU or ACA to ACC or ACG; the codon for Asn can be modified from AAU to AAC; the codon for Lys can be modified from AAA to AAG; the codons for Val can be modified from GUU or GUA to GUC or GUG; the codon for Asp can be modified from GAU to GAC; the codon for Glu can be modified from GAA to GAG; the stop codon UAA can be modified to UAG or UGA. In the case of the codons for Met (AUG) and Trp (UGG), on the other hand, there is no possibility of sequence modification. The substitutions listed above can be used either individually or in all possible combinations to increase the G/C content of the at least one mRNA of the composition of the present invention compared to its particular wild-type mRNA (i.e. the original sequence). Thus, for example, all codons for Thr occurring in the wild-type sequence can be modified to ACC (or ACG). Preferably, however, for example, combinations of the above substitution possibilities are used:

substitution of all codons coding for Thr in the original sequence (wild-type mRNA) to ACC (or ACG) and substitution of all codons originally coding for Ser to UCC (or UCG or AGC); substitution of all codons coding for Ile in the original sequence to AUC and substitution of all codons originally coding for Lys to AAG and substitution of all codons originally coding for Tyr to UAC; substitution of all codons coding for Val in the original sequence to GUC (or GUG) and substitution of all codons originally coding for Glu to GAG and substitution of all codons originally coding for Ala to GCC (or GCG) and substitution of all codons originally coding for Arg to CGC (or CGG); substitution of all codons coding for Val in the original sequence to GUC (or GUG) and substitution of all codons originally coding for Glu to GAG and substitution of all codons originally coding for Ala to GCC (or GCG) and substitution of all codons originally coding for Gly to GGC (or GGG) and substitution of all codons originally coding for Asn to AAC; substitution of all codons coding for Val in the original sequence to GUC (or GUG) and substitution of all codons originally coding for Phe to UUC and substitution of all codons originally coding for Cys to UGC and substitution of all codons originally coding for Leu to CUG (or CUC) and substitution of all codons originally coding for Gin to CAG and substitution of all codons originally coding for Pro to CCC (or CCG); etc.

Preferably, the G/C content of a coding region of the mRNA as described herein is increased by at least 7%, more preferably by at least 15%, particularly preferably by at least 20%, compared to the G/C content of the coding region of the wild-type mRNA, which codes for an antigen as defined herein or a fragment or variant thereof. According to a specific embodiment at least 5%, 10%, 20%, 30%, 40%, 50%, 60%, more preferably at least 70%, even more preferably at least 80% and most preferably at least 90%, 95% or even 100% of the substitutable codons in the region coding for an antigen as defined herein or a fragment or variant thereof or the whole sequence of the wild type mRNA sequence are substituted, thereby increasing the GC/content of said sequence. In this context, it is particularly preferable to increase the G/C content of the mRNA of the present invention, preferably of a coding region of the mRNA, to the maximum (i.e. 100% of the substitutable codons) as compared to the wild-type sequence. According to the invention, a further preferred modification of the mRNA is based on the finding that the translation efficiency is also determined by a different frequency in the occurrence of tRNAs in cells. Thus, if so-called "rare codons" are present in the mRNA to an increased extent, the corresponding modified mRNA sequence is translated to a significantly poorer degree than in the case where codons coding for relatively "frequent" tRNAs are present. According to the invention, in the modified mRNA, the region which codes for an antigen as defined herein or a fragment or variant thereof is modified compared to the corresponding region of the wild-type mRNA such that at least one codon of the wild-type sequence, which codes for a tRNA which is relatively rare in the cell, is exchanged for a codon, which codes for a tRNA which is relatively frequent in the cell and carries the same amino acid as the relatively rare tRNA. By this modification, the sequences of the RNA of the present invention is modified such that codons for which frequently occurring tRNAs are available are inserted. In other words, according to the invention, by this modification all codons of the wild-type sequence, which code for a tRNA which is relatively rare in the cell, can in each case be exchanged for a codon, which codes for a tRNA which is relatively frequent in the cell and which, in each case, carries the same amino acid as the relatively rare tRNA. Which tRNAs occur relatively frequently in the cell and which, in contrast, occur relatively rarely is known to a person skilled in the art; cf. e.g. Akashi, Curr. Opin. Genet. Dev. 2001, 11(6): 660-666. The codons, which use for the particular amino acid the tRNA which occurs the most frequently, e.g. the Gly codon, which uses the tRNA, which occurs the most frequently in the (human) cell, are particularly preferred. According to the invention, it is particularly preferable to link the sequential G/C content which is increased, in particular maximized, in the mRNA, with the "frequent" codons without modifying the amino acid sequence of the protein encoded by the coding region of the mRNA. This preferred embodiment allows provision of a particularly efficiently translated and stabilized (modified) mRNA. The determination of a modified mRNA as described above (increased G/C content; exchange of tRNAs) can be carried out using the computer program explained in WO 02/098443—the disclosure content of which is included in its full scope in the present invention. Using this computer program, the nucleotide sequence of any desired RNA can be modified with the aid of the genetic code or the degenerative nature thereof such that a maximum G/C content results, in combination with the use of codons which code for tRNAs occurring as frequently as possible in the cell, the amino acid sequence coded by the modified RNA preferably not being modified compared to the non-modified sequence. Alternatively, it is also possible to modify only the G/C content or only the codon usage compared to the original sequence. The source code in Visual Basic 6.0 (development environment used: Microsoft Visual Studio Enterprise 6.0 with Servicepack 3) is also described in WO 02/098443. In a further preferred embodiment of the present invention, the A/U content in the environment of the ribosome binding site of the mRNA is increased compared to the A/U content in the environment of the ribosome binding site of its respective wild-type mRNA. This modification (an increased A/U content around the ribosome binding site) increases the efficiency of ribosome binding to the mRNA. An effective binding of the ribosomes to the ribosome binding site (Kozak sequence) in turn has the effect of an efficient translation of the mRNA. According to a further embodiment of the present invention, the mRNA may be modified with respect to potentially destabilizing sequence elements. Particularly, the coding region and/or the 5' and/or 3' untranslated region of this mRNA may be modified compared to the respective wild-type mRNA such that it contains no destabilizing sequence elements, the encoded amino acid sequence of the modified mRNA preferably not being modified compared to its respective wild-type mRNA. It is known that, for example in sequences of eukaryotic mRNAs, destabilizing sequence elements (DSE) occur, to which signal proteins bind and regulate enzymatic degradation of RNA in vivo. For further stabilization of the modified mRNA, optionally in the region which encodes an antigen as defined herein or a fragment or variant thereof, one or more such modifications compared to the corresponding region of the wild-type mRNA can therefore be carried out, so that no or substantially no destabilizing sequence elements are contained there. According to the invention, DSE present in the untranslated regions (3'- and/or 5'-UTR) can also be eliminated from the mRNA by such modifications. Such destabilizing sequences are e.g. AU-rich sequences (AURES), which occur in 3'-UTR sections of numerous unstable RNAs (Caput et al., Proc. Natl. Acad. Sci. USA 1986, 83: 1670 to 1674). The mRNA is therefore preferably modified compared to the respective wild-type mRNA such that the mRNA as described herein contains no such destabilizing sequences. This also applies to those sequence motifs which are recognized by possible endonucleases, e.g. the sequence GAACAAG, which is contained in the 3'-UTR segment of the gene encoding the transferrin receptor (Binder et al., EMBO J. 1994, 13: 1969 to 1980). These sequence motifs are also preferably removed in the mRNA as described herein.

Sequences Adapted to Human Codon Usage:

According to the invention, a further preferred modification of the mRNA as described herein is based on the finding that codons encoding the same amino acid typically occur at different frequencies. According to the invention, in the modified mRNA as described herein, a coding sequence (coding region) as defined herein is preferably modified compared to the corresponding region of the respective wild-type mRNA such that the frequency of the codons encoding the same amino acid corresponds to the naturally occurring frequency of that codon according to the human codon usage as e.g. shown in Table 1.

For example, in the case of the amino acid alanine (Ala) present in an amino acid sequence encoded by a coding sequence of the mRNA as described herein, the wild type coding sequence is preferably adapted in a way that the codon "GCC" is used with a frequency of 0.40, the codon "GCT" is used with a frequency of 0.28, the codon "GCA" is used with a frequency of 0.22 and the codon "GCG" is used with a frequency of 0.10 etc. (see Table 2).

TABLE 1

Human codon usage table

| Amino acid | codon | fraction | /1000 |
|---|---|---|---|
| Ala | GCG | 0.10 | 7.4 |
| Ala | GCA | 0.22 | 15.8 |
| Ala | GCT | 0.28 | 18.5 |
| Ala | GCC* | 0.40 | 27.7 |
| Cys | TGT | 0.42 | 10.6 |
| Cys | TGC* | 0.58 | 12.6 |
| Asp | GAT | 0.44 | 21.8 |
| Asp | GAC* | 0.56 | 25.1 |
| Glu | GAG* | 0.59 | 39.6 |
| Glu | GAA | 0.41 | 29.0 |
| Phe | TTT | 0.43 | 17.6 |
| Phe | TTC* | 0.57 | 20.3 |
| Gly | GGG | 0.23 | 16.5 |
| Gly | GGA | 0.26 | 16.5 |
| Gly | GGT | 0.18 | 10.8 |
| Gly | GGC* | 0.33 | 22.2 |
| His | CAT | 0.41 | 10.9 |
| His | CAC* | 0.59 | 15.1 |
| Ile | ATA | 0.14 | 7.5 |
| Ile | ATT | 0.35 | 16.0 |
| Ile | ATC* | 0.52 | 20.8 |
| Lys | AAG* | 0.60 | 31.9 |
| Lys | AAA | 0.40 | 24.4 |
| Leu | TTG | 0.12 | 12.9 |
| Leu | TTA | 0.06 | 7.7 |
| Leu | CTG* | 0.43 | 39.6 |
| Leu | CTA | 0.07 | 7.2 |
| Leu | CTT | 0.12 | 13.2 |
| Leu | CTC | 0.20 | 19.6 |
| Met | ATG* | 1 | 22.0 |
| Asn | AAT | 0.44 | 17.0 |
| Asn | AAC* | 0.56 | 19.1 |
| Pro | CCG | 0.11 | 6.9 |
| Pro | CCA | 0.27 | 16.9 |
| Pro | CCT | 0.29 | 17.5 |
| Pro | CCC* | 0.33 | 19.8 |
| Gln | CAG* | 0.73 | 34.2 |
| Gln | CAA | 0.27 | 12.3 |
| Arg | AGG | 0.22 | 12.0 |
| Arg | AGA* | 0.21 | 12.1 |
| Arg | CGG | 0.19 | 11.4 |
| Arg | CGA | 0.10 | 6.2 |
| Arg | CGT | 0.09 | 4.5 |
| Arg | CGC | 0.19 | 10.4 |
| Ser | AGT | 0.14 | 12.1 |
| Ser | AGC* | 0.25 | 19.5 |
| Ser | TCG | 0.06 | 4.4 |
| Ser | TCA | 0.15 | 12.2 |
| Ser | TCT | 0.18 | 15.2 |
| Ser | TCC | 0.23 | 17.7 |
| Thr | ACG | 0.12 | 6.1 |
| Thr | ACA | 0.27 | 15.1 |
| Thr | ACT | 0.23 | 13.1 |
| Thr | ACC* | 0.38 | 18.9 |
| Val | GTG* | 0.48 | 28.1 |
| Val | GTA | 0.10 | 7.1 |
| Val | GTT | 0.17 | 11.0 |
| Val | GTC | 0.25 | 14.5 |
| Trp | TGG* | 1 | 13.2 |
| Tyr | TAT | 0.42 | 12.2 |
| Tyr | TAC* | 0.58 | 15.3 |
| Stop | TGA* | 0.61 | 1.6 |

TABLE 1-continued

Human codon usage table

| Amino acid | codon | fraction | /1000 |
|---|---|---|---|
| Stop | TAG | 0.17 | 0.8 |
| Stop | TAA | 0.22 | 1.0 |

*most frequent codon

Codon-Optimized Sequences:

As described above it is preferred according to the invention, that all codons of the wild-type sequence which code for a tRNA, which is relatively rare in the cell, are exchanged for a codon which codes for a tRNA, which is relatively frequent in the cell and which, in each case, carries the same amino acid as the relatively rare tRNA. Therefore it is particularly preferred that the most frequent codons are used for each encoded amino acid (see Table 1, most frequent codons are marked with asterisks). Such an optimization procedure increases the codon adaptation index (CAI) and ultimately maximises the CAI. In the context of the invention, sequences with increased or maximized CAI are typically referred to as "codon-optimized" sequences and/or CAI increased and/or maximized sequences. According to a preferred embodiment, the mRNA as described herein comprises at least one coding sequence, wherein the coding sequence is codon-optimized as described herein. More preferably, the codon adaptation index (CAI) of the at least one coding sequence is at least 0.5, at least 0.8, at least 0.9 or at least 0.95. Most preferably, the codon adaptation index (CAI) of the at least one coding sequence is 1.

For example, in the case of the amino acid alanine (Ala) present in the amino acid sequence encoded by the at least one coding sequence of the mRNA as described herein, the wild type coding sequence is adapted in a way that the most frequent human codon "GCC" is always used for said amino acid, or for the amino acid Cysteine (Cys), the wild type sequence is adapted in a way that the most frequent human codon "TGC" is always used for said amino acid etc.

C-Optimized Sequences:

According to another embodiment, the mRNA as described herein may be modified by modifying, preferably increasing, the cytosine (C) content of the mRNA, preferably of a coding region of the mRNA.

In a particularly preferred embodiment of the present invention, the C content of a coding region of the mRNA is modified, preferably increased, compared to the C content of the coding region of the respective wild-type RNA, i.e. the unmodified RNA. The amino acid sequence encoded by a coding sequence of the mRNA as described herein is preferably not modified as compared to the amino acid sequence encoded by the respective wild-type mRNA.

In a preferred embodiment of the present invention, the modified mRNA is modified such that at least 10%, 20%, 30%, 40%, 50%, 60%, 70% or 80%, or at least 90% of the theoretically possible maximum cytosine-content or even a maximum cytosine-content is achieved.

In further preferred embodiments, at least 10%, 20%, 30%, 40%, 50%, 60%, 70%, 80%, 90% or even 100% of the codons of the mRNA wild type sequence, which are "cytosine content optimizable" are replaced by codons having a higher cytosine-content than the ones present in the wild type sequence.

In a further preferred embodiment, some of the codons of the wild type coding sequence may additionally be modified such that a codon for a relatively rare tRNA in the cell is exchanged by a codon for a relatively frequent tRNA in the cell, provided that the substituted codon for a relatively frequent tRNA carries the same amino acid as the relatively rare tRNA of the original wild type codon. Preferably, all of the codons for a relatively rare tRNA are replaced by a codon for a relatively frequent tRNA in the cell, except codons encoding amino acids, which are exclusively encoded by codons not containing any cytosine, or except for glutamine (Gln), which is encoded by two codons each containing the same number of cytosines.

In a further preferred embodiment of the present invention, the mRNA as described herein is modified such that at least 80%, or at least 90% of the theoretically possible maximum cytosine-content or even a maximum cytosine-content is achieved by means of codons, which code for relatively frequent tRNAs in the cell, wherein the amino acid sequence remains unchanged.

Due to the naturally occurring degeneracy of the genetic code, more than one codon may encode a particular amino acid. Accordingly, 18 out of 20 naturally occurring amino acids are encoded by more than one codon (with Tryp and Met being an exception), e.g. by 2 codons (e.g. Cys, Asp, Glu), by three codons (e.g. Ile), by 4 codons (e.g. Al, Gly, Pro) or by 6 codons (e.g. Leu, Arg, Ser). However, not all codons encoding the same amino acid are utilized with the same frequency under in vivo conditions. Depending on each single organism, a typical codon usage profile is established.

The term 'cytosine content-optimizable codon' as used within the context of the present invention refers to codons, which exhibit a lower content of cytosines than other codons encoding the same amino acid. Accordingly, any wild type codon, which may be replaced by another codon encoding the same amino acid and exhibiting a higher number of cytosines within that codon, is considered to be cytosine-optimizable (C-optimizable). Any such substitution of a C-optimizable wild type codon by the specific C-optimized codon within a wild type coding region increases its overall C-content and reflects a C-enriched modified mRNA sequence. According to a preferred embodiment, the mRNA as described herein, preferably a coding sequence of the mRNA, comprises or consists of a C-maximized RNA sequence containing C-optimized codons for all potentially C-optimizable codons. Accordingly, 100% or all of the theoretically replaceable C-optimizable codons are preferably replaced by C-optimized codons over the entire length of the coding region.

In this context, cytosine-content optimizable codons are codons, which contain a lower number of cytosines than other codons coding for the same amino acid.

Any of the codons GCG, GCA, GCU codes for the amino acid Ala, which may be exchanged by the codon GCC encoding the same amino acid, and/or the codon UGU that codes for Cys may be exchanged by the codon UGC encoding the same amino acid, and/or the codon GAU which codes for Asp may be exchanged by the codon GAC encoding the same amino acid, and/or the codon that UUU that codes for Phe may be exchanged for the codon UUC encoding the same amino acid, and/or any of the codons GGG, GGA, GGU that code Gly may be exchanged by the codon GGC encoding the same amino acid, and/or the codon CAU that codes for His may be exchanged by the codon CAC encoding the same amino acid, and/or any of the codons AUA, AUU that code for Ile may be exchanged by the codon AUC, and/or any of the codons UUG, UUA, CUG, CUA, CUU coding for Leu may be exchanged by the codon CUC encoding the same amino acid, and/or the codon AAU that codes for Asn may be exchanged by the codon AAC encoding the same amino acid, and/or any of the codons CCG, CCA, CCU coding for Pro may be exchanged by the codon CCC encoding the same amino acid, and/or any of the codons AGG, AGA, CGG, CGA, CGU coding for Arg may be exchanged by the codon CGC encoding the same amino acid, and/or any of the codons AGU, AGO, UCG, UCA, UCU coding for Ser may be exchanged by the codon UCC encoding the same amino acid, and/or any of the codons ACG, ACA, ACU coding for Thr may be exchanged by the codon ACC encoding the same amino acid, and/or any of the codons GUG, GUA, GUU coding for Val may be exchanged by the codon GUC encoding the same amino acid, and/or the codon UAU coding for Tyr may be exchanged by the codon UAC encoding the same amino acid.

In any of the above instances, the number of cytosines is increased by 1 per exchanged codon. Exchange of all non C-optimized codons (corresponding to C-optimizable codons) of the coding region results in a C-maximized coding sequence. In the context of the invention, at least 70%, preferably at least 80%, more preferably at least 90%, of the non C-optimized codons within the at least one coding region of the mRNA as described herein are replaced by C-optimized codons.

It may be preferred that for some amino acids the percentage of C-optimizable codons replaced by C-optimized codons is less than 70%, while for other amino acids the percentage of replaced codons is higher than 70% to meet the overall percentage of C-optimization of at least 70% of all C-optimizable wild type codons of the coding region.

Preferably, in a C-optimized mRNA as described herein, at least 50% of the C-optimizable wild type codons for any given amino acid are replaced by C-optimized codons, e.g. any modified C-enriched RNA preferably contains at least 50% C-optimized codons at C-optimizable wild type codon positions encoding any one of the above mentioned amino acids Ala, Cys, Asp, Phe, Gly, His, Ile, Leu, Asn, Pro, Arg, Ser, Thr, Val and Tyr, preferably at least 60%.

In this context codons encoding amino acids, which are not cytosine content-optimizable and which are, however, encoded by at least two codons, may be used without any further selection process. However, the codon of the wild type sequence that codes for a relatively rare tRNA in the cell, e.g. a human cell, may be exchanged for a codon that codes for a relatively frequent tRNA in the cell, wherein both code for the same amino acid. Accordingly, the relatively rare codon GAA coding for Glu may be exchanged by the relative frequent codon GAG coding for the same amino acid, and/or the relatively rare codon AAA coding for Lys may be exchanged by the relative frequent codon AAG coding for the same amino acid, and/or the relatively rare codon CAA coding for Gln may be exchanged for the relative frequent codon CAG encoding the same amino acid.

In this context, the amino acids Met (AUG) and Trp (UGG), which are encoded by only one codon each, remain unchanged. Stop codons are not cytosine-content optimized, however, the relatively rare stop codons amber, ochre (UAA, UAG) may be exchanged by the relatively frequent stop codon opal (UGA).

The single substitutions listed above may be used individually as well as in all possible combinations in order to optimize the cytosine-content of the modified mRNA compared to the wild type mRNA sequence.

Accordingly, a coding sequence as defined herein may be changed compared to the coding region of the respective wild type RNA in such a way that an amino acid encoded by at least two or more codons, of which one comprises one additional cytosine, such a codon may be exchanged by the C-optimized codon comprising one additional cytosine, wherein the amino acid is preferably unaltered compared to the wild type sequence.

According to a particularly preferred embodiment, the invention provides an mRNA, comprising at least one coding sequence as defined herein, wherein the G/C content of the at least one coding sequence of the RNA is increased compared to the G/C content of the corresponding coding sequence of the corresponding wild-type mRNA, and/or wherein the C content of the at least one coding sequence of the mRNA is increased compared to the C content of the corresponding coding sequence of the corresponding wild-type mRNA, and/or wherein the codons in the at least one coding sequence of the mRNA are adapted to human codon usage, wherein the codon adaptation index (CAI) is preferably increased or maximised in the at least one coding sequence of the mRNA, and wherein the amino acid sequence encoded by the mRNA is preferably not being modified compared to the amino acid sequence encoded by the corresponding wild-type mRNA.

Another such feature of the mRNA construct that encodes at least one epitope of the immunogenic peptide or polypeptide, is that it can be modified to include and/or comprises, for example additionally, one or more of a 5'-CAP structure (such as m7GpppN), a poly(A) sequence and/or a poly (C) sequence. In particular of such embodiments, the mRNA construct comprises (additionally) a 5'-CAP structure and a poly(A) sequence, and optionally a poly (C) sequence. Specific non-limiting examples of certain 5'-CAP structures, poly (C) sequences and poly(A) sequences are described elsewhere herein. However, if a poly(A) sequence is included in the mRNA construct, then embodiments of such a poly(A) sequence are envisioned wherein the poly(A) sequence comprises a sequence of about 25 to about 400 adenosine nucleotides, for example a poly(A) sequence of about 50 to about 400 adenosine nucleotides, a poly(A) sequence of about 50 to about 300 adenosine nucleotides, a poly(A) sequence of about 50 to about 250 adenosine nucleotides, or a poly(A) sequence of about 60 to about 250 adenosine nucleotides; and if a poly (C) sequence is included in the mRNA construct then embodiments of such a poly (C) sequence are envisioned wherein the poly (C) sequence comprises about 10 to about 200 cytosine nucleotides, preferably about 10 to about 100 cytosine nucleotides, more preferably about 10 to about 70 cytosine nucleotides or even more preferably about 20 to about 50 or even about 20 to about 30 cytosine nucleotides. A poly(C) sequence may preferably be located 3' of the coding region comprised by a nucleic acid.

Another such feature of the mRNA construct that encodes at least one epitope of the immunogenic peptide or polypeptide, is that it can (additionally) comprise at least one histone stem-loop, such as a histone stem-loop sequence and/or a histone stem-loop structure, Such histone stem-loop sequences are preferably selected from histone stem-loop sequences as disclosed in WO2012/019780, whose disclosure is incorporated herein by reference. A histone stem-loop structure is a structure of mRNA that is formable or formed by a histone stem-loop sequence of RNA in physiological conditions eg intra-cellular and/or when included pharmaceutical formulation).

A histone stem-loop sequence, suitable to be used within the present invention, is preferably selected from at least one of the following formulae (I) or (II):

Formula (I) (Stem-Loop Sequence without Stem Bordering Elements):

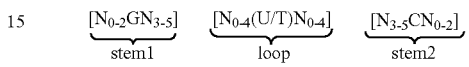

Formula (II) (Stem-Loop Sequence with Stem Bordering Elements):

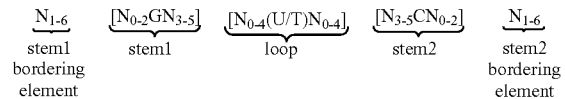

wherein:

stem1 or stem2 bordering elements $N_{1-6}$ is a consecutive sequence of 1 to 6, preferably of 2 to 6, more preferably of 2 to 5, even more preferably of 3 to 5, most preferably of 4 to 5 or 5 N, wherein each N is independently from another selected from a nucleotide selected from A, U, T, G and C, or a nucleotide analogue thereof;

stem1 $[N_{0-2}GN_{3-5}]$ is reverse complementary or partially reverse complementary with element stem2, and is a consecutive sequence between of 5 to 7 nucleotides;

wherein $N_{0-2}$ is a consecutive sequence of 0 to 2, preferably of 0 to 1, more preferably of 1 N, wherein each N is independently from another selected from a nucleotide selected from A, U, T, G and C or a nucleotide analogue thereof;

wherein $N_{3-5}$ is a consecutive sequence of 3 to 5, preferably of 4 to 5, more preferably of 4 N, wherein each N is independently from another selected from a nucleotide selected from A, U, T, G and C or a nucleotide analogue thereof, and wherein G is guanosine or an analogue thereof, and may be optionally replaced by a cytidine or an analogue thereof, provided that its complementary nucleotide cytidine in stem2 is replaced by guanosine;

loop sequence $[N_{0-4}(U/T)N_{0-4}]$ is located between elements stem1 and stem2, and is a consecutive sequence of 3 to 5 wherein each $N_{0-4}$ is independent from another a consecutive sequence of 0 to 4, preferably of 1 to 3, more preferably of 1 to 2 N, wherein each N is independently from another selected from a nucleotide selected from A, U, T, G and C or a nucleotide analogue thereof; and wherein U/T represents uridine, or optionally thymidine;

stem2 $[N_{3-5}CN_{0-2}]$ is reverse complementary or partially reverse complementary with element stem1, and is a consecutive sequence between of 5 to 7 nucleotides;

wherein $N_{3-5}$ is a consecutive sequence of 3 to 5, preferably of 4 to 5, more preferably of 4 N, wherein each N is independently from another selected from a nucleotide selected from A, U, T, G and C or a nucleotide analogue thereof;

wherein $N_{0-2}$ is a consecutive sequence of 0 to 2, preferably of 0 to 1, more preferably of 1 N, wherein each N is independently from another selected from a nucleotide selected from A, U, T, G or C or a nucleotide analogue thereof; and wherein C is cytidine or an analogue thereof, and may be optionally replaced by a guanosine or an analogue thereof provided that its complementary nucleoside guanosine in stem1 is replaced by cytidine;

wherein stem1 and stem2 are capable of base pairing with each other forming a reverse complementary sequence, wherein base pairing may occur between stem1 and stem2, e.g. by Watson-Crick base pairing of nucleotides A and U/T or G and C or by non-Watson-Crick base pairing e.g. wobble base pairing, reverse Watson-Crick base pairing, Hoogsteen base pairing, reverse Hoogsteen base pairing or are capable of base pairing with each other forming a partially reverse complementary sequence, wherein an incomplete base pairing may occur between stem1 and stem2, on the basis that one ore more bases in one stem do not have a complementary base in the reverse complementary sequence of the other stem.

According to a further preferred embodiment of the present invention, at least one histone stem-loop sequence, if included in the mRNA construct, may comprise at least one of the following specific formulae (Ia) or (IIa):

Formula (Ia) (Stem-Loop Sequence without Stem Bordering Elements):

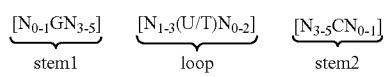

Formula (IIa) (Stem-Loop Sequence with Stem Bordering Elements):

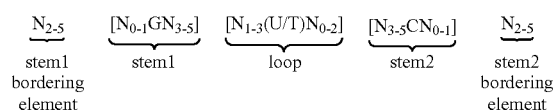

wherein:

N, C, G, T and U are as defined above.

According to a further more particularly preferred embodiment of the present invention, at least one histone stem-loop sequence, if included in the mRNA construct, may comprise at least one of the following specific formulae (Ib) or (IIb):

Formula (Ib) (Stem-Loop Sequence without Stem Bordering Elements):

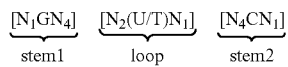

Formula (IIb) (Stem-Loop Sequence with Stem Bordering Elements):

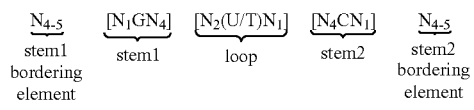

wherein:

N, C, G, T and U are as defined above.

A particular preferred histone stem-loop sequence is the nucleic acid sequence according to SEQ ID NO. 1 (or a homolog, a fragment or a variant thereof):

Histone stem-loop nucleotide sequence
(SEQ ID NO. 1)
CAAAGGCTCTTTTCAGAGCCACCA

More preferably the stem-loop sequence is the corresponding RNA sequence of the nucleic acid sequence according to SEQ ID NO. 2 (or a homolog, a fragment or a variant thereof):

Histone stem-loop RNA sequence
(SEQ ID NO. 2)
CAAAGGCUCUUUUCAGAGCCACCA

Two further such features of the mRNA construct that encodes at least one epitope of the immunogenic peptide or polypeptide, is that it can (additionally) comprise at least one of the following structural elements: a 5'- and/or 3'-untranslated region element (UTR element), particularly a 5'-UTR element which comprises or consists of a nucleic acid sequence which is derived from the 5'-UTR of a TOP gene or from a fragment, homolog or a variant thereof, or a 5'- and/or 3'-UTR element which may be derivable from a gene that provides a stable mRNA or from a homolog, fragment or variant thereof; a histone-stem-loop structure, preferably a histone-stem-loop in its 3' untranslated region; a 5'-CAP structure; a poly-A tail; or a poly(C) sequence.

Accordingly, in one such embodiment of the various aspects of the present invention the mRNA construct comprises at least one 5'- or 3'-UTR element. In this context an UTR element comprises or consists of a nucleic acid sequence which is derived from the 5'- or 3'-UTR of any naturally occurring gene or which is derived from a fragment, a homolog or a variant of the 5'- or 3'-UTR of a gene. Preferably the 5'- or 3'-UTR element used according to the present invention is heterologous to the coding region of the mRNA construct. Even if 5'- or 3'-UTR elements derived from naturally occurring genes are preferred, also synthetically engineered UTR elements may be used in the context of the present invention In respect of a 3'-UTR element, the present invention also includes mRNA constructs that include a 3'-UTR element which comprises or consists of a nucleic acid sequence derived from the 3'-UTR of a chordate gene, preferably a vertebrate gene, more preferably a mammalian gene, most preferably a human gene, or from a variant of the 3'-UTR of a chordate gene, preferably a vertebrate gene, more preferably a mammalian gene, most preferably a human gene.

The term '3'-UTR element' refers to a nucleic acid sequence which comprises or consists of a nucleic acid sequence that is derived from a 3'-UTR or from a variant of a 3'-UTR. A 3'-UTR element in the sense of the present invention may represent the 3'-UTR of an mRNA. Thus, in the sense of the present invention, preferably, a 3'-UTR element may be the 3'-UTR of an mRNA, preferably of an artificial mRNA, or it may be the transcription template for a 3'-UTR of an mRNA. Thus, a 3'-UTR element preferably is a nucleic acid sequence which corresponds to the 3'-UTR of an mRNA, preferably to the 3'-UTR of an artificial mRNA, such as an mRNA obtained by transcription of a genetically engineered vector construct. Preferably, the 3'-UTR element fulfils the function of a 3'-UTR or encodes a sequence which fulfils the function of a 3'-UTR.

In one embodiment of the present invention, the mRNA construct, if comprising a 3'-UTR, the 3'-UTR may comprises or consists of a nucleic acid sequence which is derived from a 3'-UTR of a gene providing a stable mRNA or from a homolog, or it may be a fragment or a variant of such a gene. In certain embodiments, the mRNA construct comprises a 3'-UTR element which may be derivable from a gene that relates to an mRNA with an enhanced half-life (that provides a stable mRNA), for example a 3'-UTR element as defined and described below.

For example, in a particular embodiment, the 3'-UTR element comprises or consists of a nucleic acid sequence which is derived from a 3'-UTR of a gene selected from the group consisting of an albumin gene, an α-globin gene, a β-globin gene, a tyrosine hydroxylase gene, a lipoxygenase gene, and a collagen alpha gene, such as a collagen alpha 1(I) gene, or from a variant of a 3'-UTR of a gene selected from the group consisting of an albumin gene, an α-globin gene, a β-globin gene, a tyrosine hydroxylase gene, a lipoxygenase gene, and a collagen alpha gene, such as a collagen alpha 1(I) gene according to SEQ ID NO. 1369-1390 of the patent application WO2013/143700 whose disclosure is incorporated herein by reference. In a particularly preferred embodiment, the 3'-UTR element comprises or consists of a nucleic acid sequence which is derived from a 3'-UTR of an albumin gene, preferably a vertebrate albumin gene, more preferably a mammalian albumin gene, most preferably a human albumin gene according SEQ ID No: 1369 of the patent application WO2013/143700. The mRNA sequence may comprise or consist of a nucleic acid sequence which is derived from the 3'-UTR of the human albumin gene according to GenBank Accession number NM_000477.5, or from a fragment or variant thereof.

Accordingly, in certain embodiments of the present invention the mRNA construct comprises a 3'-UTR element that comprises or consists of a nucleic acid sequence derived from a 3'-UTR of a gene selected from the group consisting of an albumin gene, an alpha-globin gene, a beta-globin gene, a tyrosine hydroxylase gene, a lipoxygenase gene, and a collagen alpha gene; or from a homolog, a fragment or a variant thereof.

Most preferably the 3'-UTR element comprises the nucleic acid sequence derived from a fragment of the human albumin gene according to SEQ ID No: 1376 of the patent application WO2013/143700, in the following referred to as SEQ ID NO. 3, or a homolog, a fragment or a variant thereof.

Nucleotide sequence of 3'-UTR element of human albumin gene
(SEQ ID NO. 3)
CATCACATTTAAAAGCATCTCAGCCTACCATGAGAATAAGAGAAAGAAAA

TGAAGATCAATAGCTTATTCATCTCTTTTTCTTTTTCGTTGGTGTAAAGC

CAACACCCTGTCTAAAAAACATAAATTTCTTTAATCATTTTGCCTCTTTT

CTCTGTGCTTCAATTAATAAAAAATGGAAAGAACCT

In another particularly preferred embodiment, the 3'-UTR element comprises or consists of a nucleic acid sequence which is derived from a 3'-UTR of an alpha-globin gene, preferably a vertebrate alpha- or beta-globin gene, more preferably a mammalian alpha- or beta-globin gene, most preferably a human alpha- or beta-globin gene according to SEQ ID NO. 1370 of the patent application WO2013/143700 (3'-UTR of *Homo sapiens* hemoglobin, alpha 1 (HBA1)), or according to SEQ ID NO. 1371 of the patent application WO2013/143700 (3'-UTR of *Homo sapiens* hemoglobin, alpha 2 (HBA2)), or according to SEQ ID NO. 1372 of the patent application WO2013/143700 (3'-UTR of *Homo sapiens* hemoglobin, beta (HBB)).

For example, the 3'-UTR element may comprise or consist of the center, alpha-complex-binding portion of the 3'-UTR of an alpha-globin gene, such as of a human alpha-globin gene, preferably according to SEQ ID NO. 4 (corresponding to SEQ ID NO. 1393 of the patent application WO2013/143700), or a homolog, a fragment or a variant thereof.

Nucleotide sequence of 3' UTR element of an alpha-globin gene
(SEQ ID NO. 4)
GCCCGATGGGCCTCCCAACGGGCCCTCCTCCCCTCCTTGCACCG Accordingly, in certain embodiments the 3'-UTR element comprises or consists of, and/or is derived or derivable from, a nucleic acid sequence according to SEQ ID NO. 3 or SEQ ID NO. 4, or from a corresponding RNA sequence, a homolog, a fragment or a variant thereof.

The term 'a nucleic acid sequence which is derived from the 3'-UTR of a [ . . . ] gene' preferably refers to a nucleic acid sequence which is based on the 3'-UTR sequence of a [ . . . ] gene or on a part thereof, such as on the 3'-UTR of an albumin gene, an alpha-globin gene, a beta-globin gene, a tyrosine hydroxylase gene, a lipoxygenase gene, or a collagen alpha gene, such as a collagen alpha 1(I) gene, preferably of an albumin gene or on a part thereof. This term includes sequences corresponding to the entire 3'-UTR sequence, i.e. the full length 3'-UTR sequence of a gene, and sequences corresponding to a fragment of the 3'-UTR sequence of a gene, such as an albumin gene, alpha-globin gene, beta-globin gene, tyrosine hydroxylase gene, lipoxygenase gene, or collagen alpha gene, such as a collagen alpha 1(I) gene, preferably of an albumin gene.

The term 'a nucleic acid sequence which is derived from a variant of the 3'-UTR of a [ . . . ] gene' preferably refers to a nucleic acid sequence which is based on a variant of the 3'-UTR sequence of a gene, such as on a variant of the 3'-UTR of an albumin gene, an alpha-globin gene, a beta-globin gene, a tyrosine hydroxylase gene, a lipoxygenase gene, or a collagen alpha gene, such as a collagen alpha 1(I) gene, or on a part thereof as described above. This term includes sequences corresponding to the entire sequence of the variant of the 3'-UTR of a gene, i.e. the full length variant 3'-UTR sequence of a gene, and sequences corresponding to a fragment of the variant 3'-UTR sequence of a gene. A fragment in this context preferably consists of a continuous stretch of nucleotides corresponding to a continuous stretch of nucleotides in the full-length variant 3'-UTR, which represents at least 20%, preferably at least 30%, more preferably at least 40%, more preferably at least 50%, even more preferably at least 60%, even more preferably at least 70%, even more preferably at least 80%, and most preferably at least 90% of the full-length variant 3'-UTR. Such a fragment of a variant, in the sense of the present invention, is preferably a functional fragment of a variant as described herein.

In particular embodiments of the various aspects of the present invention, the mRNA construct comprises (such as in a 5' to 3' direction): (a) a 5'-CAP structure (for example, m7GpppN); and (b) a coding region encoding at least one immunogenic peptide or polypeptide; and (c) a 3'-UTR element comprising or consisting of a nucleic acid sequence which is derived from an alpha-globin gene (such as one comprising the corresponding RNA sequence of the nucleic acid sequence according to SEQ ID NO. 4, or a homolog, a fragment or a variant thereof); where any of such mRNA constructs may additionally comprise one or more the features (d) to (f) as follows: (d) a poly(A) sequence (such as one comprising about 64 adenosines); (e) a poly(C) sequence (such as one comprising about 30 cytosines); and/or (f) a histone-stem-loop (such as one comprising the corresponding RNA sequence to the nucleic acid sequence according to SEQ ID NO. 1, or a homolog, a fragment or a variant thereof).

In respect of a 3'-UTR element, the present invention also includes embodiments of the mRNA construct that comprise at least one 5'-untranslated region element, the mRNA construct comprises additionally at least one a 5'-UTR element which comprises or consists of a nucleic acid sequence which is derived from the 5'-UTR of a TOP gene, or from a corresponding RNA sequence, a homolog, a fragment, or a variant thereof. In certain of such embodiments, the 5'-UTR element preferably does not comprise (eg is lacking) a 5'TOP motif or a 5'TOP (as defined above).

In further embodiments, the mRNA construct (additionally) comprises a 5'-UTR element which comprises or consists of a nucleic acid sequence which is derived from the 5'-UTR of a TOP gene, or from a corresponding RNA sequence, a homolog, a fragment, or a variant thereof. In certain of such embodiments, the 5'-UTR element preferably does not comprise (eg is lacking) a 5'TOP motif or a 5'TOP (as defined above).

In yet further embodiments, the nucleic acid sequence of the 5'-UTR element which is derived from a 5'-UTR of a TOP gene terminates at its 3'-end with a nucleotide located at position 1, 2, 3, 4, 5, 6, 7, 8, 9 or 10 upstream of the start codon (e.g. A(U/T)G) of the gene or mRNA it is derived from. Thus, the 5'-UTR element does not comprise any part of the protein coding region. Thus, preferably, the only protein coding part of the mRNA construct is provided by the coding region.

The nucleic acid sequence which is derived from the 5'-UTR of a TOP gene is preferably derived from a eukaryotic TOP gene, preferably a plant or animal TOP gene, more preferably a chordate TOP gene, even more preferably a vertebrate TOP gene, most preferably a mammalian TOP gene, such as a human TOP gene.

For example, the 5'-UTR element is preferably selected from 5'-UTR elements comprising or consisting of a nucleic acid sequence which is derived from a nucleic acid sequence selected from the group consisting of SEQ ID Nos. 1-1363, SEQ ID NO. 1395, SEQ ID NO. 1421 and SEQ ID NO. 1422 of the patent application WO2013/143700, whose disclosure is incorporated herein by reference, from the homologs of SEQ ID Nos. 1-1363, SEQ ID NO. 1395, SEQ ID NO. 1421 and SEQ ID NO. 1422 of the patent application WO2013/143700, from a variant thereof, or preferably from a corresponding RNA sequence. The term "homologs of SEQ ID Nos. 1-1363, SEQ ID NO. 1395, SEQ ID NO. 1421 and SEQ ID NO. 1422 of the patent application WO2013/143700" refers to sequences of other species than *Homo sapiens*, which are homologous to the sequences according to SEQ ID Nos. 1-1363, SEQ ID NO. 1395, SEQ ID NO. 1421 and SEQ ID NO. 1422 of the patent application WO2013/143700.

In a preferred embodiment, the 5'-UTR element comprises or consists of a nucleic acid sequence which is derived from a nucleic acid sequence extending from nucleotide position 5 (i.e. the nucleotide that is located at position 5 in the sequence) to the nucleotide position immediately 5' to the start codon (located at the 3' end of the sequences), e.g. the nucleotide position immediately 5' to the ATG sequence, of a nucleic acid sequence selected from SEQ ID Nos. 1-1363, SEQ ID NO. 1395, SEQ ID NO. 1421 and SEQ ID NO. 1422 of the patent application WO2013/143700, from the homologs of SEQ ID Nos. 1-1363, SEQ ID NO. 1395, SEQ ID NO. 1421 and SEQ ID NO. 1422 of the patent application WO2013/143700 from a variant thereof, or a corresponding RNA sequence. It is particularly preferred that the 5' UTR element is derived from a nucleic acid sequence extending from the nucleotide position immediately 3' to the 5'TOP to the nucleotide position immediately 5' to the start codon (located at the 3' end of the sequences), e.g. the nucleotide position immediately 5' to the ATG sequence, of a nucleic acid sequence selected from SEQ ID Nos. 1-1363, SEQ ID NO. 1395, SEQ ID NO. 1421 and SEQ ID NO. 1422 of the patent application WO2013/143700, from the homologs of SEQ ID Nos. 1-1363, SEQ ID NO. 1395, SEQ ID NO. 1421 and SEQ ID NO. 1422 of the patent application WO2013/143700, from a variant thereof, or a corresponding RNA sequence.

In a particularly preferred embodiment, the 5'-UTR element comprises or consists of a nucleic acid sequence which is derived from a 5'-UTR of a TOP gene encoding a ribosomal protein or from a variant of a 5'-UTR of a TOP gene encoding a ribosomal protein. For example, the 5'-UTR element comprises or consists of a nucleic acid sequence which is derived from a 5'-UTR of a nucleic acid sequence according to any of SEQ ID NOs: 67, 170, 193, 244, 259, 554, 650, 675, 700, 721, 913, 1016, 1063, 1120, 1138, and 1284-1360 of the patent application WO2013/143700, a corresponding RNA sequence, a homolog thereof, or a variant thereof as described herein, preferably lacking the 5'TOP motif. As described above, the sequence extending from position 5 to the nucleotide immediately 5' to the ATG (which is located at the 3'end of the sequences) corresponds to the 5'-UTR of said sequences.

Preferably, the 5'-UTR element comprises or consists of a nucleic acid sequence which is derived from a 5'-UTR of a TOP gene encoding a ribosomal Large protein (RPL) or from a homolog or variant of a 5'-UTR of a TOP gene encoding a ribosomal Large protein (RPL). For example, the 5'-UTR element comprises or consists of a nucleic acid sequence which is derived from a 5'-UTR of a nucleic acid sequence according to any of SEQ ID NOs: 67, 259, 1284-1318, 1344, 1346, 1348-1354, 1357, 1358, 1421 and 1422 of the patent application WO2013/143700, a corresponding RNA sequence, a homolog thereof, or a variant thereof as described herein, preferably lacking the 5'TOP motif.

In a particularly preferred embodiment, the 5'-UTR element comprises or consists of a nucleic acid sequence which is derived from the 5'-UTR of a ribosomal protein Large 32 gene, preferably from a vertebrate ribosomal protein Large 32 (L32) gene, more preferably from a mammalian ribosomal protein Large 32 (L32) gene, most preferably from a human ribosomal protein Large 32 (L32) gene, or from a variant of the 5'-UTR of a ribosomal protein Large 32 gene, preferably from a vertebrate ribosomal protein Large 32 (L32) gene, more preferably from a mammalian ribosomal protein Large 32 (L32) gene, most preferably from a human ribosomal protein Large 32 (L32) gene, wherein preferably the 5'-UTR element does not comprise the 5'TOP of said gene.

A preferred sequence for a 5'-UTR element corresponds to SEQ ID NO. 1368 of the patent application WO2013/143700 (or a homolog, a fragment or a variant thereof) and reads as follows:

```
Nucleotide sequence for 5'-UTR element
                                   (SEQ ID NO. 5)
GGCGCTGCCTACGGAGGTGGCAGCCATCTCCTTCTCGGCATC
```

Accordingly, in a particularly preferred embodiment, the 5'-UTR element comprises or consists of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the nucleic acid sequence according to SEQ ID NO. 1368 of the patent application WO2013/143700 (5'-UTR of human ribosomal protein Large 32 lacking the 5' terminal oligopyrimidine tract, SEQ ID NO. 5) or preferably to a corresponding RNA sequence, or wherein the at least one 5'-UTR element comprises or consists of a fragment of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the nucleic acid sequence according to SEQ ID NO. 9 or more preferably to a corresponding RNA sequence, wherein, preferably, the fragment is as described above, i.e. being a continuous stretch of nucleotides representing at least 20% etc. of the full-length 5'-UTR. Preferably, the fragment exhibits a length of at least about 20 nucleotides or more, preferably of at least about 30 nucleotides or more, more preferably of at least about 40 nucleotides or more. Preferably, the fragment is a functional fragment as described herein.

In some embodiments, the mRNA construct comprises a 5'-UTR element which comprises or consists of a nucleic acid sequence which is derived from the 5'-UTR of a vertebrate TOP gene, such as a mammalian, e.g. a human TOP gene, selected from RPSA, RPS2, RPS3, RPS3A, RPS4, RPS5, RPS6, RPS7, RPS8, RPS9, RPS10, RPS11, RPS12, RPS13, RPS14, RPS15, RPS15A, RPS16, RPS17, RPS18, RPS19, RPS20, RPS21, RPS23, RPS24, RPS25, RPS26, RPS27, RPS27A, RPS28, RPS29, RPS30, RPL3, RPL4, RPL5, RPL6, RPL7, RPL7A, RPL8, RPL9, RPL10, RPL10A, RPL11, RPL12, RPL13, RPL13A, RPL14, RPL15, RPL17, RPL18, RPL18A, RPL19, RPL21, RPL22, RPL23, RPL23A, RPL24, RPL26, RPL27, RPL27A, RPL28, RPL29, RPL30, RPL31, RPL32, RPL34, RPL35, RPL35A, RPL36, RPL36A, RPL37, RPL37A, RPL38, RPL39, RPL40, RPL41, RPLP0, RPLP1, RPLP2, RPLP3, RPLP0, RPLP1, RPLP2, EEF1A1, EEF1B2, EEF1D, EEF1G, EEF2, EIF3E, EIF3F, EIF3H, EIF2S3, EIF3C, EIF3K, EIF3EIP, EIF4A2, PABPC1, HNRNPA1, TPT1, TUBB1, UBA52, NPM1, ATP5G2, GNB2L1, NME2, UQCRB, or from a homolog or variant thereof, wherein preferably the 5'-UTR element does not comprise a TOP-motif or the 5'TOP of said genes, and wherein optionally the 5'-UTR element starts at its 5'-end with a nucleotide located at position 1, 2, 3, 4, 5, 6, 7, 8, 9 or 10 downstream of the 5'terminal oligopyrimidine tract (TOP) and wherein further optionally the 5'-UTR element which is derived from a 5'-UTR of a TOP gene terminates at its 3'-end with a nucleotide located at position 1, 2, 3, 4, 5, 6, 7, 8, 9 or 10 upstream of the start codon (A(U/T)G) of the gene it is derived from.

In further particularly preferred embodiments, the 5'-UTR element comprises or consists of a nucleic acid sequence which is derived from the 5'-UTR of a ribosomal protein Large 32 gene (RPL32), a ribosomal protein Large 35 gene (RPL35), a ribosomal protein Large 21 gene (RPL21), an ATP synthase, H+ transporting, mitochondrial F1 complex, alpha subunit 1, cardiac muscle (ATP5A1) gene, an hydroxysteroid (17-beta) dehydrogenase 4 gene (HSD17B4), an androgen-induced 1 gene (AIG1), cytochrome c oxidase subunit VIc gene (COX6C), or a N-acylsphingosine amidohydrolase (acid ceramidase) 1 gene (ASAH1) or from a variant thereof, preferably from a vertebrate ribosomal protein Large 32 gene (RPL32), a vertebrate ribosomal protein Large 35 gene (RPL35), a vertebrate ribosomal protein Large 21 gene (RPL21), a vertebrate ATP synthase, H+ transporting, mitochondrial F1 complex, alpha subunit 1, cardiac muscle (ATP5A1) gene, a vertebrate hydroxysteroid (17-beta) dehydrogenase 4 gene (HSD17B4), a vertebrate androgen-induced 1 gene (AIG1), a vertebrate cytochrome c oxidase subunit VIc gene (COX6C), or a vertebrate N-acyl-sphingosine amidohydrolase (acid ceramidase) 1 gene (ASAH1) or from a variant thereof, more preferably from a mammalian ribosomal protein Large 32 gene (RPL32), a ribosomal protein Large 35 gene (RPL35), a ribosomal protein Large 21 gene (RPL21), a mammalian ATP synthase, H+ transporting, mitochondrial F1 complex, alpha subunit 1, cardiac muscle (ATP5A1) gene, a mammalian hydroxysteroid (17-beta) dehydrogenase 4 gene (HSD17B4), a mammalian androgen-induced 1 gene (AIG1), a mammalian cyto-chrome c oxidase subunit VIc gene (COX6C), or a mammalian N-acylsphingosine ami-dohydrolase (acid ceramidase) 1 gene (ASAH1) or from a variant thereof, most preferably from a human ribosomal protein Large 32 gene (RPL32), a human ribosomal protein Large 35 gene (RPL35), a human ribosomal protein Large 21 gene (RPL21), a human ATP syn-thase, H+ transporting, mitochondrial F1 complex, alpha subunit 1, cardiac muscle (ATP5A1) gene, a human hydroxysteroid (17-beta) dehydrogenase 4 gene (HSD17B4), a human androgen-induced 1 gene (AIG1), a human cytochrome c oxidase subunit VIc gene (COX6C), or a human N-acylsphingosine amidohydrolase (acid ceramidase) 1 gene (ASAH1) or from a variant thereof, wherein preferably the 5'-UTR element does not comprise the 5'TOP of said gene.

Accordingly, in a particularly preferred embodiment, the 5'-UTR element comprises or consists of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the nucleic acid sequence according to SEQ ID NO. 1368, or SEQ ID NOs 1412-1420 of the patent application WO2013/143700, or a corresponding RNA sequence, or wherein the at least one 5'-UTR element comprises or consists of a fragment of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the nucleic acid sequence according to SEQ ID NO. 1368, or SEQ ID NOs 1412-1420 of the patent application WO2013/143700, wherein, preferably, the fragment is as described above, i.e. being a continuous stretch of nucleotides representing at least 20% etc. of the full-length 5'-UTR. Preferably, the fragment exhibits a length of at least about 20 nucleotides or more, preferably of at least about 30 nucleotides or more, more preferably of at least about 40 nucleotides or more. Preferably, the fragment is a functional fragment as described herein.

Accordingly, in a particularly preferred embodiment, the 5'-UTR element comprises or consists of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the nucleic acid sequence according to SEQ ID NO. 1414 of the patent application WO2013/143700 (5'-UTR of ATP5A1 lacking the 5' terminal oligopyrimidine tract) or preferably to a corresponding RNA sequence, or wherein the at least one 5'-UTR element comprises or consists of a fragment of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the nucleic acid sequence according to SEQ ID NO. 1414 of the patent application WO2013/143700 or more preferably to a corresponding RNA sequence, wherein, preferably, the fragment is as described above, i.e. being a continuous stretch of nucleotides representing at least 20% etc. of the full-length 5'-UTR. Preferably, the fragment exhibits a length of at least about 20 nucleotides or more, preferably of at least about 30 nucleotides or more, more preferably of at least about 40 nucleotides or more. Preferably, the fragment is a functional fragment as described herein.

Preferably, the at least one 5'-UTR element and the at least one 3'-UTR element act synergistically to increase protein production from the inventive mRNA sequence as described above.

As outlined above in an especially preferred embodiment of the present invention the region of the mRNA construct that encodes at least one epitope of an immunogenic peptide or polypeptide (eg such a (coding) region that encodes an immunogenic peptide or polypeptide) are optimised for the purposes of the invention, wherein the G/C content of the coding region is increased compared with the G/C content of the coding region of the wild type mRNA. In this context the modified wild type nucleotide sequence which include the modified editing site of a stretch of eight adenosine nucleotides as defined above is to be understood as wild type mRNA respectively as basis for the optimisation.

For further improvement of the resistance to e.g. in vivo degradation (e.g. by an exo- or endo-nuclease), the mRNA construct used in the context of the present invention is provided as a stabilised nucleic acid, e.g. in the form of a modified nucleic acid. In this context the G/C content is preferably increased as outlined above. According to a further embodiment of the invention it is therefore preferred that the mRNA construct is further stabilised, preferably by backbone modifications, sugar modifications and/or base modifications. All of these modifications may be introduced into the mRNA construct without impairing the mRNA's function to be translated into the antigenic function derived from the encoded peptide or polypeptide.

A backbone modification in the context of the present invention is preferably a modification in which phosphates of the backbone of the nucleotides contained in the mRNA construct are chemically modified, e.g. anionic internucleoside linkage, N3'→P5' modifications, replacement of non-bridging oxygen atoms by boranes, neutral internucleoside linkage, amide linkage of the nucleosides, methylene(methylimino) linkages, formacetal and thioformacetal linkages, introduction of sulfonyl groups, or the like.

A sugar modification in the context of the present invention is preferably a chemical modification of the sugar of the nucleotides of the mRNA construct, e.g. methylation of the ribose residue or the like.

According to a further preferred embodiment of the invention, the mRNA construct is optimized for translation, preferably optimised for translation by replacing codons for less frequent tRNAs of a given amino acid by codons for more frequently occurring tRNAs of the respective amino acid. Without being bound by theory, the translation efficiency is believed to also determined by a different frequency in the occurrence of tRNAs in cells. Thus, if so-called "less frequent codons" are present in the mRNA construct to an increased extent, the corresponding modified RNA sequence is translated to a significantly poorer degree than in the case where codons coding for more frequent tRNAs are present. Accordingly, in certain embodiments of the present invention, the coding region of the mRNA construct is modified compared to the corresponding region of the wild type mRNA sequence or coding sequence such that at least one codon of the wild type sequence which codes for a tRNA which is relatively rare or less frequent in the cell is exchanged for a codon which codes for a tRNA which is more or most frequent in the cell and carries the same amino acid as the relatively rare or less frequent tRNA. By this modification, the sequences of the mRNA construct can be modified such that codons for which more frequently occurring tRNAs are available are inserted. In other words, in the context of the present invention, by this modification all codons of the wild type sequence which code for a tRNA which is relatively rare in the cell can in each case be exchanged for a codon which codes for a respective tRNA which is relatively frequent in the cell and which, in each case, carries the same amino acid as the relatively rare tRNA. Furthermore, it is particularly preferable to link the sequential G/C content which is increased, in particular maximized, in the mRNA construct with the "frequent" codons without modifying the amino acid sequence of the peptide or polypeptide encoded by the coding region of the mRNA construct. This preferred embodiment allows provision of a particularly efficiently translated and stabilized (modified) mRNA construct.

Substitutions, additions or eliminations of bases are preferably carried out using a DNA matrix for preparation of the nucleic acid molecule by techniques of the well known site directed mutagenesis or with an oligonucleotide ligation. In such a process, for preparation of the mRNA construct as defined herein a corresponding DNA molecule may be transcribed in vitro. This DNA matrix preferably comprises a suitable promoter, e.g. a T7 or SP6 promoter, for in vitro transcription, which is followed by the desired nucleotide sequence for the mRNA construct to be prepared and a termination signal for in vitro transcription. The DNA molecule, which forms the matrix of the mRNA of interest, may be prepared by fermentative proliferation and subsequent isolation as part of a plasmid which can be replicated in bacteria. Plasmids which may be mentioned as suitable for the present invention are e.g. the plasmids pT7Ts (GenBank accession number AB255037.1; Lai et al., Development 1995, 121: 2349 to 2360), pGEM® series, e.g.

pGEM®-1 (GenBank accession number X65300.1; from Promega) and pSP64 (GenBank accession number X65327.1); cf. also Mezei and Storts, Purification of PCR Products, in: Griffin and Griffin (ed.), PCR Technology: Current Innovation, CRC Press, Boca Raton, Fla., 2001.

In particular embodiments of the various aspects of the present invention, the mRNA construct comprises (such as, in 5'- to 3'-direction) a combination of certain of such features: (a) a 5'-CAP structure (eg, m7GpppN); and (b) a 5'-UTR element which comprises or consists of a nucleic acid sequence which is derived from the 5'-UTR of a TOP gene (eg, comprising or consisting of the corresponding RNA sequence of the nucleic acid sequence according to SEQ ID NO. 5) or a homolog, a fragment or a variant thereof; and (c) a coding region encoding at least one immunogenic peptide or polypeptide; and (d) a 3'-UTR element comprising or consisting of a nucleic acid sequence which is derived from a gene providing a stable mRNA (eg, comprising or consisting of the corresponding RNA sequence of a nucleic acid sequence according to SEQ ID NO. 3) or a homolog, a fragment or a variant thereof; and (e) a poly(A) sequence (eg, one comprising about 64 adenosines); and (f) a poly(C) sequence, (eg one comprising about 30 cytosines); and (g) a histone-stem-loop (eg, comprising the corresponding RNA sequence of the nucleic acid sequence according to SEQ ID NO. 1) or a homolog, a fragment or a variant thereof.

Most preferably, the mRNA construct comprises or consists of the corresponding mRNA sequences of the following optimised nucleotide sequences: GC optimised nucleotide sequence encoding the immunogenic peptide or polypeptide with the 5'-UTR: 32L TOP UTR, and with the 3'-UTR: albumin7-A64-N5-C30-histoneSL-N5.

The coding region of the mRNA construct in respect of the various aspects of the present invention may occur as a mono-, di-, or even multicistronic mRNA, i.e. an mRNA sequence which carries the coding sequences of one, two or more proteins or peptides. Such coding sequences in di-, or even multicistronic mRNAs may be separated by at least one internal ribosome entry site (IRES) sequence. For example, the internal ribosome entry site sequence may be derived vom EMCV (encephalomyocarditis virus) or from FMDV (Foot and mouth disease virus). Furthermore signal peptides may be used which induce the cleavage of the resulting polypeptide which comprises several proteins or peptides, e.g. a signal peptide sequence derived from F2A peptide from FMDV.

The following nucleotide sequence according to SEQ ID NO. 6 shows an example of an internal ribosome entry site of EMCV usable in the context of the present invention.

```
Nucleotide sequence of IRES of EMCV
                                     (SEQ ID NO. 6)
TTGAAAGCCGGGGGTGGGAGATCCGGATTGCCAGTCTGCTCGATATCGCA

GGCTGGGTCCGTGACTACCCACTCCCCCTTTAATTCCGCCCCTCTCCCTC

CCCCCCCCTAACGTTACTGGCCGAAGCCGCTTGGAATAAGGCCGGTGTG

CGTTTGTCTATATGTTATTTTCCACCATATTGCCGTCTTTTGGCAATGTG

AGGGCCCGGAAACCTGGCCCTGTCTTCTTGACGAGCATTCCTAGGGGTCT

TTCCCCTCTCGCCAAAGGAATGCAAGGTCTGTTGAATGTCGTGAAGGAAG

CAGTTCCTCTGGAAGCTTCTTGAAGACAAACAACGTCTGTAGCGACCCTT

TGCAGGCAGCGGAACCCCCCACCTGGCGACAGGTGCCTCTGCGGCCAAA

GCCACGTGTATAAGATACACCTGCAAAGGCGGCACAACCCCAGTGCCACG

TTGTGAGTTGGATAGTTGTGGAAAGAGTCAAATGGCTCTCCTCAAGCGTA

TTCAACAAGGGGCTGAAGGATGCCCAGAAGGTACCCCATTGTATGGGATC

TGATCTGGGGCCTCGGTGCACATGCTTTACGTGTGTTTAGTCGAGGTTAA

AAAACGTCTAGGCCCCCCGAACCACGGGGACGTGGTTTTCCTTTGAAAAA

CACGATGATAATAGATCTACC
```

The following nucleotide sequence according to SEQ ID NO. 7 shows an example of an internal ribosome entry site of FMDV (GenBank: AJ133357.1, GI:6318187; 5' UTR pos. 578-1038; point mutation 86 T→C from PMID: 8389904; point mutation 454 T→A; removal of first start codon pos. 454-456) usable for the purposes of the present invention.

```
Nucleotide sequence of IRES of EMCV
                                    (SEQ ID NO. 7)
AGCAGGTTTCCCCAACTGACACAAAACGTGCAACTTGAAACTCCGCCTGG

TCTTTCCAGGTCTAGAGGGGTAACACTTTGTACTGCGTTTGGCTCCACGC

TCGATCCACTGGCGAGTGTTAGTAACAGCACTGTTGCTTCGTAGCGGAGC

ATGACGGCCGTGGGAACTCCTCCTTGGTAACAAGGACCCACGGGGCCAAA

AGCCACGCCCACACGGGCCCGTCATGTGTGCAACCCCAGCACGGCGACTT

TACTGCGAAACCCACTTTAAAGTGACATTGAAACTGGTACCCACACACTG

GTGACAGGCTAAGGATGCCCTTCAGGTACCCCGAGGTAACACGCGACACT

CGGGATCTGAGAAGGGGACTGGGGCTTCTATAAAAGCGCTCGGTTTAAAA

AGCTTCTATGCCTGAATAGGTGACCGGAGGTCGGCACCTTTCCTTTACAA

TTAAAGACCCT
```

The following nucleotide sequences according to SEQ ID Nos. 8 and 9 show examples of F2A peptides from FMDV that mediate cotranslational cleavage usable for the purposes of the present invention.

```
Nucleotide sequence of F2A peptide, version 1, of
FMDV
                                    (SEQ ID NO. 8)
GTGAAGCAGACACTCAATTTCGACCTTCTGAAGTTGGCTGGAGATGTTGA

GTCTAACCCAGGCCCC

Nucleotide sequence of F2A peptide, version 2, of
FMDV
                                    (SEQ ID NO. 9)
GTCAAACAGACCTTGAACTTCGACTTGCTCAAACTGGCCGGGGATGTGGA

GTCCAATCCTGGACCT
```

Accordingly, in further specific embodiments, the mRNA construct useful in the present invention may further comprise one or more internal ribosome entry site (IRES) sequences or IRES-motifs, which may separate several open reading frames, for example if the mRNA construct encodes for two or more antigenic peptides or proteins. An IRES-sequence may be particularly helpful if the mRNA is a bi- or multicistronic mRNA. Particularly preferred are IRES sequences according to SEQ ID NO. 6 and SEQ ID NO. 7.

In a preferred embodiment, the mRNA construct in the context of the present invention does not comprise a reporter gene or a marker gene. Preferably, the mRNA construct does not encode, for instance, luciferase; green fluorescent protein (GFP) and its variants (such as eGFP, RFP or BFP);

α-globin; hypoxanthine-guanine phosphoribosyltransferase (HGPRT); β-galactosidase; galactokinase; alkaline phosphatase; secreted embryonic alkaline phosphatase (SEAP) or a resistance gene (such as a resistance gene against neomycin, puromycin, hygromycin and zeocin). In a preferred embodiment, the mRNA construct does not encode luciferase. In another embodiment, the mRNA construct does not encode GFP or a variant thereof.

In a further preferred embodiment, the mRNA construct does not encode a protein (or a fragment of a protein) derived from a virus belonging to the family of Orthomyxoviridae. Preferably the mRNA construct does not encode a protein that is derived from an influenza virus, more preferably an influenza A virus. Preferably, mRNA construct does not encode an influenza A protein selected from the group consisting of hemagglutinin (HA), neuraminidase (NA), nucleoprotein (NP), M1, M2, NS1, NS2 (NEP: nuclear export protein), PA, PB1 (polymerase basic 1), PB1-F2 and PB2. In another preferred embodiment, the mRNA construct does not encode ovalbumin (OVA) or a fragment thereof. Preferably, the mRNA construct does not encode an influenza A protein or ovalbumin.

In certain embodiments, the mRNA construct useful in the context of the present invention may be prepared using any method known in the art, including synthetic methods such as e.g. solid phase synthesis, as well as in vitro methods, such as in vitro transcription reactions.

Methods for in vitro transcription are known in the art (Geall et al, 2013. Semin. Immunol. 25(2): 152-159; Brunelle et al, 2013. Methods Enzymol. 530:101-14). Reagents used in said method typically include:

1) a linearized DNA template with a promoter sequence that has a high binding affinity for its respective RNA polymerase such as bacteriophage-encoded RNA polymerases, 2) ribonucleoside triphosphates (NTPs) for the four bases (adenine, cytosine, guanine and uracil);

3) a cap analog leading to a 5'-CAP-structure as defined above (e.g. m7G(5')ppp(5')G (m7G));

4) a DNA-dependent RNA polymerase (e.g. T7, T3 or SP6 RNA polymerase);

5) a ribonuclease (RNase) inhibitor to inactivate any contaminating RNase;

6) a pyrophosphatase to degrade pyrophosphate, which may inhibit transcription;

7) $MgCl_2$, which supplies $Mg^{2+}$ as a co-factor for the polymerase;

8) a buffer to maintain a suitable pH value, which can also contain antioxidants and polyamines such as spermidine at optimal concentrations.

In certain embodiments, the mRNA construct useful in the context of the present invention may be purified using any method known in the art, including High Performance (High Pressure) Liquid Chromatography (HPLC) methods (WO2008/077592).

According to one embodiment of the various aspects of the present invention the mRNA construct that encodes at least one immunogenic peptide or polypeptide as outlined above may be provided (eg administered to the subject) naked without being associated with any further vehicle, transfection or complexation agent (such as one for increasing the transfection efficiency and/or the immunostimulatory properties of the mRNA construct) or of further comprised of a different nucleic acid molecule or construct.

According to an alternative embodiment of the various aspects of the present invention the mRNA construct that encodes at least one immunogenic peptide or polypeptide as outlined above may be provided (eg administered to the subject) and/or formulated together with one or more cationic or polycationic compounds, preferably with cationic or polycationic polymers, cationic or polycationic peptides or proteins, e.g. protamine, cationic or polycationic polysaccharides and/or cationic or polycationic lipids.

According to a preferred embodiment, the mRNA construct according to the present invention may be complexed with lipids to form one or more liposomes, lipoplexes, or lipid nanoparticles. Therefore, in one embodiment, the second antigenic composition comprises liposomes, lipoplexes, and/or lipid nanoparticles comprising the at least one mRNA construct.

Lipid-based formulations have been increasingly recognized as one of the most promising delivery systems for RNA due to their biocompatibility and their ease of large-scale production. Cationic lipids have been widely studied as synthetic materials for delivery of RNA. After mixing together, nucleic acids are condensed by cationic lipids to form lipid/nucleic acid complexes known as lipoplexes. These lipid complexes are able to protect genetic material from the action of nucleases and deliver it into cells by interacting with the negatively charged cell membrane. Lipoplexes can be prepared by directly mixing positively charged lipids at physiological pH with negatively charged nucleic acids.

Conventional liposomes consist of a lipid bilayer that can be composed of cationic, anionic, or neutral (phospho)lipids and cholesterol, which encloses an aqueous core. Both the lipid bilayer and the aqueous space can incorporate hydrophobic or hydrophilic compounds, respectively. Liposome characteristics and behaviour in vivo can be modified by addition of a hydrophilic polymer coating, e.g. polyethylene glycol (PEG), to the liposome surface to confer steric stabilization. Furthermore, liposomes can be used for specific targeting by attaching ligands (e.g., antibodies, peptides, and carbohydrates) to its surface or to the terminal end of the attached PEG chains (Front Pharmacol. 2015 Dec. 1; 6:286).

Liposomes are colloidal lipid-based and surfactant-based delivery systems composed of a phospholipid bilayer surrounding an aqueous compartment. They may present as spherical vesicles and can range in size from 20 nm to a few microns. Cationic lipid-based liposomes are able to complex with negatively charged nucleic acids via electrostatic interactions, resulting in complexes that offer biocompatibility, low toxicity, and the possibility of the large-scale production required for in vivo clinical applications. Liposomes can fuse with the plasma membrane for uptake; once inside the cell, the liposomes are processed via the endocytic pathway and the genetic material is then released from the endosome/carrier into the cytoplasm. Liposomes have long been perceived as drug delivery vehicles because of their superior biocompatibility, given that liposomes are basically analogs of biological membranes, and can be prepared from both natural and synthetic phospholipids (Int J Nanomedicine. 2014; 9: 1833-1843).

Cationic liposomes have been traditionally the most commonly used non-viral delivery systems for oligonucleotides, including plasmid DNA, antisense oligos, and siRNA/small hairpin RNA-shRNA). Cationic lipids, such as DOTAP, (1,2-dioleoyl-3-trimethylammonium-propane) and DOTMA (N-[1-(2,3-dioleoyloxy)propyl]-N,N,N-trimethylammonium methyl sulfate) can form complexes or lipoplexes with negatively charged nucleic acids to form nanoparticles by electrostatic interaction, providing high in vitro transfection efficiency. Furthermore, neutral lipid-based nanoliposomes for RNA delivery as e.g. neutral 1,2-dioleoyl-sn-glycero-3-phosphatidylcholine (DOPC)-based nanoliposomes were developed. (Adv Drug Deliv Rev. 2014 February; 66: 110-116.).

Therefore, in one embodiment the at least one mRNA construct of the second antigenic composition according to the present invention is complexed with cationic lipids and/or neutral lipids and thereby forms liposomes, lipid nanoparticles, lipoplexes or neutral lipid-based nanoliposomes.

Accordingly, in a further embodiment of the invention it is preferred that the mRNA construct or any other nucleic acid comprised in the antigenic composition (or vaccine component) that includes the mRNA construct is associated with or complexed with a cationic or polycationic compound or a polymeric carrier, optionally in a weight ratio selected from a range of about 6:1 (w/w) to about 0.25:1 (w/w), more preferably from about 5:1 (w/w) to about 0.5:1 (w/w), even more preferably of about 4:1 (w/w) to about 1:1 (w/w) or of about 3:1 (w/w) to about 1:1 (w/w), and most preferably a ratio of about 3:1 (w/w) to about 2:1 (w/w) of mRNA or nucleic acid to cationic or polycationic compound and/or with a polymeric carrier; or optionally in a nitrogen/phosphate ratio of mRNA or nucleic acid to cationic or polycationic compound and/or polymeric carrier in the range of about 0.1-10, preferably in a range of about 0.3-4 or 0.3-1, and most preferably in a range of about 0.5-1 or 0.7-1, and even most preferably in a range of about 0.3-0.9 or 0.5-0.9.

Thereby, the mRNA construct or any other nucleic acid comprised in the antigenic composition (or vaccine component) that includes the mRNA construct can also be associated with a vehicle, transfection or complexation agent for increasing the transfection efficiency and/or the immunostimulatory properties of the mRNA construct or of optionally comprised further included nucleic acids.

Cationic or polycationic compounds, being particularly preferred agents in this context of the present invention include protamine, nucleoline, spermine or spermidine, or other cationic peptides or proteins, such as poly-L-lysine (PLL), poly-arginine, basic polypeptides, cell penetrating peptides (CPPs), including HIV-binding peptides, HIV-1 Tat (HIV), Tat-derived peptides, Penetratin, VP22 derived or analog peptides, HSV VP22 (Herpes simplex), MAP, KALA or protein transduction domains (PTDs), PpT620, prolin-rich peptides, arginine-rich peptides, lysine-rich peptides, MPG-peptide(s), Pep-1, L-oligomers, Calcitonin peptide(s), *Antennapedia*-derived peptides (particularly from *Drosophila antennapedia*), pAntp, plsI, FGF, Lactoferrin, Transportan, Buforin-2, Bac715-24, SynB, SynB(1), pVEC, hCT-derived peptides, SAP, or histones.

Accordingly, in certain of such embodiments the mRNA construct is associated or complexed with a cationic protein or peptide; and in further of such embodiments the mRNA construct is associated or complexed with protamine.

In other embodiments the mRNA construct is associated or complexed with a cationic or polycationic proteins or peptides which may be selected from the following proteins or peptides having the following generic formula (III):

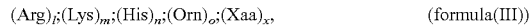

(formula(III))

wherein l+m+n+o+x=8-15, and l, m, n or o independently of each other may be any number selected from 0, 1, 2, 3, 4, 5, 6, 7, 8, 9, 10, 11, 12, 13, 14 or 15, provided that the overall content of Arg, Lys, His and Orn represents at least 50% of all amino acids of the oligopeptide; and Xaa may be any amino acid selected from native (=naturally occurring) or non-native amino acids except of Arg, Lys, His or Orn; and x may be any number selected from 0, 1, 2, 3 or 4, provided, that the overall content of Xaa does not exceed 50% of all amino acids of the oligopeptide. Particularly preferred cationic peptides in this context are e.g. $Arg_7$, $Arg_8$, $Arg_9$, $H_3R_9$, $R_9H_3$, $H_3R_9H_3$, $YSSR_9SSY$, $(RKH)_4$, $Y(RKH)_2R$, etc. In this context the disclosure of WO2009/030481 is incorporated herewith by reference.

Further preferred cationic or polycationic compounds, which can be used as transfection or complexation agent may include cationic polysaccharides, for example chitosan, polybrene, cationic polymers, e.g. polyethyleneimine (PEI), cationic lipids, e.g. DOTMA: [1-(2,3-sioleyloxy)propyl)]-N,N,N-trimethylammonium chloride, DMRIE, di-C14-amidine, DOTIM, SAINT, DC-Chol, BGTC, CTAP, DOPC, DODAP, DOPE: Dioleyl phosphatidylethanol-amine, DOSPA, DODAB, DOIC, DMEPC, DOGS: Dioctadecylamidoglicylspermin, DIMRI: Dimyristo-oxypropyl dimethyl hydroxyethyl ammonium bromide, DOTAP: dioleoyloxy-3-(trimethylammonio)propane, DC-6-14: O,O-ditetradecanoyl-N-(α-trimethylammonioacetyl) diethanolamine chloride, CLIP1: rac-[(2,3-dioctadecyloxypropyl)(2-hydroxyethyl)] dimethylammonium chloride, CLIP6: rac-[2(2,3-dihexadecyloxypropyl-oxymethyloxy)ethyl] trimethylammonium, CLIP9: rac-[2(2,3-dihexadecyloxypropyl-oxysuccinyloxy)ethyl]-trimethylammonium, oligofectamine, or cationic or polycationic polymers, e.g. modified polyaminoacids, such as β-aminoacid-polymers or reversed polyamides, etc., modified polyethylenes, such as PVP (poly(N-ethyl-4-vinylpyridinium bromide)), etc., modified acrylates, such as pDMAEMA (poly(dimethylaminoethyl methylacrylate)), etc., modified amidoamines such as pAMAM (poly(amidoamine)), etc., modified polybetaaminoester (PBAE), such as diamine end modified 1,4 butanediol diacrylate-co-5-amino-1-pentanol polymers, etc., dendrimers, such as polypropylamine dendrimers or pAMAM based dendrimers, etc., polyimine(s), such as PEI: poly(ethyleneimine), poly(propyleneimine), etc., polyallylamine, sugar backbone based polymers, such as cyclodextrin based polymers, dextran based polymers, chitosan, etc., silan backbone based polymers, such as PMOXA-PDMS copolymers, etc., blockpolymers consisting of a combination of one or more cationic blocks (e.g. selected from a cationic polymer as mentioned above) and of one or more hydrophilic or hydrophobic blocks (e.g. polyethyleneglycole); etc.

A polymeric carrier useful in the context of the present invention may be a polymeric carrier formed by disulfide-crosslinked cationic components. The disulfide-crosslinked cationic components may be the same or different from each other. The polymeric carrier can also contain further components. It is also particularly preferred that the polymeric carrier useful in the context of the present invention comprises mixtures of cationic peptides, proteins or polymers and optionally further components as defined herein, which are crosslinked by disulfide bonds as described herein. In this context the disclosure of WO2012/013326 is incorporated herewith by reference.

In this context the cationic components, which form basis for the polymeric carrier by disulfide-crosslinkage, are typically selected from any suitable cationic or polycationic peptide, protein or polymer suitable for this purpose, particular any cationic or polycationic peptide, protein or polymer capable to complex an mRNA or a nucleic acid as defined in the context of the present invention, and thereby preferably condensing the mRNA or the nucleic acid. The cationic or polycationic peptide, protein or polymer, is preferably a linear molecule, however, branched cationic or polycationic peptides, proteins or polymers may also be used.

Every disulfide-crosslinking cationic or polycationic protein, peptide or polymer of the polymeric carrier, which may be used to associate with or complex the mRNA construct or any other nucleic acid comprised in the antigenic composition (or vaccine component) that includes the mRNA construct contains at least one —SH moiety, most preferably at least one cysteine residue or any further chemical group exhibiting an —SH moiety, capable to form a disulfide linkage upon condensation with at least one further cationic or polycationic protein, peptide or polymer as cationic component of the polymeric carrier as mentioned herein.

As defined above, the polymeric carrier, which may be used to complex the mRNA construct or any further nucleic acid comprised in the inventive antigenic compositions, pharmaceutical compositions or vaccines may be formed by disulfide-crosslinked cationic (or polycationic) components.

Preferably, such cationic or polycationic peptides or proteins or polymers of the polymeric carrier, which comprise or are additionally modified to comprise at least one —SH moiety, are selected from, proteins, peptides and polymers as defined above for complexation agent.

In a further particular embodiment, the polymeric carrier which may be used to associate with or complex the mRNA construct or any other nucleic acid comprised in the antigenic compositions, pharmaceutical compositions or vaccines (or vaccine components) may be selected from a polymeric carrier molecule according to generic formula (IV):

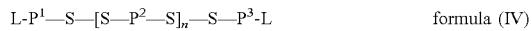  formula (IV)

wherein, $P^1$ and $P^3$ are different or identical to each other and represent a linear or branched hydrophilic polymer chain, each $P^1$ and $P^3$ exhibiting at least one —SH-moiety, capable to form a disulfide linkage upon condensation with component $P^2$, or alternatively with (AA), $(AA)_x$, or $[(AA)_x]_z$ if such components are used as a linker between $P^1$ and $P^2$ or $P^3$ and $P^2$) and/or with further components (e.g. (AA), $(AA)_x$, $[(AA)_x]_z$ or L), the linear or branched hydrophilic polymer chain selected independent from each other from polyethylene glycol (PEG), poly-N-(2-hydroxypropyl)methacrylamide, poly-2-(methacryloyloxy)ethyl phosphorylcholines, poly(hydroxyalkyl L-asparagine), poly(2-(methacryloyloxy)ethyl phosphorylcholine), hydroxyethylstarch or poly(hydroxyalkyl L-glutamine), wherein the hydrophilic polymer chain exhibits a molecular weight of about 1 kDa to about 100 kDa, preferably of about 2 kDa to about 25 kDa; or more preferably of about 2 kDa to about 10 kDa, e.g. about 5 kDa to about 25 kDa or 5 kDa to about 10 kDa;

$P^2$ is a cationic or polycationic peptide or protein, e.g. as defined above for the polymeric carrier formed by disulfide-crosslinked cationic components, and preferably having a length of about 3 to about 100 amino acids, more preferably having a length of about 3 to about 50 amino acids, even more preferably having a length of about 3 to about 25 amino acids, e.g. a length of 0.30 about 3 to 10, 5 to 15, 10 to 20 or 15 to 25 amino acids, more preferably a length of about 5 to about 20 and even more preferably a length of about 10 to about 20; or
is a cationic or polycationic polymer, e.g. as defined above for the polymeric carrier formed by disulfide-crosslinked cationic components, typically having a molecular weight of about 0.5 kDa to about 30 kDa, including a molecular weight of about 1 kDa to about 20 kDa, even more preferably of about 1.5 kDa to about 10 kDa, or having a molecular weight of about 0.5 kDa to about 100 kDa, including a molecular weight of about 10 kDa to about 50 kDa, even more preferably of about 10 kDa to about 30 kDa;

each $P^2$ exhibiting at least two —SH-moieties, capable to form a disulfide linkage upon condensation with further components $P^2$ or component(s) $P^1$ and/or $P^3$ or alternatively with further components (e.g. (AA), $(AA)_x$, or $[(AA)_x]_z$);

S—S— is a (reversible) disulfide bond (the brackets are omitted for better readability), wherein S preferably represents sulphur or a —SH carrying moiety, which has formed a (reversible) disulfide bond. The (reversible) disulfide bond is preferably formed by condensation of —SH-moieties of either components $P^1$ and $P^2$, $P^2$ and $P^2$, or $P^2$ and $P^3$, or optionally of further components as defined herein (e.g. L, (AA), $(AA)_x$, $[(AA)_x]_z$, etc); The —SH-moiety may be part of the structure of these components or added by a modification as defined below;

L is an optional ligand, which may be present or not, and may be selected independent from the other from RGD, Transferrin, Folate, a signal peptide or signal sequence, a localization signal or sequence, a nuclear localization signal or sequence (NLS), an antibody, a cell penetrating peptide, (e.g. TAT or KALA), a ligand of a receptor (e.g. cytokines, hormones, growth factors etc), small molecules (e.g. carbohydrates like mannose or galactose or synthetic ligands), small molecule agonists, inhibitors or antagonists of receptors (e.g. RGD peptidomimetic analogues), or any further protein as defined herein, etc.;

n is an integer, typically selected from a range of about 1 to 50, preferably from a range of about 1, 2 or 3 to 30, more preferably from a range of about 1, 2, 3, 4, or 5 to 25, or a range of about 1, 2, 3, 4, or 5 to 20, or a range of about 1, 2, 3, 4, or 5 to 15, or a range of about 1, 2, 3, 4, or 5 to 10, including e.g. a range of about 4 to 9, 4 to 10, 3 to 20, 4 to 20, 5 to 20, or 10 to 20, or a range of about 3 to 15, 4 to 15, 5 to 15, or 10 to 15, or a range of about 6 to 11 or 7 to 10. Most preferably, n is in a range of about 1, 2, 3, 4, or 5 to 10, more preferably in a range of about 1, 2, 3, or 4 to 9, in a range of about 1, 2, 3, or 4 to 8, or in a range of about 1, 2, or 3 to 7.

In this context the disclosure of WO2011/026641 is incorporated herewith by reference. Each of hydrophilic polymers $P^1$ and $P^3$ typically exhibits at least one —SH-moiety, wherein the at least one —SH-moiety is capable to form a disulfide linkage upon reaction with component $P^2$ or with component (AA) or $(AA)_x$, if used as linker between $P^1$ and $P^2$ or $P^3$ and $P^2$ as defined below and optionally with a further component, e.g. L and/or (AA) or $(AA)_x$, e.g. if two or more —SH-moieties are contained. The following subformulae "$P^1$—S—S—$P^2$" and "$P^2$—S—S—$P^3$" within generic formula (V) above (the brackets are omitted for better readability), wherein any of S, $P^1$ and $P^3$ are as defined herein, typically represent a situation, wherein one —SH-moiety of hydrophilic polymers $P^1$ and $P^3$ was condensed with one —SH-moiety of component $P^2$ of generic formula (V) above, wherein both sulphurs of these —SH-moieties form a disulfide bond —S—S— as defined herein in formula (V). These —SH-moieties are typically provided by each of the hydrophilic polymers $P^1$ and $P^3$, e.g. via an internal cysteine or any further (modified) amino acid or compound which carries a —SH moiety. Accordingly, the subformulae "$P^1$—S—S—$P^2$" and "$P^2$—S—S—$P^3$" may also be written as "$P^1$-Cys-Cys-$P^2$" and "$P^2$-Cys-Cys-$P^3$", if the —SH— moiety is provided by a cysteine, wherein the term Cys-Cys represents two cysteines coupled via a disulfide bond, not via a peptide bond. In this case, the term "—S—S—" in these formulae may also be written as "—S-Cys", as "-Cys-S" or as "-Cys-Cys-". In this context, the term "-Cys-Cys-" does not represent a peptide bond but a linkage of two cysteines via their —SH-moieties to form a disulfide bond. Accordingly, the term "-Cys-Cys-" also may be understood generally as "-(Cys-S)—(S-Cys)-", wherein in this specific case S indicates the sulphur of the —SH-moiety of cysteine. Likewise, the terms "—S-Cys" and "—Cys-S" indicate a disulfide bond between a —SH containing moiety and a cysteine, which may also be written as "—S—(S-Cys)" and "-(Cys-S)—S". Alternatively, the hydrophilic polymers $P^1$ and $P^3$ may be modified with a —SH moiety, preferably via a chemical reaction with a compound carrying a —SH moiety, such that each of the hydrophilic polymers $P^1$ and $P^3$ carries at least one such —SH moiety. Such a compound carrying a —SH moiety may be e.g. an (additional) cysteine or any further (modified) amino acid, which carries a —SH moiety. Such a compound may also be any non-amino compound or moiety, which contains or allows to introduce a —SH moiety into hydrophilic polymers $P^1$ and $P^3$ as defined herein. Such non-amino compounds may be attached to the hydrophilic polymers $P^1$ and $P^3$ of formula (VI) of the polymeric carrier according to the present invention via chemical reactions or binding of compounds, e.g. by binding of a 3-thio propionic acid or thioimolane, by amide formation (e.g. carboxylic acids, sulphonic acids, amines, etc), by Michael addition (e.g maleinimide moieties, $\alpha$, $\beta$ unsaturated carbonyls, etc), by click chemistry (e.g. azides or alkines), by alkene/alkine methatesis (e.g. alkenes or alkines), imine or hydrozone formation (aldehydes or ketons, hydrazins, hydroxylamins, amines), complexation reactions (avidin, biotin, protein G) or components which allow $S_n$-type substitution reactions (e.g halogenalkans, thiols, alcohols, amines, hydrazines, hydrazides, sulphonic acid esters, oxyphosphonium salts) or other chemical moieties which can be utilized in the attachment of further components. A particularly preferred PEG derivate in this context is alpha-Methoxy-omega-mercapto poly(ethylene glycol). In each case, the SH-moiety, e.g. of a cysteine or of any further (modified) amino acid or compound, may be present at the terminal ends or internally at any position of hydrophilic polymers $P^1$ and $P^3$. As defined herein, each of hydrophilic polymers $P^1$ and $P^3$ typically exhibits at least one —SH-moiety preferably at one terminal end, but may also contain two or even more —SH-moieties, which may be used to additionally attach further components as defined herein, preferably further functional peptides or proteins e.g. a ligand, an amino acid component (AA) or (AA)$_x$, antibodies, cell penetrating peptides or enhancer peptides (e.g. TAT, KALA), etc.

In this context it is particularly preferred that the mRNA construct is associated or complexed at least partially with a cationic or polycationic compound and/or a polymeric carrier, preferably cationic proteins or peptides. In this context the disclosure of WO2010/037539 and WO2012/113513 is incorporated herewith by reference. Partially, in this context, means that only a part of the mRNA construct is associated or complexed with a cationic compound and that the rest of the mRNA construct is (comprised in the an antigenic composition or vaccine of the present invention) in uncomplexed form ("free"). Preferably the ratio of complexed mRNA to free mRNA (in the antigenic compositions, pharmaceutical compositions, vaccines or vaccine compositions) is selected from a range of about 5:1 (w/w) to about 1:10 (w/w), more preferably from a range of about 4:1 (w/w) to about 1:8 (w/w), even more preferably from a range of about 3:1 (w/w) to about 1:5 (w/w) or 1:3 (w/w), and most preferably the ratio of complexed mRNA to free mRNA in the an antigenic composition or vaccine of the present invention is selected from a ratio of about 1:1 (w/w).

Accordingly, in certain embodiments, the mRNA construct is associated with or complexed at least partially with a cationic or polycationic compound and/or a polymeric carrier, preferably cationic proteins or peptides and more preferably protamine. In particular of such embodiments, the ratio of associated or complexed mRNA to free mRNA is selected from a range of about 5:1 (w/w) to about 1:10 (w/w), preferably from a range of about 4:1 (w/w) to about 1:8 (w/w), more preferably from a range of about 3:1 (w/w) to about 1:5 (w/w) or 1:3 (w/w), and most preferably the ratio of complexed mRNA to free mRNA is from a ratio of about 2:1 (w/w) to about 1:2 (w/w) such as about 1:1 (w/w).

A complexed mRNA construct when used in the context of the present invention, is preferably prepared according to a first step by complexing the mRNA construct with a cationic or polycationic compound and/or with a polymeric carrier, preferably as defined herein, in a specific ratio to form a stable complex. In this context, it is highly preferable, that no free cationic or polycationic compound or polymeric carrier or only a negligibly small amount thereof remains in the component of the complexed mRNA after complexing the mRNA. Accordingly, the ratio of the mRNA and the cationic or polycationic compound and/or the polymeric carrier in the component of the complexed mRNA is typically selected in a range that the mRNA is entirely complexed and no free cationic or polycationic compound or polymeric carrier or only a negligibly small amount thereof remains in the composition.

Preferably the ratio of the mRNA to the cationic or polycationic compound and/or the polymeric carrier, preferably as defined herein, is selected from a range of about 6:1 (w/w) to about 0.25:1 (w/w), more preferably from about 5:1 (w/w) to about 0.5:1 (w/w), even more preferably of about 4:1 (w/w) to about 1:1 (w/w) or of about 3:1 (w/w) to about 1:1 (w/w), and most preferably a ratio of about 3:1 (w/w) to about 2:1 (w/w). Alternatively, the ratio of the mRNA to the cationic or polycationic compound and/or the polymeric carrier, preferably as defined herein, in the component of the complexed mRNA, may also be calculated on the basis of the nitrogen/phosphate ratio (NIP-ratio) of the entire complex. In the context of the present invention, an N/P-ratio is preferably in the range of about 0.1-10, preferably in a range of about 0.3-4 and most preferably in a range of about 0.5-2 or 0.7-2 regarding the ratio of mRNA: cationic or polycationic compound and/or polymeric carrier, preferably as defined herein, in the complex, and most preferably in a range of about 0.7-1.5, 0.5-1 or 0.7-1, and even most preferably in a range of about 0.3-0.9 or 0.5-0.9, preferably provided that the cationic or polycationic compound in the complex is a cationic or polycationic cationic or polycationic protein or peptide and/or the polymeric carrier as defined above. In this specific embodiment the complexed mRNA is also emcompassed in the term "adjuvant component".

In a further aspect the invention provides for a second antigenic composition comprising a plurality or more than one, preferably 2 to 10, more preferably 2 to 5, most preferably 2 to 4 of the mRNA constructs as defined herein. These second antigenic compositions comprise more than one mRNA construct, preferably encoding different epitopes from different immunogenic peptides or polypeptides which comprise either the same or preferably different pathogenic antigens or fragments, variants or derivatives thereof.

In certain embodiments of the present invention the antigenic composition that comprises at least one mRNA construct may comprise a plurality or more than one mRNA construct, each as set forth herein. For example, such an antigenic composition may comprise two, three, four, five, six, seven, eight, nine, ten or more than ten (such as between about 10 and 20) of mRNA constructs, each as set forth herein.

In a related certain embodiments of the present invention, the antigenic composition that comprises at least one immunogenic peptide or polypeptide may comprise a plurality or more than one immunogenic peptide or polypeptide, each as set forth herein. For example, such an antigenic composition may comprise two, three, four, five, six, seven, eight, nine, ten or more than ten (such as between about 10 and 20) immunogenic peptides or polypeptides, each as set forth herein.

In another related certain embodiments of the present invention, the antigenic composition that comprises at least one nucleic acid construct (not being a mRNA construct) may comprise a plurality or more than one such nucleic acid construct, each as set forth herein. For example, such an antigenic composition may comprise two, three, four, five, six, seven, eight, nine, ten or more than ten (such as between about 10 and 20) such nucleic acid constructs, each as set forth herein.

Each element of such plurality of immunogenic peptide or polypeptide comprised in an antigenic composition (or encoded by a nucleic acid/mRNA construct comprised in an antigenic composition) may represent an antigen (or epitope) in respect of the same pathogen or the same condition, disorder or disease. Alternatively, one or more (such as two, three, four, five or more) elements of such plurality may represent an antigen (or epitope) in respect of a different pathogen or a different condition, disorder or disease form the other element(s) comprised in such antigenic composition. Such embodiments are, in particular, useful for the vaccination against, or to raise (in a subject) an immune response against more than one pathogen or enable treatment or prophylaxis for more than one condition, disorder or disease.

Accordingly, in a further particular preferred embodiment, the present invention also provides a second antigenic composition, that comprises a plurality of the mRNA constructs as defined herein and optionally a pharmaceutically acceptable carrier and/or vehicle.

As a first ingredient, the second antigenic composition of the present invention comprises at least one mRNA construct as defined herein; and the first antigenic composition of the present invention comprises at least an epitope of an immunogenic peptide or polypeptide (or a non-mRNA nucleic acid construct that encodes at least such an epitope). However, either (or both) of such antigenic compositions of the present invention can (additionally) comprise a second ingredient as a pharmaceutically active component. A pharmaceutically active component in this connection is a compound that has a therapeutic effect to heal, ameliorate or prevent a particular indication or disease as mentioned herein, preferably one in respect of a pathogen, a tumour or cancer, an allergy or an autoimmune disorder. Such compounds include, without implying any limitation, peptides or proteins, preferably as defined herein, nucleic acids, preferably as defined herein, (therapeutically active) low molecular weight organic or inorganic compounds (molecular weight less than 5000, preferably less than 1000), sugars, antigens or antibodies, preferably as defined herein, therapeutic agents already known in the prior art, antigenic cells, antigenic cellular fragments, cellular fractions; cell wall components (e.g. polysaccharides), modified, attenuated or de-activated (e.g. chemically or by irradiation) pathogens (virus, bacteria etc.), adjuvants, preferably as defined herein, etc.

In respect of the first (eg prime) antigenic composition of the present invention, a first certain embodiment of such first antigenic composition comprises at least one immunogenic peptide or polypeptide. For example, it may comprise an immunogenic protein, an immunogenic peptide and/or an immunogenic polypeptide (each or which may be one as set forth elsewhere herein).

In particular of such embodiments, such a first antigenic composition comprises a solution of at least one immunogenic protein, an immunogenic peptide and/or an immunogenic polypeptide. Such a solution may consist of the immunogenic protein, an immunogenic peptide and/or an immunogenic polypeptide solubilised (eg dissolved) in an aqueous (or other solvent) based solvent, which may optionally comprise additional solutes such as salts, other proteins/polypeptides/peptides, organic molecules and/or contaminating molecules.

In certain embodiments of the first antigenic composition of the present invention, an immunogenic protein, immunogenic peptide and/or immunogenic polypeptide comprised therein is provided from an isolated or in purified form. For example, such a protein/polypeptide/peptide is provided at a degree of purity selected from the list consisting of greater than about: 50%, 75%, 80%, 90, 95%, 98%, 99% or between 99% and 100% purity in respect of any undesired or contaminating molecules such as proteins. Such isolated or purified form of the protein/polypeptide/peptide may be prepared by recombinant expression of such protein/polypeptide/peptide, or by purification from natural sources. Alternatively, and particularly where the (poly) peptide has a length of less than about 100 amino acid or amino-acid like moieties, then such (poly)peptide may be prepared by synthetic methods as will be known to the person of ordinary skill.

In other certain embodiments of the first antigenic composition of the present invention, an immunogenic protein, immunogenic peptide and/or immunogenic polypeptide comprised therein is one comprised in a preparation or admixture of other molecules (such as proteins/polypeptides/proteins) that includes such immunogenic protein, immunogenic peptide and/or immunogenic polypeptide. In one such embodiment, such a preparation may be selected from the list consisting of: a virus preparation, a cell preparation and a bacteria preparation. A vaccine composition manufactured from an inactivated virus (such as RABIPUR®, prepared from inactivated rabies virus) is one non-limiting example of a first antigenic composition that comprises a virus preparation that includes at least one immunogenic protein, immunogenic peptide or immunogenic polypeptide.

In respect of the first (eg prime) antigenic composition of the present invention, in a second certain embodiment such first antigenic composition comprises at least one nucleic acid construct that encodes at least one immunogenic peptide or immunogenic polypeptide, wherein such nucleic acid construct is not an mRNA construct. With the exception of mRNA, exemplary nucleic acids are described elsewhere herein; and in one particular embodiment such a nucleic acid construct is a DNA construct.

In a further such embodiment, such a nucleic acid construct comprised in the first antigenic composition of the present invention is a vector.

Vector:

As used herein, the term "vector" refers to at least one polynucleotide or to a mixture of at least one polynucleotide and at least one protein which is capable of introducing the polynucleotide comprised therein into a cell. At least one polynucleotide comprised by the vector consists of or comprises at least one nucleic acid construct encoding at least one immunogenic peptide or polypeptide. In addition to the polynucleotide consisting of or comprising the nucleic acid construct of the present invention additional polynucleotides and/or polypeptides may be introduced into the cell. The addition of additional polynucleotides and/or polypeptides is especially desirable if said additional polynucleotides and/or polypeptides are required to introduce the nucleic acid construct of the present invention into the cell or if the introduction of additional polynucleotides and/or polypeptides increases the expression of the immunogenic peptide or polypeptide encoded by the nucleic acid construct of the present invention.

In the context of the present invention it is preferred that the immunogenic peptide or polypeptide encoded by the introduced nucleic acid construct is expressed within the cell upon introduction of the vector or vectors. Examples of suitable vectors include but are not limited to plasmids, cosmids, phages, viruses or artificial chromosomes.

In certain embodiments, the vector comprising a nucleic acid construct in the context of the present invention is selected from the group consisting of plasmids, cosmids, phages, viruses, and artificial chromosomes. More preferably, a vector suitable for use in the present invention is a phage vector, preferably lambda phage and filamentous phage vectors, or a viral vector.

Suitable viral vectors are based on naturally occurring vectors, which typically are modified to be replication incompetent also referred to as non-replicating. Non-replicating viruses require the provision of proteins in trans for replication. Typically those proteins are stably or transiently expressed in a viral producer cell line, thereby allowing replication of the virus. The viral vectors are, thus, preferably infectious and non-replicating. The skilled person is aware of how to render various viruses replication incompetent.

In a preferred embodiment of the present invention the vector is selected from the group consisting of adenovirus vectors, adeno-associated virus (AAV) vectors (e.g., AAV type 5 and type 2), alphavirus vectors (e.g., Venezuelan equine encephalitis virus (VEE), Sindbis virus (SIN), Semliki forest virus (SFV), and VEE-SIN chimeras), herpes virus vectors (e.g. vectors derived from cytomegaloviruses, like rhesus cytomegalovirus (RhCMV)), arena virus vectors (e.g. lymphocytic choriomeningitis virus (LCMV) vectors), measles virus vectors, pox virus vectors (e.g., vaccinia virus, modified vaccinia virus Ankara (MVA), NYVAC (derived from the Copenhagen strain of vaccinia), and avipox vectors: canarypox (ALVAC) and fowlpox (FPV) vectors), vesicular stomatitis virus vectors, retrovirus, lentivirus, viral like particles, and bacterial spores.

In particular embodiments, the preferred vectors are adenoviral vectors, in particular adenoviral vectors derived from human or non-human great apes and poxyviral vectors, preferably MVA. Preferred great apes from which the adenoviruses are derived are Chimpanzee (*Pan*), Gorilla (*Gorilla*) and orangutans (*Pongo*), preferably Bonobo (*Pan paniscus*) and common Chimpanzee (*Pan troglodytes*). Typically, naturally occurring non-human great ape adenoviruses are isolated from stool samples of the respective great ape. The most preferred vectors are non-replicating adenoviral vectors based on hAd5, hAdII, hAd26, hAd35, hAd49, ChAd3, ChAd4, ChAd5, ChAd6, ChAd7, ChAd8, ChAd9, ChAdIO, ChAdII, ChAdI6, ChAdI7, ChAdI9, ChAd20, ChAd22, ChAd24, ChAd26, ChAd30, ChAd31, ChAd37, ChAd38, ChAd44, ChAd55, ChAd63, ChAd 73, ChAd82, ChAd83, ChAdI46, ChAdI47, PanAdI, PanAd2, and PanAd3 vectors or replication-competent Ad4 and Ad7 vectors. The human adenoviruses hAd4, hAd5, hAd7, hAdII, hAd26, hAd35 and hAd49 are well known in the art. Vectors based on naturally occurring ChAd3, ChAd4, ChAd5, ChAd6, ChAd7, ChAd8, ChAd9, ChAdIO, ChAdII, ChAdI6, ChAdI7, ChAdI9, ChAd20, ChAd22, ChAd24, ChAd26, ChAd30, ChAd31, ChAd37, ChAd38, ChAd44, ChAd63 and ChAd82 are described in detail in WO 2005/071093. Vectors based on naturally occurring PanAdI, PanAd2, PanAd3, ChAd55, ChAd73, ChAd83, ChAdI46, and ChAdI47 are described in detail in WO 2010/086189.

The term "non-replicating adenovirus" refers to an adenovirus that has been rendered to be incapable of replication because it has been engineered to comprise at least a functional deletion, or a complete removal of, a gene product that is essential for viral replication, such as one or more of the adenoviral genes selected from E1, E2, E3 and E4.

Preferably a vector used in the context of the present invention is a poxyviral vector, particularly MVA, or an adenoviral vector, more preferably non-human great ape, e.g. a chimpanzee or bonobo, derived adenoviral vector, in particular a non-replicating adenoviral vector based on ChAd3, ChAd4, ChAd5, ChAd6, ChAd7, ChAd8, ChAd9, ChAdIO, ChAdII, ChAdI6, ChAdI7, ChAdI9, ChAd20, ChAd22, ChAd24, ChAd26, ChAd30, ChAd31, ChAd37, ChAd38, ChAd44, ChAd55, ChAd63, ChAd 73, ChAd82, ChAd83, ChAdI46, ChAdI47, PanAdI, PanAd2, and PanAd3 or replication-competent vector based on hAd4 and hAd7. A description of MVA can be found in Mayr et al, 1978; "The smallpox vaccination strain MVA: marker, genetic structure, experience gained with the parenteral vaccination and behavior in organisms with a debilitated defence mechanism." Zentralbl Bakteriol B; 167:375 and in Mayr et al, 1975; "Abstammung, Eigenschaften and Verwendung des attenuierten Vaccinia-Stammes MV" Infection 3:6.

Additional suitable vectors are described in detail in PCT/EP2011/074307. The disclosure of this application is herewith incorporated by reference with respect to its disclosure relating to the expression systems disclosed therein.

Accordingly, in certain embodiments of the invention, the nucleic acid construct—when present in the first antigenic composition—is a viral vector that is derived from a virus selected from the list consisting of: poxvirus, adenovirus, adeno-associated virus (AAV), alphavirus, herpesvirus, retrovirus, lentivirus, cytomegalovirus, sendai virus, flavivirus, parvovirus. In particular such embodiments, such viral vector is one derived from a poxvirus selected from the list consisting of: smallpox virus (variola), vaccinia virus, cowpox virus, monkeypox virus. In yet further of such embodiments, the viral vector is one derived from a vaccinia virus selected from the list consisting of: New York Attenuated Vaccinia Virus (NYVAC), ALVAC, TROVAC and Modified Vaccinia Ankara (MVA).

MVA is a highly attenuated strain of vaccinia virus that underwent multiple, fully characterised deletions during more than 570 passages in chick embryo fibroblast cells. These included host range genes and genes encoding cytokine receptors. The virus is unable to replicate efficiently in human and most other mammalian cells but the replication defect occurs at a late stage of virion assembly such that viral and recombinant gene expression is unimpaired making MVA an efficient single round expression vector incapable of causing infection in mammals.

In one embodiment, MVA is derived from the virus seed batch 460 MG obtained from 571th passage of Vaccinia Virus on CEF cells. In another embodiment, MVA is derived from the virus seed batch MVA 476 MG/14/78. In a further embodiment, MVA is derived or produced prior to 31 Dec. 1978 and is free of prion contamination.

Further in respect of the first (eg prime) antigenic composition of the present invention, a second certain embodiment the first antigenic composition comprises at least nucleic acid construct that encodes at least one immunogenic peptide or immunogenic polypeptide, wherein such nucleic acid construct is a self-replicating RNA molecule.

In certain of such embodiments, the self-replicating RNA molecule is derived from or based on an RNA virus or a retrovirus. In certain embodiments, the self-replicating RNA molecule is derived from or based on an alphavirus. Self-replicating RNA molecules are well known in the art (eg WO2013/006842, the disclosure of which is herein incorporated by reference) and can be produced by using replication elements derived from, e.g., alphaviruses, and substituting the structural viral proteins with a nucleotide sequence encoding a protein of interest.

The self-replicating RNA, when used in the context of the present invention, may contain at least one or more genes selected from the group consisting of viral replicases, viral proteases, viral helicases and other nonstructural viral proteins, and also comprise 5'- and 3'-end cz's-active replication sequences, and if desired, a heterologous sequence that encodes a desired amino acid sequence (e.g., an antigen of interest). A subgenomic promoter that directs expression of the heterologous sequence can be included in the self-replicating RNA. If desired, the heterologous sequence (e.g., an antigen of interest) may be fused in frame to other coding regions in the self-replicating RNA and/or may be under the control of an internal ribosome entry site (IRES).

In certain embodiments, a self-replicating RNA molecule is not encapsulated in a virus-like particle. Self-replicating RNA molecules of the invention can be designed so that the self-replicating RNA molecule cannot induce production of infectious viral particles. This can be achieved, for example, by omitting one or more viral genes encoding structural proteins that are necessary for the production of viral particles in the self-replicating RNA. For example, when the self-replicating RNA molecule is based on an alpha virus, such as Sindbis virus (SIN), Semliki forest virus and Venezuelan equine encephalitis virus (VEE), one or more genes encoding viral structural proteins, such as capsid and/or envelope glycoproteins, can be omitted.

If desired, self-replicating RNA molecules useful in the context of the present invention can also be designed to induce production of infectious viral particles that are attenuated or virulent, or to produce viral particles that are capable of a single round of subsequent infection.

One suitable system for achieving self-replication is to use an alphavirus-based RNA replicon. Alphaviruses comprise a set of genetically, structurally, and serologically related arthropod-borne viruses of the Togaviridae family. Twenty-six known viruses and virus subtypes have been classified within the alphavirus genus, including, Sindbis virus, Semliki Forest virus, Ross River virus, and Venezuelan equine encephalitis virus. As such, the self-replicating RNA of the invention may incorporate a RNA replicase derived from Semliki Forest virus (SFV), Sindbis virus (SIN), Venezuelan equine encephalitis virus (VEE), Ross river virus (RRV), or other viruses belonging to the alphavirus family.

An alphavirus-based "replicon" expression vectors can be useful in the context of the present invention. Replicon vectors may be utilized in several formats, including DNA, RNA, and recombinant replicon particles. Such replicon vectors have been derived from alphaviruses that include, for example, Sindbis virus (Xiong et al. (1989) Science 243: 1 188-1191; Dubensky et al, (1996) J. Virol. 70:508-519; Hariharan et al. (1998) J. Virol. 72:950-958; Polo et al. (1999) PNAS 96:4598-4603), Semliki Forest virus (Liljestrom (1991) Bio/Technology 9: 1356-1361; Berglund et al. (1998) Nat. Biotech. 16:562-565), and Venezuelan equine encephalitis virus (Pushko et al. (1997) Virology 239:389-401).

Alphaviruses-derived replicons are generally quite similar in overall characteristics (e.g., structure, replication), individual alphaviruses may exhibit some particular property (e.g., receptor binding, interferon sensitivity, and disease profile) that is unique. Therefore, chimeric alphavirus replicons made from divergent virus families may also be useful.

Alphavirus-based replicons are (+)-stranded replicons that can be translated after delivery to a cell to give rise of a replicase (or replicase-transcriptase). The replicase is translated as a polyprotein which auto-cleaves to provide a replication complex which creates genomic (−)-strand copies of the +-strand delivered RNA. These (−)-strand transcripts can themselves be transcribed to give further copies of the (+)-stranded parent RNA and also to give a subgenomic transcript which encodes the desired gene product. Translation of the subgenomic transcript thus leads to in situ expression of the desired gene product by the infected cell. Suitable alphavirus replicons can use a replicase from a Sindbis virus, a Semliki Forest virus, an Eastern equine encephalitis virus, a Venezuelan equine encephalitis virus, etc.

A preferred self-replicating RNA molecule thus encodes (i) a RNA-dependent RNA polymerase which can transcribe RNA from the self-replicating RNA molecule and (ii) a (immunogenic) peptide or polypeptide (antigen). The polymerase can be an alphavirus replicase e.g. comprising alphavirus protein nsP4.

A self-replicating RNA molecule useful in the context of the present invention may have two open reading frames. The first (5') open reading frame encodes a replicase; the second (3') open reading frame encodes a (immunogenic) peptide or polypeptide (antigen). In some embodiments the RNA may have additional (downstream) open reading frames, e.g. that encode another such desired gene product. A self-replicating RNA molecule can have a 5' sequence which is compatible with the encoded replicase.

In other embodiments, a self-replicating RNA molecule is derived from or based on a virus other than an alphavirus, preferably, a positive-stranded RNA virus, and more preferably a picornavirus, flavivirus, rubivirus, pestivirus, hepacivirus, calicivirus, or coronavirus. Suitable wild-type alphavirus sequences are well-known and are available from sequence depositories, such as the American Type Culture Collection, Rockville, Md.

Representative examples of suitable alphaviruses include Aura (ATCC VR-368), Bebaru virus (ATCC VR-600, ATCC VR-1240), Cabassou (ATCC VR-922), Chikungunya virus (ATCC VR-64, ATCC VR-1241), Eastern equine encephalomyelitis virus (ATCC VR-65, ATCC VR-1242), Fort Morgan (ATCC VR-924), Getah virus (ATCC VR-369, ATCC VR-1243), Kyzylagach (ATCC VR-927), Mayaro (ATCC VR-66), Mayaro virus (ATCC VR-1277), Middleburg (ATCC VR-370), Mucambo virus (ATCC VR-580, ATCC VR-1244), Ndumu (ATCC VR-371), Pixuna virus (ATCC VR-372, ATCC VR-1245), Ross River virus (ATCC VR-373, ATCC VR-1246), Semliki Forest (ATCC VR-67, ATCC VR-1247), Sindbis virus (ATCC VR-68, ATCC VR-1248), Tonate (ATCC VR-925), Triniti (ATCC VR-469), Una (ATCC VR-374), Venezuelan equine encephalomyelitis (ATCC VR-69, ATCC VR-923, ATCC VR-1250 ATCC VR-1249, ATCC VR-532), Western equine encephalomyelitis (ATCC VR-70, ATCC VR-1251, ATCC VR-622, ATCC VR-1252), Whataroa (ATCC VR-926), and Y-62-33 (ATCC VR-375).

A self-replicating RNA molecule useful in the context of the present invention may be larger than other types of RNA (e.g. mRNA). Typically, the self-replicating RNA molecules useful in the context of the present invention contain at least about 4 kb. For example, the self-replicating RNA can contain at least about 5 kb, at least about 6 kb, at least about 7 kb, at least about 8 kb, at least about 9 kb, at least about 10 kb, at least about 11 kb, at least about 12 kb or more than 12 kb. In certain examples, the self-replicating RNA is about 4 kb to about 12 kb, about 5 kb to about 12 kb, about 6 kb to about 12 kb, about 7 kb to about 12 kb, about 8 kb to about 12 kb, about 9 kb to about 12 kb, about 10 kb to about 12 kb, about 11 kb to about 12 kb, about 5 kb to about 1 kb, about 5 kb to about 10 kb, about 5 kb to about 9 kb, about 5 kb to about 8 kb, about 5 kb to about 7 kb, about 5 kb to about 6 kb, about 6 kb to about 12 kb, about 6 kb to about 11 kb, about 6 kb to about 10 kb, about 6 kb to about 9 kb, about 6 kb to about 8 kb, about 6 kb to about 7 kb, about 7 kb to about 11 kb, about 7 kb to about 10 kb, about 7 kb to about 9 kb, about 7 kb to about 8 kb, about 8 kb to about 11 kb, about 8 kb to about 10 kb, about 8 kb to about 9 kb, about 9 kb to about 11 kb, about 9 kb to about 10 kb, or about 10 kb to about 11 kb.

The self-replicating RNA molecules useful in the context of the present invention may comprise one or more chemical or sequence modifications, such as those described elsewhere herein in the context of mRNA. In particular, such self-replicating RNA molecules may comprise one or more modified nucleotides (e.g., pseudouridine, N6-methyladenosine, 5-methylcytidine, 5-methyluridine).

In one alternative embodiment, the nucleic acid construct comprised in the first antigenic composition is not a viral vector (such as not being one or more of those described—generically or specifically—above), for example the nucleic acid construct is not an MVA vector, in particular it is not MVA derived from the virus seed batch 460 MG obtained from 571th passage of Vaccinia Virus on CEF cells, and/or is not MVA derived from the virus seed batch MVA 476 MG/14/78, and/or is not MVA derived or produced prior to 31 Dec. 1978 and is free of prion contamination.

In an alternative or additional alternative embodiment, the nucleic acid construct comprised in the first antigenic composition is not a self-replicating RNA molecule (such as not being one or more of those described—generically or specially—above), In the context of the present invention at least one epitope of the immunogenic peptide or polypeptide comprised in—or encoded by the nucleic acid construct comprised in—the first (prime) antigenic composition is immunologically equivalent to the at least one epitope of the immunogenic peptide or polypeptide encoded by the mRNA construct of the second (boost) antigenic composition. In certain embodiments of the various aspects of the present invention, the amino acid sequence of the epitope encoded in the mRNA construct—comprised in the second (boost) antigenic composition—is similar to the amino acid sequence of the epitope encoded in the nucleic acid construct—comprised in the first (prime) antigenic composition; or is similar to the amino acid sequence (or sequence of amino-acid-like moieties) of the epitope of the immunogenic peptide or polypeptide comprised in the first (prime) antigenic composition.

In this context, one amino acid sequence (or epitope or peptide/polypeptide/protein) is "similar" to another amino acid sequence (or epitope or peptide/polypeptide/protein) if one is a variant or the other. For example, in certain embodiments an amino acid sequence (or epitope or peptide/polypeptide/protein) is similar to another amino acid sequence (or epitope or peptide/polypeptide/protein) if at least about 70%, 75%, 80%, 85%, 90%, 95%, 98% or 99% amino acid identity over a stretch of about 10, 20, 30, 50, 75 or 100 amino acids of such sequence, epitope, peptide, polypeptide or protein. In the case of amino-acid-like moieties that are substituted to mimic the structure or others features of a given amino acid, the person of ordinary skill will recognise that such amino-acid-like moiety (or moieties) will be—in this context—be recognised as having "identify" to the amino acid(s) that is (or are) being mimicked.

Accordingly, in such embodiments, the amino acid sequence of at least the epitope of the immunogenic peptide or polypeptide comprised in the first antigenic composition, or encoded by the nucleic acid construct comprised in the first antigenic composition, is similar to the amino acid sequence of at least the epitope of the immunogenic peptide or polypeptide encoded by the mRNA construct comprised in the second antigenic composition. In particular of such embodiments, a portion of the amino acid sequence of the immunogenic peptide or polypeptide comprised in the first antigenic composition, or encoded by the nucleic acid construct comprised in the first antigenic composition, is similar to a portion the amino acid sequence of the immunogenic peptide or polypeptide encoded by the mRNA construct comprised in the second antigenic composition. In this context, the term "portion" may reflect about 20%, 30%, 40%, 50%, 60%, 70%, 75%, 80%, 85%, 90%, 85%, 98% or even 100% of the respective immunogenic peptide or polypeptide, or it may reflect a contiguous length of amino acids that has a length of between about: 20 to 50, 50 to 100, 100 to 150, 150 to 200, 250 to 250 to 300, 300, 350 to 400, 400 to 450 or over 450 (such as up to 1000) amino acids.

In all aspects of the present invention, an epitope, antigen, immunogenic peptide and/or immunogenic polypeptide useful in the present invention may be from (such as isolated from, derived from, in respect of or has a sequence that is homologous to or a variant of) an amino acid sequence from a pathogen, for example an infectious agent that causes disease or illness to the subject. In particular such embodiments, the epitope, antigen, immunogenic peptide and/or immunogenic polypeptide useful in the present invention may be from a pathogen of humans (eg, an infectious agent that is pathogenic to humans). In alternative embodiments, the epitope, antigen, immunogenic peptide and/or immunogenic polypeptide useful in the present invention may be from a pathogen of a non-human animal, such as a domesticated mammal, domesticated bird or farmed fish. In other embodiments, the epitope, antigen, immunogenic peptide and/or immunogenic polypeptide useful in the present invention may be from (such as isolated from, derived from, in respect of or has a sequence that is homologous to or a variant of) an amino acid sequence of a pathogenic antigen.

Accordingly, in certain embodiments the amino acid sequence of at least the epitope may be from a pathogen, or a homolog, a fragment or a variant thereof. In particular of such embodiments, the immunogenic peptide or polypeptide comprised in the first antigenic composition, or encoded by the nucleic acid construct comprised in the first antigenic composition, and the immunogenic peptide or polypeptide encoded by the mRNA construct comprised in the second antigenic composition may be from a pathogen or a pathogenic antigens, or a homolog, a fragment or a variant thereof.

Particular types of pathogens from which, in all embodiments, the pathogen from which the amino acid of the epitope, immunogenic peptide and/or immunogenic polypeptide may be from includes a pathogen selected from the list consisting of: a virus, a bacterium, a fungus and a protozoan, in particular any of such pathogens that is pathogenic to a human subject.

In all of such embodiments, an epitope, antigen, immunogenic peptide and/or immunogenic polypeptide from a pathogen may alternatively be described as a "pathogenic antigen".

Accordingly, in the various aspects of the present invention the epitope, immunogenic peptide and/or immunogenic polypeptide from a pathogen may be, may comprise or may be comprised in a pathogenic antigen or a fragment, variant or a derivative thereof. Such pathogenic antigens are derived from pathogenic organisms, in particular bacterial, viral or protozoological (multicellular) pathogenic organisms, which evoke an immunological reaction by subject, in particular a mammalian subject, more particularly a human. More specifically, pathogenic antigens are preferably surface antigens, e.g. proteins (or fragments of proteins, e.g. the exterior portion of a surface antigen) located at the surface of the virus or the bacterial or protozoological organism.

Pathogenic antigens are peptide or protein antigens preferably derived from a pathogen associated with infectious disease which are preferably selected from antigens derived from the pathogens *Acinetobacter baumannii, Anaplasma* genus, *Anaplasma phagocytophilum, Ancylostoma braziliense, Ancylostoma duodenale, Arcanobacterium haemolyticum, Ascaris lumbricoides, Aspergillus* genus, Astroviridae, *Babesia* genus, *Bacillus anthracis, Bacillus cereus, Bartonella henselae,* BK virus, *Blastocystis hominis, Blastomyces dermatitidis, Bordetella pertussis, Borrelia burgdorferi, Borrelia* genus, *Borrelia* spp, *Brucella* genus, *Brugia malayi,* Bunyaviridae family, *Burkholderia cepacia* and other *Burkholderia* species, *Burkholderia mallei, Burkholderia pseudomallei,* Caliciviridae family, *Campylobacter* genus, *Candida albicans, Candida* spp, *Chlamydia trachomatis, Chlamydophila pneumoniae, Chlamydophila psittaci,* CJD prion, *Clonorchis sinensis, Clostridium botulinum, Clostridium difficile, Clostridium perfringens, Clostridium perfringens, Clostridium* spp, *Clostridium tetani, Coccidioides* spp, coronaviruses, *Corynebacterium diphtheriae, Coxiella burnetii,* Crimean-Congo hemorrhagic fever virus, *Cryptococcus neoformans, Cryptosporidium* genus, Cytomegalovirus (CMV), Dengue viruses (DEN-1, DEN-2, DEN-3 and DEN-4), *Dientamoeba fragilis,* Ebolavirus (EBOV), *Echinococcus* genus, *Ehrlichia chaffeensis, Ehrlichia ewingii, Ehrlichia* genus, *Entamoeba histolytica, Enterococcus* genus, Enterovirus genus, Enteroviruses, mainly Coxsackie A virus and Enterovirus 71 (EV71), *Epidermophyton* spp, Epstein-Barr Virus (EBV), *Escherichia coli* 0157:H7, OI 1 1 and O104:H4, *Fasciola hepatica* and *Fasciola gigantica,* FFI prion, Filarioidea superfamily, Flaviviruses, *Francisella tularensis, Fusobacterium* genus, *Geotrichum candidum, Giardia intestinalis, Gnathostoma* spp, GSS prion, Guanarito virus, *Haemophilus ducreyi, Haemophilus influenzae, Helicobacter pylori,* Henipavirus (Hendra virus Nipah virus), Hepatitis A Virus, Hepatitis B Virus (HBV), Hepatitis C Virus (HCV), Hepatitis D Virus, Hepatitis E Virus, Herpes simplex virus 1 and 2 (HSV-1 and HSV-2), *Histoplasma capsulatum,* HIV (Human immunodeficiency virus), *Hortaea werneckii,* Human bocavirus (HBoV), Human herpesvirus 6 (HHV-6) and Human herpesvirus 7 (HHV-7), Human metapneumovirus (hMPV), Human papillomavirus (HPV), Human parainfluenza viruses (HPIV), Japanese encephalitis virus, JC virus, Junin virus, *Kingella kingae, Klebsiella granulomatis,* Kuru prion, Lassa virus, *Legionella pneumophila, Leishmania* genus, *Leptospira* genus, *Listeria monocytogenes,* Lymphocytic choriomeningitis virus (LCMV), Machupo virus, *Malassezia* spp, Marburg virus, Measles virus, *Metagonimus yokagawai,* Microsporidia phylum, Molluscum contagiosum virus (MCV), Mumps virus, *Mycobacterium leprae* and *Mycobacterium lepromatosis, Mycobacterium tuberculosis, Mycobacterium ulcerans, Mycoplasma pneumoniae, Naegleria fowleri, Necator americanus, Neisseria gonorrhoeae, Neisseria meningitidis, Nocardia asteroides, Nocardia* spp, *Onchocerca volvulus, Orientia tsutsugamushi,* Orthomyxoviridae family (Influenza), *Paracoccidioides brasiliensis, Paragonimus* spp, *Paragonimus westermani,* Parvovirus B19, *Pasteurella* genus, *Plasmodium* genus, *Pneumocystis jirovecii,* Poliovirus, Rabies virus, Respiratory syncytial virus (RSV), Rhinovirus, rhinoviruses, *Rickettsia akari, Rickettsia* genus, *Rickettsia prowazekii, Rickettsia rickettsii, Rickettsia typhi,* Rift Valley fever virus, Rotavirus, Rubella virus, Sabia virus, *Salmonella* genus, *Sarcoptes scabiei,* SARS coronavirus, *Schistosoma* genus, *Shigella* genus, Sin Nombre virus, Hantavirus, *Sporothrix schenckii, Staphylococcus* genus, *Staphylococcus* genus, *Streptococcus agalactiae, Streptococcus pneumoniae, Streptococcus pyogenes, Strongyloides stercoralis, Taenia* genus, *Taenia solium,* Tick-borne encephalitis virus (TBEV), *Toxocara canis* or *Toxocara cati, Toxoplasma gondii, Treponema pallidum, Trichinella spiralis, Trichomonas vaginalis, Trichophyton* spp, *Trichuris trichiura, Trypanosoma brucei, Trypanosoma cruzi, Ureaplasma urealyticum,* Varicella zoster virus (VZV), Varicella zoster virus (VZV), Variola major or Variola minor, vCJD prion, Venezuelan equine encephalitis virus, *Vibrio cholerae,* West Nile virus, Western equine encephalitis virus, *Wuchereria bancrofti,* Yellow fever virus, *Yersinia enterocolitica, Yersinia pestis,* and *Yersinia pseudotuberculosis.*

In this context particularly preferred are antigens from the pathogens selected from Influenza virus, respiratory syncytial virus (RSV), Herpes simplex virus (HSV), human Papilloma virus (HPV), Human immunodeficiency virus (HIV), Plasmodium, Staphylococcus aureus, Dengue virus, *Chlamydia trachomatis,* Cytomegalovirus (CMV), Hepatitis B virus (HBV), *Mycobacterium tuberculosis,* Rabies virus, and Yellow Fever Virus.

According to an alternative embodiment, the first antigenic composition and/or the second antigenic composition as described herein do not comprise an antigen (or a fragment or variant thereof) derived from RSV, preferably from a respiratory pathogen. Alternatively, the first antigenic composition and/or the second antigenic composition as described herein do preferably not comprise an antigen (or a fragment or variant thereof) derived from HIV. In this context, an antigen may be a peptide or protein or a nucleic acid encoding a peptide or protein derived from RSV or HIV, respectively.

Furthermore, the pathogenic antigen (antigen derived from a pathogen associated with infectious disease) may be preferably selected from the following antigens: Outer membrane protein A OmpA, biofilm associated protein Bap, transport protein MucK (*Acinetobacter baumannii, Acinetobacter* infections)); variable surface glycoprotein VSG, microtubule-associated protein MAPP1 5, trans-sialidase TSA (*Trypanosoma brucei*, African sleeping sickness (African trypanosomiasis)); HIV p24 antigen, HIV envelope proteins (Gp120, Gp41, Gp160), polyprotein GAG, negative factor protein Nef, transactivator of transcription Tat (HIV (Human immunodeficiency virus), AIDS (Acquired immunodeficiency syndrome)); galactose-inhibitable adherence protein GIAP, 29 kDa antigen Eh29, Gal/GalNAc lectin, protein CRT, 125 kDa immunodominant antigen, protein M1 7, adhesin ADH1 12, protein STIRP (*Entamoeba histolytica*, Amoebiasis); Major surface proteins 1-5 (MSP1 a, MSP1 b, MSP2, MSP3, MSP4, MSP5), type IV secreotion system proteins (VirB2, VirB7, VirB1 1 VirD4) (*Anaplasma* genus, Anaplasmosis); protective Antigen PA, edema factor EF, lethal facotor LF, the S-layer homology proteins SLH (*Bacillus anthracis*, Anthrax); acranolysin, phospholipase D, collagen-binding protein CbpA (*Arcanobacterium haemolyticum, Arcanobacterium haemolyticum* infection); nucleocapsid protein NP, glycoprotein precursor GPC, glycoprotein GP1, glycoprotein GP2 Gunin virus, Argentine hemorrhagic fever); chitin-protein layer proteins, 14 kDa surface antigen A14, major sperm protein MSP, MSP polymerization-organizing protein MPOP, MSP fiber protein 2 MFP2, MSP polymerization-activating kinase MPAK, ABA-1-like protein ALB, protein ABA-1, cuticulin CUT-1 (*Ascaris lumbricoides*, Ascariasis); 41 kDa allergen Asp v1 3, allergen Asp f3, major conidial surface protein rodlet A, protease PepI p, GPI-anchored protein Gel1 p, GPI-anchored protein Crfl p (*Aspergillus* genus, Aspergillosis); family VP26 protein, VP29 protein (Astroviridae, Astrovirus infection); Rhoptry-associated protein 1 RAP-1, merozoite surface antigens MSA-1, MSA-2 (a1, a2, b, c), 12D3, 1 1 C5, 21 B4, P29, variant erythrocyte surface antigen VESA1, Apical Membrane Antigen 1 AMA-1 (*Babesia* genus, Babesiosis); hemolysin, enterotoxin C, PX01-51, glycolate oxidase, ABC-transporter, penicillin-bingdn protein, zinc transporter family protein, pseudouridine synthase Rsu, plasmid replication protein RepX, oligoendopeptidase F, prophage membrane protein, protein HemK, flagellar antigen H, 28.5-kDa cell surface antigen (*Bacillus cereus, Bacillus cereus* infection); large T antigen LT, small T antigen, capsid protein VP1, capsid protein VP2 (BK virus, BK virus infection); 29 kDa-protein, caspase-3-like antigens, glycoproteins (*Blastocystis hominis, Blastocystis hominis* infection); yeast surface adhesin WI-1 (*Blastomyces dermatitidis*, Blastomycosis); nucleoprotein N, polymerase L, matrix protein Z, glycoprotein GP (Machupo virus, Bolivian hemorrhagic fever); outer surface protein A OspA, outer surface protein OspB, outer surface protein OspC, decorin binding protein A DbpA, decorin binding protein B DbpB, flagellar filament 41 kDa core protein Fla, basic membrane protein A precursor BmpA (Immunodominant antigen P39), outer surface 22 kDa lipoprotein precursor (antigen IPLA7), variable surface lipoprotein vlsE (*Borrelia* genus, *Borrelia* infection); Botulinum neurotoxins BoNT/AI, BoNT/A2, BoNT/A3, BoNT/B, BoNT/C, BoNT/D, BoNT/E, BoNT/F, BoNT/G, recombinant botulinum toxin F He domain FHc (*Clostridium botulinum*, Botulism (and Infant botulism)); nucleocapsid, glycoprotein precursor (Sabia virus, Brazilian hemorrhagic fever); copper/Zinc superoxide dismutase SodC, bacterioferritin Bfr, 50S ribosomal protein pIL, OmpA-like transmembrane domain-containing protein Omp31, immunogenic 39-kDa protein M5 P39, zinc ABC transporter periplasmic zinc-binding protein znuA, periplasmic immunogenic protein Bp26, 30S ribosomal protein SI 2 RpsL, glyceraldehyde-3-phosphate dehydrogenase Gap, 25 kDa outer-membrane immunogenic protein precursor Omp25, invasion protein B IaIB, trigger factor Tig, molecular chaperone DnaK, putative peptidyl-prolyl cis-trans isomerase SurA, lipoprotein Omp19, outer membrane protein MotY Omp1 6, conserved outer membrane protein D15, malate dehydrogenase Mdh, component of the Type-IV secretion system (T4SS) VirJ, lipoprotein of unknown function BAB1_0187 (*Brucella* genus, Brucellosis); members of the ABC transporter family (LoIC, OppA, and PotF), putative lipoprotein releasing system transmembrane protein LoIC E, flagellin FliC, *Burkholderia* intracellular motility A BimA, bacterial Elongation factor-Tu EF-Tu, 1 7 kDa OmpA-like protein, boaA coding protein, boaB coding protein (*Burkholderia cepacia* and other *Burkholderia* species, *Burkholderia* infection); mycolyl-transferase Ag85A, heat-shock protein Hsp65, protein TB10.4, 19 kDa antigen, protein PstS3, heat-shock protein Hsp70 (*Mycobacterium ulcerans*, Buruli ulcer); norovirus major and minor viral capsid proteins VP1 and VP2, genome polyprotein, Sapoviurus capsid protein VP1, protein Vp3, geome polyprotein (Caliciviridae family, Calicivirus infection (Norovirus and Sapovirus)); major outer membrane protein PorA, flagellin FlaA, surface antigen CjaA, fibronectin binding protein CadF, aspartate/glutamate-binding ABC transporter protein PebI A, protein FspA1, protein FspA2 (*Campylobacter* genus, Campylobacteriosis); glycolytic enzyme enolase, secreted aspartyl proteinases SAP1-10, glycophosphatidylinositol (GPO-linked cell wall protein, protein Hyr1, complement receptor 3-related protein CR3-RP, adhesin Als3p, heat shock protein 90 kDa hsp90, cell surface hydrophobicity protein CSH (usually *Candida albicans* and other *Candida* species, Candidiasis); 1 7-kDa antigen, protein P26, trimeric autotransporter adhesins TAAs, *Bartonella* adhesin A BadA, variably expressed outer-membrane proteins Vomps, protein Pap3, protein HbpA, envelope-associated protease HtrA, protein OMP89, protein GroEL, protein LaIB, protein OMP43, dihydrolipoamide succinyltransferase SucB (*Bartonella henselae*, Cat-scratch disease); amastigote surface protein-2, amastigote-specific surface protein SSP4, cruzipain, trans-sialidase TS, trypomastigote surface glycoprotein TSA-1, complement regulatory protein CRP-10, protein G4, protein G2, paraxonemal rod protein PAR2, paraflagellar rod component Pari, mucin-Associated Surface Proteins MPSP (*Trypanosoma cruzi*, Chagas Disease (American trypanosomiasis)); envelope glycoproteins (gB, gC, gE, gH, gI, gK, gI_) (Varicella zoster virus (VZV), Chickenpox); major outer membrane protein MOMP, probable outer membrane protein PMPC, outer membrane complex protein B OmcB, heat shock proteins Hsp60 HSP10, protein IncA, proteins from the type Ill secretion system, ribonucleotide reductase small chain protein NrdB, plasmid protein Pgp3, chlamydial outer protein N CopN, antigen CT521, antigen CT425, antigen CT043, antigen TC0052, antigen TC0189, antigen TC0582, antigen TC0660, antigen TC0726, antigen TC0816, antigen TC0828 (*Chlamydia trachomatis, Chlamydia*); low calcium response protein E LCrE, chlamydial outer protein N CopN, serine/threonine-protein kinase PknD, acyl-carrier-protein S-malonyltransferase FabD, single-stranded DNA-binding protein Ssb, major outer membrane protein MOMP, outer membrane protein 2 Omp2, polymorphic membrane protein family (Pmp1, Pmp2, Pmp3, Pmp4, Pmp5, Pmp6, Pmp7, Pmp8, Pmp9, Pmp10, Pmp11, Pmp12, Pmp13, Pmp14, Pmp15, Pmp16, Pmp17, Pmp18, Pmp19, Pmp20, Pmp21) (*Chlamydophila pneumoniae, Chlamydophila pneumoniae* infection); cholera toxin B CTB, toxin coregulated pilin A TcpA, toxin coregulated pilin TcpF, toxin coregulated pilus biosynthesis ptrotein F TcpF, cholera enterotoxin subunit A, cholera enterotoxin subunit B, Heat-stable enterotoxin ST, mannose-sensitive hemagglutinin MSHA, outer membrane protein U Porin ompU, Poring B protein, polymorphic membrane protein-D (*Vibrio cholerae*, Cholera); propionyl-CoA carboxylase PCC, 14-3-3 protein, prohibitin, cysteine proteases, glutathione transferases, gelsolin, cathepsin L proteinase CatL, Tegumental Protein 20.8 kDa TP20.8, tegumental protein 31 0.8 kDa TP31 0.8, lysophosphatidic acid phosphatase LPAP, (*Clonorchis sinensis*, Clonorchiasis); surface layer proteins SLPs, glutamate dehydrogenase antigen GDH, toxin A, toxin B, cysteine protease Cwp84, cysteine protease Cwp13, cysteine protease Cwp19, Cell Wall Protein CwpV, flagellar protein FliC, flagellar protein FliD (*Clostridium difficile, Clostridium difficile* infection); rhinoviruses: capsid proteins VP1, VP2, VP3, VP4; coronaviruses: spike proteins S, envelope proteins E, membrane proteins M, nucleocapsid proteins N (usually rhinoviruses and coronaviruses, Common cold (Acute viral rhinopharyngitis; Acute coryza)); prion protein Prp (CJD prion, Creutzfeldt-Jakob disease (CJD)); envelope protein Gc, envelope protein Gn, nucleocapsid proteins (Crimean-Congo hemorrhagic fever virus, Crimean-Congo hemorrhagic fever (CCHF)); virulence-associated DEAD-box RNA helicase VAD1, galactoxylomannan-protein GalXM, glucuronoxylomannan GXM, mannoprotein MP (*Cryptococcus neoformans*, Cryptococcosis); acidic ribosomal protein P2 CpP2, mucin antigens Mud Muc2, Muc3 Muc4, Muc5, Muc6, Muc7, surface adherence protein CP20, surface adherence protein CP23, surface protein CP12, surface protein CP21, surface protein CP40, surface protein CP60, surface protein CP15, surface-associated glycopeptides gp40, surface-associated glycopeptides gp1 5, oocyst wall protein AB, profilin PRF, apyrase (*Cryptosporidium* genus, Cryptosporidiosis); fatty acid and retinol binding protein-1 FAR-1, tissue inhibitor of metalloproteinase TIMP, (TMP), cysteine proteinase ACEY-1, cysteine proteinase ACCP-1, surface antigen Ac-1 6, secreted protein 2 ASP-2, metalloprotease 1 MTP-1, aspartyi protease inhibitor API-1, surface-associated antigen SAA-1, adult-specific secreted factor Xa serine protease inhibitor anticoagulant AP, cathepsin D-like aspartic protease ARR-1 (usually *Ancylostoma braziliense*; multiple other parasites, Cutaneous larva migrans (CLM)); cathepsin L-like proteases, 53/25-kDa antigen, 8 kDa family members, cysticercus protein with a marginal trypsin-like activity TsAg5, oncosphere protein TSOL18, oncosphere protein TSOL45-1 A, lactate dehydrogenase A LDHA, lactate dehydrogenase B LDHB (*Taenia solium*, Cysticercosis); pp65 antigen, membrane protein pp15, capsid-proximal tegument protein pp150, protein M45, DNA polymerase UL54, helicase UL105, glycoprotein gM, glycoprotein gN, glcoprotein H, glycoprotein B gB, protein UL83, protein UL94, protein UL99 (Cytomegalovirus (CMV), Cytomegalovirus infection); capsid protein C, premembrane protein prM, membrane protein M, envelope protein E (domain I, domain II, domain II), protein NS1, protein NS2A, protein NS2B, protein NS3, protein NS4A, protein 2K, protein NS4B, protein NS5 (Dengue viruses (DEN-1, DEN-2, DEN-3 and DEN-4)-Flaviviruses, Dengue fever); 39 kDa protein (*Dientamoeba fragilis*, Dientamoebiasis); diphtheria toxin precursor Tox, diphteria toxin DT, pilin-specific sortase SrtA, shaft pilin protein SpaA, tip pilin protein SpaC, minor pilin protein SpaB, surface-associated protein DIP1281 (*Corynebacterium diphtheriae*, Diphtheria); glycoprotein GP, nucleoprotein NP, minor matrix protein VP24, major matrix protein VP40, transcription activator VP30, polymerase cofactor VP35, RNA polymerase L (Ebolavirus (EBOV), Ebola hemorrhagic fever); prion protein (vCJD prion, Variant Creutzfeldt-Jakob disease (vCJD, nvCJD)); UvrABC system protein B, protein FIpI, protein FIp2, protein FIp3, protein TadA, hemoglobin receptor HgbA, outer membrane protein TdhA, protein CpsRA, regulator CpxR, protein SapA, 18 kDa antigen, outer membrane protein NcaA, protein LspA, protein LspA1, protein LspA2, protein LspB, outer membrane component DsrA, lectin DItA, lipoprotein Hip, major outer membrane protein OMP, outer membrane protein OmpA2 (*Haemophilus ducreyi*, Chancroid); aspartyi protease 1 Pep1, phospholipase B PLB, alpha-mannosidase 1 AMN1, glucanosyltransferase GEL1, urease URE, peroxisomal matrix protein PmpI, proline-rich antigen Pra, humal T-cell reactive protein TcrP (*Coccidioides immitis* and *Coccidioides posadasii*, Coccidioidomycosis); allergen Tri r 2, heat shock protein 60 Hsp60, fungal actin Act, antigen Tri r2, antigen Tri r4, antigen Tri t1, protein IV, glycerol-3-phosphate dehydrogenase GpdI, osmosensor HwShol A, osmosensor HwShol B, histidine kinase HwHhk7B, allergen *Mala* s 1, allergen *Mala* s 1 1, thioredoxin Trx *Mala* s 13, allergen *Mala* f, allergen *Mala* s (usually *Trichophyton* spp, *Epidermophyton* spp., *Malassezia* spp., *Hortaea werneckii*, Dermatophytosis); protein EG95, protein EG10, protein EG18, protein EgA31, protein EM18, antigen EPC1, antigen B, antigen 5, protein P29, protein 14-3-3, 8-kDa protein, myophilin, heat shock protein 20 HSP20, glycoprotein GP-89, fatty acid binding protein FAPB (*Echinococcus* genus, Echinococcosis); major surface protein 2 MSP2, major surface protein 4 MSP4, MSP variant SGV1, MSP variant SGV2, outer membrane protein OMP, outer membrane protein 19 OMP-19, major antigenic protein MAPI, major antigenic protein MAP1-2, major antigenic protein MAPI B, major antigenic protein MAP1-3, Erum2510 coding protein, protein GroEL, protein GroES, 30-kDA major outer membrane proteins, GE 100-kDa protein, GE 130-kDa protein, GE 1 60-kDa protein (*Ehrlichia* genus, Ehrlichiosis); secreted antigen SagA, sagA-like proteins SalA and SalB, collagen adhesin Scm, surface proteins Fms1 (EbpA(fm), Fms5 (EbpB(fm), Fms9 (EpbC(fm) and Fms10, protein EbpC(fm), 96 kDa immunoprotective glycoprotein G1 (*Enterococcus* genus, *Enterococcus* infection); genome polyprotein, polymerase 3D, viral capsid protein VP1, viral capsid protein VP2, viral capsid protein VP3, viral capsid protein VP4, protease 2A, protease 3C (Enterovirus genus, Enterovirus infection); outer membrane proteins OM, 60 kDa outer membrane protein, cell surface antigen OmpA, cell surface antigen OmpB (sca5), 134 kDa outer membrane protein, 31 kDa outer membrane protein, 29.5 kDa outer membrane protein, cell surface protein SCA4, cell surface protein AdrI (RP827), cell surface protein Adr2 (RP828), cell surface protein SCA1, Invasion protein invA, cell division protein fts, secretion proteins sec Ofamily, virulence proteins virB, tlyA, tlyC, parvulin-like protein Pip, preprotein translocase SecA, 120-kDa surface protein antigen SPA, 138 kD complex antigen, major 100-kD protein (protein I), intracytoplasmic protein D, protective surface protein antigen SPA (*Rickettsia prowazekii*, Epidemic typhus); Epstein-Barr nuclear antigens (EBNA-1, EBNA-2, EBNA-3A, EBNA-3B, EBNA-3C, EBNA-leader protein (EBNA-LP)), latent membrane proteins (LMP-1, LMP-2A, LMP-2B), early antigen EBV-EA, membrane antigen EBV-MA, viral capsid antigen EBV-VCA, alkaline nuclease EBV-AN, glycoprotein H, glycoprotein gp350, glycoprotein gpH O, glycoprotein gp42, glycoprotein gHgL, glycoprotein gB (Epstein-Barr Virus (EBV), Epstein-Barr Virus Infectious Mononucleosis); capsid protein VP2, capsid protein VP1, major protein NS1 (Parvovirus B19, Erythema infectiosum (Fifth disease)); pp65 antigen, glycoprotein 105, major capsid protein, envelope glycoprotein H, protein U51 (Human herpesvirus 6 (HHV-6) and Human herpesvirus 7 (HHV-7), Exanthem subitum); thioredoxin-glutathione reductase TGR, cathepsins L1 and L2, Kunitz-type protein KTM, leucine aminopeptidase LAP, cysteine proteinase Fas2, saposin-like protein-2 SAP-2, thioredoxin peroxidases TPx, Prx-1, Prx-2, cathepsin I cysteine proteinase CL3, protease cathepsin L CL1, phosphoglycerate kinase PGK, 27-kDa secretory protein, 60 kDa protein HSP35alpha, glutathione transferase GST, 28.5 kDa tegumental antigen 28.5 kDa TA, cathepsin B3 protease CatB3, Type I cystatin stefin-1, cathepsin L5, cathepsin LI g and cathepsin B, fatty acid binding protein FABP, leucine aminopeptidases LAP (*Fasciola hepatica* and *Fasciola gigantica*, Fasciolosis); prion protein (FFI prion, Fatal familial insomnia (FFI)); venom allergen homolog-like protein VAL-1, abundant larval transcript ALT-1, abundant larval transcript ALT-2, thioredoxin peroxidase TPX, vespid allergen homologue VAH, thiordoxin peroxidase 2 TPX-2, antigenic protein SXP (peptides N, N1, N2, and N3), activation associated protein-1 ASP-1, Thioredoxin TRX, transglutaminase BmTGA, glutathione-S-transferases GST, myosin, vespid allergen homologue VAH, 1 75 kDa collagenase, glyceraldehyde-3-phosphate dehydrogenase GAPDH, cuticular collagen Col-4, secreted larval acidic proteins SLAPs, chitinase CHI-1, maltose binding protein MBP, glycolytic enzyme fructose-1,6-bisphosphate aldolase Fba, tropomyosin TMY-1, nematode specific gene product OvB20, onchocystatin CPI-2, Cox-2 (Filarioidea superfamily, Filariasis); phospholipase C PLC, heat-labile enterotoxin B, Iota toxin component Ib, protein CPE1281, pyruvate ferredoxin oxidoreductase, elongation factor G EF-G, perfringolysin O Pfo, glyceraldehyde-3-phosphate dehydrogenase GapC, Fructose-bisphosphate aldolase Alf2, *Clostridium perfringens* enterotoxin CPE, alpha toxin AT, alpha toxoid ATd, epsilon-toxoid ETd, protein HP, large cytotoxin TpeL, endo-beta-N-acetylglucosaminidase Naglu, phosphoglyceromutase Pgm (*Clostridium perfringens*, Food poisoning by *Clostridium perfringens*); leukotoxin IktA, adhesion FadA, outer membrane protein RadD, high-molecular weight arginine-binding protein (*Fusobacterium* genus, *Fusobacterium* infection); phospholipase C PLC, heat-labile enterotoxin B, Iota toxin component Ib, protein CPE1281, pyruvate ferredoxin oxidoreductase, elongation factor G EF-G, perfringolysin O Pfo, glyceraldehyde-3-phosphate dehydrogenase GapC, fructose-bisphosphate aldolase Alf2, *Clostridium perfringens* enterotoxin CPE, alpha toxin AT, alpha toxoid ATd, epsilon-toxoid ETd, protein HP, large cytotoxin TpeL, endo-beta-N-acetylglucosaminidase Naglu, phosphoglyceromutase Pgm (usually *Clostridium perfringens*; other *Clostridium* species, Gas gangrene (Clostridial myonecrosis)); lipase A, lipase B, peroxidase Dec1 (*Geotrichum candidum*, Geotrichosis); prion protein (GSS prion, Gerstmann-Straussler-Scheinker syndrome (GSS)); cyst wall proteins CWPI, CWP2, CWP3, variant surface proteins VSP, VSPI, VSP2, VSP3, VSP4, VSP5, VSP6, 56 kDa antigen, pyruvate ferredoxin oxidoreductase PFOR, alcohol dehydrogenase E ADHE, alpha-giardin, alpha8-giardin, alphal-guiardin, beta-giardin, cystein proteases, glutathione-S-transferase GST, arginine deiminase ADI, fructose-1,6-bisphosphat aldolase FBA, *Giardia* trophozoite antigens GTA (GTA1, GTA2), ornithine carboxyl transferase OCT, striated fiber-asseblin-like protein SALP, uridine phosphoryl-like protein UPL, alpha-tubulin, beta-tubulin (*Giardia intestinalis*, Giardiasis); members of the ABC transporter family (LoIC, OppA, and PotF), putative lipoprotein releasing system transmembrane protein LoIC/E, flagellin FliC, *Burkholderia* intracellular motility A BimA, bacterial Elongation factor-Tu EF-Tu, 1 7 kDa OmpA-like protein, boaA coding protein (*Burkholderia mallei*, Glanders); cyclophilin CyP, 24 kDa third-stage larvae protein GS24, excretion-secretion products ESPs (40, 80, 120 and 208 kDa) (*Gnathostoma spinigerum* and *Gnathostoma hispidum*, Gnathostomiasis); pilin proteins, minor pilin-associated subunit pilC, major pilin subunit and variants pilE, pilS, phase variation protein porA, Porin B PorB, protein TraD, Neisserial outer membrane antigen H.8, 70 kDa antigen, major outer membrane protein PI, outer membrane proteins PIA and PIB, W antigen, surface protein A NspA, transferrin binding protein TbpA, transferrin binding protein TbpB, PBP2, mtrR coding protein, ponA coding protein, membrane permease FbpBC, FbpABC protein system, LbpAB proteins, outer membrane protein Opa, outer membrane transporter FetA, iron-repressed regulator MpeR (*Neisseria gonorrhoeae*, Gonorrhea); outer membrane protein A OmpA, outer membrane protein C OmpC, outer membrane protein K17 OmpK17 (*Klebsiella granulomatis*, Granuloma inguinale (Donovanosis)); fibronectin-binding protein Sfb, fibronectin/fibrinogen-binding protein FBP54, fibronectin-binding protein FbaA, M protein type 1 EmmI, M protein type 6 Emm6, immunoglobulin-binding protein 35 Sib35, Surface protein R28 Spr28, superoxide dismutase SOD, C5a peptidase ScpA, antigen I/II AgI/II, adhesin AspA, G-related alpha2-macroglobulin-binding protein GRAB, surface fibrillar protein M5 (*Streptococcus pyogenes*, Group A streptococcal infection); C protein β antigen, arginine deiminase proteins, adhesin BibA, 105 kDA protein BPS, surface antigens c, surface antigens R, surface antigens X, trypsin-resistant protein R1, trypsin-resistant protein R3, trypsin-resistant protein R4, surface immunogenic protein Sip, surface protein Rib, Leucine-rich repeats protein LrrG, serine-rich repeat protein Srr-2, C protein alpha-antigen Bca, Beta antigen Bag, surface antigen Epsilon, alpha-like protein ALP1, alpha-like protein ALP5 surface antigen delta, alpha-like protein ALP2, alpha-like protein ALP3, alpha-like protein ALP4, Cbeta protein Bac (*Streptococcus agalactiae*, Group B streptococcal infection); transferrin-binding protein 2 Tbp2, phosphatase P4, outer membrane protein P6, peptidoglycan-associated lipoprotein Pal, protein D, protein E, adherence and penetration protein Hap, outer membrane protein 26 Omp26, outer membrane protein P5 (Fimbrin), outer membrane protein D15, outer membrane protein OmpP2, 5'-nucleotidase NucA, outer membrane protein PI, outer membrane protein P2, outer membrane lipoprotein Pep, Lipoprotein E, outer membrane protein P4, fuculokinase FucK, [Cu,Zn]-superoxide dismutase SodC, protease HtrA, protein 0145, alpha-galactosylceramide (*Haemophilus influenzae, Haemophilus influenzae* infection); polymerase 3D, viral capsid protein VP1, viral capsid protein VP2, viral capsid protein VP3, viral capsid protein VP4, protease 2A, protease 3C (Enteroviruses, mainly Coxsackie A virus and Enterovirus 71 (EV71), Hand, foot and mouth disease (HFMD)); RNA polymerase L, protein L, glycoprotein Gn, glycoprotein Gc, nucleocapsid protein S, envelope glycoprotein G1, nucleoprotein NP, protein N, polyprotein M (Sin Nombre virus, Hantavirus, Hantavirus Pulmonary Syndrome (HPS)); heat shock protein HspA, heat shock protein HspB, citrate synthase GItA, protein UreB, heat shock protein Hsp60, neutrophil-activating protein NAP, catalase KatA, vacuolating cytotoxin VacA, urease alpha UreA, urease beta Ureb, protein Cpn10, protein groES, heat shock protein HspI O, protein MopB, cytotoxicity-associated 10 kDa protein CAG, 36 kDa antigen, beta-lactamase HcpA, Beta-lactamase HcpB (Helicobacter pylori, Helicobacter pylori infection); integral membrane proteins, aggregation-prone proteins, O-antigen, toxin-antigens Stx2B, toxin-antigen StxI B, adhesion-antigen fragment Int28, protein EspA, protein EspB, Intimin, protein Tir, protein IntC300, protein Eae (*Escherichia coli* 0157:H7, 01 1 1 and O104:H4, Hemolytic-uremic syndrome (HUS)); RNA polymerase L, protein L, glycoprotein Gn, glycoprotein Gc, nucleocapsid protein S, envelope glycoprotein G1, nucleoprotein NP, protein N, polyprotein M (Bunyaviridae family, Hemorrhagic fever with renal syndrome (HFRS)); glycoprotein G, matrix protein M, nucleoprotein N, fusion protein F, polymerase L, protein W, proteinC, phosphoprotein p, non-structural protein V (Henipavirus (Hendra virus Nipah virus), Henipavirus infections); polyprotein, glycoprotein Gp2, hepatitis A surface antigen HBAg, protein 2A, virus protein VP1, virus protein VP2, virus protein VP3, virus protein VP4, protein P1 B, protein P2A, protein P3AB, protein P3D (Hepatitis A Virus, Hepatitis A); hepatitis B surface antigen HBsAg, Hepatitis B core antigen HbcAg, polymerase, protein Hbx, preS2 middle surface protein, surface protein L, large S protein, virus protein VP1, virus protein VP2, virus protein VP3, virus protein VP4 (Hepatitis B Virus (HBV), Hepatitis B); envelope glycoprotein E1 gp32 gp35, envelope glycoprotein E2 NS1 gp68 gp70, capsid protein C, core protein Core, polyprotein, virus protein VP1, virus protein VP2, virus protein VP3, virus protein VP4, antigen G, protein NS3, protein NSSA, (Hepatitis C Virus, Hepatitis C); virus protein VP1, virus protein VP2, virus protein VP3, virus protein VP4, large hepatitis delta antigen, small hepatitis delta antigen (Hepatitis D Virus, Hepatitis D); virus protein VP1, virus protein VP2, virus protein VP3, virus protein VP4, capsid protein E2 (Hepatitis E Virus, Hepatitis E); glycoprotein L UL1, uracil-DNA glycosylase UL2, protein UL3, protein UL4, DNA replication protein UL5, portal protein UL6, virion maturation protein UL7, DNA helicase UL8, replication origin-binding protein UL9, glycoprotein M UL10, protein UL1 1, alkaline exonuclease UL12, serine-threonine protein kinase UL1 3, tegument protein UL14, terminase UL1 5, tegument protein UL1 6, protein UL1 7, capsid protein VP23 UL18, major capsid protein VP5 UL19, membrane protein UL20, tegument protein UL21, Glycoprotein H (UL22), Thymidine Kinase UL23, protein UL24, protein UL25, capsid protein P40 (UL26, VP24, VP22A), glycoprotein B (UL27), ICP18.5 protein (UL28), major DNA-binding protein ICP8 (UL29), DNA polymerase UL30, nuclear matrix protein UL31, envelope glycoprotein UL32, protein UL33, inner nuclear membrane protein UL34, capsid protein VP26 (UL35), large tegument protein UL36, capsid assembly protein UL37, VP19C protein (UL38), ribonucleotide reductase (Large subunit) UL39, ribonucleotide reductase (Small subunit) UL40, tegument protein/virion host shutoff VHS protein (UL41), DNA polymerase processivity factor UL42, membrane protein UL43, glycoprotein C (UL44), membrane protein UL45, tegument proteins VP1 1/12 (UL46), tegument protein VP13/14 (UL47), virion maturation protein VP16 (UL48, Alpha-TIF), envelope protein UL49, dUTP diphosphatase UL50, tegument protein UL51, DNA helicase/primase complex protein UL52, glycoprotein K (UL53), transcriptional regulation protein IE63 (ICP27, UL54), protein UL55, protein UL56, viral replication protein ICP22 (IE68, US1), protein US2, serine/threonine-protein kinase US3, glycoprotein G (US4), glycoprotein J (US5), glycoprotein D (US6), glycoprotein I (US7), glycoprotein E (US8), tegument protein US9, capsid/tegument protein US10, Vmw21 protein (US1 1), ICP47 protein (IE12, US12), major transcriptional activator ICP4 (IE1 75, RSI), E3 ubiquitin ligase ICPO (IE1 10), latency-related protein 1 LRP1, latency-related protein 2 LRP2, neurovirulence factor RL1 (ICP34.5), latency-associated transcript LAT (Herpes simplex virus 1 and 2 (HSV-1 and HSV-2), Herpes simplex); heat shock protein Hsp60, cell surface protein H1 C, dipeptidyl peptidase type IV DppIV, M antigen, 70 kDa protein, 1 7 kDa histone-like protein (*Histoplasma capsulatum*, Histoplasmosis); fatty acid and retinol binding protein-1 FAR-1, tissue inhibitor of metal Ioproteinase TIMP (TMP), cysteine proteinase ACEY-1, cysteine proteinase ACCP-1, surface antigen Ac-16, secreted protein 2 ASP-2, metal Ioprotease 1 MTP-1, aspartyl protease inhibitor API-1, surface-associated antigen SAA-1, surface-associated antigen SAA-2, adult-specific secreted factor Xa, serine protease inhibitor anticoagulant AP, cathepsin D-like aspartic protease ARR-1, glutathione S-transferase GST, aspartic protease APR-1, acetylcholinesterase AChE (*Ancylostoma duodenale* and *Necator americanus*, Hookworm infection); protein NSI, protein NPI, protein VPI, protein VP2, protein VP3 (Human bocavirus (HBoV), Human bocavirus infection); major surface protein 2 MSP2, major surface protein 4 MSP4, MSP variant SGV1, MSP variant SGV2, outer membrane protein OMP, outer membrane protein 19 OMP-19, major antigenic protein MAPI, major antigenic protein MAPI-2, major antigenic protein MAPI B, major antigenic protein MAPI-3, Erum2510 coding protein, protein GroEL, protein GroES, 30-kDA major outer membrane proteins, GE 100-kDa protein, GE 130-kDa protein, GE 160-kDa protein (*Ehrlichia ewingii, Human ewingii* ehrlichiosis); major surface proteins 1-5 (MSPI a, MSPI b, MSP2, MSP3, MSP4, MSP5), type IV secreotion system proteins VirB2, VirB7, VirBI I, VirD4 (*Anaplasma phagocytophilum*, Human granulocytic anaplasmosis (HGA)); protein NSI, small hydrophobic protein NS2, SH protein, fusion protein F, glycoprotein G, matrix protein M, matrix protein M2-1, matrix protein M2-2, phosphoprotein P, nucleoprotein N, polymerase L (Human metapneumovirus (hMPV), Human metapneumovirus infection); major surface protein 2 MSP2, major surface protein 4 MSP4, MSP variant SGV1, MSP variant SGV2, outer membrane protein OMP, outer membrane protein 19 OMP-19, major antigenic protein MAPI, major antigenic protein MAPI-2, major antigenic protein MAP1 B, major antigenic protein MAPI-3, Erum2510 coding protein, protein GroEL, protein GroES, 30-kDA major outer membrane proteins, GE 100-kDa protein, GE 1 30-kDa protein, GE 1 60-kDa protein (*Ehrlichia chaffeensis*, Human monocytic ehrlichiosis); replication protein E1, regulatory protein E2, protein E3, protein E4, protein E5, protein E6, protein E7, protein E8, major capsid protein LI, minor capsid protein L2 (Human papillomavirus (HPV), Human papillomavirus (HPV) infection); fusion protein F, hemagglutinin-neuramidase HN, glycoprotein G, matrix protein M, phosphoprotein P, nucleoprotein N, polymerase L (Human parainfluenza viruses (HPIV), Human parainfluenza virus infection); Hemagglutinin (HA), Neuraminidase (NA), Nucleoprotein (NP), M1 protein, M2 protein, NS1 protein, NS2 protein (NEP protein: nuclear export protein), PA protein, PB1 protein (polymerase basic 1 protein), PB1-F2 protein and PB2 protein (Orthomyxoviridae family, Influenza virus (flu)); genome polyprotein, protein E, protein M, capsid protein C Gapanese encephalitis virus, Japanese encephalitis); RTX toxin, type IV pili, major pilus subunit PilA, regulatory transcription factors PilS and PilR, protein sigma54, outer membrane proteins (*Kingella kingae*, *Kingella kingae* infection); prion protein (Kuru prion, Kuru); nucleoprotein N, polymerase L, matrix protein Z, glycoprotein GP (Lassa virus, Lassa fever); peptidoglycan-associated lipoprotein PAL, 60 kDa chaperonin Cpn60 (groEL, HspB), type IV pilin PilE, outer membrane protein MIP, major outer membrane protein MompS, zinc metalloproteinase MSP (*Legionella pneumophila*, Legionellosis (Legionnaires' disease, Pontiac fever)); P4 nuclease, protein WD, ribonucleotide reductase M2, surface membrane glycoprotein Pg46, cysteine proteinase CP, glucose-regulated protein 78 GRP-78, stage-specific S antigen-like protein A2, ATPase FI, beta-tubulin, heat shock protein 70 Hsp70, KMP-1 1, glycoprotein GP63, protein BT1, nucleoside hydrolase NH, cell surface protein B1, ribosomal protein PI-like protein PI, sterol 24-c-methyltransferase SMT, LACK protein, histone H1, SPB1 protein, thiol specific antioxidant TSA, protein antigen STI1, signal peptidase SP, histone H2B, suface antigen PSA-2, cystein proteinase b Cpb (*Leishmania* genus, Leishmaniasis); major membrane protein I, serine-rich antigen-45 kDa, 10 kDa caperonin GroES, HSP kDa antigen, amino-oxononanoate synthase AONS, protein recombinase A RecA, Acetyl-/propionyl-coenzyme A carboxylase alpha, alanine racemase, 60 kDa chaperonin 2, ESAT-6-like protein EcxB (L-ESAT-6), protein Lsr2, protein ML0276, Heparin-binding hemagglutinin HBHA, heat-shock protein 65 Hsp65, mycP1 or ML0041 coding protein, htrA2 or ML01 76 coding protein, htrA4 or ML2659 coding protein, gcp or ML0379 coding protein, cIpC or ML0235 coding protein (*Mycobacterium leprae* and *Mycobacterium lepromatosis*, Leprosy); outer membrane protein LipL32, membrane protein LIC10258, membrane protein LP30, membrane protein LIC12238, Ompa-like protein Lsa66, surface protein LigA, surface protein LigB, major outer membrane protein OmpLI, outer membrane protein LipL41, protein LigAni, surface protein LcpA, adhesion protein LipL53, outer membrane protein UpL32, surface protein Lsa63, flagellin FlaB1, membrane lipoprotein LipL21, membrane protein pL40, leptospiral surface adhesin Lsa27, outer membrane protein OmpL36, outer membrane protein OmpL37, outer membrane protein OmpL47, outer membrane protein OmpL54, acy transferase LpxA (*Leptospira* genus, Leptospirosis); listeriolysin O precursor HIy (LLO), invasion-associated protein Iap (P60), Listeriolysin regulatory protein PrfA, Zinc metal loproteinase MpI, phosphatidylinositol-specific phospholipase C PLC (PIcA, PIcB), O-acetyltransferase Oat, ABC-transporter permease Im.G_1 771, adhesion protein LAP, LAP receptor Hsp60, adhesin LapB, haemolysin listeriolysin O LLO, protein ActA, Internalin A InIA, protein InIB (*Listeria monocytogenes*, Listeriosis); outer surface protein A OspA, outer surface protein OspB, outer surface protein OspC, decorin binding protein A DbpA, decorin binding protein B DbpB, flagellar filament 41 kDa core protein Fla, basic membrane protein A BmpA (Immunodominant antigen P39), outer surface 22 kDa lipoprotein precursor (antigen IPLA7), variable surface lipoprotein vIsE (usually *Borrelia burgdorferi* and other *Borrelia* species, Lyme disease (Lyme borreliosis)); venom allergen homolog-like protein VAL-1, abundant larval transcript ALT-1, abundant larval transcript ALT-2, thioredoxin peroxidase TPX, vespid allergen homologue VAH, thiordoxin peroxidase 2 TPX-2, antigenic protein SXP (peptides N, N1, N2, and N3), activation associated protein-1 ASP-1, thioredoxin TRX, transglutaminase BmTGA, glutathione-S-transferases GST, myosin, vespid allergen homologue VAH, 1 75 kDa collagenase, glyceraldehyde-3-phosphate dehydrogenase GAPDH, cuticular collagen Col-4, Secreted Larval Acidic Proteins SLAPs, chitinase CHI-1, maltose binding protein MBP, glycolytic enzyme fructose-1,6-bisphosphate aldolase Fba, tropomyosin TMY-1, nematode specific gene product OvB20, onchocystatin CPI-2, protein Cox-2 (*Wuchereria bancrofti* and *Brugia malayi*, Lymphatic filariasis (Elephantiasis)); glycoprotein GP, matrix protein Z, polymerase L, nucleoprotein N (Lymphocytic choriomeningitis virus (LCMV), Lymphocytic choriomeningitis); thrombospondin-related anonymous protein TRAP, SSP2 Sporozoite surface protein 2, apical membrane antigen 1 AMA1, rhoptry membrane antigen RMA1, acidic basic repeat antigen ABRA, cell-traversal protein PF, protein Pvs25, merozoite surface protein 1 MSP-1, merozoite surface protein 2 MSP-2, ring-infected erythrocyte surface antigen RESALiver stage antigen 3 LSA-3, protein Eba-1 75, serine repeat antigen 5 SERA-5, circumsporozoite protein CS, merozoite surface protein 3 MSP3, merozoite surface protein 8 MSP8, enolase PF10, hepatocyte erythrocyte protein 1 7 kDa HEP1 7, erythrocyte membrane protein 1 EMP1, protein Kbetamerozoite surface protein 4/5 MSP 4/5, heat shock protein Hsp90, glutamate-rich protein GLURP, merozoite surface protein 4 MSP-4, protein STARP, circumsporozoite protein-related antigen precursor CRA (*Plasmodium* genus, Malaria); nucleoprotein N, membrane-associated protein VP24, minor nucleoprotein VP30, polymerase cofactor VP35, polymerase L, matrix protein VP40, envelope glycoprotein GP (Marburg virus, Marburg hemorrhagic fever (MHF)); protein C, matrix protein M, phosphoprotein P, non-structural protein V, hemagglutinin glycoprotein H, polymerase L, nucleoprotein N, fusion protein F (Measles virus, Measles); members of the ABC transporter family (LoIC, OppA, and PotF), putative lipoprotein releasing system transmembrane protein LoIC/E, flagellin FliC, *Burkholderia* intracellular motility A BimA, bacterial Elongation factor-Tu EF-Tu, 1 7 kDa OmpA-like protein, boaA coding protein, boaB coding protein (*Burkholderia pseudomallei*, Melioidosis (Whitmore's disease)); pilin proteins, minor pi I in-associated subunit pilC, major pilin subunit and variants pilE, pilS, phase variation protein porA, Porin B PorB, protein TraD, Neisserial outer membrane antigen H.8, 70 kDa antigen, major outer membrane protein PI, outer membrane proteins PIA and PIB, W antigen, surface protein A NspA, transferrin binding protein TbpA, transferrin binding protein TbpB, PBP2, mtrR coding protein, ponA coding protein, membrane permease FbpBC, FbpABC protein system, LbpAB proteins, outer membrane protein Opa, outer membrane transporter FetA, iron-repressed regulator MpeR, factor H-binding protein fHbp, adhesin NadA, protein NhbA, repressor FarR (*Neisseria meningitidis*, Meningococcal disease); 66 kDa protein, 22 kDa protein (usually *Metagonimus yokagawai*, Metagonimiasis); polar tube proteins (34, 75, and 1 70 kDa in Glugea, 35, 55 and 1 50 kDa in Encephalitozoon), kinesin-related protein, RNA polymerase II largest subunit, similar of integral membrane protein YIPA, anti-silencing protein 1, heat shock transcription factor HSF, protein kinase, thymidine kinase, NOP-2 like nucleolar protein (Microsporidia phylum, Microsporidiosis); CASP8 and FADD-like apoptosis regulator, Glutathione peroxidase GPX1, RNA helicase NPH-II NPH2, Poly(A) polymerase catalytic subunit PAPL, Major envelope protein P43K, early transcription factor 70 kDa subunit VETFS, early transcription factor 82 kDa subunit VETFL, metalloendopeptidase G1-type, nucleoside triphosphatase I NPH1, replication protein A28-like MC134L, RNA polymease 7 kDa subunit RP07 (Molluscum contagiosum virus (MCV), Molluscum contagiosum (MQ); matrix protein M, phosphoprotein PN, small hydrophobic protein SH, nucleoprotein N, protein V, fusion glycoprotein F, hemagglutinin-neuraminidase HN, RNA polymerase L (Mumps virus, Mumps); Outer membrane proteins OM, cell surface antigen OmpA, cell surface antigen OmpB (sca5), cell surface protein SCA4, cell surface protein SCA1, intracytoplasmic protein D, crystalline surface layer protein SLP, protective surface protein antigen SPA (*Rickettsia typhi*, Murine typhus (Endemic typhus)); adhesin P1, adhesion P30, protein p1 1 6, protein P40, cytoskeletal protein HMW1, cytoskeletal protein HMW2, cytoskeletal protein HMW3, MPN152 coding protein, MPN426 coding protein, MPN456 coding protein, MPN-500 coding protein (*Mycoplasma pneumoniae*, Mycoplasma pneumonia); NocA, Iron dependent regulatory protein, VapA, VapD, VapF, VapG, caseinolytic protease, filament tip-associated 43-kDa protein, protein P24, protein P61, 15-kDa protein, 56-kDa protein (usually *Nocardia asteroides* and other *Nocardia* species, Nocardiosis); venom allergen homolog-like protein VAL-1, abundant larval transcript ALT-1, abundant larval transcript ALT-2, thioredoxin peroxidase TPX, vespid allergen homologue VAH, thiordoxin peroxidase 2 TPX-2, antigenic protein SXP (peptides N, N1, N2, and N3), activation associated protein-1 ASP-1, Thioredoxin TRX, transglutaminase BmTGA, glutathione-S-transferases GST, myosin, vespid allergen homologue VAH, 1 75 kDa collagenase, glyceraldehyde-3-phosphate dehydrogenase GAPDH, cuticular collagen Col-4, Secreted Larval Acidic Proteins SLAPs, chitinase CHI-1, maltose binding protein MBP, glycolytic enzyme fructose-1,6-bisphosphate aldolase Fba, tropomyosin TMY-1, nematode specific gene product OvB20, onchocystatin CPI-2, Cox-2 (*Onchocerca volvulus*, Onchocerciasis (River blindness)); 43 kDa secreted glycoprotein, glycoprotein gpO, glycoprotein gp75, antigen Pb27, antigen Pb40, heat shock protein Hsp65, heat shock protein Hsp70, heat shock protein Hsp90, protein P10, triosephosphate isomerase TPI, N-acetyl-glucosamine-binding lectin Paracoccin, 28 kDa protein Pb28 (*Paracoccidioides brasiliensis*, Paracoccidioidomycosis (South American blastomycosis)); 28-kDa cruzipain-like cystein protease Pw28CCP (usually *Paragonimus westermani* and other *Paragonimus* species, Paragonimiasis); outer membrane protein OmpH, outer membrane protein Omp28, protein PM1539, protein PM0355, protein PM141 7, repair protein MutL, protein BcbC, protein PM0305, formate dehydrogenase-N, protein PM0698, protein PM1422, DNA gyrase, lipoprotein PlpE, adhesive protein Cp39, heme aquisition system receptor HasR, 39 kDa capsular protein, iron-regulated OMP IROMP, outer membrane protein OmpA87, fimbria! protein Ptf, fimbrial subunit protein PtfA, transferrin binding protein TbpI, esterase enzyme MesA, *Pasteurella multocida* toxin PMT, adhesive protein Cp39 (*Pasteurella* genus, Pasteurellosis); "filamentous hemagglutinin FhaB, adenylate cyclase CyaA, pertussis toxin subunit 4 precursor PtxD, pertactin precursor Prn, toxin subunit 1 PtxA, protein Cpn60, protein brkA, pertussis toxin subunit 2 precursor PtxB, pertussis toxin subunit 3 precursor PtxC, pertussis toxin subunit 5 precursor PtxE, pertactin Prn, protein Fim2, protein Fim3;" (*Bordetella pertussis*, Pertussis (Whooping cough)); "F1 capsule antigen, virulence-associated V antigen, secreted effector protein LcrV, V antigen, outer membrane protease Pla, secreted effector protein YopD, putative secreted protein-tyrosine phosphatase YopH, needle complex major subunit YscF, protein kinase YopO, putative autotransporter protein YapF, inner membrane ABC-transporter YbtQ (Irp7), putative sugar binding protein YP00612, heat shock protein 90 HtpG, putative sulfatase protein YdeN, outer-membrane lipoprotein carrier protein LoIA, secretion chaperone YerA, putative lipoprotein YPO0420, hemolysin activator protein HpmB, pesticin/yersiniabactin outer membrane receptor Psn, secreted effector protein YopE, secreted effector protein YopF, secreted effector protein YopK, outer membrane protein YopN, outer membrane protein YopM, Coagulase/fibrinolysin precursor PIa;" (*Yersinia pestis*, Plague); protein PhpA, surface adhesin PsaA, pneumolysin Ply, ATP-dependent protease CIp, lipoate-protein ligase LpIA, cell wall surface anchored protein psrP, sortase SrtA, glutamyl-tRNA synthetase GItX, choline binding protein A CbpA, pneumococcal surface protein A PspA, pneumococcal surface protein C PspC, 6-phosphogluconate dehydrogenase Gnd, iron-binding protein PiaA, Murein hydrolase LytB, proteon LytC, protease A1 (*Streptococcus pneumoniae*, Pneumococcal infection); major surface protein B, kexin-like protease KEX1, protein A12, 55 kDa antigen P55, major surface glycoprotein Msg (*Pneumocystis jirovecii, Pneumocystis* pneumonia (PCP)); genome polyprotein, polymerase 3D, viral capsid protein VP1, viral capsid protein VP2, viral capsid protein VP3, viral capsid protein VP4, protease 2A, protease 3C (Poliovirus, Poliomyelitis); protein Nfa1, exendin-3, secretory lipase, cathepsin B-like protease, cysteine protease, cathepsin, peroxiredoxin, protein Cryl Ac (usually *Naegleria fowleri*, Primary amoebic meningoencephalitis (PAM)); agnoprotein, large T antigen, small T antigen, major capsid protein VP1, minor capsid protein Vp2 (JC virus, Progressive multifocal leukoencephalopathy); low calcium response protein E LCrE, chlamydial outer protein N CopN, serine/threonine-protein kinase PknD, acyl-carrier-protein S-malonyltransferase FabD, single-stranded DNA-binding protein Ssb, major outer membrane protein MOMP, outer membrane protein 2 Omp2, polymorphic membrane protein family (Pmp1, Pmp2, Pmp3, Pmp4, Pmp5, Pmp6, Pmp7, Pmp8, Pmp9, Pmp10, PmpI I, Pmp12, Pmp13, Pmp14, Pmp15, Pmp16, Pmp17, Pmp18, Pmp19, Pmp20, Pmp21) (*Chlamydophila psittaci*, Psittacosis); outer membrane protein PI, heat shock protein B HspB, peptide ABC transporter, GTP-binding protein, protein IcmB, ribonuclease R, phosphatas SixA, protein DsbD, outer membrane protein ToIC, DNA-binding protein PhoB, ATPase DotB, heat shock protein B HspB, membrane protein ComI, 28 kDa protein, DNA-3-methyladenine glycosidase I, pouter membrane protein OmpH, outer membrane protein AdaA, glycine cleavage system T-protein (*Coxiella burnetii*, Q fever); nucleoprotein N, large structural protein L, phophoprotein P, matrix protein M, glycoprotein G (Rabies virus, Rabies); fusionprotein F, nucleoprotein N, matrix protein M, matrix protein M2-1, matrix protein M2-2, phophoprotein P, small hydrophobic protein SH, major surface glycoprotein G, polymerase L, non-structural protein 1 NS1, nonstructural protein 2 NS2 (Respiratory syncytial virus (RSV), Respiratory syncytial virus infection); genome polyprotein, polymerase 3D, viral capsid protein VP1, viral capsid protein VP2, viral capsid protein VP3, viral capsid protein VP4, protease 2A, protease 3C (Rhinovirus, Rhinovirus infection); outer membrane proteins OM, cell surface antigen OmpA, cell surface antigen OmpB (sca5), cell surface protein SCA4, cell surface protein SCA1, protein PS120, intracytoplasmic protein D, protective surface protein antigen SPA (*Rickettsia* genus, Rickettsial infection); outer membrane proteins OM, cell surface antigen OmpA, cell surface antigen OmpB (sca5), cell surface protein SCA4, cell surface protein SCA1, intracytoplasmic protein D (*Rickettsia akari*, Rickettsialpox); envelope glycoprotein GP, polymerase L, nucleoprotein N, non-structural protein NSS (Rift Valley fever virus, Rift Valley fever (RVF)); outer membrane proteins OM, cell surface antigen OmpA, cell surface antigen OmpB (sca5), cell surface protein SCA4, cell surface protein SCA1, intracytoplasmic protein D (*Rickettsia rickettsii*, Rocky mountain spotted fever (RMSF)); "non-structural protein 6 NS6, non-structural protein 2 NS2, intermediate capsid protein VP6, inner capsid protein VP2, non-structural protein 3 NS3, RNA-directed RNA polymerase L, protein VP3, non-structural protein 1 NS1, non-structural protein 5 NS5, outer capsid glycoprotein VP7, non-structural glycoprotein 4 NS4, outer capsid protein VP4;" (Rotavirus, Rotavirus infection); polyprotein P200, glycoprotein E1, glycoprotein E2, protein NS2, capsid protein C (Rubella virus, Rubella); chaperonin GroEL (MopA), inositol phosphate phosphatase SopB, heat shock protein HsIU, chaperone protein DnaJ, protein TviB, protein IroN, flagellin FliC, invasion protein SipC, glycoprotein gp43, outer membrane protein LamB, outer membrane protein PagC, outer membrane protein ToIC, outer membrane protein NmpC, outer membrane protein FadL, transport protein SadA, transferase WgaP, effector proteins SifA, SteC, SseL, SseJ and SseF (*Salmonella* genus, *Salmonellosis*); "protein 14, non-structural protein NS7b, non-structural protein NS8a, protein 9b, protein 3a, nucleoprotein N, non-structural protein NS3b, non-structural protein NS6, protein 7a, non-structural protein NS8b, membrane protein M, envelope small membrane protein EsM, replicase polyprotein 1 a, spike glycoprotein S, replicase polyprotein I ab;" (SARS coronavirus, SARS (Severe Acute Respiratory Syndrome)); serin protease, Atypical *Sarcoptes* Antigen 1 ASA1, glutathione S-transferases GST, cystein protease, serine protease, apolipoprotein (*Sarcoptes scabiei*, Scabies); glutathione S-transferases GST, paramyosin, hemoglbinase SM32, major egg antigen, 14 kDa fatty acid-binding protein SmI 4, major larval surface antigen P37, 22.6 kDa tegumental antigen, calpain CANP, triphospate isomerase Tim, surface protein 9B, outer capsid protein VP2, 23 kDa integral membrane protein Sm23, Cu/Zn-superoxide dismutase, glycoprotein Gp, myosin (*Schistosoma* genus, Schistosomiasis (Bilharziosis)); 60 kDa chaperonin, 56 kDa type-specific antigen, pyruvate phosphate di kinase, 4-hydroxybenzoate octaprenyltransferase (*Orientia tsutsugamushi*, Scrub typhus); dehydrogenase GuaB, invasion protein Spa32, invasin IpaA, invasin IpaB, invasin IpaC, invasin IpaD, invasin IpaH, invasin IpaJ (*Shigella* genus, Shigellosis (Bacillary dysentery)); protein P53, virion protein US10 homolog, transcriptional regulator IE63, transcriptional transactivator IE62, protease P33, alpha trans-inducing factor 74 kDa protein, deoxyuridine 5'-triphosphate nucleotidohydrolase, transcriptional transactivator IE4, membrane protein UL43 homolog, nuclear phosphoprotein UL3 homolog, nuclear protein UL4 homolog, replication origin-binding protein, membrane protein 2, phosphoprotein 32, protein 57, DNA polymerase processivity factor, portal protein 54, DNA primase, tegument protein UL14 homolog, tegument protein UL21 homolog, tegument protein UL55 homolog, tripartite terminase subunit UL33 homolog, tripartite terminase subunit UL15 homolog, capsid-binding protein 44, virion-packaging protein 43 (Varicella zoster virus (VZV), Shingles (Herpes zoster)); truncated 3-beta hydroxy-5-ene steroid dehydrogenase homolog, virion membrane protein A13, protein A1 9, protein A31, truncated protein A35 homolog, protein A37.5 homolog, protein A47, protein A49, protein A51, semaphorin-like protein A43, serine proteinase inhibitor 1, serine proteinase inhibitor 2, serine proteinase inhibitor 3, protein A6, protein B15, protein C1, protein C5, protein C6, protein F7, protein F8, protein F9, protein F1 1, protein F14, protein F1 5, protein F1 6 (Variola major or Variola minor, Smallpox (Variola)); adhesin/glycoprotein gp70, proteases (*Sporothrix schenckii*, Sporotrichosis); heme-iron binding protein IsdB, collagen adhesin Cna, clumping factor A CIfA, protein MecA, fibronectin-binding protein A FnbA, enterotoxin type A EntA, enterotoxin type B EntB, enterotoxin type C EntCI, enterotoxin type C EntC2, enterotoxin type D EntD, enterotoxin type E EntE, Toxic shock syndrome toxin-1 TSST-1, Staphylokinase, Penicillin binding protein 2a PBP2a (MecA), secretory antigen SssA (*Staphylococcus* genus, Staphylococcal food poisoning); heme-iron binding protein IsdB, collagen adhesin Cna, clumping factor A CIfA, protein MecA, fibronectin-binding protein A FnbA, enterotoxin type A EntA, enterotoxin type B EntB, enterotoxin type C EntCI, enterotoxin type C EntC2, enterotoxin type D EntD, enterotoxin type E EntE, Toxic shock syndrome toxin-1 TSST-1, Staphylokinase, Penicillin binding protein 2a PBP2a (MecA), secretory antigen SssA (*Staphylococcus* genus e.g. *aureus*, Staphylococcal infection); antigen Ss-IR, antigen NIE, strongylastacin, Na+-K+ ATPase Sseat-6, tropomysin SsTmy-1, protein LEC-5, 41 kDa antigen P5, 41-kDa larval protein, 31-kDa larval protein, 28-kDa larval protein (*Strongyloides stercoralis*, Strongyloidiasis); glycerophosphodiester phosphodiesterase GlpQ (Gpd), outer membrane protein TmpB, protein Tp92, antigen TpF1, repeat protein Tpr, repeat protein F TprF, repeat protein G TprG, repeat protein I Tprl, repeat protein J TprJ, repeat protein K TprK, treponemal membrane protein A TmpA, lipoprotein, 15 kDa Tpp15, 47 kDa membrane antigen, miniferritin TpF1, adhesin Tp0751, lipoprotein TP0136, protein TpN1 7, protein TpN47, outer membrane protein TP0136, outer membrane protein TP0155, outer membrane protein TP0326, outer membrane protein TP0483, outer membrane protein TP0956 (*Treponema pallidum*, Syphilis); Cathepsin L-like proteases, 53/25-kDa antigen, 8 kDa family members, cysticercus protein with a marginal trypsin-like activity TsAg5, oncosphere protein TSOL18, oncosphere protein TSOL45-1 A, lactate dehydrogenase A LDHA, lactate dehydrogenase B LDHB (*Taenia* genus, Taeniasis); tetanus toxin TetX, tetanus toxin C TTC, 140 kDa S layer protein, flavoprotein beta-subunit CT3, phospholipase (lecithinase), phosphocarrier protein HPr (*Clostridium tetani*, Tetanus (Lockjaw)); genome polyprotein, protein E, protein M, capsid protein C (Tick-borne encephalitis virus (TBEV), Tick-borne encephalitis); 58-kDa antigen, 68-kDa antigens, *Toxocara* larvae excretory-secretory antigen TES, 32-kDa glycoprotein, glycoprotein TES-70, glycoprotein GP31, excretory-secretory antigen TcES-57, perienteric fluid antigen Pe, soluble extract antigens Ex, excretory/secretory larval antigens ES, antigen TES-120, polyprotein allergen TBA-1, cathepsin L-like cysteine protease c-cpI-1, 26-kDa protein (*Toxocara canis* or *Toxocara cati*, Toxocariasis (Ocular Larva Migrans (OLM) and Visceral Larva Migrans (VLM))); microneme proteins (MIC1, MIC2, MIC3, MIC4, MIC5, MIC6, MIC7, MIC8), rhoptry protein Rop2, rhoptry proteins (Rop1, Rop2, Rop3, Rop4, Rop5, Rop6, Rop7, Rop16, Rjop1 7), protein SR1, surface antigen P22, major antigen p24, major surface antigen p30, dense granule proteins (GRA1, GRA2, GRA3, GRA4, GRA5, GRA6, GRA7, GRA8, GRA9, GRA10), 28 kDa antigen, surface antigen SAG1, SAG2 related antigen, nucleoside-triphosphatase 1, nucleoside-triphosphatase 2, protein Stt3, HesB-like domain-containing protein, rhomboid-like protease 5, toxomepsin 1 (*Toxoplasma gondii*, Toxoplasmosis); 43 kDa secreted glycoprotein, 53 kDa secreted glycoprotein, paramyosin, antigen Ts21, antigen Ts87, antigen p46000, TSL-1 antigens, caveolin-1 CAV-1, 49 kDa newborn larva antigen, prosaposin homologue, serine protease, serine proteinase inhibitor, 45-kDa glycoprotein Gp45 (*Trichinella spiralis*, Trichinellosis); Myb-like transcriptional factors (Myb1, Myb2, Myb3), adhesion protein AP23, adhesion protein AP33, adhesin protein AP33-3, adhesins AP51, adhesin AP65, adhesion protein AP65-1, alpha-actinin, kinesin-associated protein, teneurin, 62 kDa proteinase, subtilisin-like serine protease SUB1, cysteine proteinase gene 3 CP3, alpha-enolase Enol, cysteine proteinase CP30, heat shock proteins (Hsp70, Hsp60), immunogenic protein P270, (*Trichomonas vaginalis*, Trichomoniasis); beta-tubulin, 47-kDa protein, secretory leukocyte-like proteinase-1 SLP-1, 50-kDa protein I[T50, 1 7 kDa antigen, 43/47 kDa protein (*Trichuris trichiura*, Trichuriasis (Whipworm infection)); protein ESAT-6 (EsxA), 10 kDa filtrate antigen EsxB, secreted antigen 85-B FBPB, fibronectin-binding protein A FbpA (Ag85A), serine protease PepA, PPE family protein PPE18, fibronectin-binding protein D FbpD, immunogenic protein MPT64, secreted protein MPT51, catalase-peroxidase-peroxynitritase T KATG, periplasmic phosphate-binding lipoprotein PSTS3 (PBP-3, Phos-1), iron-regulated heparin binding hemagglutinin Hbha, PPE family protein PPE14, PPE family protein PPE68, protein Mtb72F, protein Apa, immunogenic protein MPT63, periplasmic phosphate-binding lipoprotein PSTS1 (PBP-1), molecular chaperone DnaK, cell surface lipoprotein Mpt83, lipoprotein P23, phosphate transport system permease protein pstA, 14 kDa antigen, fibronectin-binding protein C FbpCI, Alanine dehydrogenase TB43, Glutamine synthetase 1, ESX-1 protein, protein CFP10, TBI 0.4 protein, protein MPT83, protein MTB12, protein MTBE, Rpf-like proteins, protein MTB32, protein MTB39, crystallin, heat-shock protein HSP65, protein PST-S (usually *Mycobacterium tuberculosis*, Tuberculosis); outer membrane protein FobA, outer membrane protein FobB, intracellular growth locus IgICI, intracellular growth locus IgIC2, aminotransferase WbtI, chaperonin GroEL, 1 7 kDa major membrane protein TUL4, lipoprotein LpnA, chitinase family 18 protein, isocitrate dehydrogenase, Nif3 family protein, type IV pili glycosylation protein, outer membrane protein toIC, FAD binding family protein, type IV pilin multimeric outer membrane protein, two component sensor protein KdpD, chaperone protein DnaK, protein ToIQ (*Francisella tularensis*, Tularemia); "MB antigen, urease, protein GyrA, protein GyrB, protein ParC, protein ParE, lipid associated membrane proteins LAMP, thymidine kinase TK, phospholipase PL-A1, phospholipase PL-A2, phospholipase PL-C, surface-expressed 96-kDa antigen;" (*Ureaplasma urealyticum, Ureaplasma urealyticum* infection); non-structural polyprotein, structural polyprotein, capsid protein CP, protein E1, protein E2, protein E3, protease PI, protease P2, protease P3 (Venezuelan equine encephalitis virus, Venezuelan equine encephalitis); glycoprotein GP, matrix protein Z, polymerase L, nucleoprotein N (Guanarito virus, Venezuelan hemorrhagic fever); polyprotein, protein E, protein M, capsid protein C, protease NS3, protein NS1, protein NS2A, protein AS2B, protein NS4A, protein NS4B, protein NS5 (West Nile virus, West Nile Fever); capsid protein CP, protein E1, protein E2, protein E3, protease P2 (Western equine encephalitis virus, Western equine encephalitis); genome polyprotein, protein E, protein M, capsid protein C, protease NS3, protein NS1, protein NS2A, protein AS2B, protein NS4A, protein NS4B, protein NS5 (Yellow fever virus, Yellow fever); putative Yop targeting protein YobB, effector protein YopD, effector protein YopE, protein YopH, effector protein YopJ, protein translocation protein YopK, effector protein YopT, protein YpkA, flagellar biosyntheses protein FIhA, peptidase M48, potassium efflux system KefA, transcriptional regulatoer RovA, adhesin Ifp, translocator portein LcrV, protein PcrV, invasin Inv, outer membrane protein OmpF-like porin, adhesin YadA, protein kinase C, phospholipase CI, protein PsaA, mannosyltransferase-like protein WbyK, protein YscU, antigen YPMa (*Yersinia pseudotuberculosis, Yersinia pseudotuberculosis* infection); effector protein YopB, 60 kDa chaperonin, protein WbcP, tyrosin-protein phosphatase YopH, protein YopQ, enterotoxin, Galactoside permease, reductaase NrdE, protein YasN, Invasin Inv, adhesin YadA, outer membrane porin F OmpF, protein UspAI, protein EibA, protein Hia, cell surface protein Ail, chaperone SycD, protein LcrD, protein LcrG, protein LcrV, protein SycE, protein YopE, regulator protein TyeA, protein YopM, protein YopN, protein YopO, protein YopT, protein YopD, protease CIpP, protein MyfA, protein FiIA, and protein PsaA (*Yersinia enterocolitica*, Yersiniosis); where, in brackets is the particular pathogen or the family of pathogens of which the antigen(s) is/are derived and the infectious disease with which the pathogen is associated.

Accordingly, in one certain embodiment, the first antigenic composition and/or the second antigenic composition is for (or is useful for) the treatment or prophylaxis of infection from one or more of the pathogens listed herein; or it is for (or is useful for) the treatment or prophylaxis of a condition, disorder or disease associated with such a pathogen.

In all aspects of the present invention, an epitope, antigen, immunogenic peptide and/or immunogenic polypeptide useful in the present invention may alternatively be from (such as isolated from, derived from, in respect of or has a sequence that is homologous to or a variant of) an amino acid sequence from a tumour or cancer cell.

The terms "tumour" and "cancer" will be well undated to the person of ordinary skill, and includes the meaning of an amount of tissue that has grown (or is growing) abnormally, and cancer includes meaning of a malignant tumor, ie a group of diseases involving abnormal cell growth together with the potential to invade or spread to other parts of the body of the subject. However, not all tumors are cancerous; benign tumors do not spread to other parts of the body of the subject. A tumour cell or a cancer cell therefore includes the meaning of a cell that is (or was) comprised in the tumour or the cancer, respectively, eg including cancer cells that form or give rise to metastases.

Accordingly, and in certain embodiments of the first antigenic composition and/or the second antigenic composition, the amino acid sequence of at least the epitope is from a tumour or cancer cell, or a homolog, a fragment or a variant thereof. In certain of such embodiments, the immunogenic peptide or polypeptide comprised in the first antigenic composition, or encoded by the nucleic acid construct comprised in the first antigenic composition, and the immunogenic peptide or polypeptide encoded by the mRNA construct comprised in the second antigenic composition is from a tumour or cancer cell, or a homolog, a fragment or a variant thereof.

In all of such embodiments, an epitope, antigen, immunogenic peptide and/or immunogenic polypeptide from a tumour or cancer cell may alternatively be described as a "tumour antigen".

Tumour antigens are preferably located on the surface of the (tumour) cell characterizing a mammalian, in particular human tumour (in e.g. systemic or solid tumour diseases). Tumour antigens may also be selected from proteins, which are overexpressed in tumour cells compared to a normal cell. Furthermore, tumour antigens also includes antigens expressed in cells which are (were) not themselves (or originally not themselves) degenerated but are associated with the supposed tumour. Antigens which are connected with tumour-supplying vessels or (re)formation thereof, in particular those antigens which are associated with neovascularization, e.g. growth factors, such as VEGF, bFGF etc., are also included herein. Antigens connected with a tumour furthermore include antigens from cells or tissues, typically embedding the tumour. Further, some substances (usually proteins or peptides) are expressed in patients suffering (knowingly or not-knowingly) from a cancer disease and they occur in increased concentrations in the body fluids of said patients. These substances are also referred to as "tumour antigens", however they are not antigens in the stringent meaning of an immune response inducing substance. The class of tumour antigens can be divided further into tumour-specific antigens (TSAs) and tumour-associated-antigens (TAAs). TSAs can only be expressed by tumour cells and never by normal "healthy" cells. They typically result from a tumour specific mutation. TAAs, which are more common, are usually expressed by both tumour and healthy cells. These antigens are recognized and the antigen-expressing cell can be destroyed by cytotoxic T cells. Additionally, tumour antigens can also occur on the surface of the tumour in the form of, e.g., a mutated receptor. In this case, they can be recognized by antibodies.

Further, tumour associated antigens may be classified as tissue-specific antigens, also called melanocyte-specific antigens, cancer-testis antigens and tumour-specific antigens. Cancer-testis antigens are typically understood to be peptides or proteins of germ-line associated genes which may be activated in a wide variety of tumours. Human cancer-testis antigens may be further subdivided into antigens which are encoded on the X chromosome, so-called CT-X antigens, and those antigens which are not encoded on the X chromosome, the so-called (non-X CT antigens). Cancer-testis antigens which are encoded on the X-chromosome comprises, for example, the family of melanoma antigen genes, the so-called MAGE-family. The genes of the MAGE-family may be characterised by a shared MAGE homology domain (MHD). Each of these antigens, i.e. melanocyte-specific antigens, cancer-testis antigens and tumour-specific antigens, may elicit autologous cellular and humoral immune response. Accordingly, the tumour antigen encoded by the inventive nucleic acid sequence is preferably a melanocyte-specific antigen, a cancer-testis antigen or a tumour-specific antigens, preferably it may be a CT-X antigen, a non-X CT-antigens, a binding partner for a CT-X antigen or a binding partner for a non-X CT-antigen or a tumour-specific antigen, more preferably a CT-X antigen, a binding partner for a non-X CT-antigen or a tumour-specific antigen. Particular preferred tumour antigens are selected from the list consisting of 5T4, 707-AP, 9D7, AFP, AIbZIP HPG1, alpha-5-beta-1-integrin, alpha-5-beta-6-integrin, alpha-actinin-4/m, alpha-methylacyl-coenzyme A racemase, ART-4, ARTC1/m, B7H4, BAGE-1, BCL-2, bcr/abl, beta-catenin/m, BING-4, BRCA1/m, BRCA2/m, CA 15-3/CA 27-29, CA 19-9, CA72-4, CA125, calreticulin, CAMEL, CASP-8/m, cathepsin B, cathepsin L, CD1, CD20, CD22, CD25, CDE30, CD33, CD4, CD52, CD55, CD56, CD80, CDC27/m, CDK4/m, CDKN2A/m, CEA, CLCA2, CML28, CML66, COA-1/m, coactosin-like protein, collage XXIII, COX-2, CT-9/BRD6, Cten, cyclin B1, cyclin D1, cyp-B, CYPB1, DAM-10, DAM-6, DEK-CAN, EFTUD2/m, EGFR, ELF2/m, EMMPRIN, EpCam, EphA2, EphA3, ErbB3, ETV6-AML1, EZH2, FGF-5, FN, Frau-1, G250, GAGE-1, GAGE-2, GAGE-3, GAGE-4, GAGE-5, GAGE-6, GAGE7b, GAGE-8, GDEP, GnT-V, gpl OO, GPC3, GPNMB/m, HAGE, HAST-2, hepsin, Her2/neu, HERV-K-MEL, HLA-A*0201-R1 71, HLA-A1 1/m, HLA-A2/m, HNE, homeobox NKX3.1, HOM-TES-14/SCP-1, HOM-TES-85, HPV-E6, HPV-E7, HSP70-2M, HST-2, hTERT, iCE, IGF-1 R, IL-13Ra2, IL-2R, IL-5, immature laminin receptor, kallikrein-2, kallikrein-4, Ki67, KIAA0205, KIAA0205/m, KK-LC-1, K-Ras/m, LAGE-A1, LDLR-FUT, MAGE-A1, MAGE-A2, MAGE-A3, MAGE-A4, MAGE-A6, MAGE-A9, MAGE-A10, MAGE-A12, MAGE-B1, MAGE-B2, MAGE-B3, MAGE-B4, MAGE-B5, MAGE-B6, MAGE-B10, MAGE-B16, MAGE-B17, MAGE-C1, MAGE-C2, MAGE-C3, MAGE-D1, MAGE-D2, MAGE-D4, MAGE-E1, MAGE-E2, MAGE-F1, MAGE-H1, MAGEL2, mammaglobin A, MART-1/melan-A, MART-2, MART-2/m, matrix protein 22, MC1 R, M-CSF, MEI/m, mesothelia, MG50/PXDN, MMP1 1, MN/CA IX-antigen, MRP-3, MUC-1, MUC-2, MUM-1/m, MUM-2/m, MUM-3/m, myosin class I/m, NA88-A, N-acetylglucosaminyltransferase-V, Neo-PAP, Neo-PAP/m, NFYC/m, NGEP, NMP22, NPM/ALK, N-Ras/m, NSE, NY-ESO-B, NY-ESO-1, OA1, OFA-iLRP, OGT, OGT/m, OS-9, OS-9/m, osteocalcin, osteopontin, pi 5, p190 minor bcr-abl, p53, p53/m, PAGE-4, PAI-1, PAI-2, PAP, PART-1, PATE, PDEF, Pim-1-Kinase, Pin-1, Pml/PARalpha, POTE, PRAME, PRDXS/m, prostein, proteinase-3, PSA, PSCA, PSGR, PSM, PSMA, PTPRK m, RAGE-1, RBAF600/m, RHAMM/CD1 68, RU1, RU2, S-100, SAGE, SART-1, SART-2, SART-3, SCC, SIRT2/m, Sp17, SSX-1, SSX-2/HOM-MEL-40, SSX-4, STAMP-1, STEAP-1, survivin, survivin-2B, SYT-SSX-1, SYT-SSX-2, TA-90, TAG-72, TARP, TEL-AML1, TGFbeta, TGFbetaRII, TGM-4, TPI/m, TRAG-3, TRG, TRP-1, TRP-2/6b, TRP/INT2, TRP-p8, tyrosinase, UPA, VEGFR1, VEGFR-2/FLK-1, and VVT1. Such tumour antigens preferably may be selected from the group consisting of p53, CA125, EGFR, Her2/neu, hTERT, PAP, MAGE-A1, MAGE-A3, Mesothelin, MUC-1, GP100, MART-1, Tyrosinase, PSA, PSCA, PSMA, STEAP-1 VEGF, VEGFR1, VEGFR2, Ras, CEA or WT1, and more preferably from PAP, MAGE-A3, WT1, and MUC-1. Such tumour antigens preferably may be selected from the group consisting of MAGE-A1 (e.g. MAGE-A1 according to accession number M77481), MAGE-A2, MAGE-A3, MAGE-A6 (e.g. MAGE-A6 according to accession number NM_005363), MAGE-C1, MAGE-C2, melan-A (e.g. melan-A according to accession number NM_00551 1), GP100 (e.g. GP100 according to accession number M77348), tyrosinase (e.g. tyrosinase according to accession number NM_000372), surviving (e.g. survivin according to accession number AF077350), CEA (e.g. CEA according to accession number NM_004363), Her-2/neu (e.g. Her-2/neu according to accession number M1 1 730), WT1 (e.g. WT1 according to accession number NM_000378), PRAME (e.g. PRAME according to accession number NM_0061 15), EGFRI (epidermal growth factor receptor 1) (e.g. EGFRI (epidermal growth factor receptor 1) according to accession number AF288738), MUC1, mucin-1 (e.g. mucin-1 according to accession number NMJD02456), SEC61 G (e.g. SEC61 G according to accession number NM_014302), hTERT (e.g. hTERT accession number NM_198253), 5T4 (e.g. 5T4 according to accession number NM_006670), TRP-2 (e.g. TRP-2 according to accession number NM_001922), STEAP1, PCA, PSA, PSMA, etc.

Furthermore tumour antigens also may encompass idiotypic antigens associated with a cancer or tumour disease, particularly lymphoma or a lymphoma associated disease, wherein said idiotypic antigen is an immunoglobulin idiotype of a lymphoid blood cell or a T cell receptor idiotype of a lymphoid blood cell.

Tumour antigens for the treatment of cancer or tumour diseases, are typically proteins of mammalian origin, preferably of human origin. Their selection for treatment of the subject depends on the tumour type to be treated and the expression profile of the individual tumour. A human suffering from prostate cancer, is e.g. preferably treated by a tumour antigen, which is typically expressed (or overexpressed) in prostate carcinoma or specifically overexpressed in the subject to be treated, e.g. any of PSMA, PSCA, and/or PSA.

In particular embodiments, the tumour or cancer cell is a cell that is (or was) one from a cancer or tumour disease which preferably includes one from e.g. Acute lymphoblastic leukemia, Acute myeloid leukemia, Adrenocortical carcinoma, AIDS-related cancers, AIDS-related lymphoma, Anal cancer, Appendix cancer, Astrocytoma, Basal cell carcinoma, Bile duct cancer, Bladder cancer, Bone cancer, Osteosarcoma/Malignant fibrous histiocytoma, Brainstem glioma, Brain tumor, cerebellar astrocytoma, cerebral astrocytoma/malignant glioma, ependymoma, medulloblastoma, supratentorial primitive neuroectodermal tumors, visual pathway and hypothalamic glioma, Breast cancer, Bronchial adenomas/carcinoids, Burkitt lymphoma, childhood Carcinoid tumor, gastrointestinal Carcinoid tumor, Carcinoma of unknown primary, primary Central nervous system lymphoma, childhood Cerebellar astrocytoma, childhood Cerebral astrocytoma/Malignant glioma, Cervical cancer, Childhood cancers, Chronic lymphocytic leukemia, Chronic myelogenous leukemia, Chronic myeloproliferative disorders, Colon Cancer, Cutaneous T-cell lymphoma, Desmoplastic small round cell tumor, Endometrial cancer, Ependymoma, Esophageal cancer, Ewing's sarcoma in the Ewing family of tumors, Childhood Extracranial germ cell tumor, Extragonadal Germ cell tumor, Extrahepatic bile duct cancer, Intraocular melanoma, Retinoblastoma, Gallbladder cancer, Gastric (Stomach) cancer, Gastrointestinal Carcinoid Tumor, Gastrointestinal stromal tumor (GIST), extracranial, extragonadal, or ovarian Germ cell tumor, Gestational trophoblastic tumor, Glioma of the brain stem, Childhood Cerebral Astrocytoma, Childhood Visual Pathway and Hypothalamic Glioma, Gastric carcinoid, Hairy cell leukemia, Head and neck cancer, Heart cancer, Hepatocellular (liver) cancer, Hodgkin lymphoma, Hypopharyngeal cancer, childhood Hypothalamic and visual pathway glioma, Intraocular Melanoma, Islet Cell Carcinoma (Endocrine Pancreas), Kaposi sarcoma, Kidney cancer (renal cell cancer), Laryngeal Cancer, Leukemias, acute lymphoblastic Leukemia, acute myeloid Leukemia, chronic lymphocytic Leukemia, chronic myelogenous Leukemia, hairy cell Leukemia, Lip and Oral Cavity Cancer, Liposarcoma, Liver Cancer, Non-Small Cell Lung Cancer, Small Cell Lung Cancer, Lymphomas, AIDS-related Lymphoma, Burkitt Lymphoma, cutaneous T-Cell Lymphoma, Hodgkin Lymphoma, Non-Hodgkin Lymphomas, Primary Central Nervous System Lymphoma, Waldenstrom Macroglobulinemia, Malignant Fibrous Histiocytoma of Bone/Osteosarcoma, Childhood Medulloblastoma, Melanoma, Intraocular (Eye) Melanoma, Merkel Cell Carcinoma, Adult Malignant Mesothelioma, Childhood Mesothelioma, Metastatic Squamous Neck Cancer with Occult Primary, Mouth Cancer, Childhood Multiple Endocrine Neoplasia Syndrome, Multiple Myeloma/Plasma Cell Neoplasm, Mycosis Fungoides, Myelodysplastic Syndromes, Myelodysplastic/Myeloproliferative Diseases, Chronic Myelogenous Leukemia, Adult Acute Myeloid Leukemia, Childhood Acute Myeloid Leukemia, Multiple Myeloma (Cancer of the Bone-Marrow), Chronic Myeloproliferative Disorders, Nasal cavity and paranasal sinus cancer, Nasopharyngeal carcinoma, Neuroblastoma, Oral Cancer, Oropharyngeal cancer, Osteosarcoma/malignant fibrous histiocytoma of bone, Ovarian cancer, Ovarian epithelial cancer (Surface epithelial-stromal tumor), Ovarian germ cell tumor, Ovarian low malignant potential tumor, Pancreatic cancer, islet cell Pancreatic cancer, Paranasal sinus and nasal cavity cancer, Parathyroid cancer, Penile cancer, Pharyngeal cancer, Pheochromocytoma, Pineal astrocytoma, Pineal germinoma, childhood Pineoblastoma and supratentorial primitive neuroectodermal tumors, Pituitary adenoma, Plasma cell neoplasia Multiple myeloma, Pleuropulmonary blastoma, Primary central nervous system lymphoma, Prostate cancer, Rectal cancer, Renal cell carcinoma (kidney cancer), Cancer of the Renal pelvis and ureter, Retinoblastoma, childhood Rhabdomyosarcoma, Salivary gland cancer, Sarcoma of the Ewing family of tumors, Kaposi Sarcoma, soft tissue Sarcoma, uterine Sarcoma, Sezary syndrome, Skin cancer (nonmelanoma), Skin cancer (melanoma), Merkel cell Skin carcinoma, Small intestine cancer, Squamous cell carcinoma, metastatic Squamous neck cancer with occult primary, childhood Supratentorial primitive neuroectodermal tumor, Testicular cancer, Throat cancer, childhood Thymoma, Thymoma and Thymic carcinoma, Thyroid cancer, childhood Thyroid cancer, Transitional cell cancer of the renal pelvis and ureter, gestational Trophoblastic tumor, Urethral cancer, endometrial Uterine cancer, Uterine sarcoma, Vaginal cancer, childhood Visual pathway and hypothalamic glioma, Vulvar cancer, Waldenstrom macroglubulinemia, and childhood Wilms tumor (kidney cancer).

In particular of such embodiments, the tumour or cancer cell is a cell from a tumour or cancer selected from the list consisting of: prostate cancer, lung cancer, breast cancer, brain cancer, colon cancer, stomach cancer, liver cancer, pancreas cancer, ovary cancer, lymphoma, leukemia, and myeloma.

Accordingly, in another certain embodiment of the present invention, the first antigenic composition and/or the second antigenic composition is for (or is useful for) the treatment or prophylaxis of a tumour or cancer (such as one or more of those described herein); or it is for (or is useful for) the treatment or prophylaxis of a condition, disorder or disease associated with one or more of the tumours or cancers disclosed herein.

In all aspects of the present invention, an epitope, antigen, immunogenic peptide and/or immunogenic polypeptide useful in the present invention may yet further alternatively be from (such as isolated from, derived from, in respect of or has a sequence that is homologous to or a variant of) an amino acid sequence from an allergenic antigen or an autoimmune self-antigen or a fragment, variant or derivative thereof.

Allergenic antigens may be selected from antigens derived from different sources, e.g. from animals, plants, fungi, bacteria, etc. Sources of allergens in this context include e.g. grasses, pollens, molds, drugs, or numerous environmental triggers, etc. Allergenic antigens typically belong to different classes of compounds, such as nucleic acids and their fragments, proteins or peptides and their fragments, carbohydrates, polysaccharides, sugars, lipids, phospholipids, etc. Of particular interest in the context of the present invention are protein or peptide antigens and their fragments or epitopes, or nucleic acids and their fragments, particularly nucleic acids and their fragments, encoding such protein or peptide antigens and their fragments or epitopes.

Antigens associated with allergy or allergic disease (allergens or allergenic antigens) are preferably derived from a source selected from the list consisting of:

*Acarus* spp (Aca s 1, Aca s 10, Aca s 10.0101, Aca s 13, Aca s 13.0101, Aca s 2, Aca s 3, Aca s 7, Aca s 8), *Acanthocybium* spp (Aca so 1), *Acanthocheilonema* spp (Aca v 3, Aca v 3.0101), *Acetes* spp (Ace ja 1), *Actinidia* spp (Act a 1, Act c 1, Act c 10, Act c 10.0101, Act c 2, Act c 4, Act c 5, Act c 5.0101, Act c 8, Act c 8.0101, Act c Chitinase, Act d 1, Act d 1.0101, Act d 10, Act d 10.0101, Act d 10.0201, Act d 11, Act d 11.0101, Act d 2, Act d 2.0101, Act d 3, Act d 3.0101, Act d 3.02, Act d 4, Act d 4.0101, Act d 5, Act d 5.0101, Act d 6, Act d 6.0101, Act d 7, Act d 7.0101, Act d 8, Act d 8.0101, Act d 9, Act d 9.0101, Act d Chitinase, Act e 1, Act e 5), *Acyrthosiphon* spp (Acy pi 7, Acy pi 7.0101, Acy pi 7.0102), *Adenia* spp (Ade v RIP), *Aedes* spp (Aed a 1, Aed a 1.0101, Aed a 2, Aed a 2.0101, Aed a 3, Aed a 3.0101, Aed a 4, Aed a 7, Aed a 7.0101, Aed a 7.0102, Aed a 7.0103, Aed a 7.0104, Red a 7.0105, Aed a 7.0106, Aed a 7.0107, Aed a 7.0108, Aed a 7.0109, Aed a 7.0110, Aed a 7.0111, Aed al 1, Aed al 3, Aed al 37 kD, Aed v 37 kD, Aed v 63 kD), *Aegilops* spp (Aeg ta 28, Aeg ta alpha_Gliadin, Aeg urn 28, Aeg un 28), *Aethaloperca* spp (Aet ro 1), *Agropyron* spp (Agr c 7), *Agrostis* spp (Agr ca 1, Agr ca 5, Agr g 1, Agr g 4, Agr s 5), *Agrobacterium* spp (Agr sp CP4 EPSPS), *Ailuropoda* spp (Ail me Phosvitin, Ail me TCTP), *Aix* spp (*Aix* ga 1, *Aix* sp 1), *Aleuroglyphus* spp (Ale o 1, Ale o 10, Ale o 10.0101, Ale o 10.0102, Ale o 13, Ale o 14, Ale o 2, Ale o 20, Ale o 3, Ale o 5, Ale o 7, Ale o 8, Ale o 9), *Allium* spp (All a 3, All a Alliin lyase, All c 3, All c 30 kD, All c 4, All c Alliin lyase, All p Alliin lyase, All s Alliin lyase), *Alnus* spp (Aln g 1, Aln g 1.0101, Aln g 1/Bet v 1/Cor a 1 TPC7, Aln g 1/Bet v 1/Cor a 1 TPC9, Aln g 2, Aln g 4, Aln g 4.0101), *Alopochen* spp (Alo ae 1), *Alopecurus* spp (Alo p 1, Alo p 5), *Alternaria* spp (Alt a 1, Alt a 1.0101, Alt a 1.0102, Alt a 10, Alt a 10.0101, Alt a 12, Alt a 12.0101, Alt a 13, Alt a 13.0101, Alt a 2, Alt a 3, Alt a 3.0101, Alt a 4, Alt a 4.0101, Alt a 5, Alt a 5.0101, Alt a 6, Alt a 6.0101, Alt a 7, Alt a 7.0101, Alt a 70 kD, Alt a 8, Alt a 8.0101, Alt a 9, Alt a MnSOD, Alt a NTF2, Alt a TCTP, Alt ar 1, Alt arg 1, Alt b 1, Alt bl 1, Alt br 1, Alt c 1, Alt ca 1, Alt ce 1, Alt ch 1, Alt ci 1, Alt co 1, Alt cr 1, Alt ct 1, Alt cu 1, Alt cy 1, Alt d 1, Alt du 1, Alt e 1, Alt et 1, Alt eu 1, Alt ga 1, Alt gr 1, Alt j 1, Alt l 1, Alt lo 1, Alt m 1, Alt me 1, Alt mi 1, Alt mo 1, Alt o 1, Alt p 1, Alt ph 1, Alt po 1, Alt ps 1, Alt r 1, Alt s 1, Alt se 1, Alt sm 1, Alt so 1, Alt su 1, Alt t 1, Alt to 1, Alt to 1), *Amaranthus* spp (Ama r 2, Ama r 2.0101, Ama v 2, Ama v 2.0101, Ama v 2.0201), *Ambrosia* spp (Amb a 1, Amb a 1.0101, Amb a 1.0201, Amb a 1.0202, Amb a 1.0301, Amb a 1.0302, Amb a 1.0303, Amb a 1.0304, Amb a 1.0305, Amb a 1.0401, Amb a 1.0402, Amb a 1.0501, Amb a 1.0502, Amb a 10, Amb a 10.0101, Amb a 3, Amb a 3.0101, Amb a 4, Amb a 4.0101, Amb a 5, Amb a 5.0101, Amb a 6, Amb a 6.0101, Amb a 7, Amb a 7.0101, Amb a 8, Amb a 8.0101, Amb a 8.0102, Amb a 9, Amb a 9.0101, Amb a 9.0102, Amb a CPI, Amb p 1, Amb p 5, Amb p 5.0101, Amb p 5.0201, Amb t 5, Amb t 5.0101, Amb t 8), *Ammothea* spp (Amm h 7, Amm h 7.0101), *Anadara* spp (Ana br 1), *Ananas* spp (Ana c 1, Ana c 1.0101, Ana c 2, Ana c 2.0101, Ana c 2.0101 (MUXF3)), *Anas* spp (Ana ca 1), *Anarhichas* spp (Ana l 1), *Anacardium* spp (Ana o 1, Ana o 1.0101, Ana o 1.0102, Ana o 2, Ana o 2.0101, Ana o 3, Ana o 3.0101), *Anas* spp (Ana p 1, Ana p 2, Ana p 3), *Anguilla* spp (Ang a 1, Ang j 1), *Anisakis* spp (Ani s 1, Ani s 1.0101, Ani s 10, Ani s 10.0101, Ani s 11, Ani s 11.0101, Ani s 12, Ani s 12.0101, Ani s 2, Ani s 2.0101, Ani s 24 kD, Ani s 3, Ani s 3.0101, Ani s 4, Ani s 4.0101, Ani s 5, Ani s 5.0101, Ani s 6, Ani s 6.0101, Ani s 7, Ani s 7.0101, Ani s 8, Ani s 8.0101, Ani s 9, Ani s 9.0101, Ani s CCOS3, Ani s Cytochrome B, Ani s FBPP, Ani s NADHDS4L, Ani s NARaS, Ani s PEPB, Ani s Troponin), *Annona* spp (Ann c Chitinase), *Anopheles* spp (Ano da 17, Ano da 17.0101, Ano da 27, Ano da 27.0101, Ano da 7, Ano da 7.0101, Ano g 7, Ano g 7.0101), *Anser* spp (Ans a 1, Ans a 2, Ans a 3, Ans in 1), *Anthoxanthum* spp (Ant o 1, Ant o 1.0101, Ant o 12, Ant o 13, Ant o 2, Ant o 4, Ant o 5, Ant o 6, Ant o 7), *Apis* spp (Api c 1, Api c 1.0101, Api c 10, Api c 2, Api c 4, Api d 1, Api d 1.0101, Api d 4, Api fl 4), *Apium* spp (Api g 1, Api g 1.0101, Api g 1.0201, Api g 2, Api g 2.0101, Api g 3, Api g 3.0101, Api g 4, Api g 4.0101, Api g 5, Api g 5.0101, Api g 6, Api g 6.0101), *Apis* spp (Api m 1, Api m 1.0101, Api m 10, Api m 10.0101, Api m 11, Api m 11.0101, Api m 11.0201, Api m 13 kD, Api m 2, Api m 2.0101, Api m 3, Api m 3.0101, Api m 4, Api m 4.0101, Api m 5, Api m 5.0101, Api m 6, Api m 6.0101, Api m 7, Api m 7.0101, Api m 8, Api m 8.0101, Api m 9, Api m 9.0101, Api m A1-A2, Api m A1-A2-A3, Api m Apalbumin 1, Api m Apalbumin 2, Api me 1, Api me 4), *Arachis* spp (Ara d 2, Ara d 6, Ara f 3, Ara f 4, Ara h 1, Ara h 1.0101, Ara h 10, Ara h 10.0101, Ara h 10.0102, Ara h 11, Ara h 11.0101, Ara h 2, Ara h 2.0101, Ara h 2.0102, Ara h 2.0201, Ara h 2.0202, Ara h 3, Ara h 3.0101, Ara h 4, Ara h 4.0101, Ara h 5, Ara h 5.0101, Ara h 6, Ara h 6.0101, Ara h 7, Ara h 7.0101, Ara h 7.0201, Ara h 7.0202, Ara h 8, Ara h 8.0101, Ara h 8.0201, Ara h 9, Ara h 9.0101, Ara h 9.0201, Ara h Agglutinin, Ara h Oleosin 18 kD, Ara i 2, Ara i 6), *Arabidopsis* spp (Ara t 3, Ara t 8, Ara t GLP), *Archosargus* spp (Arc pr 1), *Archaeopotamobius* spp (Arc s 8, Arc s 8.0101), *Aequipecten* spp (Arg i 1), *Argas* spp (Arg r 1, Arg r 1.0101), *Ariopsis* spp (Ari fe 1), *Armoracia* spp (Arm r HRP), *Arrhenatherum* spp (Arr e 1, Arr e 5), *Artemisia* spp (Art a 1, Art ap 1), *Artemia* spp (Art fr 1, Art fr 1.0101, Art fr 5, Art fr 5.0101), *Arthrobacter* spp (Art gl CO), *Achorion* spp (Art gy 7), *Artocarpus* spp (Art h 17 kD, Art h 4), *Arthrospira* spp (Art pl beta_Phycocyanin), *Artemisia* spp (Art v 1, Art v 1.0101, Art v 1.0102, Art v 1.0103, Art v 1.0104, Art v 1.0105, Art v 1.0106, Art v 1.0107, Art v 2, Art v 2.0101, Art v 3, Art v 3.0101, Art v 3.0201, Art v 3.0202, Art v 3.0301, Art v 4, Art v 4.0101, Art v 4.0201, Art v 47 kD, Art v 5, Art v 5.0101, Art v 6, Art v 6.0101, Art v 60 kD), *Arthroderma* spp (Art va 4), *Ascaris* spp (Asc 13, Asc l 3.0101, Asc l 3.0102, Asc l 34 kD, Asc s 1, Asc s 1.0101, Asc s 3, Asc s 3.0101, Asc s GST), *Aspergillus* spp (Asp aw Glucoamylase, Asp c 22, Asp f 1, Asp f 1.0101, Asp f 10, Asp f 10.0101, Asp f 11, Asp f 11.0101, Asp f 12, Asp f 12.0101, Asp f 13, Asp f 13.0101, Asp f 15, Asp f 15.0101, Asp f 16, Asp f 16.0101, Asp f 17, Asp f 17.0101, Asp f 18, Asp f 18.0101, Asp f 2, Asp f 2.0101, Asp f 22, Asp f 22.0101, Asp f 23, Asp f 23.0101, Asp f 27, Asp f 27.0101, Asp f 28, Asp f 28.0101, Asp f 29, Asp f 29.0101, Asp f 3, Asp f 3.0101, Asp f 34, Asp f 34.0101, Asp f 4, Asp f 4.0101, Asp f 5, Asp f 5.0101, Asp f 56 kD, Asp f 6, Asp f 6.0101, Asp f 7, Asp f 7.0101, Asp f8, Asp f 8.0101, Asp f 9, Asp f 9.0101, Asp f AfCalAp, Asp f AT_V, Asp f Catalase, Asp f Chitosanase, Asp f CP, Asp f DPPV, Asp f FDH, Asp f gamma_Actin, Asp f Glucosidase, Asp f GPI, Asp f GST, Asp f GT, Asp f IAO, Asp f IPMI, Asp f LPL1, Asp f LPL3, Asp f Mannosidase, Asp f MDH, Asp f PL, Asp f PUP, Asp f RPS3, Asp f SXR, Asp fl 13, Asp fl 13.0101, Asp fl 18, Asp fl 2, Asp fl 21, Asp fl 3, Asp fl 4, Asp fl 7, Asp fl 8, Asp fl 9, Asp me Seaprose, Asp n 14, Asp n 14.0101, Asp n 18, Asp n 18.0101, Asp n 25, Asp n 25.0101, Asp n 30, Asp n Glucoamylase, Asp n Hemicellulase, Asp n Pectinase, Asp o 13, Asp o 13.0101, Asp o 21, Asp o 21.0101, Asp o 3, Asp o 4, Asp o 7, Asp o 8, Asp o Lactase, Asp o Lipase, Asp oc 13, Asp r 1, Asp sa AP, Asp sp Glucoamylase, Asp sp Glucoseoxidase, Asp sp PL, Asp sp PME, Asp sy 13, Asp v 13, Asp v 13.0101, Asp v Catalase A, Asp v Enolase, Asp v GAPDH, Asp v MDH, Asp v SXR), *Asparagus* spp (Aspa o 1, Aspa o 1.01, Aspa o 1.02, Aspa o 17 kD, Aspa o 4), *Aspergillus* spp (Aspe ni 2, Aspe ni 3, Aspe ni 4, Aspe ni 7, Aspe ni 8, Aspe ni 9), *Avena* spp (Ave s 1, Ave s 12, Ave s 13, Ave s 2, Ave s 4, Ave s 5, Ave s 7), *Babylonia* spp (Bab ja 1), *Bacillus* spp (Bac al Subtilisin, Bac cl Subtilisin, Bac l Subtilisin, Bac li aA, Bac li Subtilisin), *Bactrocera* spp (Bac of 27, Bac ol 27.0101), *Bacillus* spp (Bac sp aA1, Bac sp aA3, Bac sp Decarboxylase, Bac st amyM, Bac su Subtilisin, Bac t CrylAb, Bac t CrylFa, Bac t Cry3Bb1, Bac t Cry9c), *Bagre* spp (Bag ma 1), *Batistes* spp (Bal ca 1), *Balanus* spp (Bal r 1, Bal r 1.0101), *Beauveria* spp (Bea b Ald, Bea b Enol, Bea b f2, Bea b Hex), *Bertholletia* spp (Ber e 1, Ber e 1.0101, Ber e 2, Ber e 2.0101), *Beryx* spp (Ber sp 1), *Betula* spp (Bet ab 1, Bet al 1, Bet ch 1, Bet co 1, Bet da 1, Bet gr 1, Bet hu 1, Bet le 1, Bet me 1, Bet n 1, Bet p 1, Bet pa 1, Bet po 1, Bet pu 1, Bet pu 2, Bet pu 4, Bet pu 6, Bet pu 7, Bet sc 1, Bet ut 1, Bet v 1, Bet v 1 B1-B1-B1, Bet v 1 fv Mal 4x, Bet v 1.0101, Bet v 1.0102, Bet v 1.0103, Bet v 1.0201, Bet v 1.0301, Bet v 1.0401, Bet v 1.0402, Bet v 1.0501, Bet v 1.0601, Bet v 1.0602, Bet v 1.0701, Bet v 1.0801, Bet v 1.0901, Bet v 1.1001, Bet v 1.1101, Bet v 1.1201, Bet v 1.1301, Bet v 1.1401, Bet v 1.1402, Bet v 1.1501, Bet v 1.1502, Bet v 1.1601, Bet v 1.1701, Bet v 1.1801, Bet v 1.1901, Bet v 1.2001, Bet v 1.2101, Bet v 1.2201, Bet v 1.2301, Bet v 1.2401, Bet v 1.2501, Bet v 1.2601, Bet v 1.2701, Bet v 1.2801, Bet v 1.2901, Bet v 1.3001, Bet v 1.3101, Bet v 2, Bet v 2.0101, Bet v 3, Bet v 3.0101, Bet v 4, Bet v 4.0101, Bet v 6, Bet v 6.0101, Bet v 6.0102, Bet v 7, Bet v 7.0101, Bet v 8, Bet v Glucanase), *Beta* spp (Beta v 1, *Beta* v 1.0101, *Beta* v 2, *Beta* v 2.0101), *Blattella* spp (Bla g 1, Bla g 1.0101, Bla g 1.0102, Bla g 1.0103, Bla g 1.0201, Bla g 1.0202, Bla g 2, Bla g 2.0101, Bla g 2.0201, Bla g 36 kD, Bla g 4, Bla g 4.0101, Bla g 4.0201, Bla g 5, Bla g 5.0101, Bla g 5.0201, Bla g 6, Bla g 6.0101, Bla g 6.0201, Bla g 6.0301, Bla g 7, Bla g 7.0101, Bla g 8, Bla g 8.0101, Bla g 9, Bla g Enolase, Bla g GSTD1, Bla g RACK1, Bla g TPI, Bla g Trypsin, Bla g Vitellogenin), *Blatta* spp (Bla o 1, Bla o 7), *Blomia* spp (Blo t 1, Blo t 1.0101, Blo t 1.0201, Blo t 10, Blo t 10.0101, Blo t 10.0102, Blo t 11, Blo t 11.0101, Blo t 12, Blo t 12.0101, Blo t 12.0102, Blo t 13, Blo t 13.0101, Blo t 14, Blo t 15, Blo t 18, Blo t 19, Blo t 19.0101, Blo t 2, Blo t 2.0101, Blo t 2.0102, Blo t 2.0103, Blo t 20, Blo t 21, Blo t 21.0101, Blo t 3, Blo t 3.0101, Blo t 4, Blo t 4.0101, Blo t 5, Blo t 5.0101, Blo t 6, Blo t 6.0101, Blo t 7, Blo t 8, Blo t 9, Blo t HSP70), *Bombus* spp (Bom ar 4, Bom by 4, Bom p 1, Bom p 1.0101, Bom p 2, Bom p 3, Bom p 4, Bom p 4.0101, Bom t 1, Bom t 1.0101, Bom t 4, Bom t 4.0101), *Bombyx* spp (Bomb m 1, Bomb m 1.0101, Bomb m 7, Bomb m 7.0101, Bomb m 7.0102, Bomb m 7.0103, Bomb m 7.0104, Bomb m 7.0105, Bomb m 7.0106), *Boophilus* spp (Boo m 1, Boo m 7, Boo m 7.0101), *Bos* spp (Bos d 2, *Bos* d 2.0101, *Bos* d 2.0102, *Bos* d 2.0103, *Bos* d 3, *Bos* d 3.0101, *Bos* d 4, *Bos* d 4.0101, *Bos* d 5, *Bos* d 5.0101, *Bos* d 5.0102, *Bos* d 6, *Bos* d 6 (MDA), *Bos* d 6.0101, *Bos* d 7, *Bos* d 7.0101, *Bos* d 8, *Bos* d 8 alphaS1, *Bos* d 8 alphaS2, *Bos* d 8 beta, *Bos* d 8 kappa, *Bos* d alpha21, *Bos* d alpha21.0101, *Bos* d Chymosin, *Bos* d Fibrin, *Bos* d Gelatin, *Bos* d HG, *Bos* d Insulin, *Bos* d Lactoferrin, *Bos* d Lactoperoxidase, *Bos* d Myoglobin, *Bos* d OBP, *Bos* d OSCP, *Bos* d Phosvitin, *Bos* d PLA2, *Bos* d PRVB, *Bos* d Thrombin, *Bos* d TI, *Bos* gr ALA, *Bos* gr Myoglobin), *Bothrops* spp (Bot as 1, Bot at 1), *Bouteloua* spp (Bou g 1), *Biting* spp (Boy ov 1), *Brama* spp (Bra du 1), *Brassica* spp (Bra j 1, Bra j 1.0101, Bra n 1, Bra n 1.0101, Bra n 4, Bra n 7, Bra n 8, Bra n PG, Bra ni 8, Bra o 3, Bra o 3.0101, Bra r 1, Bra r 1.0101, Bra r 2, Bra r 2.0101, Bra r 3, Bra r 4, Bra r 7), *Bromus* spp (Bro a 1, Bro a 4), *Brosme* spp (Bro br 1), *Bromus* spp (Bro i 1, Bro i 5, Bro i 7), *Brugia* spp (Bru m 3, Bru m 3.0101, Bru m Bm33), *Bubalus* spp (Bub b ALA, Bub b BLG, Bub b Casein, Bub b Casein alphaS1, Bub b Casein alphaS2, Bub b Casein beta, Bub b Casein kappa), *Caenorhabditis* spp (Cae b 3, Cae b 3.0101, Cae br 3, Cae br 3.0101, Cae e 3, Cae e 3.0101, Cae e 3.0102, Cae re 13, Cae re 13.0101), *Cajanus* spp (Caj c 1), *Caligus* spp (Cal cl 1, Cal cl 1.0101, Cal cl 1.0102), *Calamus* spp (Cal le 1), *Callinectes* spp (Cal s 2), *Camelus* spp (Cam d ALA, Cam d Casein, Cam d Casein alphaS1, Cam d Casein alphaS2, Cam d Casein beta, Cam d Casein kappa), *Camponotus* spp (Cam fl 7, Cam fl 7.0101), *Canis* spp (Can f 1, Can f 1.0101, Can f 2, Can f 2.0101, Can f 3, Can f 3.0101, Can f 4, Can f 4.0101, Can f 5, Can f 5.0101, Can f 6, Can f 6.0101, Can f Feld1-like, Can f Homs2-like, Can f Phosvitin, Can f TCTP), *Canthidermis* spp (Can ma 1), *Cancer* spp (Can mg 2, Can p 1), *Cannabis* spp (Can s 3), *Candida* spp (Cand a 1, Cand a 1.0101, Cand a 3, Cand a 3.0101, Cand a CAAP, Cand a CyP, Cand a Enolase, Cand a FPA, Cand a MnSOD, Cand a PGK, Cand b 2, Cand b 2.0101, Cand b FDH, Cand r Lipase), *Capsicum* spp (Cap a 1, Cap a 1.0101, Cap a 17 kD, Cap a 2, Cap a 2.0101, Cap a 30 kD, Cap a Glucanase, Cap ch 17 kD), *Caprella* spp (Cape 1), *Capra* spp (Cap h ALA, Cap h BLG, Cap h Casein, Cap h Casein alphaS1, Cap h Casein alphaS2, Cap h Casein beta, Cap h Casein kappa, Cap h GSA), *Capitulum* spp (Cap m 1), *Carassius* spp (Car au 1), *Carpinus* spp (Car b 1, Car b 1.0101, Car b 1.0102, Car b 1.0103, Car b 1.0104, Car b 1.0105, Car b 1.0106, Car b 1.0107, Car b 1.0108, Car b 1.0109, Car b 1.0110, Car b 1.0111, Car b 1.0112, Car b 1.0113, Car b 1.0201, Car b 1.0301, Car b 1.0302, Car b 2, Car b 4), *Caranx* spp (Car cr 1), *Carya* spp (Car i 1, Car i 1.0101, Car i 2, Car i 4, Car i 4.0101), *Carcinus* spp (Car ma 2), *Caryota* spp (Car mi 2), *Carica* spp (Car p 1, Car p Chitinase, Car p Chymopapain, Car p Endoproteinase), *Castanea* spp (Cas c 24 kD, Cas s 1, Cas s 1.0101, Cas s 1.0102, Cas s 1.0103, Cas s 2, Cas s 5, Cas s 5.0101, Cas s 8, Cas s 8.0101, Cas s 9, Cas s 9.0101), *Catharanthus* spp (Cat r 1, Cat r 1.0101, Cat r 17 kD, Cat r 2), *Caulolatilus* spp (Cau ch 1), *Cavia* spp (Cav p 1, Cav p 1.0101, Cav p 2, Cav p 2.0101, Cav p 3, Cav p 3.0101, Cav p Gelatin, Cav p GSA), *Centropristis* spp (Cen s 1), *Cephalopholis* spp (Cep so 1), *Charybdis* spp (Cha f 1, Cha f 1.0101), *Chaetodipterus* spp (Cha fa 1), *Chamaecyparis* spp (Cha o 1, Cha o 1.0101, Cha o 2, Chao 2.0101), *Chenopodium* spp (Che a 1, Che a 1.0101, Che a 2, Che a 2.0101, Che a 3, Che a 3.0101), *Chironomus* spp (Chi k 1, Chi k 10, Chi k 10.0101), *Chinchilla* spp (Chi l 21 kD_a, Chi l 21 kD_b), *Chionoecetes* spp (Chi o 1, Chi o 1.0101, Chi o 2, Chi o 4, Chi o 6, Chi o alpha_Actin, Chi o SERCA), *Chironomus* spp (Chi t 1, Chi t 1.0101, Chi t 1.0201, Chi t 2, Chi t 2.0101, Chi t 2.0102, Chi t 3, Chi t 3.0101, Chi t 4, Chi t 4.0101, Chi t 5, Chi t 5.0101, Chi t 6, Chi t 6.0101, Chi t 6.0201, Chi t 7, Chi t 7.0101, Chi t 8, Chi t 8.0101, Chi t 9, Chi t 9.0101), *Chlamys* spp (Chl n 1), *Chloephaga* spp (Chl pi 1), *Chortoglyphus* spp (Cho a 10), *Chrysomela* spp (Chr tr 7, Chr tr 7.0101), *Cicer* spp (Cic a 2S Albumin, Cic a Albumin), *Cichorium* spp (Cic i 1), *Cimex* spp (Cim l Nitrophorin), *Citrus* spp (Cit l 1, Cit l 3, Cit l 3.0101), *Citrullus* spp (Cit la 2, Cit la MDH, Cit la TPI), *Citrus* spp (Cit r 3, Cit r 3.0101, Cit s 1, Cit s 1.0101, Cit s 2, Cit s 2.0101, Cit s 3, Cit s 3.0101, Cit s 3.0102, Cit s IFR), *Cladosporium* spp (Cla c 14, Cla c 14.0101, Cla c 9, Cla c 9.0101, Cla h 1, Cla h 10, Cla h 10.0101, Cla h 12, Cla h 12.0101, Cla h 2, Cla h 2.0101, Cla h 42 kD, Cla h 5, Cla h 5.0101, Cla h 6, Cla h 6.0101, Cla h 7, Cla h 7.0101, Cla h 8, Cla h 8 CSP, Cla h 8.0101, Cla h 9, Cla h 9.0101, Cla h abH, Cla h GST, Cla h HCh1, Cla h HSP70, Cla h NTF2, Cla h TCTP), *Clostridium* spp (Clo hi Collagenase, Clo t Toxoid), *Clupea* spp (Clu h 1, Clu h 1.0101, Clu h 1.0201, Clu h 1.0301), *Cocos* spp (Coc n 2, Coc n 4, Coc n 5), *Coccidioides* spp (Coc po 8), *Coffea* spp (Cof a 1, Cof a 1.0101), *Columba* spp (Col l PSA), *Coprinus* spp (Cop c 1, Cop c 1.0101, Cop c 2, Cop c 2.0101, Cop c 3, Cop c 3.0101, Cop c 4, Cop c 5, Cop c 5.0101, Cop c 6, Cop c 7, Cop c 7.0101), *Corylus* spp (Cor a 1, Cor a 1.0101, Cor a 1.0102, Cor a 1.0103, Cor a 1.0104, Cor a 1.0201, Cor a 1.0301, Cor a 1.0401, Cor a 1.0402, Cor a 1.0403, Cor a 1.0404, Cor a 10, Cor a 10.0101, Cora 11, Cora 11.0101, Cora 12, Cora 12.0101, Cora 13, Cora 13.0101, Cor a 14, Cora 14.0101, Cora 2, Cora 2.0101, Cora 2.0102, Cora 8, Cora 8.0101, Cora 9, Cor a 9.0101), *Corynebacterium* spp (Cor d Toxoid), *Corylus* spp (Cor he 1), *Coryphaena* spp (Cor hi 1), *Coriandrum* spp (Cor s 1, Cor s 11 kD, Cor s 2), *Cotoneaster* spp (Cot l 3), *Crangon* spp (Cra c 1, Cra c 1.0101, Cra c 2, Cra c 2.0101, Cra c 4, Cra c 4.0101, Cra c 5, Cra c 5.0101, Cra c 6, Cra c 6.0101, Cra c 8, Cra c 8.0101), *Crassostrea* spp (Cra g 1), *Cricetus* spp (Cri c HSA), *Crivellia* spp (Cri pa 1), *Crocus* spp (Cro s 1, Cro s 1.0101, Cro s 2, Cro s 2.0101, Cro s 3, Cro s 3.01, Cro s 3.02), *Cryptomeria* spp (Cry j 1, Cry j 1.0101, Cry j 1.0102, Cry j 1.0103, Cry j 2, Cry j 2.0101, Cry j 2.0102, Cry j 3, Cry j 3.1, Cry j 3.2, Cry j 3.3, Cry j 3.4, Cry j 3.5, Cry j 3.6, Cry j 3.7, Cry j 3.8, Cry j 4, Cry j AP, Cry j Chitinase, Cry j CPA9, Cry j IFR, Cry j LTP, Cry j P1-P2), *Cryphonectria* spp (Cry p AP), *Ctenocephalides* spp (Cte f 1, Cte f 1.0101, Cte f 2, Cte f 2.0101, Cte f 3, Cte f 3.0101), *Ctenopharyngodon* spp (Cte id 1), *Cucumis* spp (Cuc m 1, Cuc m 1.0101, Cuc m 2, Cuc m 2.0101, Cuc m 3, Cuc m 3.0101, Cuc m Lec17, Cuc m MDH), *Cucurbita* spp (Cuc ma 18 kD, Cuc ma 2, Cuc p 2, Cuc p AscO), *Cucumis* spp (Cuc s 2), *Culicoides* spp (Cul n 1, Cul n 10, Cul n 11, Cul n 2, Cul n 3, Cul n 4, Cul n 5, Cul n 6, Cul n 7, Cul n 8, Cul n 9, Cul n HSP70), *Culex* spp (Cul q 28 kD, Cul q 35 kD, Cul q 7, Cul q 7.0101, Cul q 7.0102), *Culicoides* spp (Cul so 1), *Cuminum* spp (Cum c 1, Cum c 2), *Cupressus* spp (Cup a 1, Cup a 1.0101, Cup a 1.02, Cup a 2, Cup a 3, Cup a 4, Cup a 4.0101, Cup s 1, Cup s 1.0101, Cups 1.0102, Cups 1.0103, Cups 1.0104, Cups 1.0105, Cups 3, Cups 3.0101, Cup s 3.0102, Cup s 3.0103, Cup s 8), *Cochliobolus* spp (Cur l 1, Cur l 1.0101, Cur l 2, Cur l 2.0101, Cur l 3, Cur l 3.0101, Cur l 4, Cur l 4.0101, Cur l ADH, Cur l GST, Cur l MnSOD, Cur l Oryzin, Cur l Trx, Cur l ZPS1), *Cyanochen* spp (Cya cy 1), *Cynoscion* spp (Cyn ar 1), *Cynosurus* spp (Cyn cr 1, Cyn cr 5), *Cynodon* spp (Cyn d 1, Cyn d 1.0101, Cyn d 1.0102, Cyn d 1.0103, Cyn d 1.0104, Cyn d 1.0105, Cyn d 1.0106, Cyn d 1.0107, Cyn d 1.0201, Cyn d 1.0202, Cyn d 1.0203, Cyn d 1.0204, Cyn d 10, Cyn d 11, Cyn d 12, Cyn d 12.0101, Cyn d 13, Cyn d 15, Cyn d 15.0101, Cyn d 2, Cyn d 22, Cyn d 22.0101, Cyn d 23, Cyn d 23.0101, Cyn d 24, Cyn d 24.0101, Cyn d 4, Cyn d 5, Cyn d 6, Cyn d 7, Cyn d 7.0101), *Cynoscion* spp (Cyn ne 1), *Cynomys* spp (Cyn sp Lipocalin), *Cyprinus* spp (Cyp c 1, Cyp c 1.01, Cyp c 1.02), *Daboia* spp (Dab ru 1), *Dactylis* spp (Dac g 1, Dac g 1.01, Dac g 1.0101, Dac g 1.02, Dac g 12, Dac g 13, Dac g 2, Dac g 2.0101, Dac g 3, Dac g 3.0101, Dac g 4, Dac g 4.0101, Dac g 5, Dac g 5.0101, Dac g 7), *Dama* spp (Dam d CSA), *Danio* spp (Dan re 1, Dan re 2, Dan re alpha21, Dan re CK), *Dasyatis* spp (Das ak 1, Das am 1, Das sa 1), *Daucus* spp (Dau c 1, Dau c 1.0101, Dau c 1.0102, Dau c 1.0103, Dau c 1.0104, Dau c 1.0105, Dau c 1.0201, Dau c 1.0301, Dau c 3, Dau c 4, Dau c 4.0101, Dau c CyP), *Decapterus* spp (Dec ru 1), *Dendronephthya* spp (Den n 1, Den n 1.0101), *Dermatophagoides* spp (Der f 1, Der f 1.0101, Der f 1.0102, Der f 1.0103, Der f 1.0104, Der f 1.0105, Der f 1.0106, Der f 1.0107, Der f 1.0108, Der f 1.0109, Der f 1.0110, Der f 10, Der f 10.0101, Der f 10.0102, Der f 11, Der f 11.0101, Der f 13, Der f 13.0101, Der f 14, Der f 14.0101, Der f 15, Der f 15.0101, Der f 16, Der f 16.0101, Der f 17, Der f 17.0101, Der f 18, Der f 18.0101, Der f 2, Der f 2.0101, Der f 2.0102, Der f 2.0103, Der f 2.0104, Der f 2.0105, Der f 2.0106, Der f 2.0107, Der f 2.0108, Der f 2.0109, Der f 2.0110, Der f 2.0111, Der f 2.0112, Der f 2.0113, Der f 2.0114, Der f 2.0115, Der f 2.0116, Der f 2.0117, Der f 20, Der f 21, Der f 22, Der f 22.0101, Der f 3, Der f 3.0101, Der f 4, Der f 5, Der f 6, Der f 6.0101, Der f 7, Der f 7.0101, Der f 8, Der f 9, Der f HSP70), *Dermanyssus* spp (Der g 10, Der g 10.0101), *Dermatophagoides* spp (Der m 1, Der m 1.0101, Der p 1, Der p 1.0101, Der p 1.0102, Der p 1.0103, Der p 1.0104, Der p 1.0105, Der p 1.0106, Der p 1.0107, Der p 1.0108, Der p 1.0109, Der p 1.0110, Der p 1.0111, Der p 1.0112, Der p 1.0113, Der p 1.0114, Der p 1.0115, Der p 1.0116, Der p 1.0117, Der p 1.0118, Der p 1.0119, Der p 1.0120, Der p 1.0121, Der p 1.0122, Der p 1.0123, Der p 1.0124, Der p 10, Der p 10.0101, Der p 10.0102, Der p 10.0103, Der p 11, Der p 11.0101, Der p 13, Der p 14, Der p 14.0101, Der p 15, Der p 18, Der p 2, Der p 2.0101, Der p 2.0102, Der p 2.0103, Der p 2.0104, Der p 2.0105, Der p 2.0106, Der p 2.0107, Der p 2.0108, Der p 2.0109, Der p2.0110, Der p 2.0111, Der p 2.0112, Der p 2.0113, Der p 2.0114, Der p 2.0115, Der p 20, Der p 20.0101, Der p 21, Der p 21.0101, Der p 23, Der p 23.0101, Der p 3, Der p 3.0101, Der p 4, Der p 4.0101, Der p 5, Der p 5.0101, Der p 5.0102, Der p 6, Der p 6.0101, Der p 7, Der p 7.0101, Der p 8, Der p 8.0101, Der p 9, Der p 9.0101, Der p 9.0102, Der p P1-P2, Der p P2-P1, Der s 1, Der s 2, Der s 3), *Dianthus* spp (Dia c RIP), *Dicranopteris* spp (Dic l 2S Albumin), *Diospyros* spp (Dio k 17 kD, Dio k 4, Dio k IFR), *Dioscorea* spp (Dio p TSP), *Diplodus* spp (Dip ho 1), *Distichlis* spp (Dis s 1, Dis s 7), *Ditrema* spp (Dit to 1), *Dolichovespula* spp (Dol a 1, Dol a 2, Dol a 5, Dol a 5.0101), *Dolichos* spp (Dol b Agglutinin), *Dolichovespula* spp (Dol m 1, Dol m 1.0101, Dol m 1.02, Dol m 2, Dol m 2.0101, Dol m 5, Dol m 5.0101, Dol m 5.02), *Drosophila* spp (Dro an 7, Dro an 7.0101, Dro er 7, Dro er 7.0101, Dro er 7.0102, Dro gr 7, Dro gr 7.0101, Dro gr 7.0102, Dro m 7, Dro m 7.0101, Dro m 7.0102, Dro m 7.0103, Dro m 7.0104, Dro m 7.0105, Dro m 7.0106, Dro m 7.0107, Dro m 7.0108, Dro m 7.0109, Dro m 7.0110, Dro m 7.0111, Dro m 7.0112, Dro m 7.0113, Dro m 9, Dro m MnSOD, Dro mo 7, Dro mo 7.0101, Dro pp 7, Dro pp 7.0101, Dro se 7, Dro se 7.0101, Dro si 7, Dro si 7.0101, Dro si 7.0102, Dro vi 7, Dro vi 7.0101, Dro wi 7, Dro wi 7.0101, Dro y 7, Dro y 7.0101, Dro y 7.0102, Dro y 7.0103), *Echium* spp (Ech p Cytochrome C), *Elaeis* spp (Ela g 2, Ela g Bd31 kD), *Elops* spp (Elo sa 1), *Embellisia* spp (Emb a 1, Emb i 1, Emb nz 1, Emb t 1), *Engraulis* spp (Eng e 1), *Enteroctopus* spp (Ent d 1), *Epinephelus* spp (Epi bl 1, Epi co 1, Epi fl 1, Epi mc 1, Epi mo 1), *Epicoccum* spp (Epi p 1, Epi p 1.0101, Epi p 12 kD, Epi p GST), *Epinephelus* spp (Epi po 1, Epi un 1), *Equisetum* spp (Equ a 17 kD), *Equus* spp (Equ as 4, Equ as DSA, Equ bu 4, Equ c 1, Equ c 1.0101, Equ c 2, Equ c 2.0101, Equ c 2.0102, Equ c 3, Equ c 3.0101, Equ c 4, Equ c 4.0101, Equ c 5, Equ c 5.0101, Equ c ALA, Equ c BLG, Equ c Casein, Equ c Casein beta, Equ c Casein kappa, Equ c PRVB, Equ he 4, Equ z ZSA), *Erimacrus* spp (Eri i 1, Eri i 1.0101, Eri i 1.0102), *Eriocheir* spp (Eri s 1, Eri s 1.0101, Eri s 2), *Erwinia* spp (Erw ch Asparaginase), *Escherichia* spp (Esc c Asparaginase, Esc s c beta GAL), *Esox* spp (Eso l 1), *Euphausia* spp (Eup p 1, Eup p 1.0101), *Euphasia* spp (Eup s 1, Eup s 1.0101), *Euroglyphus* spp (Eur m 1, Eur m 1.0101, Eur m 1.0102, Eur m 1.0103, Eur m 10, Eur m 14, Eur m 14.0101, Eur m 2, Eur m 2.0101, Eur m 2.0102, Eur m 3, Eur m 3.0101, Eur m 4, Eur m 4.0101), *Evynnis* spp (Evy j 1), *Fagopyrum* spp (Fag e 1, Fag e 1.0101, Fag e 10 kD, Fag e 19 kD, Fag e 2, Fag e 2.0101, Fag e TI), *Fagus* spp (Fag s 1, Fag s 1.0101, Fag s 2, Fag s 4), *Fagopyrum* spp (Fag t 1, Fag t 10 kD, Fag t 2, Fag t 2.0101), *Felis* spp (Fel d 1, Fel d 1.0101, Fel d 2, Fel d 2.0101, Fel d 3, Fel d 3.0101, Fel d 4, Fel d 4.0101, Fel d 5, Fel d 5.0101, Fel d 6, Fel d 6.0101, Fel d 7, Fel d 7.0101, Fel d 8, Fel d 8.0101, Fel d IgG), *Fenneropenaeus* spp (Fen c 1, Fen c 2, Fen me 1, Fen me 1.0101), *Festuca* spp (Fes e 1, Fes e 13, Fes e 4, Fes e 5, Fes e 7, Fes p 1, Fes p 13, Fes p 4, Fes p 4.0101, Fes p 5, Fes r 1, Fes r 5), *Ficus* spp (Fic c 17 kD, Fic c 4, Fic c Ficin), *Foeniculum* spp (Foe v 1, Foe v 2), *Forsythia* spp (For s 1), *Forcipomyia* spp (For t 1, For t 1.0101, For t 2, For t 2.0101, For t 7, For t FPA, For t Myosin, For t TPI), *Fragaria* spp (Fra a 1, Fra a 1.0101, Fra a 3, Fra a 3.0101, Fra a 3.0102, Fra a 3.0201, Fra a 3.0202, Fra a 3.0203, Fra a 3.0204, Fra a 3.0301, Fra a 4, Fra a 4.0101, Fra c 1), *Fraxinus* spp (Fra e 1, Fra e 1.0101, Fra e 1.0102, Fra e 1.0201, Fra e 12, Fra e 2, Fra e 3, Fra e 9), *Fragaria* spp (Fra v 1), *Fusarium* spp (Fus c 1, Fus c 1.0101, Fus c 2, Fus c 2.0101, Fus c 3, Fus s 1, Fus s 45 kD, Fus sp Lipase), *Gadus* spp (Gad c 1, Gad c 1.0101, Gad c APDH, Gad m 1, Gad m 1.0101, Gad m 1.0102, Gad m 1.0201, Gad m 1.0202, Gad m 45 kD, Gad m Gelatin, Gad ma 1), *Gallus* spp (Gal d 1, Gal d 1.0101, Gal d 2, Gal d 2.0101, Gal d 3, Gal d 3.0101, Gal d 4, Gal d 4.0101, Gal d 5, Gal d 5.0101, Gal d 6, Gal d 6.0101, Gal d Apo I, Gal d Apo VI, Gal d GPI, Gal d HG, Gal d IgY, Gal d L-PGDS, Gal d Ovomucin, Gal d Phosvitin, Gal d PRVB, Gal la 4), *Galleria* spp (Gal m 18 kD, Gal m 24 kD), *Gallus* spp (Gal so 4), *Gammarus* spp (Gam s TM), *Gelonium* spp (Gel m RIP), *Geothelphusa* spp (Geo de 1), *Glossina* spp (Glo m 5, Glo m 5.0101, Glo m 7, Glo m 7.0101, Glo m 7.0102, Glo m 7.0103), *Glycine* spp (Gly a Bd30K, Gly ar Bd30K, Gly ca Bd30K, Gly cl Bd30K, Gly cu Bd30K, Gly cy Bd30K), *Glycyphagus* spp (Gly d 10, Gly d 10.0101, Gly d 13, Gly d 2, Gly d 2.0101, Gly d 2.0201, Gly d 2.03, Gly d 2/Lep d 2 L1, Gly d 2/Lep d 2 L2, Gly d 2/Lep d 2 L3, Gly d 2/Lep d 2 L4, Gly d 2/Lep d 2 R1, Gly d 2/Lep d 2 R2, Gly d 2/Lep d 2 R3, Gly d 2/Lep d 2 R4, Gly d 2/Lep d 2 R5, Gly d 20, Gly d 3, Gly d 5, Gly d 5.01, Gly d 5.02, Gly d 7, Gly d 8), *Glycine* spp (Gly f Bd30K, Gly l Bd30K, Gly m 1, Gly m 1.0101, Gly m 1.0102, Gly m 2, Gly m 2.0101, Gly m 2S Albumin, Gly m 3, Gly m 3.0101, Gly m 3.0102, Gly m 39 kD, Gly m 4, Gly m 4.0101, Gly m 5, Gly m 5.0101, Gly m 5.0201, Gly m 5.0301, Gly m 5.0302, Gly m 50 kD, Gly m 6, Gly m 6.0101, Gly m 6.0201, Gly m 6.0301, Gly m 6.0401, Gly m 6.0501, Gly m 68 kD, Gly m Agglutinin, Gly m Bd28K, Gly m Bd30K, Gly m Bd60K, Gly m CPI, Gly m EAP, Gly m TI, Gly mi Bd30K, Gly s Bd30K, Gly t Bd30K, Gly to Bd30K), *Gossypium* spp (Gos h Vicilin), *Haemophilus* spp (Hae in P6), *Haemaphysalis* spp (Hae 17, Hae 17.0101, Hae q 7, Hae q 7.0101), *Haliotis* spp (Hal a 1, Hal d 1, Hal di 1, Hal di PM, Hal m 1, Hal m 1.0101, Hal r 1, Hal r 49 kD, Hal ru 1), *Harmonia* spp (Har a 1, Har a 1.0101, Har a 2, Har a 2.0101), *Harpegnathos* spp (Har sa 7, Har sa 7.0101, Har sa 7.0102), *Helianthus* spp (Hel a 1, Hel a 1.0101, Hel a 2, Hel a 2.0101, Hel a 2S Albumin, Hel a 3, Hel a 3.0101, Hel a 4), *Helix* spp (Hel ap 1, Hel as 1, Hel as 1.0101), *Heligmosomoides* spp (Hel p 3, Hel p 3.0101), *Helianthus* spp (Hel to 1), *Hemanthias* spp (Hem le 1), *Hemifusus* spp (Hem t 1), *Heterodera* spp (Het g 3, Het g 3.0101), *Hevea* spp (Hev b 1, Hev b 1.0101, Hev b 10, Hev b 10.0101, Hev b 10.0102, Hev b 10.0103, Hev b 11, Hev b 11.0101, Hev b 11.0102, Hev b 12, Hev b 12.0101, Hev b 13, Hev b 13.0101, Hev b 14, Hev b 14.0101, Hev b 2, Hev b 2.0101, Hev b 3, Hev b 3.0101, Hev b 4, Hev b 4.0101, Hev b 5, Hev b 5.0101, Hev b 6, Hev b 6.01, Hev b 6.02, Hev b 6.0202, Hev b 6.03, Hev b 7, Hev b 7.01, Hev b 7.02, Hev b 7.D2, Hev b 7.S2, Hev b 8, Hev b 8.0101, Hev b 8.0102, Hev b 8.0201, Hev b 8.0202, Hev b 8.0203, Hev b 8.0204, Hev b 9, Hev b 9.0101, Hev b Citrate binding Protein, Hev b GAPDH, Hev b HSP80, Hev b IFR, Hev b Proteasome subunit, Hev b Rotamase, Hev b SPI, Hev b Trx, Hev b UDPGP), *Hexagrammos* spp (Hex of 1), *Hippoglossus* spp (Hip h 1), *Hippoglossoides* spp (Hip pl 1), *Hippoglossus* spp (Hip st 1), *Hirudo* spp (Hir me Hirudin), *Holcus* spp (Hol l 1, Hol l 1.0101, Hol l 1.0102, Hol l 2, Hol l 4, Hol l 5, Hol l 5.0101, Hol l 5.0201), *Holocnemus* spp (Hol pl 9, Hol pl Hemocyanin), *Homarus* spp (Hom a 1, Hom a 1.0101, Hom a 1.0102, Hom a 1.0103, Hom a 3, Hom a 3.0101, Hom a 4, Hom a 6, Hom a 6.0101, Hom g 1, Hom g 2), *Homo* spp (Hom s 1, Hom s 1.0101, Hom s 2, Hom s 2.0101, Hom s 3, Hom s 3.0101, Hom s 4, Hom s 4.0101, Hom s 5, Hom s 5.0101, Hom s AAT, Hom s ACTH, Hom s Adalimumab, Hom s ALA, Hom s alpha_Actin, Hom s alpha-Galactosidase, Hom s APDH, Hom s Arylsulfatase B, Hom s Casein, Hom s CyP A, Hom s CyP B, Hom s CyP C, Hom s DSF70, Hom s DSG3, Hom s eIF6, Hom s Etanercept, Hom s Factor IX, Hom s Factor VII, Hom s Factor VIII, Hom s G-CSF, Hom s Glucocerebrosidase, Hom s Glucosidase, Hom s HLA-DR-alpha, Hom s HSA, Hom s Iduronidase, Hom s Idursulfase, Hom s IgA, Hom s Insulin, Hom s Lactoferrin, Hom s Laminin gamma_2, Hom s MnSOD, Hom s Oxytocin, Hom s P2, Hom s Phosvitin, Hom s Profilin, Hom s PSA, Hom s RP1, Hom s TCTP, Hom s TL, Hom s TPA, Hom s TPO, Hom s Transaldolase, Hom s Trx, Hom s Tubulin-alpha, Hom s/*Mus* m Basiliximab, Hom s/*Mus* m Cetuximab, Hom s/*Mus* m Cetuximab (Gal-Gal), Hom s/*Mus* m Infliximab, Hom s/*Mus* m Natalizumab, Hom s/*Mus* m Omalizumab, Hom s/*Mus* m Palivizumab, Hom s/*Mus* m Rituximab, Hom s/*Mus* m Tocilizumab, Hom s/*Mus* m Trastuzumab), *Hoplostethus* spp (Hop a 1), *Hordeum* spp (Hor v 1, Hor v 12, Hor v 12.0101, Hor v 13, Hor v 14, Hor v 15, Hor v 15.0101, Hor v 16, Hor v 16.0101, Hor v 17, Hor v 17.0101, Hor v 18 kD, Hor v 2, Hor v 21, Hor v 21.0101, Hor v 28, Hor v 33, Hor v 4, Hor v 5, Hor v 5.0101, Hor v BDAI, Hor v BTI), *Humicola* spp (Hum in Cellulase), *Humulus* spp (Hum j 1, Hum j 1.0101, Hum j 10 kD, Hum j 2), *Huso* spp (Hus h 1), *Hylocereus* spp (Hyl un LTP), *Hymenocephalus* spp (Hym st 1), *Hyperoglyphe* spp (Hyp by 1), *Hypophthalmichthys* spp (Hyp mo 1), *Hypophthalmichthy* spp (Hyp no 1), *Ictalurus* spp Oct fu 1, Ict p 1), *Imperata* spp (Imp c 4, Imp c 5, Imp c VIIIe1), *Ixodes* spp (Ixo r 2, Ixo sc 7, Ixo sc 7.0101), *Jasus* spp (Jas la 1, Jas la 1.0101, Jas Ia 1.0102), *Juglans* spp (Jug ca 1, Jug ca 2, Jug ci 1, Jug ci 2, Jug n 1, Jug n 1.0101, Jug n 2, Jug n 2.0101, Jug r 1, Jug r 1.0101, Jug r 2, Jug r 2.0101, Jug r 3, Jug r 3.0101, Jug r 4, Jug r 4.0101, Jug r 5), *Juniperus* spp (Jun a 1, Jun a 1.0101, Jun a 1.0102, Jun a 2, Jun a 2.0101, Jun a 3, Jun a 3.0101, Jun c 1, Jun o 1, Jun o 4, Jun o 4.0101, Jun r 3, Jun r 3.1, Jun r 3.2, Jun v 1, Jun v 1.0101, Jun v 1.0102, Jun v 3, Jun v 3.0101, Jun v 3.0102, Jun v 4), *Katsuwonus* spp (Kat p 1), *Kyphosus* spp (Kyp se 1), *Lachnolaimus* spp (Lac ma 1), *Lachesis* spp (Lac mu 1), *Lactuca* spp (Lac s 1, Lac s 1.0101), *Lagocephalus* spp (Lag Ia 1), *Larus* spp (Lar a 1, Lar a 2, Lar a 3), *Larimichthys* spp (Lar po 1), *Lates* spp (Lat c 1), *Lateolabrax* spp (Lat ja 1), *Lathyrus* spp (Lat oc Agglutinin), *Leiostomus* spp (Lei xa 1), *Lens* spp (Len c 1, Len c 1.0101, Len c 1.0102, Len c 1.0103, Len c 2, Len c 2.0101, Len c 3, Len c 3.0101, Len c Agglutinin), *Leopardus* spp (Leo p 1), *Lepidoglyphus* spp (Lep d 10, Lep d 10.0101, Lep d 12, Lep d 13, Lep d 13.0101, Lep d 2, Lep d 2.0101, Lep d 2.0102, Lep d 2.0201, Lep d 2.0202, Lep d 3, Lep d 39 kD, Lep d 5, Lep d 5.0101, Lep d 5.0102, Lep d 5.0103, Lep d 7, Lep d 7.0101, Lep d 8, Lep d alpha Tubulin), *Lepomis* spp (Lep gi 1), *Leptomelanosoma* spp (Lep i 1), *Lepomis* spp (Lep ma 1), *Lepisma* spp (Lep s 1, Lep s 1.0101, Lep s 1.0102), *Lepeophtheirus* spp (Lep sa 1, Lep sa 1.0101, Lep sa 1.0102, Lep sa 1.0103), *Leptailurus* spp (Lep se 1), *Lepidorhombus* spp (Lep w 1, Lep w 1.0101), *Lethocerus* spp (Let in 7, Let in 7.0101, Let in 7.0102), *Leuciscus* spp (Leu ce 1), *Lewia* spp (Lew in 1), *Ligustrum* spp (Lig v 1, Lig v 1.0101, Lig v 1.0102, Lig v 2), *Lilium* spp (Lil l 2, Lil l PG), *Limanda* spp (Lim fe 1), *Limnonectes* spp (Lim m 1), *Limulus* spp (Lim p 1, Lim p 1.0101, Lim p 2, Limp LPA), *Liposcelis* spp (Lip b 1, Lip b 1.0101), *Litchi* spp (Lit c 1, Lit c 1.0101, Lit c IFR, Lit c TPI), *Lithobates* spp (Lit ca 1), *Litopenaeus* spp (Lit se 1, Lit v 1, Lit v 1.0101, Lit v 2, Lit v 2.0101, Lit v 3, Lit v 3.0101, Lit v 4, Lit v 4.0101), *Filiaria* spp (Loa lo 3, Loa lo 3.0101), *Lobotes* spp (Lob su 1), *Locusta* spp (Loc m 7, Loc m 7.0101), *Loligo* spp (Lol b 1, Lol e 1), *Lolium* spp (Lol m 2, Lol m 5, Lol p 1, Lol p 1.0101, Lol p 1.0102, Lol p 1.0103, Lol p 10, Lol p 11, Lol p 11.0101, Lol p 12, Lol p 13, Lol p 2, Lol p 2.0101, Lol p 3, Lol p 3.0101, Lol p 4, Lol p 4.0101, Lol p 5, Lol p 5.0101, Lol p 5.0102, Lol p 7, Lol p CyP, Lol p FT, Lol p Legumin), *Lonomia* spp (Lon o 7, Lon o 7.0101), *Lophodytes* spp (Lop cu 1), *Lophonetta* spp (Lop sp 1), *Lupinus* spp (Lup a 1, Lup a alpha_Conglutin, Lup a delta_Conglutin, Lup a gamma_Conglutin, Lup an 1, Lup an 1.0101, Lup an alpha_Congiutin, Lup an delta_Conglutin, Lup an gamma_Conglutin, Lup l 17 kD), *Lutjanus* spp (Lut a 1, Lut c 1, Lut cy 1, Lut gr 1, Lut gu 1, Lut jo 1), *Lutraria* spp (Lut p 1), *Lutjanus* spp (Lut pu 1, Lut sy 1), *Lycopersicon* spp (Lyc e 1, Lyc e 1.0101, Lyc e 11S Globulin, Lyc e 2, Lyc e 2.0101, Lyc e 2.0102, Lyc e 3, Lyc e 3.0101, Lyc e 4, Lyc e 4.0101, Lyc e ARP60S, Lyc e Chitinase, Lyc e Glucanase, Lyc e Peroxidase, Lyc e PG, Lyc e PME, Lyc e PR23, Lyc e Vicilin), *Maconellicoccus* spp (Mac h 7, Mac h 7.0101), *Macruronus* spp (Mac ma 1, Mac n 1), *Maclura* spp (Mac po 17 kD), *Macrobrachium* spp (Mac ro 1, Mac ro 1.0101, Mac ro Hemocyanin), *Macropus* spp (Macy s Gelatin), *Malus* spp (Mal d 1, Mal d 1.0101, Mal d 1.0102, Mal d 1.0103, Mal d 1.0104, Mal d 1.0105, Mal d 1.0106, Mal d 1.0107, Mal d 1.0108, Mal d 1.0109, Mal d 1.0201, Mal d 1.0202, Mal d 1.0203, Mal d 1.0204, Mal d 1.0205, Mal d 1.0206, Mal d 1.0207, Mal d 1.0208, Mal d 1.0301, Mal d 1.0302, Mal d 1.0303, Mal d 1.0304, Mal d 1.0401, Mal d 1.0402, Mal d 1.0403, Mal d 2, Mal d 2.0101, Mal d 3, Mal d 3.0101, Mal d 3.0102, Mal d 3.0201, Mal d 3.0202, Mal d 3.0203, Mal d 4, Mal d 4.0101, Mal d 4.0102, Mal d 4.0201, Mal d 4.0202, Mal d 4.0301, Mal d 4.0302), *Malpighia* spp (Mal g 4, Mal g Hevein), *Malus* spp (Mal p 1), *Malassezia* spp (Mala f 2, Mala f 2.0101, Mala f 3, Mala f 3.0101, Mala f 4, Mala f 4.0101, Mala g 10, Mala s 1, Mala s 1.0101, Mala s 10, Mala s 10.0101, Mala s 11, Mala s 11.0101, Mala s 12, Mala s 12.0101, Mala s 13, Mala s 13.0101, Mala s 5, Mala s 5.0101, Mala s 6, Mala s 6.0101, Mala s 7, Mala s 7.0101, Mala s 8, Mala s 8.0101, Mala s 9, Mala s 9.0101), *Manihot* spp (Man e 5, Man e 5.0101, Man e FPA, Man e GAPDH), *Mangifera* spp (Man i 1, Man i 14 kD, Man i 2, Man i 3, Man i 3.01, Man i 3.02, Man i Chitinase), *Marsupenaeus* spp (Mar j 1, Mar j 1.0101, Mar j 2, Mar j 4), *Matricaria* spp (Mat c 17 kD), *Mecopoda* spp (Mec e 7), *Megalobrama* spp (Meg am 2, Meg am CK), *Megathura* spp (Meg c Hemocyanin), *Megalops* spp (Meg sp 1), *Melanogrammus* spp (Mel a 1), *Meleagris* spp (Mel g 1, Mel g 2, Mel g 3, Mel g PRVB, Mel g TSA), *Melicertus* spp (Mel l 1), *Menticirrhus* spp (Men am 1), *Mercurialis* spp (Mer a 1, Mer a 1.0101), *Merluccius* spp (Mer ap 1, Mer au 1, Mer bi 1, Mer ca 1, Mer ga 1, Mer hu 1), *Merlangius* spp (Mer me 1), *Merluccius* spp (Mer mr 1, Mer pa 1, Mer po 1, Mer pr 1, Mer se 1), *Meriones* spp (Mer un 23 kD), *Metarhizium* spp (Met a 30), *Metapenaeopsis* spp (Met ba 1), *Metapenaeus* spp (Met e 1, Met e 1.0101, Met e 2), *Metasequoia* spp (Met gl 2), *Metapenaeus* spp (Met j 1, Met j 2), *Metanephrops* spp (Met ja 1), *Metapenaeopsis* spp (Met la 1), *Metanephrops* spp (Met t 2), *Micromesistius* spp (Mic po 1), *Micropogonias* spp (Mic un 1), *Mimachlamys* spp (Mim n 1), *Momordica* spp (Mom c RIP), *Morus* spp (Mor a 17 kD, Mor a 4), *Morone* spp (Mor am 1), *Morus* spp (Mor n 3, Mor n 3.0101), *Morone* spp (Mor sa 1, Mor sc 1), *Mugil* spp (Mug c 1), *Muraenolepis* spp (Mur mi 1), *Musa* spp (*Mus a 1*, *Mus a 1.0101*, *Mus a 2*, *Mus a 2.0101*, *Mus a 3*, *Mus a 3.0101*, *Mus a 4*, *Mus a 4.0101*, *Mus a 5*, *Mus a 5.0101*, *Mus a 5.0102*), *Mus* spp (*Mus m 1*, *Mus m 1.0101*, *Mus m 1.0102*, *Mus m 2*, *Mus m Gelatin*, *Mus m IgG*, *Mus m MSA*, *Mus m Muromonab*, *Mus m Phosvitin*), *Mustela* spp (*Mus p 17 kD*), *Musa* spp (*Mus xp 1*, *Mus xp 2*, *Mus xp 5*), *Mycteroperca* spp (Myc bo 1, Myc mi 1, Myc ph 1), *Myceliophthora* spp (Myc sp Laccase), *Myrmecia* spp (Myr p 1, Myr p 1.0101, Myr p 2, Myr p 2.0101, Myr p 2.0102, Myr p 3, Myr p 3.0101), *Mytilus* spp (Myt e 1, Myt g 1, Myt g PM), *Myzus* spp (Myz p 7, Myz p 7.0101), *Nemorhedus* spp (Nae go Hya), *Necator* spp (Nec a Calreticulin), *Nemipterus* spp (Nem vi 1), *Neosartorya* spp (Neo fi 1, Neo fi 22), *Neochen* spp (Neo ju 1), *Neoscona* spp (Neo n 7, Neo n 7.0101), *Nephelium* spp (Nep l GAPDH), *Nephrops* spp (Nep n 1, Nep n DF9), *Neptunea* spp (Nep po 1, Nep po 1.0101), *Nicotiana* spp (Nic t 8, Nic t Osmotin, Nic t Villin), *Nimbya* spp (Nim c 1, Nim s 1), *Nippostrongylus* spp (Nip b Ag1), *Nycticebus* spp (Nyc c 1), *Octopus* spp (Oct f 1, Oct l 1, Oct v 1, Oct v 1.0101, Oct v PM), *Ocyurus* spp (Ocy ch 1), *Olea* spp (Ole e 1, Ole e 1.0101, Ole e 1.0102, Ole e 1.0103, Ole e 1.0104, Ole e 1.0105, Ole e 1.0106, Ole e 1.0107, Ole e 10, Ole e 10.0101, Ole e 11, Ole e 11.0101, Ole e 11.0102, Ole e 12, Ole e 13, Ole e 2, Ole e 2.0101, Ole e 3, Ole e 3.0101, Ole e 36 kD, Ole e 4, Ole e 4.0101, Ole e 5, Ole e 5.0101, Ole e 6, Ole e 6.0101, Ole e 7, Ole e 7.0101, Ole e 8, Ole e 8.0101, Ole e 9, Ole e 9.0101), *Ommastrephes* spp (Omm b 1, Omm b 1.0101), *Oncorhynchus* spp (Onc ke 1, Onc ke 18 kD, Onc ke alpha2I, Onc ke Vitellogenin, Onc m 1, Onc m 1.0101, Onc m 1.0201, Onc m alpha2I, Onc m Protamine, Onc m Vitellogenin, Onc ma 1, Onc ma FPA, Onc ma FSA, Onc ma TPI, Onc n 1), *Onchocerca* spp (Onc o 3, Onc o 3.0101), *Oncorhynchus* spp (Onc is 1), *Onchocerca* spp (Onc v 3, Onc v 3.0101), *Oratosquilla* spp (Ora o 1, Ora o 1.0101), *Oreochromis* spp (Ore a 1, Ore mo 1, Ore mo 2, Ore mo FPA, Ore mo SCAF7145, Ore nil, Ore ni 18 kD, Ore ni 45 kD), *Ornithonyssus* spp (Orn sy 10, Orn sy 10.0101, Orn sy 10.0102), *Oryctolagus* spp (Ory c 1, Ory c 1.0101, Ory c 2, Ory c Casein, Ory c Phosvitin, Ory c RSA), *Oryza* spp (Ory s 1, Ory s 1.0101, Ory s 11, Ory s 12, Ory s 12.0101, Ory s 13, Ory s 14, Ory s 17 kD, Ory s 19 kD, Ory s 2, Ory s 23, Ory s 3, Ory s 7, Ory s aA_TI, Ory s GLP52, Ory s GLP63, Ory s Glyoxalase l, Ory s NRA), *Ostrya* spp (Ost c 1, Ost c 1.0101), *Ovis* spp (Ovi a ALA, Ovi a BLG, Ovi a Casein, Ovi a Casein alphaS1, Ovi a Casein alphaS2, Ovi a Casein beta, Ovi a Casein kappa, Ovi a Phosvitin, Ovi a SSA), *Pachycondyla* spp (Pac c 3), *Pagrus* spp (Pag m 1, Pag pa 1), *Pampus* spp (Pam ar 1, Pam c 1), *Pandalus* spp (Pan b 1, Pan b 1.0101), *Pangasius* spp (Pan bo 1), *Pandalus* spp (Pan e 1, Pan e 1.0101, Pan e 4), *Panulirus* spp (Pan h 1, Pan hy 1), *Pangasius* spp (Pan hy 18 kD, Pan hy 45 kD), *Panulirus* spp (Pan j 1), *Panthera* spp (Pan 11, Pan o 1, Pan p 1), *Panulirus* spp (Pans 1, Pan s 1.0101), *Panthera* spp (Pan t 1), *Pan* spp (Pan tr TCTP), *Papaver* spp (Pap s 17 kD, Pap s 2, Pap s 34 kD), *Papilio* spp (Pap xu 7, Pap xu 7.0101, Pap xu 7.0102), *Paralichthys* spp (Par a 1), *Parasilurus* spp (Par as 1, Par c 1), *Paralithodes* spp (Par c 1.0101, Par c 1.0102, Par f 1), *Parthenium* spp (Par h 1), *Parietaria* spp (Par j 1, Par j 1.0101, Par j 1.0102, Par j 1.0103, Par j 1.0201, Par j 2, Par j 2.0101, Par j 2.0102, Par j 3, Par j 3.0101, Par j 3.0102, Par j 4, Par j 4.0101, Par j J1-J2), *Paralichthys* spp (Par le 1), *Parietaria* spp (Par m 1, Par o 1, Par o 1.0101), *Paralichthys* spp (Par ol 1, Par ol alpha2I), *Parahucho* spp (Par pe Vitellogenin), *Passiflora* spp (Pas e Chitinase, Pas e Hevein), *Paspalum* spp (Pas n 1, Pas n 1.0101, Pas n 13), *Patinopecten* spp (Pat y 1), *Pediculus* spp (Ped h 7, Ped h 7.0101), *Penaeus* spp (Pen a 1, Pen a 1.0101, Pen a 1.0102, Pen a 1.0102 (103-117), Pen a 1.0102 (109-123), Pen a 1.0102 (1-15), Pen a 1.0102 (115-129), Pen a 1.0102 (121-135), Pen a 1.0102 (127-141), Pen a 1.0102 (13-27), Pen a 1.0102 (133-147), Pen a 1.0102 (139-153), Pen a 1.0102 (145-159)), *Farfantepenaeus* spp (Pen a 1.0102 (151-165)), *Penaeus* spp (Pen a 1.0102 (157-171), Pen a 1.0102 (163-177), Pen a 1.0102 (169-183), Pen a 1.0102 (175-189), Pen a 1.0102 (181-195), Pen a 1.0102 (187-201), Pen a 1.0102 (193-207), Pen a 1.0102 (19-33), Pen a 1.0102 (199-213), Pen a 1.0102 (205-219), Pen a 1.0102 (211-225), Pen a 1.0102 (217-231), Pen a 1.0102 (223-237), Pen a 1.0102 (229-243)), *Farfantepenaeus* spp (Pen a 1.0102 (235-249)), *Penaeus* spp (Pen a 1.0102 (241-255), Pen a 1.0102 (247-261), Pen a 1.0102 (253-267), Pen a 1.0102 (25-39), Pen a 1.0102 (259-273), Pen a 1.0102 (265-279), Pen a 1.0102 (270-284), Pen a 1.0102 (31-45), Pen a 1.0102 (37-51), Pen a 1.0102 (43-57), Pen a 1.0102 (49-63)), *Farfantepenaeus* spp (Pen a 1.0102 (55-69)), *Penaeus* spp (Pen a 1.0102 (61-75), Pen a 1.0102 (67-81), Pen a 1.0102 (7-21), Pen a 1.0102 (73-87), Pen a 1.0102 (79-93), Pen a 1.0102 (85-99), Pen a 1.0102 (91-105), Pen a 1.0102 (97-111), Pen a 1.0103), *Penicillium* spp (Pen b 13, Pen b 13.0101, Pen b 26, Pen b 26.0101, Pen c 1, Pen c 13, Pen c 13.0101, Pen c 18, Pen c 19, Pen c 19.0101, Pen c 2, Pen c 22, Pen c 22.0101, Pen c 24, Pen c 24.0101, Pen c 3, Pen c 3.0101, Pen c 30, Pen c 30.0101, Pen c 32, Pen c 32.0101, Pen c MnSOD, Pen ch 13, Pen ch 13.0101, Pen ch 18, Pen ch 18.0101, Pen ch 20, Pen ch 20.0101, Pen ch 31, Pen ch 31.0101, Pen ch 33, Pen ch 33.0101, Pen ch 35, Pen ch 35.0101, Pen ch MnSOD), *Penaeus* spp (Pen i 1, Pen i 1.0101, Pen m 1, Pen m 1.0101, Pen m 1.0102, Pen m 2, Pen m 2.0101, Pen m 3, Pen m 3.0101, Pen m 4, Pen m 4.0101, Pen m 6, Pen m 6.0101), *Penicillium* spp (Pen o 18, Pen o 18.0101), *Penaeus* spp (Pena o 1, Pena o 1.0101), *Periplaneta* spp (Per a 1, Per a 1.0101, Per a 1.0102, Per a 1.0103, Per a 1.0104, Per a 1.0105, Per a 1.0201, Per a 10, Per a 10.0101, Per a 2, Per a 3, Per a 3.0101, Per a 3.0201, Per a 3.0202, Per a 3.0203, Per a 4, Per a 5, Per a 6, Per a 6.0101, Per a 7, Per a 7.0101, Per a 7.0102, Per a 7.0103, Per a 9, Per a 9.0101, Per a Cathepsin, Per a FABP, Per a Trypsin, Per f 1, Per f 7, Per f 7.0101), *Perna* spp (Per v 1), *Persea* spp (Pers a 1, Pers a 1.0101, Pers a 4), *Petroselinum* spp (Pet c 1, Pet c 2, Pet c 3), *Phalaris* spp (Pha a 1, Pha a 1.0101, Pha a 5, Pha a 5.0101, Pha a 5.02, Pha a 5.03, Pha a 5.04), *Phaseolus* spp (Pha v 3, Pha v 3.0101, Pha v 3.0201, Pha v aAI, Pha v aAI.0101, Pha v Chitinase, Pha v PHA, Pha v Phaseoiin), *Phleum* spp (Phl p 1, Phl p 1.0101, Phl p 1.0102, Phl p 11, Phl p 11.0101, Phl p12, Phl p 12.0101, Phl p 12.0102, Phl p 12.0103, Phl p 13, Phi p 13.0101, Phl p 2, Phl p 2.0101, Phl p 3, Phl p 3.0101, Phl p 3.0102, Phl p 4, Phi p 4.0101, Phl p 4.0102, Phl p 4.0201, Phl p 4.0202, Phl p 4.0203, Phl p 4.0204, Phi p 5, Phl p 5.0101, Phl p 5.0102, Phl p 5.0103, Phl p 5.0104, Phl p 5.0105, Phl p 5.0106, Phl p 5.0107, Phl p 5.0108, Phl p 5.0109, Phl p 5.0201, Phl p 5.0202, Phl p 5.0203, Phl p 5.0204, Phl p 5.0205, Phl p 5.0206, Phl p 5.0207, Phl p 6, Phl p 6.0101, Phl p 6.0102, Phl p 7, Phl p 7.0101, Phl p P1-P2-P5-P6, Phl p P2-P6, Phl p P5-P1, Phl p P6-P2), *Phoenix* spp (Pho d 2, Pho d 2.0101, Pho d 40 kD, Pho d 90 kD), *Phodopus* spp (Pho s 21 kD), *Phoma* spp (Pho t 1), *Phragmites* spp (Phr a 1, Phr a 12, Phr a 13, Phr a 4, Phr a 5), *Phytolacca* spp (Phy a RIP), *Pimpinella* spp (Pim a 1, Pim a 2), *Pinna* spp (Pin a 1), *Piper* spp (Pip n 14 kD, Pip n 28 kD), *Pisum* spp (Pis s 1, Pis s 1.0101, Pis s 1.0102, Pis s 2, Pis s 2.0101, Pis s 5, Pis s Agglutinin, Pis s Albumin), *Pistacia* spp (Pis v 1, Pis v 1.0101, Pis v 2, Pis v 2.0101, Pis v 2.0201, Pis v 3, Pis v 3.0101, Pis v 4, Pis v 4.0101, Pis v 5, Pis v 5.0101), *Platanus* spp (Pla a 1, Pla a 1.0101, Pla a 2, Pla a 2.0101, Pla a 3, Pla a 3.0101, Pla a 8), *Platichthys* spp (Pla f 1), *Plantago* spp (Pla l 1, Pla l 1.0101, Pla l 1.0102, Pla l 1.0103, Pla l Cytochrome C), *Platanus* spp (Pla oc 1, Pla or 1, Pla or 1.0101, Pla or 2, Pla or 2.0101, Pla or 3, Pla or 3.0101, Pla or 4, Pla or CyP, Pla r 1), *Plectropomus* spp (Ple ar 1), *Pleospora* spp (Ple h 1), *Plectropomus* spp (Ple le 1), *Plodia* spp (Plo i 1, Plo i 1.0101, Plo i 2, Plo i 2.0101), *Poa* spp (Poa p 1, Poa p 1.0101, Poa p 10, Poa p 12, Poa p 13, Poa p 2, Poa p 4, Poa p 5, Poa p 5.0101, Poa p 6, Poa p 7), *Polistes* spp (Pol a 1, Pol a 1.0101, Pol a 2, Pol a 2.0101, Pol a 5, Pol a 5.0101, Pol d 1, Pol d 1.0101, Pol d 1.0102, Pol d 1.0103, Pol d 1.0104, Pol d 4, Pol d 4.0101, Pol d 5, Pol d 5.0101, Pole 1, Pol e 1.0101, Pol e 2, Pol e 4, Pol e 4.0101, Pol e 5, Pol e 5.0101, Pol f 5, Pol f 5.0101, Pol g 1, Pol g 1.0101, Pol g 2, Pol g 4, Pol g 5, Pol g 5.0101, Pol he MLT, Pol m 5, Pol m 5.0101), *Polypedilum* spp (Pol n 1), *Pollicipes* spp (Pol po 1), *Pollachius* spp (Pol vi 1), *Polybia* spp (Poly p 1, Poly p 1.0101, Poly p 2, Poly p 5, Poly s 5, Poly s 5.0101), *Pomatomus* spp (Pom sa 1), *Pongo* spp (Pon ab HSA), *Pontastacus* spp (Pon l 4, Pon l 4.0101, Pon l 7, Pon 17.0101), *Portunus* spp (Per s 1, Por s 1.0101, Por s 1.0102, Por tr 1, Por tr 1.0101), *Protortonia* spp (Pro ca 38 kD), *Procumbarus* spp (Pro cl 1, Pro cl 1.0101, Pro cl 21 kD), *Prosopis* spp (Pro j 20 kD), *Prunus* spp (Pru ar 1, Pru ar 1.0101, Pru ar 3, Pru ar 3.0101, Pru av 1, Pru av 1.0101, Pru av 1.0201, Pru av 1.0202, Pru av 1.0203, Pru av 2, Pru av 2.0101, Pru av 3, Pru av 3.0101, Pru av 4, Pru av 4.0101, Pru c 1, Pru d 1, Pru d 2, Pru d 3, Pru d 3.0101, Pru d 4, Pru du 1, Pru du 2, Pru du 2S Albumin, Pru du 3, Pru du 3.0101, Pru du 4, Pru du 4.0101, Pru du 4.0102, Pru du 5, Pru du 5.0101, Pru du 6, Pru du 6.0101, Pru du 6.0201, Pru du Congiutin, Pru p 1, Pru p 1.0101, Pru p 2, Pru p 2.0101, Pru p 2.0201, Pru p 2.0301, Pru p 3, Pru p 3.0101, Pru p 3.0102, Pru p 4, Pru p 4.0101, Pru p 4.0201, Pru sa 3), *Psilocybe* spp (Psi c 1, Psi c 1.0101, Psi c 2, Psi c 2.0101), *Psoroptes* spp (Pso o 1, Pso o 10, Pso o 10.0101, Pso o 11, Pso o 13, Pso o 14, Pso o 2, Pso o 21, Pso o 3, Pso o 5, Pso o 7), *Puma* spp (Pum c 1), *Punica* spp (Pun g 3), *Pyrus* spp (Pyr c 1, Pyr c 1.0101, Pyr c 3, Pyr c 3.0101, Pyr c 4, Pyr c 4.0101, Pyr c 5, Pyr c 5.0101, Pyr py 2), *Quercus* spp (Que a 1, Que a 1.0101, Que a 1.0201, Que a 1.0301, Que a 1.0401, Que a 2, Que a 4), *Rachycentron* spp (Rac ca 1), *Rana* spp (Ran e 1, Ran e 1.0101, Ran e 2, Ran e 2.0101), *Ranina* spp (Ran ra 1), *Rangifer* spp (Ran t BLG), *Rattus* spp (Rat n 1, Rat n 1.0101, Rat n Casein, Rat n Gelatin, Rat n IgG, Rat n Phosvitin, Rat n RSA, Rat n Transferrin), *Rhizomucor* spp (Rhi m AP), *Rhizopus* spp (Rhi nv Lipase, Rhi o Lipase), *Rhomboplites* spp (Rho au 1), *Rhodotorula* spp (Rho m 1, Rho m 1.0101, Rho m 2, Rho m 2.0101), *Ricinus* spp (Ric c 1, Ric c 1.0101, Ric c 2, Ric c 3, Ric c 8, Ric c RIP), *Rivulus* spp (Riv ma 1), *Robinia* spp (Rob p 2, Rob p 4, Rob p Glucanase), *Rosa* spp (Ros r 3), *Roystonea* spp (Roy e 2), *Rubus* spp (Rub i 1, Rub i 1.0101, Rub i 3, Rub i 3.0101, Rub i Chitinase, Rub i CyP), *Saccharomyces* spp (Sac c Carboxypeptidase Y, Sac c CyP, Sac c Enolase, Sac c Glucosidase, Sac c Invertase, Sac c MnSOD, Sac c P2, Sac c Profilin), *Salvelinus* spp (Sal f 1), *Salsola* spp (Sal k 1, Sal k 1.0101, Sal k 1.0201, Sal k 1.0301, Sal k 1.0302, Sal k 2, Sal k 2.0101, Sal k 3, Sal k 3.0101, Sal k 4, Sal k 4.0101, Sal k 4.0201, Sal k 5, Sal k 5.0101), *Salvelinus* spp (Sal le Vitellogenin), *Salmo* spp (Sal s 1, Sal s 1.0101, Sal s 1.0201, Sal s 2, Sal s 2.0101, Sal s Gelatin), *Sambucus* spp (Sam n 1), *Sander* spp (San lu 1), *Saponaria* spp (Sap o RIP), *Sardinops* spp (Sar m 1), *Sarkidiornis* spp (Sar ml 1), *Sardina* spp (Sar p 1), *Sarcoptes* spp (Sar s 1, Sar s 14, Sar s 3, Sar s GST, Sar s PM), *Sardinops* spp (Sar sa 1, Sar sa 1.0101), *Schistosoma* spp (Sch j GST, Sch j PM, Sch j Sj22, Sch j Sj67, Sch ma Sm20, Sch ma Sm21, Sch ma Sm22, Sch ma Sm31), *Sciaenops* spp (Sci oc 1), *Scomber* spp (Sco a 1), *Scombermorus* spp (Sco ca 1), *Scomberomorus* spp (Sco g 1), *Scomber* spp (Sco j 1, Sco ma 1, Sco s 1), *Scolopendra* spp (Sco y 7, Sco y 7.0101), *Scylla* spp (Scy o 1, Scy o 1.0101, Scy o 2, Scy pa 1, Scy pa 2, Scy s 1, Scy s 1.0101, Scy s 2), *Sebastes* spp (Seb fa 1, Seb in 1, Seb m 1, Seb m 1.0101, Seb m 1.0201), *Secale* spp (Sec c 1, Sec c 12, Sec c 13, Sec c 2, Sec c 20, Sec c 20.0101, Sec c 20.0201, Sec c 28, Sec c 3, Sec c 4, Sec c 4.0101, Sec c 4.0201, Sec c 5, Sec c 5.0101, Sec c aA_TI, Sec c aATI.0101), *Senecio* spp (Sen j MDH, Sen j PL), *Sepia* spp (Sep e 1, Sep e 1.0101), *Sepioteuthis* spp (Sep l 1, Sep l 1.0101), *Sepia* spp (Sep m 1), *Seriola* spp (Ser d 1, Ser la 1), *Sergestes* spp (Ser lu 1), *Seriola* spp (Ser q 1, Ser ri 1), *Sesamum* spp (Ses i 1, Ses i 1.0101, Ses i 2, Ses i 2.0101, Ses i 3, Ses i 3.0101, Ses i 4, Ses i 4.0101, Ses i 5, Ses i 5.0101, Ses i 6, Ses i 6.0101, Ses i 7, Ses i 7.0101, Ses i 8), *Shigella* spp (Shi bo GST, Shi dy GST), *Simulia* spp (Sim vi 1, Sim vi 2, Sim vi 3, Sim vi 4, Sim vi 70 kD), *Sinapis* spp (Sin a 1, Sin a 1.0101, Sin a 1.0104, Sin a 1.0105, Sin a 1.0106, Sin a 1.0107, Sin a 1.0108, Sin a 2, Sin a 2.0101, Sin a 3, Sin a 3.0101, Sin a 4, Sin a 4.0101), *Sinonovacula* spp (Sin c 1, Sin c 1.0101), *Solenopsis* spp (Sol g 2, Sol g 2.0101, Sol g 3, Sol g 3.0101, Sol g 4, Sol g 4.0101, Sol g 4.0201, Sol i 1, Sol i 1.0101, Sol i 2, Sol i 2.0101, Sol i 3, Sol i 3.0101, Soli 4, Sol i 4.0101), *Solenocera* spp (Sol me 1), *Solenopsis* spp (Sol r 1, Sol r 2, Sol r 2.0101, Sol r 3, Sol r 3.0101, Sol s 2, Sol s 2.0101, Sol s 3, Sol s 3.0101, Sol s 4), *Solea* spp (Sol so 1, Sol so TPI), *Solanum* spp (Sola t 1, Sola t 1.0101, Sola t 2, Sola t 2.0101, Sola t 3, Sola t 3.0101, Sola t 3.0102, Sola t 4, Sola t 4.0101, Sola t 8, Sola t Glucanase), *Sorghum* spp (Sorb 1, Sor h 1, Sor h 1.0101, Sor h 12, Sor h 7), *Sparus* spp (Spa a 1), *Sphyrna* spp (Sph ti 1), *Spirulina* spp (Spi mx beta_Phycocyanin), *Spinacia* spp (Spi o 2, Spi o RuBisCP), *Squilla* spp (Squ ac 1, Squ ac 1.0101, Squ o 1, Squ o 1.0101), *Staphylococcus* spp (Sta a FBP, Sta a SEA, Sta a SEB, Sta a SEC, Sta a SED, Sta a SEE, Sta a TSST), *Stachybotrys* spp (Sta c 3, Sta c 3.0101, Sta c Cellulase, Sta c Hemolysin, Sta c SchS34, Sta c Stachyrase A), *Stemphylium* spp (Ste b 1, Ste c 1, Ste v 1), *Stolephorus* spp (Sto i 1), *Struthio* spp (Str c 1, Str c 2, Str c 3), *Streptococcus* spp (Str dy Streptokinase), *Streptomyces* spp (Str g Pronase), *Streptococcus* spp (Str pn PspC), *Strongylocentrotus* spp (Str pu 18 kD, Str pu Vitellogenin), *Streptococcus* spp (Str py SPEA, Str py SPEC, Str py Streptokinase), *Strongyloides* spp (Str st 45 kD), *Streptomyces* spp (Str v PAT), *Styela* spp (Sty p 1), *Suidasia* spp (Sui m 1, Sui m 13, Sui m 2, Sui m 3, Sui m 5, Sui m 5.01, Sui m 5.02, Sui m 5.03, Sui m 6, Sui m 7, Sui m 8, Sui m 9), *Sus* spp (Sus s ACTH, Sus s ALA, Sus s Amylase, Sus s BLG, Sus s Casein, Sus s Casein alphaS1, Sus s Casein alphaS2, Sus s Casein beta, Sus s Casein kappa, Sus s Gelatin, Sus s HG, Sus s Insulin, Sus s Lipase, Sus s Pepsin, Sus s Phosvitin, Sus s PRVB, Sus s PSA, Sus s TCTP), *Syntelopodeuma* spp (Syn y 7, Syn y 7.0101), *Syringa* spp (Syr v 1, Syr v 1.0101, Syr v 1.0102, Syr v 1.0103, Syr v 2, Syr v 3, Syr v 3.0101), *Tabanus* spp (Tab y 1, Tab y 1.0101, Tab y 2, Tab y 2.0101, Tab y 5, Tab y 5.0101), *Tadorna* spp (Tad ra 1), *Talaromyces* spp (Tal st 22, Tal st 3, Tal st 8), *Taraxacum* spp (Tar o 18 kD), *Taxodium* spp (Tax d 2), *Tegenaria* spp (Teg d Hemocyanin), *Teladorsagia* spp (Tel ci 3), *Thaumetopoea* spp (Tha p 1, Tha p 1.0101, Tha p 2, Tha p 2.0101), *Theragra* spp (The c 1), *Thermomyces* spp (The l Lipase, The sp Lipase, The sp Xylanase), *Thunnus* spp (Thu a 1, Thu a 1.0101, Thu a Collagen, Thu al 1, Thu at 1, Thu o 1, Thu o Collagen), *Thuja* spp (Thu oc 3, Thu p 1), *Thunnus* spp (Thu t 1, Thu to 1), *Thyrsites* spp (Thy at 1), *Thyrophygus* spp (Thy y 7, Thy y 7.0101), *Todarodes* spp (Tod p 1, Tod p 1.0101, Tod p 1.0102), *Toxoptera* spp (Tox c 7, Tox c 7.0101), *Toxocara* spp (Tox ca TES120, Tox ca TES26, Tox ca TES30), *Toxoplasma* spp (Tox g HSP70), *Trachypenaeus* spp (Tra c 1), *Trachinotus* spp (Tra ca 1), *Trachurus* spp (Tra j 1, Tra j Gelatin, Tra tr Gelatin), *Triticum* spp (Tri a 1, Tri a 10 kD, Tri a 12, Tri a 12.0101, Tri a 12.0102, Tri a 12.0103, Tri a 12.0104, Tri a 13, Tri a 14, Tri a 14.0101, Tri a 14.0201, Tri a 15, Tri a 15.0101, Tri a 18, Tri a 18.0101, Tri a 19, Tri a 19.0101, Tri a 2, Tri a 21, Tri a 21.0101, Tri a 23 kd, Tri a 25, Tri a 25.0101, Tri a 26, Tri a 26.0101, Tri a 27, Tri a 27.0101, Tri a 28, Tri a 28.0101, Tri a 29, Tri a 29.0101, Tri a 29.0201, Tri a 3, Tri a 30, Tri a 30.0101, Tri a 31, Tri a 31.0101, Tri a 32, Tri a 32.0101, Tri a 33, Tri a 33.0101, Tri a 34, Tri a 34.0101, Tri a 35, Tri a 35.0101, Tri a 36, Tri a 36.0101, Tri a 37, Tri a 37.0101, Tri a 4, Tri a 4.0101, Tri a 4.0201, Tri a 5, Tri a 7, Tri a aA_SI, Tri a alpha_Gliadin, Tri a bA, Tri a Bd36K, Tri a beta_Gliadin, Tri a Chitinase, Tri a CM16, Tri a DH, Tri a Endochitinase, Tri a gamma_Gliadin, Tri a Germin, Tri a Gliadin, Tri a GST, Tri a LMW Glu, Tri a LMW-GS B16, Tri a LMW-GS P42, Tri a LMW-GS P73, Tri a LTP2, Tri a omega2_Gliadin, Tri a Peroxidase, Tri a Peroxidase 1, Tri a SPI, Tri a TLP, Tri a Tritin, Tri a XI), *Tritirachium* spp (Tri al Proteinase K), *Tribolium* spp (Tri ca 17, Tri ca 17.0101, Tri ca 7, Tri ca 7.0101), *Trichostrongylus* spp (Tri co 3, Tri co 3.0101), *Trichophyton* spp (Tri eq 4), *Trigonella* spp (Tri fg 1, Tri fg 2, Tri fg 3, Tri fg 4), *Trichosanthes* spp (Tri k RIP), *Trichiurus* spp (Tri le 1), *Triticum* spp (Tri m Peroxidase), *Trichophyton* spp (Tri me 2, Tri me 4), *Trisetum* spp (Tri p 1, Tri p 5), *Trichinella* spp (Tri ps 3, Tri ps 3.0101), *Trichophyton* spp (Tri r 2, Tri r 2.0101, Tri r 4, Tri r 4.0101), *Trichoderma* spp (Tri rs Cellulase), *Triticum* spp (Tri s 14), *Trichophyton* spp (Tri sc 2, Tri sc 4, Tri so 2), *Trichinella* spp (Tri sp 3, Tri sp 3.0101, Tri sp 3.0102, Tri sp 3.0103, Tri sp 3.0104, Tri sp 3.0105, Tri sp 3.0106), *Trichophyton* spp (Tri t 1, Tri t 1.0101, Tri t 4, Tri t 4.0101), *Triticum* spp (Tri td 14, Tri td aA_TI), *Trichoderma* spp (Tri v Cellulase), *Trichophyton* spp (Tri ve 4), *Triatoma* spp (Tria p 1, Tria p 1.0101), *Triplochiton* spp (Trip s 1), *Turbo* spp (Tur c 1, Tur c PM), *Tyrophagus* spp (Tyr p 1, Tyr p 10, Tyr p 10.0101, Tyr p 10.0102, Tyr p 13, Tyr p 13.0101, Tyr p 2, Tyr p 2.0101, Tyr p 24, Tyr p 24.0101, Tyr p 3, Tyr p 3.0101, Tyr p 4, Tyr p 5, Tyr p 5.01, Tyr p 5.02, Tyr p 5.03, Tyr p 7, Tyr p alpha Tubulin), *Ulocladium* spp (Ulo a 1, Ulo at 1, Ulo b 1, Ulo c 1, Ulo co 1, Ulo cu 1, Ulo mu 1, Ulo ob 1, Ulo se 1, Ulo su 1, Ulo to 1), *Uncia* spp (Unc u 1), *Urophycis* spp (Uro to 1), *Vaccinium* spp (Vac m 3), *Varroa* spp (Var j 13 kD), *Venerupis* spp (Ven ph 1, Ven ph 1.0101), *Vespula* spp (Ves f 1, Ves f 2, Ves f 5, Ves f 5.0101, Ves g 1, Ves g 2, Ves g 5, Ves g 5.0101, Ves m 1, Ves m 1.0101, Ves m 2, Ves m 2.0101, Ves m 5, Ves m 5.0101, Ves m MLT, Vesp 1, Vesp 2, Vesp 5, Vesp 5.0101, Ves s 1, Ves s 1.0101, Ves s 2, Ves s 5, Ves s 5.0101, Ves v 1, Ves v 1.0101, Ves v 2, Ves v 2.0101, Ves v 2.0201, Ves v 3, Ves v 3.0101, Ves v 5, Ves v 5.0101, Ves v 5-Pol a 5, Ves vi 5, Ves vi 5.0101), *Vespa* spp (Vesp c 1, Vesp c 1.0101, Vesp c 2, Vesp c 5, Vesp c 5.0101, Vesp c 5.0102, Vesp m 1, Vesp m 1.0101, Vesp m 5, Vesp m 5.0101, Vesp ma 1, Vesp ma 2, Vesp ma 5, Vesp ma MLT, Vesp v MLT), *Vigna* spp (Vig r 1, Vig r 1.0101, Vig r 17 kD, Vig r 5, Vig r 8S Globulin, Vig r Albumin, Vig r beta-Conglycinin), *Vitis* spp (Vit v 1, Vit v 1.0101, Vit v 4, Vit v 5, Vit v Glucanase, Vit v TLP), *Xiphias* spp (Xip g 1, Xip g 1.0101, Xip g 25 kD), *Zea* spp (Zea m 1, Zea m 1.0101, Zea m 11, Zea m 12, Zea m 12.0101, Zea m 12.0102, Zea m 12.0103, Zea m 12.0104, Zea m 12.0105, Zea m 13, Zea m 14, Zea m 14.0101, Zea m 14.0102, Zea m 2, Zea m 20S, Zea m 22, Zea m 25, Zea m 25.0101, Zea m 27 kD Zein, Zea m 3, Zea m 4, Zea m 5, Zea m 50 kD Zein, Zea m 7, Zea m Chitinase, Zea m G1, Zea m G2, Zea m PAO, Zea m Zm13), *Zeus* spp (Zeu fa 1), *Ziziphus* spp (Ziz m 1, Ziz m 1.0101), *Zoarces* spp (Zoa a ISP III), *Zygophyllum* spp (Zyg f 2)

In this context the terms in brackets indicate the particular preferred allergenic antigens (allergens) from the particular source.

Most preferably the allergenic antigen is preferably derived from a source (e.g. a plant (e.g. grass or a tree), a natural product (e.g. milk, nuts etc.), a fungal source (e.g. *Aspergillus*) or a bacterial source or from an animal source or animal poison (e.g. cat, dog, venom of bees etc.), preferably selected from the list consisting of grass pollen (e.g. pollen of rye), tree pollen (e.g. pollen of hazel, birch, alder, ash), flower pollen, herb pollen (e.g. pollen of mugwort), dust mite (e.g. Der f 1, Der p 1, Eur m 1, Der m 1 Der f 2, Der p 2, Eur m 2, Tyr p 2, Lep d 2), mold (e.g. allergens of *Acremonium, Aspergillus, Cladosporium, Fusarium, Mucor, Penicillium, Rhizopus, Stachybotrys, Trichoderma*, or *Alternaria*), animals (e.g Fel dl, Fel d 2, Fel d3, or Fel d4 of cats), food (e.g. allergens of fish (e.g. bass, cod, flounder), seafood (e.g. crab, lobster, shrimps), egg, wheat, nuts (e.g. peanuts, almonds, cashews, walnuts), soya, milk, etc.) or insect venom (e.g. allergens from the venom of wasps, bees, hornets, ants, mosquitos, or ticks).

Autoimmune self-antigens, i.e. antigens associated with autoimmune disease or autoantigens, may be associated with an autoimmune disease affecting at least one or more of the following organ systems: the circulatory system, the digestive system, the endocrine system, the excretory system, the immune system, the integumentary system, the muscular system, the nervous system, the reproductive system, the respiratory system, the skeletal system, preferably with the cardiovascular system, the neuroendocrine system, the musculoskeletal system or gastrointestinal system. Therein the circulatory system is the organ system which enables pumping and channeling blood to and from the body and lungs with heart, blood and blood vessels. The digestive system enables digestion and processing food with salivary glands, esophagus, stomach, liver, gallbladder, pancreas, intestines, colon, rectum and anus. The endocrine system enables communication within the body using hormones made by endocrine glands such as the hypothalamus, pituitary or pituitary gland, pineal body or pineal gland, thyroid gland, parathyroid gland and adrenal glands. The excretory system comprises kidneys, ureters, bladder and urethra and is involved in fluid balance, electrolyte balance and excretion of urine. The immune system comprises structures involved in the transfer of lymph between tissues and the blood stream, the lymph and the nodes and vessels which may be responsible for transport of cellular and humoral components of the immune system. It is responsible for defending against disease-causing agents and comprises amongst others leukocytes, tonsils, adenoids, thymus and spleen. The integumentary system comprises skin, hair and nails. The muscular system enables movement with muscles together with the skeletal system which comprises bones, cartilage, ligaments and tendons and provides structural support. The nervous system is responsible for collecting, transferring and processing information and comprises the brain, spinal cord and nerves. The reproductive system comprises the sex organs, such as ovaries, fallopian tubes, uterus, vagina, mammary glands, testes, vas deferens, seminal vesicles, prostate and penis. The respiratory system comprises the organs used for breathing, the pharynx, larynx, trachea, bronchi, lungs and diaphragm and acts together with the circulation system.

Autoimmune self-antigens (antigens associated with autoimmune disease or autoantigens) are selected from autoantigens associated with autoimmune diseases selected from Addison disease (autoimmune adrenalitis, Morbus Addison), alopecia areata, Addison's anemia (Morbus Biermer), autoimmune hemolytic anemia (AIHA), autoimmune hemolytic anemia (AIHA) of the cold type (cold hemagglutinine disease, cold autoimmune hemolytic anemia (AIHA) (cold agglutinin disease), (CHAD)), autoimmune hemolytic anemia (AIHA) of the warm type (warm AIHA, warm autoimmune haemolytic anemia (AIHA)), autoimmune hemolytic Donath-Landsteiner anemia (paroxysmal cold hemoglobinuria), antiphospholipid syndrome (APS), atherosclerosis, autoimmune arthritis, arteriitis temporalis, Takayasu arteriitis (Takayasu's disease, aortic arch disease), temporal arteriitis/giant cell arteriitis, autoimmune chronic gastritis, autoimmune infertility, autoimmune inner ear disease (AIED), Basedow's disease (Morbus Basedow), Bechterew's disease (Morbus Bechterew, ankylosing spondylitis, spondylitis ankylosans), Behcet's syndrome (Morbus Behcet), bowel disease including autoimmune inflammatory bowel disease (including colitis ulcerosa (Morbus Crohn, Crohn's disease), cardiomyopathy, particularly autoimmune cardiomyopathy, idiopathic dilated cardiomyopathy (DCM), celiac sprue dermatitis (gluten mediated enteropathia), chronic fatigue immune dysfunction syndrome (CFIDS), chronic inflammatory demyelinating polyneuropathy (CIDP), chronic polyarthritis, Churg-Strauss syndrome, cicatricial pemphigoid, Cogan syndrome, CREST syndrome (syndrom with Calcinosis cutis, Raynaud phenomenon, motility disorders of the esophagus, sklerodaktylia and teleangiectasia), Crohn's disease (Morbus Crohn, colitis ulcerosa), dermatitis herpetiformis during, dermatologic autoimmune diseases, dermatomyositis, Diabetes, Diabetes mellitus Type 1 (type I diabetes, insuline dependent Diabetes mellitus), Diabetes mellitus Type 2 (type II diabetes), essential mixed cryoglobulinemia, essential mixed cryoglobulinemia, fibromyalgia, fibromyositis, Goodpasture syndrome (anti-GBM mediated glomerulonephritis), graft versus host disease, Guillain-Barré syndrome (GBM, Polyradikuloneuritis), haematologic autoimmune diseases, Hashimoto thyroiditis, hemophilia, acquired hemophilia, hepatitis, autoimmune hepatitis, particularly autoimmune forms of chronic hepatitis, idiopathic pulmonary fibrosis (IPF), idiopathic thrombocytopenic purpura, Immuno-thrombocytopenic purpura (Morbus Werlhof; ITP), IgA nephropathy, infertility, autoimmune infertility, juvenile rheumatoid arthritis (Morbus Still, Still syndrome), Lambert-Eaton syndrome, lichen planus, lichen sclerosus, lupus erythematosus, systemic lupus erythematosus (SLE), lupus erythematosus (discoid form), Lyme arthritis (Lyme disease, *borrelia* arthritis), Mëniere's disease (Morbus Mëniere); mixed connective tissue disease (MCTD), multiple sclerosis (MS, encephalomyelitis disseminate, Charcot's disease), Myasthenia gravis (myasthenia, MG), myosits, polymyositis, neural autoimmune diseases, neurodermitis, pemphigus vulgaris, bullous pemphigoid, scar forming pemphigoid; polyarteriitis nodosa (periarteiitis nodosa), polychondritis (panchondritis), polyglandular (autoimmune) syndrome (PGA syndrome, Schmidt's syndrome), Polymyalgia rheumatica, primary agammaglobulinemia, primary biliary cirrhosis PBC, primary autoimmune cholangitis), progressive systemic sclerosis (PSS), Psoriasis, Psoriasis vulgaris, Raynaud's phenomena, Reiter's syndrome (Morbus Reiter, urethral conjunctive synovial syndrome)), rheumatoid arthritis (RA, chronic polyarthritis, rheumatic disease of the joints, rheumatic fever), sarcoidosis (Morbus Boeck, Besnier-Boeck-Schaumann disease), stiff-man syndrome, Sclerodermia, Scleroderma, Sjögren's syndrome, sympathetic ophtalmia; Transient gluten intolerance, transplanted organ rejection, uveitis, autoimmune uveiitis, Vasculitis, Vitiligo, (leucoderma, piebold skin), and Wegner's disease (Morbus Wegner, Wegner's granulomatosis).

These and other proteins acting as autoimmune self-antigens are understood to be therapeutic, as they are meant to treat the subject, in particular a mammal, more particularly a human being, by vaccinating with a self-antigen which is expressed by the mammal, e.g. the human, itself and which triggers an undesired immune response, which is not raised in a healthy subject. Accordingly, such proteins acting as self-antigens are typically of mammalian, in particular human origin.

Particularly preferred in this context are autoimmune self-antigens (autoantigens) selected from:

myelin basic protein (MBP), proteolipid protein (PLP), and myelinoligodendrocyte glycoprotein (MOG), in each case associated with multiple sclerosis (MS);

CD44, preproinsulin, proinsulin, insulin, glutamic acid decaroxylase (GAD65), tyrosine phosphatase-like insulinoma antigen 2 (IA2), zinc transporter ((ZnT8), and heat shock protein 60 (HSP60), in each case associated with diabetes Typ I;

interphotoreceptor retinoid-binding protein (IRBP) associated with autoimmune uveitis;

acetylcholine receptor AchR, and insulin-like growth factor-1 receptor (IGF-1 R), in each case associated with Myasthenia gravis;

M-protein from beta-hemolytic streptocci (pseudo-autoantigen) associated with Rheumatic Fever;

Macrophage migration inhibitory factor associated with Arthritis;

Ro/La RNP complex, alpha- and beta-fodrin, islet cell autoantigen, poly(ADP)ribose polymerase (PARP), NuMA, NOR-90, Ro60 autoantigen, and p27 antigen, in each case associated with Sjogren's syndrome;

Ro60 autoantigen, low-density lipoproteins, Sm antigens of the U-1 small nuclear ribonucleoprotein complex (B/B', D1, D2, D3, E, F, G), and RNP ribonucleoproteins, in each case associated with lupus erythematosus;

oxLDL, beta(2)GPI, HSP60/65, and oxLDL/beta(2)GPI, in each case associated with Atherosclerosis;

cardiac beta(1)-adrenergic receptor associated with idiopathic dilated cardiomyopathy (DCM);

histidyl-tRNA synthetase (HisRS) associated with myositis;

topoisomerase I associated with scleroderma disease.

Furthermore, in other embodiments said autoimmune self-antigen is associated with the respective autoimmune disease, like e.g. IL-1 7, heat shock proteins, and/or any idiotype pathogenic T cell or chemokine receptor which is expressed by immune cells involved in the autoimmune response in said autoimmune disease (such as any autoimmune diseases described herein).

In the context of each of the various aspects of the present invention, certain embodiments of the methods, compositions, vaccines or kits may (additionally) comprise or comprise the use of an adjuvant. In this context, an adjuvant may be understood as any compound, which is suitable to initiate or increase an immune response of the innate immune system, i.e. a non-specific immune response. With other words, when administered, the antigenic compositions, pharmaceutical composition and/or vaccines of the present invention preferably elicit an innate immune response due to the adjuvant, optionally contained therein. Preferably, such an adjuvant may be selected from an adjuvant known to a skilled person and suitable for the present case, i.e. supporting the induction of an innate immune response in a mammal, e.g. an adjuvant protein as defined above or an adjuvant as defined in the following.

Particularly preferred as adjuvants suitable for depot and delivery are cationic or polycationic compounds as defined above for the inventive mRNA sequence as vehicle, transfection or complexation agent.

Furthermore, other embodiments of the various aspects of the present invention may comprise (or comprise the use of) one or more additional adjuvants which are suitable to initiate or increase an immune response of the innate immune system, i.e. a non-specific immune response, particularly by binding to pathogen-associated molecular patterns (PAMPs). With other words, when administered, the pharmaceutical composition or vaccine preferably elicits an innate immune response due to the adjuvant, optionally contained therein. Preferably, such an adjuvant may be selected from an adjuvant known to a skilled person and suitable for the present case, i.e. supporting the induction of an innate immune response in a mammal, e.g. an adjuvant protein as defined above or an adjuvant as defined in the following. According to one embodiment such an adjuvant may be selected from an adjuvant as defined above.

Also such an adjuvant may be selected from any adjuvant known to a skilled person and suitable for the present case, i.e. supporting the induction of an innate immune response in a mammal and/or suitable for depot and delivery of the components of the inventive pharmaceutical composition or vaccine. Preferred as adjuvants suitable for depot and delivery are cationic or polycationic compounds as defined above. Likewise, the adjuvant may be selected from the group consisting of, e.g., cationic or polycationic compounds as defined above, from chitosan, TDM, MDP, muramyl dipeptide, pluronics, alum solution, aluminium hydroxide, ADJUMER™ (polyphosphazene); aluminium phosphate gel; glucans from algae; algammulin; aluminium hydroxide gel (alum); highly protein-adsorbing aluminium hydroxide gel; low viscosity aluminium hydroxide gel; AF or SPT (emulsion of squalane (5%), Tween 80 (0.2%), Pluronic L121 (1.25%), phosphate-buffered saline, pH 7.4);

AVRIDINE™ (propanediamine); BAY R1005™ ((N-(2-deoxy-2-L-leucylaminob-D-glucopyranosyl)-N-octadecyl-dodecanoyl-amide hydroacetate); CALCITRIOL™ (1-alpha, 25-dihydroxy-vitamin D3); calcium phosphate gel; CAP™ (calcium phosphate nanoparticles); cholera holotoxin, cholera-toxin-A1-protein-A-D-fragment fusion protein, sub-unit B of the cholera toxin; CRL 1005 (block copolymer P1205); cytokine-containing liposomes; DDA (dimethyldioctadecylammonium bromide); DHEA (dehydroepiandrosterone); DMPC (dimyristoylphosphatidylcholine); DM PG (dimyristoylphosphatidylglycerol); DOC/alum complex (deoxycholic acid sodium salt); Freund's complete adjuvant; Freund's incomplete adjuvant; gamma inulin; Gerbu adjuvant (mixture of: i) N-acetylglucosaminyl-(P1-4)-N-acetylmuramyl-L-alanyl-D35 glutamine (GMDP), ii) dimethyldioctadecylammonium chloride (DDA), iii) zinc-L-proline salt complex (ZnPro-8); GM-CSF); GMDP (N-acetylglucosaminyl-(b1-4)-N-acetylmuramyl-L47 alanyl-D-isoglutamine); imiquimod (1-(2-methypropyl)-1H-imidazo[4,5-c]quinoline-4-amine); ImmTher™ (N-acetylglucosaminyl-N-acetylmuramyl-L-Ala-D-isoGlu-L-Ala-glycerol dipalmitate); DRVs (immunoliposomes prepared from dehydration-rehydration vesicles); interferongamma; interleukin-1beta; interleukin-2; interleukin-7; interleukin-12; ISCOMS™; ISCOPREP 7.0.3.™; liposomes; LOXORIBINE™ (7-allyl-8-oxoguanosine); LT 5 oral adjuvant (*E. coli* labile enterotoxin-protoxin); microspheres and microparticles of any composition; MF59™; (squalenewater emulsion); MONTANIDE ISA 51™ (purified incomplete Freund's adjuvant); MONTANIDE ISA720™ (metabolisable oil adjuvant); MPL™ (3-Q-desacyl-4'-monophosphoryl lipid A); MTP-PE and MTP-PE liposomes ((N-acetyl-L-alanyl-D-isoglutaminyl-L-alanine-2-(1,2-dipalmitoyl-sn-glycero-3-(hydroxyphosphoryloxy))-ethylamide, monosodium salt); MURAMETIDE™ (Nac-Mur-L-Ala-D-Gln-OCH3); MURAPALMITINE™ and DMURAPALMITINE™ (Nac-Mur-L-Thr-D-isoGln-sn-glyceroldipalmitoyl); NAGO (neuraminidase-galactose oxidase); nanospheres or nanoparticles of any composition; NISVs (non-ionic surfactant vesicles); PLEURAN™ (β-glucan); PLGA, PGA and PLA (homo- and co-polymers of lactic acid and glycolic acid; microspheres/nanospheres); PLURONIC L121™ PMMA (polymethylmethacrylate); PODDS™ (proteinoid microspheres); polyethylene carbamate derivatives; poly-rA: poly-rU (polyadenylic acid-polyuridylic acid complex); polysorbate 80 (Tween 80); protein cochleates (Avanti Polar Lipids, Inc., Alabaster, Ala.); STIMULON™ (QS-21); Quil-A (Quil-A saponin); S-28463 (4-amino-otec-dimethyl-2-ethoxymethyl-1H-imidazo[4,5-c]quinoline-1-ethanol); SAF-1™ ("Syntex adjuvant formulation"); Sendai proteoliposomes and Sendai containing lipid matrices; Span-85 (sorbitan trioleate); Specol (emulsion of Marcol 52, Span 85 and Tween 85); squalene or Robane® (2,6,10,15,19,23-hexamethyltetracosan and 2,6,10,15,19,23-hexamethyl-2,6,10,14,18,22-tetracosahexane); stearyltyrosine (octadecyltyrosine hydrochloride); Theramid® (N-acetylglucosaminyl-N-acetylmuramyl-L-Ala-D-isoGlu-L-Aladipalmitoxypropylamide); Theronyl-MDP (Termurtide™ or [thr 1]-MDP; N-acetylmuramyl-Lthreonyl-D-isoglutamine); Ty particles (Ty-VLPs or virus-like particles); Walter-Reed liposomes (liposomes containing lipid A adsorbed on aluminium hydroxide), and lipopeptides, including Pam3Cys, in particular aluminium salts, such as Adju-phos, Alhydrogel, Rehydragel; emulsions, including CFA, SAF, IFA, MF59, Provax, TiterMax, Montanide, Vaxfectin; copolymers, including Optivax (CRL1005), L121, Poloaxmer4010), etc.; liposomes, including Stealth, cochleates, including BIORAL; plant derived adjuvants, including QS21, Quil A, Iscomatrix, ISCOM; adjuvants suitable for costimulation including Tomatine, biopolymers, including PLG, PMM, Inulin, microbe derived adjuvants, including Romurtide, DETOX, MPL, CWS, Mannose, CpG nucleic acid sequences, CpG7909, ligands of human TLR 1-10, ligands of murine TLR 1-13, ISS-1018, 35 IC31, Imidazoquinolines, Ampligen, Ribi529, IMOxine, IRIVs, VLPs, cholera toxin, heat-labile toxin, Pam3Cys, Flagellin, GPI anchor, LNFPIII/Lewis X, antimicrobial peptides, UC-1V150, RSV fusion protein, cdiGMP; and adjuvants suitable as antagonists including CGRP neuropeptide.

Particularly preferred, an adjuvant may be selected from adjuvants, which support induction of a Th1-immune response or maturation of naïve T-cells, such as GM-CSF, IL-12, IFNg, any immunostimulatory nucleic acid as defined above, preferably an immunostimulatory RNA, CpG DNA, etc.

In further preferred embodiments it is also possible that in this context, the present invention contains (or comprises the use of) besides the antigen-providing mRNA, and/or other nucleic acid construct or immunogenic polypeptide, further components which are selected from the group comprising: further antigens or further antigen-providing nucleic acids; a further immunotherapeutic agent; one or more auxiliary substances; or any further compound, which is known to be immunostimulating due to its binding affinity (as ligands) to human Toll-like receptors; and/or an adjuvant nucleic acid, preferably an immunostimulatory RNA (isRNA).

In other preferred embodiments it is also possible that in this context, the present invention additionally contains (or additionally comprises the use of) one or more auxiliary substances in order to increase its immunogenicity or immunostimulatory capacity, if desired. A synergistic action of the inventive mRNA sequence as defined herein and of an auxiliary substance, which may be optionally contained in the inventive pharmaceutical composition, is preferably achieved thereby. Depending on the various types of auxiliary substances, various mechanisms can come into consideration in this respect. For example, compounds that permit the maturation of dendritic cells (DCs), for example lipopolysaccharides, TNF-alpha or CD40 ligand, form a first class of suitable auxiliary substances. In general, it is possible to use as auxiliary substance any agent that influences the immune system in the manner of a "danger signal" (LPS, GP96, etc.) or cytokines, such as GM-CFS, which allow an immune response to be enhanced and/or influenced in a targeted manner. Particularly preferred auxiliary substances are cytokines, such as monokines, lymphokines, interleukins or chemokines, that further promote the innate immune response, such as IL-1, IL-2, IL-3, IL-4, IL-5, IL-6, IL-7, IL-8, IL-9, IL-10, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IFN-alpha, IFN-beta, IFN-gamma, GM-CSF, G-CSF, M-CSF, LT-beta or TNF-alpha, growth factors, such as hGH, Also included are embodiments of the various aspects of the present invention that (additionally) contain (or additionally comprise the use of) any further compound, which is known to be immunostimulating due to its binding affinity (as ligands) to human Toll-like receptors TLR1, TLR2, TLR3, TLR4, TLR5, TLR6, TLR7, TLR8, TLR9, TLR10, or due to its binding affinity (as ligands) to murine Toll-like receptors TLR1, TLR2, TLR3, TLR4, TLR5, TLR6, TLR7, TLR8, TLR9, TLR10, TLR11, TLR12 or TLR13.

In this context it is particularly preferred that embodiments of the present invention that additionally comprise or contain (or that additionally comprise the use of) an adjuvant component comprises (or comprises the use of) the same mRNA sequence or construct as that comprised in second antigenic composition, e.g. an mRNA coding for the same epitope of (or the same) immunogenic peptide or polypeptide, or fragments, variants or derivatives thereof.

Despite, the various aspects of the present invention may comprise (or comprise the use of) further components for facilitating administration and uptake of components of the applicable (antigenic) composition and/or treatment regimen of the present invention. Such further components may be an appropriate carrier or vehicle, additional adjuvants for supporting any immune response, antibacterial and/or antiviral agents.

Alternatively, in the context of each of the various aspects of the present invention, certain other embodiments of the methods, compositions, vaccines or kits may not comprise or comprise the use of one or more of the adjuvants listed herein, or may not contain, comprise or comprise the use of an adjuvant (such as none of those listed herein). That is, such embodiments of these aspects of the invention operate and/or provide utility without one or more such an additional agent or composition that modifies (eg enhances) the efficacy of the other agents comprised or used (such as an antigenic composition as set forth herein).

In certain embodiments of each of the various aspects of the present invention, the methods, compositions, vaccines or kits may (additionally) comprise or comprise the use of a pharmaceutically acceptable carrier and/or vehicle.

Such a pharmaceutically acceptable carrier typically includes the liquid or non-liquid basis of a composition comprising the components of the inventive pharmaceutical composition. If the composition is provided in liquid form, the carrier will typically be pyrogen-free water; isotonic saline or buffered (aqueous) solutions, e.g. phosphate, citrate etc. buffered solutions. The injection buffer may be hypertonic, isotonic or hypotonic with reference to the specific reference medium, i.e. the buffer may have a higher, identical or lower salt content with reference to the specific reference medium, wherein preferably such concentrations of the afore mentioned salts may be used, which do not lead to damage of cells due to osmosis or other concentration effects. Reference media are e.g. liquids occurring in "in vivo" methods, such as blood, lymph, cytosolic liquids, or other body liquids, or e.g. liquids, which may be used as reference media in "in vitro" methods, such as common buffers or liquids. Such common buffers or liquids are known to a skilled person. Ringer-Lactate solution is particularly preferred as a liquid basis.

However, one or more compatible solid or liquid fillers or diluents or encapsulating compounds, which are suitable for administration to a subject (such as a human patient) to be treated, may be used as well for the pharmaceutical composition according to the invention. The term "compatible" as used here means that these constituents of the inventive pharmaceutical composition are capable of being mixed with the components of the inventive pharmaceutical composition in such a manner that no interaction occurs which would substantially reduce the pharmaceutical effectiveness of the pharmaceutical composition under typical use conditions.

A further component of (or for use in) the various aspects of the present invention may be an immunotherapeutic agent that can be selected from immunoglobulins, preferably IgGs, monoclonal or polyclonal antibodies, polyclonal serum or sera, etc, most preferably immunoglobulins directed against a pathogen or tumour or cancer cell, such as one or more of those described herein. Preferably, such a further immunotherapeutic agent may be provided as a peptide/protein or may be encoded by a nucleic acid, preferably by a DNA or an RNA, more preferably an mRNA. Such an immunotherapeutic agent allows providing passive vaccination additional to active vaccination triggered by the inventive antigen-providing mRNA.

Furthermore, in specific embodiments, additionally to the antigen-providing mRNA further antigens can be included in or used in the various aspects of the present invention and are typically substances such as cells, cell lysates, viruses, attenuated viruses, inactivated viruses, proteins, peptides, nucleic acids or other bio- or macromolecules or fragments thereof. Preferably, antigens may be proteins and peptides or fragments thereof, such as epitopes of those proteins or peptides, preferably having 5 to 15, more preferably 6 to 9, amino acids. Particularly, said proteins, peptides or epitopes may be derived from a glycoprotein (GP) and/or a matrix protein (such as VP40) and/or a nucleoprotein (NP) of a virus pathogen or from fragments, variants or derivatives thereof. Further, antigens may also comprise any other biomolecule, e.g., lipids, carbohydrates, etc. Preferably, the antigen is a protein or (poly-) peptide antigen, a nucleic acid, a nucleic acid encoding a protein or (poly-) peptide antigen, a polysaccharide antigen, a polysaccharide conjugate antigen, a lipid antigen, a glycolipid antigen, a carbohydrate antigen, a bacterium, a cell (vaccine), or killed or attenuated viruses. Particularly preferred in this context is the addition of anti-virus vaccines comprising inactivated virus.

The various aspects of the present invention defined herein may furthermore comprise or comprise the use of further additives or additional compounds. Further additives which may be included in the pharmaceutical composition are emulsifiers, such as, for example, Tween®; wetting agents, such as, for example, sodium lauryl sulfate; colouring agents; taste-imparting agents, pharmaceutical carriers; tablet-forming agents; stabilizers; antioxidants; preservatives, RNase inhibitors and/or an anti-bacterial agent or an anti-viral agent. Additionally the inventive pharmaceutical composition may comprise small interfering RNA (siRNA) directed against genes of a pathogen or of a tumour of cancer cell, e.g. siRNA directed against the gene encoding a glycoprotein (GP) or a matrix protein (such as VP40) or a nucleoprotein (NP) of a viral pathogen.

The various aspects of the present invention typically comprises or comprise the use or administration of an effective amount of the components of one or other (or both) of the antigenic compositions, particularly of the mRNA contruct(s) as defined herein. As used herein, an "effective amount" also means an amount of the mRNA construct(s) as defined herein as such that is sufficient to significantly induce an immune respeoce and/or a positive modification of a disease or disorder or to prevent a disease, preferably a pathogen diseased, a turnout or cancer disease, an allergy disease or an autoimmune disease as defined herein. In further embodiments, a "safe and effective amount" is an "effective amount" (as defined anywhere herein) that is small enough to avoid serious side-effects and to permit a sensible relationship between advantage and risk. The determination of these limits typically lies within the scope of sensible medical judgment.

The various aspects of the present invention may be used for human and also for veterinary medical purposes, preferably for human medical purposes, as a pharmaceutical composition in general or as a vaccine.

In another particularly preferred aspect, the first antigenic composition may be provided or used as a vaccine; and/or the second antigenic composition may be provided or used as a vaccine Accordingly, in one additional aspect, the present invention relates to a first vaccine composition comprising a first antigenic composition as described, defined or claimed herein; and in another additional aspect, the present invention also relates to a second vaccine composition comprising a second antigenic composition as described, defined or claimed herein; and in yet another aspect the present invention also relates to a vaccine combination comprising both of the following two (separate) components: (x) a first antigenic composition or a first vaccine composition, in each case as described, defined or claimed herein; and (y) a second antigenic composition or a second vaccine composition, in each case as described, defined or claimed herein.

Typically, such a vaccine, vaccine composition or vaccine combination is as defined above for pharmaceutical compositions. Additionally, such a vaccine, vaccine composition or vaccine combination in respect of the second antigenic composition typically contains an mRNA construct as defined herein or a plurality of mRNA construct as defined herein.

Such inventive vaccines, vaccine compositions or vaccine combinations may also comprise a pharmaceutically acceptable carrier, adjuvant, and/or vehicle as defined herein above. In the specific context of the vaccines, vaccine compositions or vaccine combinations of the present invention, the choice of a pharmaceutically acceptable carrier is determined in principle by the manner in which such vaccine, vaccine composition or vaccine combination is administered. A vaccine, vaccine composition or vaccine combination of the present invention can be administered, for example, systemically or locally. Routes for systemic administration in general include, for example, transdermal, oral, parenteral routes, including subcutaneous, intravenous, intramuscular, intraarterial, intradermal and intraperitoneal injections and/or intranasal administration routes. Routes for local administration in general include, for example, topical administration routes but also intradermal, transdermal, subcutaneous, or intramuscular injections or intralesional, intracranial, intrapulmonal, intracardial, and sublingual injections. More preferably, vaccines, vaccine compositions or vaccine combinations of the present invention may be administered by an intradermal, subcutaneous, or intramuscular route. Inventive vaccines, vaccine compositions or vaccine combinations of the present invention are therefore preferably formulated in liquid (or sometimes in solid) form. Preferably, a vaccine, vaccine composition or vaccine combination of the present invention may be administered by conventional needle injection or needle-free jet injection. In a preferred embodiment an inventive vaccine, vaccine composition or vaccine combination may be administered by jet injection as defined herein, preferably intramuscularly or intradermally, more preferably intradermally.

A vaccine, vaccine composition or vaccine combination of the present invention can additionally contain one or more auxiliary substances in order to increase its immunogenicity or immunostimulatory capacity, if desired. Particularly preferred are adjuvants as auxiliary substances or additives as defined for the pharmaceutical composition.

In a further aspect, the present invention relates to a kit or kit of parts comprising: (x) a first antigenic composition or a first vaccine composition, in each case as described, defined or claimed herein; and (y) a second antigenic composition or a second vaccine composition, in each case as described, defined or claimed herein. In certain embodiments, such kit or kit of parts comprises a plurality (such a two or more) containers the contents of at least two or more of such containers differing from each other in whole or in part: the first of such containers containing a first antigenic composition or a first vaccine composition, in each case as described, defined or claimed herein; and the second of such containers containing a second antigenic composition or a second vaccine composition, in each case as described, defined or claimed herein.

In certain embodiments of the kit or kit of parts of the present invention, such kit/kit of parts optionally includes (eg may additionally comprise) instructions, such as instructions that comprise information on the administration and dosage of one or more of components of the kit/kit of parts.

In yet another aspect, the present invention also relates to a packaged vaccine that comprises: (x) a first antigenic composition or a first vaccine composition, in each case as described, defined or claimed herein; and/or (y) a second antigenic composition or a second vaccine composition, in each case as described, defined or claimed herein; wherein preferably when both such components are included, such components are contained in separate containers; and wherein the package additionally comprises instructions, such as instructions that comprise information on the administration and dosage of one or more of components of the packaged vaccine.

In particular embodiments of the present invention, a kit/kit of parts or a packaged vaccine of the present invention; or the first or second antigenic composition of the present invention; or the first or second vaccine composition of the present invention is for use in a prime-boost vaccination regimen, such as in a prime-boost regimen disclosed described or used herein, for example in any of the methods of the present invention.

In certain embodiments, the instructions of the kit/kit of parts or of the packaged vaccine of the present invention can further include (eg can additionally comprise) information to: (a) administer to a subject at least once an effective amount of the first antigenic composition or first vaccine composition; and (b) subsequently administer to the subject at least once an effective amount of the second antigenic composition or second vaccine composition. In particular of such instructions, the subject is a human subject and/or one that is in need of such administration.

In particular of such embodiments, the instructions (additionally) comprise instructions (eg information) to administer the first and/or second antigenic compositions (or the first and/or second vaccine compositions) as set forth herein, such as in a prime-boost regimen disclosed described or used herein, for example in any of the methods of the present invention.

As used herein, the term "container" includes the meaning of any receptacle for holding a composition or vaccine of the present invention. For example, in certain embodiments, the container is the packaging that directly contains such composition or vaccine (ie the packaging is in direct contact with composition or vaccine; "primary packaging"), such as a vial, syringe, ampule, blister-pack and the like. In other embodiments, the container is not the packaging that directly contains the pharmaceutical composition, i.e., the container is a receptacle, such as a box or vial that contains the (primary) packaged composition or vaccine (ie, "secondary packaging"), such as a paper or plastic box or bag. Packaging techniques for both primary and secondary packaging are well-known in the art.

It should be understood that the instructions for use of the compositions, vaccine or components of the kit/kit of parts or packaged vaccine may be contained on the packaging containing such compositions or vaccine and as such the instructions form an increased functional relationship to the packaged product. However, it should be understood that the instructions can contain information pertaining to the composition's or vaccine's ability to perform its intended function, e.g., treating, ameliorating, or preventing a condition, disorder or disease in a subject. The instructions may alternatively, or additionally include at least one of the following information: description of the therapeutic agent; dosage schedule and administration for treatment or prevention of a condition, disorder or disease or symptoms thereof; precautions; warnings; indications; counter-indications; overdosage information; adverse reactions; animal pharmacology; suitable subject population such as age, sex, weight and/or health, physiological or genetic status.

"Instructions", as that term is used herein, includes the meaning of printed words, numbers and/or figures, a publication, a recording, a diagram, or any other medium of expression which can be used to communicate information on the usefulness of, or other aspects in respect of, a composition or vaccine of the present invention, such as one in a kit/kit of parts or packaged vaccine. Such instructions of a kit or package may, for example, be affixed to or comprise a surface of a container that contains a composition or vaccine of the present invention (such as one the primary or secondary packaging of such kit/kit of parts or packaged vaccine) or the instructions can be separate to the packaging but shipped together with (such as inside) a container which contains a composition or vaccine of the present invention. Examples of such instructions include a patient information sheet, a package-insert, prescribing information and or a summary of product characteristics. Alternatively, the instructions may be shipped separately from the container with the intention that the recipient uses such instructions and a composition or vaccine of the present invention cooperatively. In such embodiment, delivery of the instructions may be, for example, by physical delivery of the information sheet, publication or other medium of expression communicating the usefulness of, or other aspects in respect of, the kit such as computer readable memory containing information to enable a computer to display or record the instructions in human understandable form, such as on a screen or to speak verbal instructions, or may alternatively be achieved by electronic transmission, for example by means of a computer, such as by electronic mail, or download from a website.

It is to be understood that application of the teachings of the present invention to a specific problem or environment, and the inclusion of variations of the present invention or additional features thereto (such as further aspects and embodiments), will be within the capabilities of one having ordinary skill in the art in light of the teachings contained herein.

Unless context dictates otherwise, the descriptions and definitions of the features set out above are not limited to any particular aspect or embodiment of the invention and apply equally to all aspects and embodiments which are described.

All references, patents, and publications cited herein are hereby incorporated by reference in their entirety.

Certain aspects and embodiments of the invention will now be illustrated by way of example and with reference to the description, figures and tables set out herein. Such examples of the methods, uses and other aspects of the present invention are representative only, and should not be taken to limit the scope of the present invention to only such representative examples.

FIGURES

The figures shown in the following are merely illustrative and shall describe the present invention in a further way. These figures shall not be construed to limit the present invention thereto.

FIG. 1: shows box-plots of IFN-gamma spots from various treatment groups of mice as described in Example 1. A significant increase in immune response in mice (number of IFN-gamma spots, determined as described in Example 1) results from the specifically-ordered protein prime:mRNA boost vaccination regimen of the invention (treatment group D) compared to the inverse vaccination regimen of mRNA prime:protein boost vaccination (treatment group C) and also compared to a homologous vaccination regimen of protein prime:protein boost (treatment group B). Treatment groups A and E represent homologous prime:boost regimens with Ringer Lactate buffer (as control) and mRNA respectively.

Figure 2A:
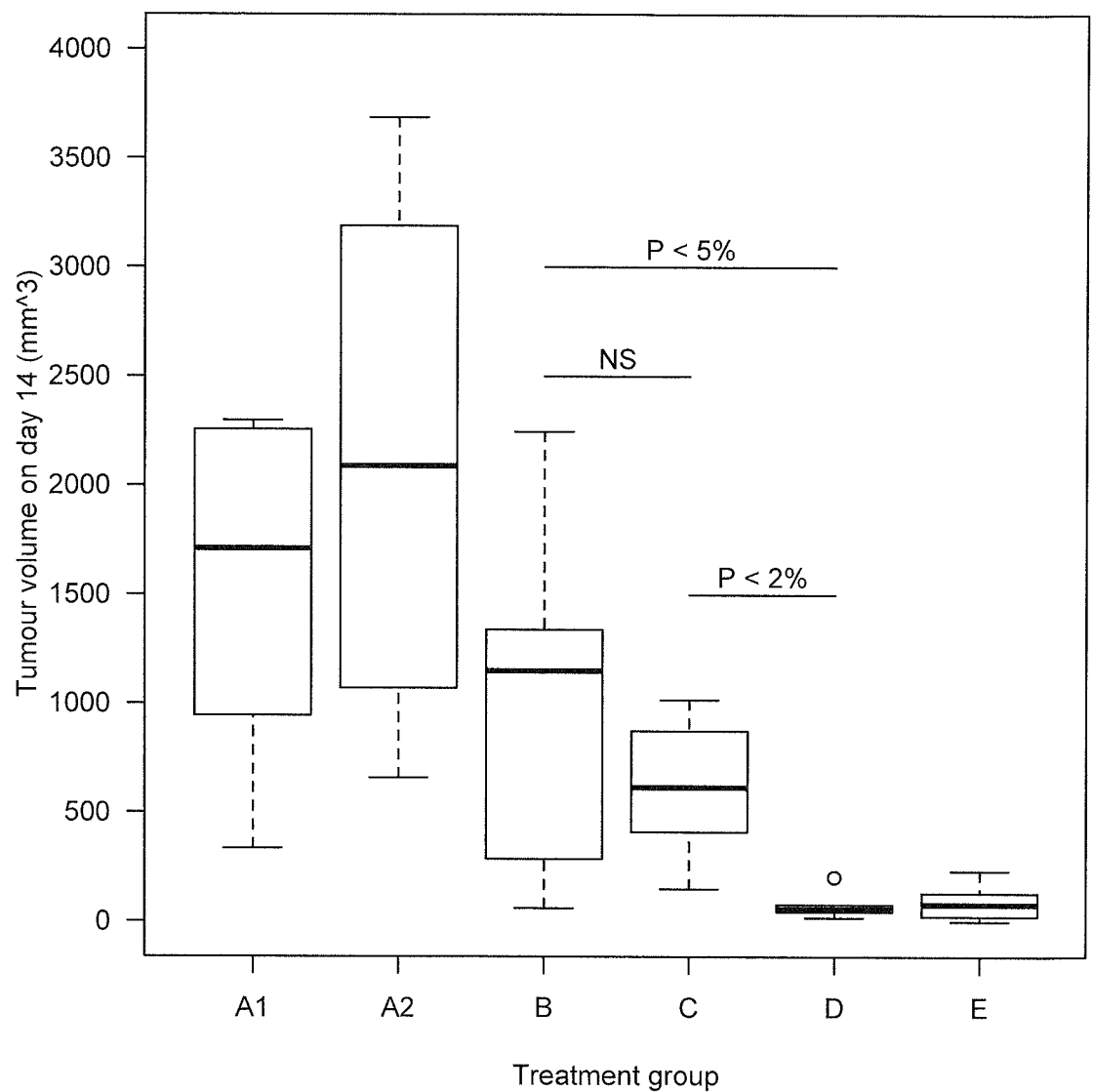

FIG. 2a: shows box-plots of tumour volume 14 days following tumour challenge from various treatment groups of mice as described in Example 2. A significant increase in tumour protection (tumour volume 14 days after challenge, determined as briefly described below) results from the specifically-ordered protein prime:mRNA boost vaccination regimen of the invention (treatment group D) compared to the inverse vaccination regimen represented by the mRNA prime:protein boost (treatment group C) and also compared to a homologous vaccination regimen of protein prime: protein boost (treatment group B). Treatment groups A1, A2 and E represent homologous prime:boost regimens with Ringer Lactate buffer, CpG-DNA adjuvant (as controls) and mRNA respectively.

Figure 2B:
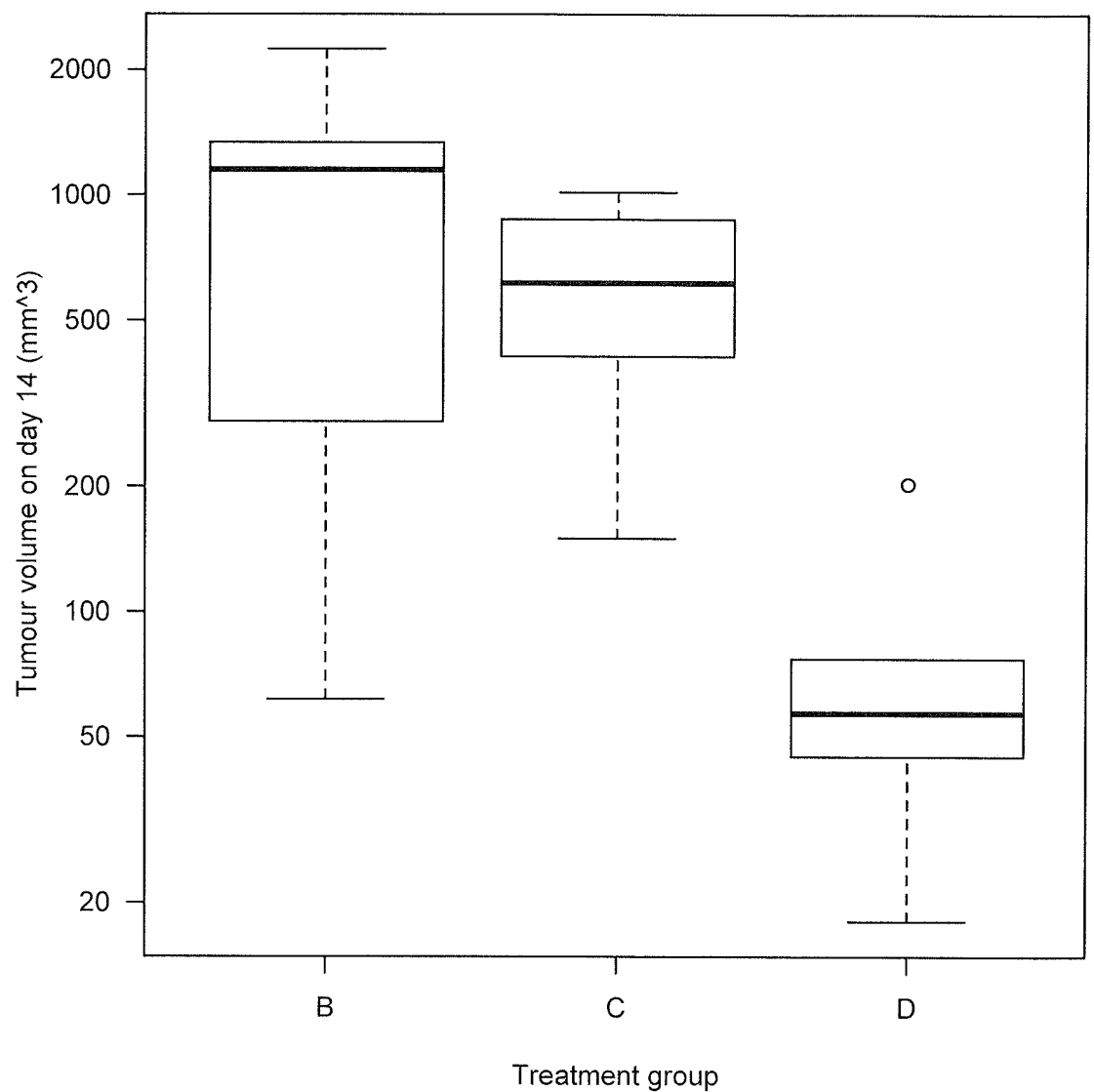

FIG. 2b: shows box-plots of the same data for treatment groups B, C and D (respectively protein prime:protein boost, mRNA prime:protein boost and protein prime:mRNA boost) as shown in FIG. 1, but plotted using a log-scale so as to more readily observe the significant improvement on tumour protection conferred by the specifically-ordered heterologous vaccination regimen of protein prime:mRNA boost of the present invention (treatment group D).

EXAMPLES

The examples shown in the following are merely illustrative and shall describe the present invention in a further way. These examples shall not be construed to limit the present invention thereto.

Example 1: Improved T-Cell Response after Heterologous Prime-Boost Vaccination Involving Administration of a Boosting Composition that Includes an mRNA Construct Encoding at Least One Immunogenic Protein The inventors made the surprising finding that the administration of an mRNA construct encoding ovalbumin protein after (ie, as a vaccination "boost") the administration of ovalbumin protein (ie as a vaccination "prime") resulted in a significant increase in immune response (as measured by IFN-gamma secretion in splenocytes) as compared to the inverse vaccination regimen where the mRNA construct is administered as the vaccination prime before the administration of ovalbumin protein as the vaccination boost.

FIG. 1 shows a significant increase in the number of IFN-gamma spots (a measure of immune response, and determined as briefly described below) in the protein prime:mRNA boost treatment group (D) compared to the inverse vaccination regimen represented by the mRNA prime:protein boost treatment group (C) (two-tailed Wilcoxon rank sum test: p-value=0.01587). Given that many currently available vaccination therapies include a protein-based vaccination, it is highly relevant to observe the yet more significant difference between the low immune response produced by homologous vaccination regimen of protein prime:protein boost (treatment group B) compared to that produced by the specifically-ordered heterologous vaccination regimen of protein prime:mRNA boost of the present invention (treatment group D) (two-tailed Wilcoxon rank sum test: p-value=0.007937). Treatment groups A and E represent homologous prime:boost regimens with buffer and mRNA respectively, each administered i.d.

Briefly, for each treatment group five C57BL/6 mice (10 weeks old) were vaccinated intradermally (i.d.) with OVA-RNActive R1710 (32 µg/mouse/vaccination day, prepared as described in WO2010/037539) and/or intramuscularly (i.m.) with adjuvanted ovalbumin protein (5 µg/mouse/vaccination day, adjuvanted with CureVac's RNA-based adjuvant (R711+CR12C 2:1), and prepared as described in WO2012/013326) according to the following vaccination schedule (Table 1). As a control, one treatment group was administered i.d. with Ringer Lactate (RiLa) buffer.

The OVA-encoding mRNA construct comprised the following features, further specific or alternative embodiments of such features (or other features of the mRNA) are described elsewhere herein: The construct was prepared by modifying the wild type coding sequence by introducing a GC-optimized sequence for stabilization, followed by a stabilizing sequence derived from the alpha-globin-3'-UTR (muag (mutated alpha-globin-3'-UTR)), a stretch of 64 adenosines (poly-A-sequence), a stretch of 30 cytosines (poly-C-sequence), and a histone stem loop.

TABLE 1

Animal treatment groups (five mice/group)

| Group | Prime vaccination | | Boost vaccination | | Readout |
|---|---|---|---|---|---|
| | day 0 | day 13 | day 27 | day 41 | day 48 |
| A | RiLa 4 × 20 µl i.d | RiLa 4 × 20 µl i.d | RiLa 4 × 20 µl i.d | RiLa 4 × 20 µl i.d | Ex vivo ELISpot |
| B | Ovalbumin protein 30 µl i.m. left side | Ovalbumin protein 30 µl i.m. right side | — | Ovalbumin protein 30 µl i.m. left side | Ovalbumin protein 30 µl i.m. right side | |
| C | R1710 mRNA 4 × 20 µl i.d | R1710 mRNA 4 × 20 µl i.d | — | Ovalbumin protein 30 µl i.m. left side | Ovalbumin protein 30 µl i.m.. right side | |
| D | Ovalbumin protein 30 µl i.m. left side | Ovalbumin protein 30 µl i.m. right side | — | R1710 mRNA 4 × 20 µl i.d | R1710 mRNA 4 × 20 µl i.d | |
| E | R1710 mRNA 4 × 20 µl i.d | R1710 mRNA 4 × 20 µl i.d | — | R1710 mRNA 4 × 20 µl i.d | R1710 mRNA 4 × 20 µl i.d | |

For analysis, splenocytes were isolated from each mouse and analysed by ELISPOT assay after stimulation with a MHC I specific SIINFEKL peptide (Fotin-Mleczek et al, 2012; J Gene Med 14:428). Data-visualisation and statistical analyses and were conducted using R version 3.1.2 (The R Foundation for Statistical Computing, 2014). The distribution of the number of IFN-gamma spots for the five mice in each treatment group is represented by box-plots (for each group, the median of the data-points is shown by dark line, the rectangles represent the interquartile range (IQR) of the data-points, the whiskers extent to the most extreme data-points within 1.5 of the IQR and any data-points lying outside of such a range are shown individually).

Example 2: Improved Anti-Tumour Protection Following Heterologous Prime-Boost Anti-Cancer Vaccination Involving Administration of a Boosting Composition that Includes an mRNA Construct Encoding at Least One Immunogenic Protein Not only did the inventors show an improved immune response by the novel prime-boost regimen of the invention (as described in Example 1 above), they were further surprised to find that another novel prime-boost regimen of the invention provided increased tumour protection: administration of mRNA construct encoding ovalbumin protein after (ie, as a vaccination "boost") the administration of ovalbumin protein (ie as a vaccination "prime") resulted in a significant increase in tumour protection (as measured by the resulting tumor volume after challenge) as compared to the inverse vaccination regimen where the mRNA construct is administered as the vaccination prime before the administration of ovalbumin protein as the vaccination boost.

FIG. 2a shows a significant increase in tumour protection (as measured by the resulting tumour volume 14 days after challenge, and determined as briefly described below) in the protein prime:mRNA boost treatment group (D) compared to the inverse vaccination regimen represented by the mRNA prime:protein boost treatment group (C) (two-tailed Wilcoxon rank sum test: p-value=0.01587). Furthermore, while there was no significant difference in the tumour protection conferred by the homologous vaccination regimen of protein prime:protein boost (treatment group B) and the inverse vaccination regimen represented by the mRNA prime:protein boost treatment group (C) (two-tailed Wilcoxon rank sum test: p-value=0.5476), there was a significant difference in the tumour protection conferred by the homologous vaccination regimen of protein prime:protein boost (treatment group B) and the specifically-ordered heterologous vaccination regimen of protein prime:mRNA boost of the present invention (treatment group D) (two-tailed Wilcoxon rank sum test: p-value=0.03175). Treatment groups A1, A2 and E represent homologous prime:boost regimens with buffer, adjuvant and mRNA respectively.

FIG. 2b shows the same data for treatment groups B, C and D (respectively protein prime:protein boost, mRNA prime:protein boost and protein prime:mRNA boost) plotted uses a log-scale so as to more readily observe the significant improvement on tumour protection conferred by the specifically-ordered heterologous vaccination regimen of protein prime:mRNA boost of the present invention (treatment group D).

Briefly, for each treatment group five C57BL/6 mice (10 weeks old) were vaccinated intramuscularly (i.m.) with OVA-RNActive R1710 (20 µg/mouse/vaccination day, as described in WO2010/037539) and/or subcutaneously (s.c.) with adjuvanted ovalbumin protein (10 µg/mouse/vaccination day plus 10 µg CpG-DNA per mouse and vaccination day, and prepared as described below) according to the following vaccination schedule (Table 2). As controls, one treatment group was administered i.m. with Ringer Lactate (RiLa) buffer and another administered s.c. with CpG-DNA (10 μg/mouse and vaccination day).

TABLE 2

Animal treatment groups (five mice/group)

| Group | Prime vaccination day 0 | Prime vaccination day 2 | — | Boost vaccination day 14 | Boost vaccination day 16 | Readout |
|---|---|---|---|---|---|---|
| A1 | RiLa 2 × 25 μl i.m | RiLa 2 × 25 μl i.m | — | RiLa 2 × 25 μl i.m | RiLa 2 × 25 μl i.m | Described below |
| A2 | — | 10 μg CpG-DNA 100 μl s.c in IFA | — | — | 10 μg CpG-DNA 100 μl s.c in IFA | |
| B | — | Ovalbumin protein 10 μg + 10 μg CpG-DNA in IFA 100 μl s.c | — | — | Ovalbumin protein 10 μg + 10 μg CpG-DNA in IFA 100 μl s.c | |
| C | R1710 mRNA (20 μg) 2 × 25 μl i.m | R1710 mRNA (20 μg) 2 × 25 μl i.m | — | — | Ovalbumin protein 10 μg + 10 μg CpG-DNA in IFA 100 μl s.c | |
| D | — | Ovalbumin protein 10 μg + 10 μg CpG-DNA in IFA 100 μl s.c | — | R1710 mRNA (20 μg) 2 × 25 μl i.m | R1710 mRNA (20 μg) 2 × 25 μl i.m | |
| E | R1710 mRNA (20 μg) 2 × 25 μl i.m | R1710 mRNA (20 μg) 2 × 25 μl i.m | — | R1710 mRNA (20 μg) 2 × 25 μl i.m | R1710 mRNA (20 μg) 2 × 25 μl i.m | |

Further details on preparation of one or more of the compositions administrated during this example 2 are as follows:

mRNA composition: Ova-RNA 20 μg/mouse, 1:8 complexed with protamine (25 μl were injected per muscle), prepared as described in WO2010/037539.

Protein composition: Ovalbumin 10 μg/mouse+CpG-DNA 10 μg/mouse with Incomplete Freund's Adjuvant (IFA) to 100 μl per mouse.

CpG-DNA composition: CpG-DNA (1826) 10 μg/mouse with Incomplete Freund's Adjuvant (IFA) to 100 μl per mouse.

CpG DNA (1826) was prepared as described in (Scheel et al, 2004; Eur J Immunol 34:537).

Tumour challenge was performed essentially as described previously (Fotin-Mleczek et al, 2012; J Gene Med 14:428). Briefly, eight days after the last vaccination, mice were challenged subcutaneously with 1×10$^6$ syngeneic E.G7-OVA tumour cells into the flank and tumour growth was monitored by measuring the tumour size in three dimensions using callipers, with readout taken as tumour volume (in mm$^3$) 14 days after challenge.

Data-visualisation and statistical analyses were performed as described in Example 1.

Example 3 [Prophetic]: Improved T-Cell Response after Heterologous Prime-Boost Vaccination Involving Administration of a Priming Composition that Includes a Viral Vector Encoding an Immunogenic Protein and Subsequent Administration of a Boosting Composition that Includes an mRNA Construct Encoding the Immunogenic Protein An improvement in immune response is also shown with a further heterologous prime:boost vaccination regimen of the present invention, in this case a regime comprising administration of a priming composition that includes a viral vector that encodes an immunogenic protein and subsequent administration of a boosting composition that includes an mRNA construct encoding the immunogenic protein.

Briefly, the immune response of such an inventive prime:boost vaccination regimen is shown generally as described in Example 1, except that: (1) the adjuvanted ovalbumin composition is replaced by the recombinant adenovirus vector Bonobo Adenovirus type 3, PanAd3, encoding the respiratory syncytial virus (RSV) F-protein and administered intranasally or intramuscularly (10$^8$ virus particles per mouse); and (2) the OVA-RNActive R1710 composition is replaced by an RSV-F protein (or an RSV-F mutant) encoding mRNA composition (RSV-F RNActive). The adenoviral vector is administered on day 0 and the RSV-F RNActive composition is administered 4 weeks later intradermally.

The first composition including the recombinant Bonobo Adenovirus type 3, PanAd3 vector encoding the RSV-F protein is prepared as described in WO2014/006191.

The second composition, including the RSV-F RNActive encoding the RSV-F protein or a mutant thereof is prepared as described in WO2015/024668. An example of an RSV-F mutant is the deletion mutant RSV-Fdel 554-574 long protein (Oomens et al, 2006; J Virol 80:10465). Such mRNA construct comprises the following features, further specific or alterative embodiments of such features (or other features of the mRNA) are described elsewhere herein: The construct is prepared by modifying the wild type coding sequence by introducing a GC-optimized sequence for stabilization, followed by a stabilizing sequence derived from the alpha-globin-3'-UTR (muag (mutated alpha-globin-3'-UTR)), a stretch of 64 adenosines (poly-A-sequence), a stretch of 30 cytosines (poly-C-sequence), and a histone stem loop.

Vaccine Design

To design a vaccine antigen for use in the present invention, protein sequences of the F0-, N-, and M2-1- proteins of RSV are retrieved from the National Center for Biotechnology Information (NCBI) RSV Resource database (available on the world wide web at ncbi.nlm.nih.gov). Protein sequences are chosen from different RSV subtype A strains.

A F0 consensus sequence is derived by alignment of all non-identical sequences of the F-protein using MUSCLE version 3.6 and applying the majority rule. The vaccine's F0 consensus sequence is designed on the basis of the alignment of the different RSV sequences. The sequence similarity of the vaccine consensus F0 sequence is measured performing BLAST analysis, which stands for Basic Local Alignment Search Tool and is publicly available through the NCBI. The highest average similarity of the consensus sequence, calculated compared to all RSV sequences in the database, is 100% with respect to the human respiratory syncytial virus A2 strain. Further, the vaccine's F0 sequence lacks the transmembrane (TM) region residing in amino acids 525 to 574 (F0deltaTM) to allow for the secretion of F0deltaTM. Finally, the vaccine's F0deltaTM sequence is codon-optimized for expression in eukaryotic cells.

The vaccine's N consensus sequence is derived by alignment of all non-identical sequences of the N-protein using MUSCLE version 3.6 and applying the majority rule. BLAST analysis of the N consensus sequence finds the best alignment with the human respiratory syncytial virus A2 strain. The vaccine's N sequence is then codon-optimized for expression in eukaryotic cells.

A M2-1 consensus sequence is derived by alignment of all non-identical sequences of the M2-1-protein using MUSCLE version 3.6 and applying the majority rule. BLAST analysis of the M2-1 consensus sequence finds the best alignment with the human respiratory syncytial virus A2 strain. Finally, the vaccine's M2-1 sequence is codon-optimized for expression in eukaryotic cells.

The vaccine's F0deltaTM sequence and N sequence are spaced by the cleavage sequence 2A of the Foot and Mouth Disease virus. The vaccine's N sequence and M2-1 sequence are separated by a flexible linker (GGGSGGG; SEQ ID NO: 10).

Finally, the codon-optimized viral genes are cloned as the single open reading frame F0deltaTM-N-M2-1.

Generation of DNA Plasmids Encoding F0deltaTM and F0deltaTM-N-M2-1

Consensus F0deltaTM, N and M2-1 sequences are optimized for mammalian expression, including the addition of a Kozak sequence and codon optimization. The DNA sequence encoding the multi-antigen vaccine is chemically synthesized and then sub-cloned by suitable restriction enzymes EcoRV and NotI into the pVJTetOCMV shuttle vector under the control of the CMV promoter.

Generation of PanAd3 Viral-Vectored RSV Vaccine

A viral-vectored RSV vaccine PanAd3/F0deltaTM-N-M2-1 is generated which contains a 809 amino acid polyprotein (SEQ ID NO: 7 of WO2014/006191) coding for the consensus F0deltaTM, N and M2-1 proteins fused by a flexible linker. Bonobo Adenovirus type 3 (PanAd3) is a novel adenovirus strain with improved seroprevalence and has been described previously.

Cloning of F0deltaTM-N-M2-1 from the plasmid vector pVJTetOCMV/F0deltaTM-N-M2-1 into the PanAd3 pre-Adeno vector is performed by cutting out the antigen sequences flanked by homologous regions and enzymatic in vitro recombination. Cloning of F0deltaTM-N-M2-1 from the shuttle plasmid vector p94-F0deltaTM-N-M2-1 into the MVA vector is performed by two steps of enzymatic in vitro recombination and selection of the positive recombinant virus by fluorescence microscopy.

Prime with PanAd3-RSV and Boost with RSV-F RNActive in Mice

1. Materials and Methods

Groups of 5 BALB/c mice are immunised with 10exp8 virus particles of PanAd3-RSV by instillation in the nose or by intramuscular injection. Another group is intradermally immunised with 20 µg of RSV-F RNActive as described below. Four weeks later all animals receive intradermally 20 µg of RSV-F RNActive. After four weeks all animals are bled and serum is prepared. A pool of sera of the animals in each group is analysed by F protein ELISA: Briefly, 96 well microplates are coated with 0.5 µg protein F (Sino Biologicals Inc. cat n. I 1049-V08B) and incubated with serial dilutions of the sera. After extensive washes, the specific binding is revealed by a secondary anti-mouse IgG antibody conjugated with alkaline phosphatase. Background is determined using BALB/c pre-immune sera. Antibody titres are expressed as the dilution giving a value equal to background plus 3 times the standard deviation. Neutralising antibodies are measured by a FACS-based infection assay. Briefly, a recombinant RSV-A virus expressing GFP (Chen et al, 2010; J Immunological Methods 362:180) is used to infect cultured Hep-2 cells for 24 hours at a Multiplicity of infection (MOI) giving 20% infected cells. A serial dilution of pools of mice sera is incubated with the virus 1 hour at 37° C. before addition to the cells. 24 hours later the percentage of infected cells is measured by whole-cell FACS analysis. Antibody titre is expressed as the serum dilution giving 50% inhibition of infection (EC50). T cell responses are measured by IFN-gamma T cell Elispot: briefly, spleen and lung lymphocytes are plated on 96 well microplates coated with anti-IFNgamma antibody and stimulated ex vivo with peptide pools spanning the whole RSV vaccine antigen. After extensive washes, the secreted IFN-gamma forming a spot on the bottom of the plate is revealed by a secondary antibody conjugated to alkaline phosphatase. The number of spots is counted by an automatic Elispot reader.

2. Results

The simian adenovirus PanAd3-RSV containing the RSV antigens F, N and M2-1 is administered to groups of BALB/c mice either by the intranasal route or by the intramuscular route. A separate group is immunised with the RSV-F RNActive by intradermal injection. Four weeks later, the three groups of mice are boosted with the RSV-F RNActive by intradermal injection. Four weeks after the boost, sera of mice are analyzed by F-protein ELISA and the neutralising antibody titers are measured by a FACS based RSV neutralisation assay. T cell responses in spleen and lung are measured by IFN-gamma T cell Elispot.

Example 4 [Prophetic]: Improved T-Cell Response after Heterologous Prime-Boost Vaccination Involving Administration of a Priming Composition that Includes an Immunogenic Peptide and Subsequent Administration of a Boosting Composition that Includes an mRNA Construct Encoding the Immunogenic Peptide An improvement in immune response is also shown with a further heterologous prime:boost vaccination regimen of the present invention, in this case a regime comprising administration of a priming composition that includes an immunogenic peptide and subsequent administration of a boosting composition that includes an mRNA construct encoding the immunogenic peptide.

Briefly, the immune response of such an inventive prime:boost vaccination regimen is shown generally as described in Example 1, except that: (1) the adjuvanted ovalbumin composition is replaced by a composition containing an ovalbumin-derived peptide with the amino acid sequence SIINFEKL (SIINFEKL peptide) and administered subcutaneously (s.c.) (10 µg/mouse/vaccination day); (2) the OVA-RNActive R1710 composition is replaced by an SIINFEKL-encoding RNActive composition and administered intramuscularly (i.m.) (20 µg/mouse/vaccination day); and (3) the vaccination schedule is as follows: The peptide vaccine is administered on day 0 and the SIINFEKL-encoding RNActive composition is administered on day 14. As a control, one treatment group is administered i.d. with Ringer Lactate (RiLa) buffer.

The composition including the immunogenic ovalbumin-derived peptide (SIINFEKL) is prepared as follows: Peptide: SIINFEKL peptide 10 µg/mouse with Incomplete Freund's Adjuvant (IFA) to 100 µl per mouse.

The RNActive composition including the mRNA encoding the immunogenic ovalbumin peptide is prepared essentially in the same way as the OVA-RNActive of Example 2 with the difference that the open reading frame (ORF) does not encode the ovalbumin protein but only the SIINFEKL peptide. The OVA-RNActive construct may be prepared using the non-OVA-specific features as described in Example 1 of WO2015/024668. Such an OVA-mRNA construct would then comprise the following features, further specific or alterative embodiments of such features (or other features of the mRNA) are described elsewhere herein: The construct is prepared by modifying the wild type coding sequence by introducing a GC-optimized sequence for stabilization, followed by a stabilizing sequence derived from the alpha-globin-3'-UTR (muag (mutated alpha-globin-3'-UTR)), a stretch of 64 adenosines (poly-A-sequence), a stretch of 30 cytosines (poly-C-sequence), and a histone stem loop.

In view of the above, it will be appreciated that: (x) described herein are; and/or (y) the present invention also relates to, the following first set of items:

1. A method for inducing an immune response in a subject; the method comprising the steps:
   (a) administering to a subject in need thereof at least once an effective amount of a first antigenic composition that comprises at least one immunogenic peptide or polypeptide and/or that comprises at least one nucleic acid construct that encodes at least one immunogenic peptide or polypeptide; and
   (b) subsequently administering to the subject at least once an effective amount of a second antigenic composition that comprises at least one mRNA construct that encodes at least one immunogenic peptide or polypeptide,
   wherein:
      the nucleic acid construct, if comprised in the first antigenic composition, is not an mRNA construct; and
      at least one epitope of the immunogenic peptide or polypeptide comprised in, or encoded by the nucleic acid construct comprised in, the first antigenic composition is immunologically equivalent to at least one epitope of the immunogenic peptide or polypeptide encoded by the mRNA construct of the second antigenic composition.
2. The method of item 1, wherein the first antigenic composition and the second antigenic composition are administered to the subject, respectively, in a prime-boost immunisation regime.
3. The method of item 2, wherein the second antigenic composition is subsequently administered within about 28, 14 or 7 days of administration of the first antigenic composition, preferably about 27, 24, 21, 18, 15, 12, 10, 9, 8, 7, 6, 5, 4, 3, 2 or 1 day(s) after administration of the first antigenic composition.
4. The method of any one of items 1 to 3, wherein:
   the first antigenic composition is administered in two or more doses prior to the administration of the second antigenic composition, and/or
   the second antigenic composition is administered in two or more doses subsequently to the administration of the first antigenic composition,
   preferably, wherein the first antigenic composition and/or the second antigenic composition is administered in a number of doses selected from the list consisting of: 2, 3, 4, 5, 6, 7, 8, 9 and 10 times.
5. The method of item 4, wherein the interval between the administration of one or more pairs of consecutive doses is from about 5 to 120 days.
6. The method of any one of items 1 to 5, wherein the first antigenic composition and/or the second antigenic composition is administered by subcutaneous, intramuscular and/or intradermal injection.
7. The method of item 6, wherein the injection is carried out using conventional needle injection and/or using jet injection.
8. The method of any one of items 1 to 7, wherein the G/C content of the region of the mRNA construct encoding at least one epitope of the immunogenic peptide or polypeptide is increased compared with the G/C content of the region of the wild type mRNA that encodes the epitope of the immunogenic peptide or polypeptide, preferably wherein the amino acid sequence of the immunogenic peptide or polypeptide encoded by the G/C-enriched mRNA is not modified compared with the amino acid sequence of the epitope of the immunogenic peptide or polypeptide encoded by the wild type mRNA.
9. The method of any one of items 1 to 8, wherein the mRNA construct comprises additionally:
   (a) a 5'-CAP structure;
   (b) a poly(A) sequence; and
   (c) optionally a poly (C) sequence.
10. The method of item 9, wherein the poly(A) sequence comprises a sequence of about 25 to about 400 adenosine nucleotides, preferably a sequence of about 50 to about 400 adenosine nucleotides, more preferably a sequence of about 50 to about 300 adenosine nucleotides, even more preferably a sequence of about 50 to about 250 adenosine nucleotides, most preferably a sequence of about 60 to about 250 adenosine nucleotides.
11. The method of any one of items 1 to 10, wherein the mRNA construct comprises additionally at least one histone stem-loop, preferably comprising the corresponding RNA sequence to the nucleic acid sequence according to SEQ ID NO. 1, or a homolog, a fragment or a variant thereof.
12. The method of any one of items 1 to 11, wherein the mRNA construct comprises additionally a 3'-UTR element.
13. The method of item 12, wherein the 3'-UTR element comprises or consists of a nucleic acid sequence which is derived from a 3'-UTR of a gene providing a stable mRNA or from a homolog, a fragment or a variant thereof.
14. The method of item 13, wherein the 3'-UTR element comprises or consists of a nucleic acid sequence derived from a 3'-UTR of a gene selected from the group consisting of an albumin gene, an alpha-globin gene, a beta-globin gene, a tyrosine hydroxylase gene, a lipoxygenase gene, and a collagen alpha gene; or from a homolog, a fragment or a variant thereof.
15. The method of item 13 or 14, wherein the 3'-UTR element is derived from a nucleic acid sequence according to SEQ ID NO. 3 or SEQ ID NO. 4, or from a corresponding RNA sequence, a homolog, a fragment or a variant thereof.
16. The method of any one of items 1 to 15, wherein the mRNA construct comprises, preferably in 5'- to 3'-direction:
   (a) a 5'-CAP structure, preferably m7GpppN;
   (b) a coding region encoding at least one immunogenic peptide or polypeptide;

(c) a 3'-UTR element comprising or consisting of a nucleic acid sequence which is derived from an alpha-globin gene, preferably comprising the corresponding RNA sequence of the nucleic acid sequence according to SEQ ID NO. 4; or a homolog, a fragment or a variant thereof;

(d) optionally a poly(A) sequence, preferably comprising about 64 adenosines;

(e) optionally a poly(C) sequence, preferably comprising about 30 cytosines; and (f) optionally a histone-stem-loop, preferably comprising the corresponding RNA sequence to the nucleic acid sequence according to SEQ ID NO. 1, or a homolog, a fragment or a variant thereof.

17. The method of any one of items 1 to 16, wherein the mRNA construct comprises additionally a 5'-UTR element which comprises or consists of a nucleic acid sequence which is derived from the 5'-UTR of a TOP gene, or from a corresponding RNA sequence, a homolog, a fragment, or a variant thereof, preferably lacking the 5'TOP motif.

18. The method of item 17, wherein the 5'-UTR element comprises or consists of a nucleic acid sequence which is derived from a 5'-UTR of a TOP gene encoding a ribosomal protein, or from a corresponding RNA sequence or from a homolog, a fragment or a variant thereof, preferably lacking the 5'TOP motif.

19. The method of item 18, wherein the 5'-UTR element comprises or consists of a nucleic acid sequence which is derived from a 5'-UTR of a TOP gene encoding a ribosomal Large protein (RPL) or from a homolog, a fragment or variant thereof, preferably lacking the 5'TOP motif and more preferably comprising or consisting of a corresponding RNA sequence of the nucleic acid sequence according to SEQ ID NO. 5, or a homolog, a fragment or a variant thereof.

20. The method of item 19, wherein the mRNA construct comprises, preferably in 5'- to 3'-direction:

(a) a 5'-CAP structure, preferably m7GpppN;

(b) a 5'-UTR element which comprises or consists of a nucleic acid sequence which is derived from the 5'-UTR of a TOP gene, preferably comprising or consisting of the corresponding RNA sequence of the nucleic acid sequence according to SEQ ID NO. 5, or a homolog, a fragment or a variant thereof;

(c) a coding region encoding at least one immunogenic peptide or polypeptide;

(d) a 3'-UTR element comprising or consisting of a nucleic acid sequence which is derived from a gene providing a stable mRNA, preferably comprising or consisting of the corresponding RNA sequence of a nucleic acid sequence according to SEQ ID NO. 3, or a homolog, a fragment or a variant thereof;

(e) a poly(A) sequence preferably comprising about 64 adenosines;

(f) a poly(C) sequence, preferably comprising about 30 cytosines; and (g) a histone-stem-loop, preferably comprising the corresponding RNA sequence of the nucleic acid sequence according to SEQ ID NO. 1, or a homolog, a fragment or a variant thereof.

21. The method of any one of items 1 to 20, wherein the mRNA construct is associated with or complexed with a cationic or polycationic compound or a polymeric carrier, preferably in a weight ratio selected from a range of about 6:1 (w/w) to about 0.25:1 (w/w), more preferably from about 5:1 (w/w) to about 0.5:1 (w/w), more preferably of about 4:1 (w/w) to about 1:1 (w:w) or of about 3:1 (w/w) to about 1:1 (w/w), and most preferably a ratio of about 3:1 (w/w) to about 2:1 (w/w) of mRNA to cationic or polycationic compound and/or with a polymeric carrier; or optionally in a nitrogen/phosphate ratio of mRNA to cationic or polycationic compound and/or polymeric carrier in the range of about 0.1-10, preferably in a range of about 0.3-4 or 0.3-1, more preferably in a range of about 0.5-1 or 0.7-1, and most preferably in a range of about 0.3-0.9 or 0.5-0.9.

22. The method of item 21, wherein the mRNA construct is associated or complexed with a cationic protein or peptide, preferably protamine.

23. The method of any one of items 1 to 22, wherein the second antigenic composition comprises a plurality or more than one mRNA construct, each as set forth in any one of items 1 to 22.

24. The method of any one of items 1 to 23, wherein the mRNA construct is complexed at least partially with a cationic or polycationic compound and/or a polymeric carrier, preferably cationic proteins or peptides and most preferably protamine.

25. The method of item 24, wherein the ratio of complexed mRNA to free mRNA is selected from a range of about 5:1 (w/w) to about 1:10 (w/w), preferably from a range of about 4:1 (w/w) to about 1:8 (w/w), more preferably from a range of about 3:1 (w/w) to about 1:5 (w/w) or 1:3 (w/w), and most preferably the ratio of complexed mRNA to free mRNA is from a ratio of about 2:1 (w/w) to about 1:2 (w/w) such as about 1:1 (w/w).

26. The method of any one of items 1 to 25, wherein the first antigenic composition comprises at least one immunogenic peptide or polypeptide, preferably an immunogenic protein or an immunogenic peptide.

27. The method of item 26, wherein the first antigenic composition comprises a solution of at least one immunogenic peptide or polypeptide, preferably comprises a solution of at least one immunogenic protein and/or at least one immunogenic peptide.

28. The method of item 26 or 27, wherein the first antigenic composition comprises at least one preparation comprising at least one immunogenic peptide or polypeptide, preferably wherein the preparation is selected from the list consisting of: a virus preparation, a cell preparation and a bacteria preparation.

29. The method of any one of items 1 to 28, wherein the first antigenic composition comprises at least one nucleic acid construct that encodes at least one immunogenic peptide or polypeptide, preferably wherein the nucleic acid construct is a DNA construct.

30. The method of item 29, wherein said nucleic acid construct is a viral vector.

31. The method of item 30, wherein the viral vector is one derived from a virus selected from the list consisting of: poxvirus, adenovirus, adeno-associated virus (AAV), alphavirus, herpesvirus, retrovirus, lentivirus, cytomegalovirus, sendai virus, flavivirus, parvovirus.

32. The method of item 31, wherein the viral vector is one derived from a poxvirus selected from the list consisting of: smallpox virus (variola), vaccinia virus, cowpox virus, monkeypox virus.

33. The method of item 32, wherein the viral vector is one derived from a vaccinia virus selected from the list consisting of: New York Attenuated Vaccinia Virus (NY-VAC), ALVAC, TROVAC and Modified Vaccinia Ankara (MVA).

34. The method of item 33, wherein the viral vector is one derived from MVA that is derived from the virus seed batch 460 MG obtained from the 571th passage of vaccina virus in chick embryo fibroblast cells or is derived from the virus seed batch MVA 476 MG/14/78, and/or is derived or produced prior to 31 Dec. 1978 and is free from prion contamination.
35. The method of item 29, wherein said nucleic acid construct is a self-replicating RNA molecule.
36. The method of item 29, wherein said nucleic acid construct is not a viral vector and/or is not a self-replicating RNA molecule.
37. The method of any one of items 1 to 36, wherein the amino acid sequence of at least the epitope of the immunogenic peptide or polypeptide comprised in the first antigenic composition, or encoded by the nucleic acid construct comprised in the first antigenic composition, is similar to the amino acid sequence of at least the epitope of the immunogenic peptide or polypeptide encoded by the mRNA construct comprised in the second antigenic composition, preferably wherein the amino acid sequence of the immunogenic peptide or polypeptide comprised in the first antigenic composition, or encoded by the nucleic acid construct comprised in the first antigenic composition, is similar to the amino acid sequence of the immunogenic peptide or polypeptide encoded by the mRNA construct comprised in the second antigenic composition.
38. The method of any one of items 1 to 37, wherein the amino acid sequence of at least the epitope is from a pathogen, or a homolog, a fragment or a variant thereof, preferably wherein the immunogenic peptide or polypeptide comprised in the first antigenic composition, or encoded by the nucleic acid construct comprised in the first antigenic composition, and the immunogenic peptide or polypeptide encoded by the mRNA construct comprised in the second antigenic composition is from a pathogen, or a homolog, a fragment or a variant thereof.
39. The method of item 38, wherein the pathogen is one selected from the list consisting of: a virus, a bacterium, a fungus and a protozoan.
40. The method of item 38 or 39 for the treatment or prophylaxis of infection from the pathogen, or of a condition, disorder or disease associated therewith.
41. The method of any one of items 1 to 37, wherein the amino acid sequence of at least the epitope is from a tumour or cancer cell, or a homolog, a fragment or a variant thereof, preferably wherein the immunogenic peptide or polypeptide comprised in the first antigenic composition, or encoded by the nucleic acid construct comprised in the first antigenic composition, and the immunogenic peptide or polypeptide encoded by the mRNA construct comprised in the second antigenic composition is from a tumour or cancer cell, or a homolog, a fragment or a variant thereof.
42. The method of item 41, wherein the tumour or cancer cell is a cell from a tumour cancer selected from the list consisting of: prostate cancer, lung cancer, breast cancer, brain cancer, colon cancer, stomach cancer, liver cancer, pancreas cancer, ovary cancer, lymphoma, leukemia, and myeloma.
43. The method of item 41 or 42 for the treatment or prophylaxis of the tumour or cancer, or of a condition, disorder or disease associated therewith.
44. The method of any one of items 1 to 43, wherein the first and/or the second antigenic composition comprises additionally an adjuvant.
45. The method of any one of items 1 to 44, wherein the first antigenic composition and/or the second antigenic composition is a pharmaceutical composition, optionally comprising additionally a pharmaceutically acceptable carrier.

The present invention is further preferably defined by the following items:

1. A second antigenic composition that comprises at least one mRNA construct that encodes at least one immunogenic peptide or polypeptide, for use in administering to a subject in need thereof at least once an effective amount of the second antigenic composition subsequently to administration to the subject at least once of an effective amount of a first antigenic composition that comprises at least one immunogenic peptide or polypeptide and/or that comprises at least one nucleic acid construct that encodes at least one immunogenic peptide or polypeptide,
wherein:
the nucleic acid construct, if comprised in the first antigenic composition, is not an mRNA construct; and
at least one epitope of the immunogenic peptide or polypeptide comprised in, or encoded by the nucleic acid construct comprised in, the first antigenic composition is immunologically equivalent to at least one epitope of the immunogenic peptide or polypeptide encoded by the mRNA construct of the second antigenic composition.
2. A first antigenic composition that comprises at least one immunogenic peptide or polypeptide and/or that comprises at least one nucleic acid construct that encodes at least one immunogenic peptide or polypeptide, for use in administering to a subject in need thereof at least once an effective amount of the first antigenic composition and prior to administration to the subject at least once an effective amount of a second antigenic composition that comprises at least one mRNA construct that encodes at least one immunogenic peptide or polypeptide,
wherein:
the nucleic acid construct, if comprised in the first antigenic composition, is not an mRNA construct; and
at least one epitope of the immunogenic peptide or polypeptide comprised in, or encoded by the nucleic acid construct comprised in, the first antigenic composition is immunologically equivalent to at least one epitope of the immunogenic peptide or polypeptide encoded by the mRNA construct of the second antigenic composition.
3. The second antigenic composition of item 1 or the first antigenic composition of item 2, wherein the first antigenic composition and the second antigenic composition are administered to the subject, respectively, in a prime-boost immunisation regimen.
4. The second antigenic composition of item 1 or 3 or the first antigenic composition of item 2 or 3, wherein the second antigenic composition is subsequently administered within about 28, 14 or 7 days of administration of the first antigenic composition, preferably about 27, 24, 21, 18, 15, 12, 10, 9, 8, 7, 6, 5, 4, 3, 2 or 1 day(s) after administration of the first antigenic composition.
5. The second antigenic composition of any one of items 1, 3 or 4 or the first antigenic composition of any one of items 2 to 4, wherein:
the first antigenic composition is administered in two or more doses prior to the administration of the second antigenic composition, and/or the second antigenic composition is administered in two or more doses subsequently to the administration of the first antigenic composition,
preferably, wherein the first antigenic composition and/or the second antigenic composition is administered in a number of doses selected from the list of consisting of: 2, 3, 4, 5, 6, 7, 8, 9 and 10 times.

6. The first or second antigenic composition of item 5, wherein the interval between the administration of one or more pairs of consecutive doses is from about 5 to 120 days.

7. The second antigenic composition of any one of items 1 or 3 to 6 or the first antigenic composition of any one of items 2 to 6, wherein the first antigenic composition and/or the second antigenic composition is administered by subcutaneous, intramuscular and/or intradermal injection.

8. The first or second antigenic composition of item 7, wherein the injection is carried out using jet injection.

9. The second antigenic composition of any one of items 1 or 3 to 8 or the first antigenic composition of any one of items 2 to 8, wherein the G/C content of the region of the mRNA construct encoding at least one epitope of the immunogenic peptide or polypeptide is increased compared with the G/C content of the region of the wild type mRNA that encodes the epitope of the immunogenic peptide or polypeptide, preferably wherein the amino acid sequence of the epitope of the immunogenic peptide or polypeptide encoded by the G/C-enriched mRNA is not modified compared with the amino acid sequence of the epitope of the immunogenic peptide or polypeptide encoded by the wild type mRNA.

10. The second antigenic composition of any one of items 1 or 3 to 9 or the first antigenic composition of any one of items 2 to 9, wherein the mRNA construct comprises additionally:
(a) a 5'-CAP structure;
(b) a poly(A) sequence; and
(c) optionally a poly (C) sequence.

11. The first or second antigenic composition of item 10, wherein the poly(A) sequence comprises a sequence of about 25 to about 400 adenosine nucleotides, preferably a sequence of about 50 to about 400 adenosine nucleotides, more preferably a sequence of about 50 to about 300 adenosine nucleotides, even more preferably a sequence of about 50 to about 250 adenosine nucleotides, most preferably a sequence of about 60 to about 250 adenosine nucleotides.

12. The second antigenic composition of any one of items 1 or 3 to 11 or the first antigenic composition of any one of items 2 to 11, wherein the mRNA construct comprises additionally at least one histone stem-loop, preferably comprising the corresponding RNA sequence to the nucleic acid sequence according to SEQ ID NO. 1, or a homolog, a fragment or a variant thereof.

13. The second antigenic composition of any one of items 1 or 3 to 12 or the first antigenic composition of any one of items 2 to 12, wherein the mRNA construct comprises additionally a 3'-UTR element.

14. The first or second antigenic composition of item 13, wherein the 3'-UTR element comprises or consists of a nucleic acid sequence which is derived from a 3'-UTR of a gene providing a stable mRNA or from a homolog, a fragment or a variant thereof.

15. The first or second antigenic composition of item 14, wherein the 3'-UTR element comprises or consists of a nucleic acid sequence derived from a 3'-UTR of a gene selected from the group consisting of an albumin gene, an alpha-globin gene, a beta-globin gene, a tyrosine hydroxylase gene, a lipoxygenase gene, and a collagen alpha gene; or from a homolog, a fragment or a variant thereof.

16. The first or second antigenic composition of item 14 or 15, wherein the 3'-UTR element is derived from a nucleic acid sequence according to SEQ ID NO. 3 or SEQ ID NO. 4, or from a corresponding RNA sequence, a homolog, a fragment or a variant thereof.

17. The second antigenic composition of any one of items 1 or 3 to 16 or the first antigenic composition of any one of items 2 to 16, wherein the mRNA construct comprises, preferably in 5'- to 3'-direction:
(a) a 5'-CAP structure, preferably m7GpppN;
(b) a coding region encoding at least one immunogenic peptide or polypeptide;
(c) a 3'-UTR element comprising or consisting of a nucleic acid sequence which is derived from an alpha-globin gene, preferably comprising the corresponding RNA sequence of the nucleic acid sequence according to SEQ ID NO. 4; or a homolog, a fragment or a variant thereof;
(d) optionally a poly(A) sequence, preferably comprising about 64 adenosines;
(e) optionally a poly(C) sequence, preferably comprising about 30 cytosines; and
(f) optionally a histone-stem-loop, preferably comprising the corresponding RNA sequence to the nucleic acid sequence according to SEQ ID NO. 1, or a homolog, a fragment or a variant thereof.

18. The second antigenic composition of any one of items 1 or 3 to 17 or the first antigenic composition of any one of items 2 to 17, wherein the mRNA construct comprises additionally a 5'-UTR element which comprises or consists of a nucleic acid sequence which is derived from the 5'-UTR of a TOP gene, or from a corresponding RNA sequence, a homolog, a fragment, or a variant thereof, preferably lacking the 5'TOP motif.

19. The first or second antigenic composition of item 18, wherein the 5'-UTR element comprises or consists of a nucleic acid sequence which is derived from a 5'-UTR of a TOP gene encoding a ribosomal protein, or from a corresponding RNA sequence or from a homolog, a fragment or a variant thereof, preferably lacking the 5'TOP motif.

20. The first or second antigenic composition of item 19, wherein the 5'-UTR element comprises or consists of a nucleic acid sequence which is derived from a 5'-UTR of a TOP gene encoding a ribosomal Large protein (RPL) or from a homolog, a fragment or variant thereof, preferably lacking the 5'TOP motif and more preferably comprising or consisting of a corresponding RNA sequence of the nucleic acid sequence according to SEQ ID NO. 5, or a homolog, a fragment or a variant thereof.

21. The first or second antigenic composition of item 20, wherein the mRNA construct comprises, preferably in 5'- to 3'-direction:
(a) a 5'-CAP structure, preferably m7GpppN;
(b) a 5'-UTR element which comprises or consists of a nucleic acid sequence which is derived from the 5'-UTR of a TOP gene, preferably comprising or consisting of the corresponding RNA sequence of the nucleic acid sequence according to SEQ ID NO. 5, or a homolog, a fragment or a variant thereof;
(c) a coding region encoding at least one immunogenic peptide or polypeptide;

(d) a 3'-UTR element comprising or consisting of a nucleic acid sequence which is derived from a gene providing a stable mRNA, preferably comprising or consisting of the corresponding RNA sequence of a nucleic acid sequence according to SEQ ID NO. 3, or a homolog, a fragment or a variant thereof;
(e) a poly(A) sequence preferably comprising about 64 adenosines;
(f) a poly(C) sequence, preferably comprising about 30 cytosines; and
(g) a histone-stem-loop, preferably comprising the corresponding RNA sequence of the nucleic acid sequence according to SEQ ID NO. 1, or a homolog, a fragment or a variant thereof.

22. The second antigenic composition of any one of items 1 or 3 to 21 or the first antigenic composition of any one of items 2 to 21, wherein the mRNA construct is associated with or complexed with a cationic or polycationic compound or a polymeric carrier, preferably in a weight ratio selected from a range of about 6:1 (w/w) to about 0.25:1 (w/w), more preferably from about 5:1 (w/w) to about 0.5:1 (w/w), even more preferably of about 4:1 (w/w) to about 1:1 (w:w) or of about 3:1 (w/w) to about 1:1 (w/w), and most preferably a ratio of about 3:1 (w/w) to about 2:1 (w/w) of mRNA to cationic or polycationic compound and/or with a polymeric carrier; or optionally in a nitrogen/phosphate ratio of mRNA to cationic or polycationic compound and/or polymeric carrier in the range of about 0.1-10, preferably in a range of about 0.3-4 or 0.3-1, more preferably in a range of about 0.5-1 or 0.7-1, and most preferably in a range of about 0.3-0.9 or 0.5-0.9.

23. The first or second antigenic composition of item 22, wherein the mRNA construct is associated or complexed with a cationic protein or peptide, preferably protamine.

24. The second antigenic composition of any one of items 1 or 3 to 23 or the first antigenic composition of any one of items 2 to 23, wherein the second antigenic composition comprises a plurality or more than one mRNA construct, each as set forth in any one of items 1 to 23.

25. The second antigenic composition of any one of items 1 or 3 to 24 or the first antigenic composition of any one of items 2 to 24, wherein the mRNA construct is complexed at least partially with a cationic or polycationic compound and/or a polymeric carrier, preferably cationic proteins or peptides and most preferably protamine.

26. The first or second antigenic composition of item 25, wherein the ratio of complexed mRNA to free mRNA is selected from a range of about 5:1 (w/w) to about 1:10 (w/w), preferably from a range of about 4:1 (w/w) to about 1:8 (w/w), more preferably from a range of about 3:1 (w/w) to about 1:5 (w/w) or 1:3 (w/w), and most preferably the ratio of complexed mRNA to free mRNA is from a ratio of about 2:1 (w/w) to about 1:2 (w/w) such as about 1:1 (w/w).

27. The second antigenic composition of any one of items 1 or 3 to 26 or the first antigenic composition of any one of items 2 to 26, wherein the first antigenic composition comprises at least one immunogenic peptide or polypeptide, preferably an immunogenic protein or an immunogenic peptide.

28. The first or second antigenic composition of item 27, wherein the first antigenic composition comprises a solution of at least one immunogenic peptide or polypeptide, preferably comprises a solution of at least one immunogenic protein and/or at least one immunogenic peptide.

29. The first or second antigenic composition of item 27 or 28, wherein the first antigenic composition comprises at least one preparation comprising at least one immunogenic peptide or polypeptide, preferably wherein the preparation is selected from the list consisting of: a virus preparation, a cell preparation and a bacteria preparation.

30. The second antigenic composition of any one of items 1 or 3 to 29 or the first antigenic composition of any one of items 2 to 29, wherein the first antigenic composition comprises at least one nucleic acid construct that encodes at least one immunogenic peptide or polypeptide, preferably wherein the nucleic acid construct is a DNA construct.

31. The first or second antigenic composition of item 30, wherein said nucleic acid construct is a viral vector.

32. The first or second antigenic composition of item 31, wherein the viral vector is one derived from a virus selected from the list consisting of: poxvirus, adenovirus, adeno-associated virus (AAV), alphavirus, herpesvirus, retrovirus, lentivirus, cytomegalovirus, sendai virus, flavivirus, parvovirus.

33. The first or second antigenic composition of item 32, wherein the viral vector is one derived from a poxvirus selected from the list consisting of: smallpox virus (variola), vaccinia virus, cowpox virus, monkeypox virus.

34. The first or second antigenic composition of item 33, wherein the viral vector is one derived from a vaccinia virus selected from the list consisting of: New York Attenuated Vaccinia Virus (NYVAC), ALVAC, TROVAC and Modified Vaccinia Ankara (MVA).

35. The first or second antigenic composition of item 34, wherein the viral vector is one derived from MVA that is derived from the virus seed batch 460 MG obtained from the 571th passage of vaccina virus in chick embryo fibroblast cells or is derived from the virus seed batch MVA 476 MG/14/78, and/or is derived or produced prior to 31 Dec. 1978 and is free from prion contamination.

36. The first or second antigenic composition of item 30, wherein said nucleic acid construct is a self-replicating RNA molecule.

37. The first or second antigenic composition of item 30, wherein said nucleic acid construct is not a viral vector and/or is not a self-replicating RNA molecule.

38. The second antigenic composition of any one of items 1 or 3 to 37 or the first antigenic composition of any one of items 2 to 37, wherein the amino acid sequence of at least the epitope of the immunogenic peptide or polypeptide comprised in the first antigenic composition, or encoded by the nucleic acid construct comprised in the first antigenic composition, is similar to the amino acid sequence of at least the epitope of the immunogenic peptide or polypeptide encoded by the mRNA construct comprised in the second antigenic composition, preferably wherein the amino acid sequence of the immunogenic peptide or polypeptide comprised in the first antigenic composition, or encoded by the nucleic acid construct comprised in the first antigenic composition, is similar to the amino acid sequence of the immunogenic peptide or polypeptide encoded by the mRNA construct comprised in the second antigenic composition.

39. The second antigenic composition of any one of items 1 or 3 to 38 or the first antigenic composition of any one of items 2 to 38, wherein the amino acid sequence of at least the epitope is from a pathogen, or a homolog, a fragment or a variant thereof, preferably wherein the immunogenic peptide or polypeptide comprised in the first antigenic composition, or encoded by the nucleic acid construct comprised in the first antigenic composition, and the immunogenic peptide or polypeptide encoded by the mRNA construct comprised in the second antigenic composition is from a pathogen, or a homolog, a fragment or a variant thereof.
40. The first or second antigenic composition of item 39, wherein the pathogen is one selected from the list consisting of: a virus, a bacterium, a fungus and a protozoan.
41. The first or second antigenic composition of item 39 or 40 for the treatment or prophylaxis of infection from the pathogen, or of a condition, disorder or disease associated therewith.
42. The second antigenic composition of any one of items 1 or 3 to 38 or the first antigenic composition of any one of items 2 to 38, wherein the amino acid sequence of at least the epitope is from a tumour or cancer cell, or a homolog, a fragment or a variant thereof, preferably wherein the immunogenic peptide or polypeptide comprised in the first antigenic composition, or encoded by the nucleic acid construct comprised in the first antigenic composition, and the immunogenic peptide or polypeptide encoded by the mRNA construct comprised in the second antigenic composition is from a tumour or cancer cell, or a homolog, a fragment or a variant thereof.
43. The first or second antigenic composition of item 42, wherein the tumour or cancer cell is a cell from a tumour or cancer selected from the list consisting of: prostate cancer, lung cancer, breast cancer, brain cancer, colon cancer, stomach cancer, liver cancer, pancreas cancer, ovary cancer, lymphoma, leukemia, and myeloma.
44. The first or second antigenic composition of item 42 or 43 for the treatment or prophylaxis of the tumour or cancer, or of a condition, disorder or disease associated therewith.
45. The second antigenic composition of any one of items 1 or 3 to 44 or the first antigenic composition of any one of items 2 to 44, wherein the first and/or the second antigenic composition comprises additionally an adjuvant.
46. The second antigenic composition of any one of items 1 or 3 to 45 or the first antigenic composition of any one of items 2 to 45, wherein the first antigenic composition and/or the second antigenic composition is a pharmaceutical composition, optionally comprising additionally a pharmaceutically acceptable carrier.
47. A first vaccine composition comprising a first antigenic composition as set forth in any one of items 1 to 46.
48. A second vaccine composition comprising a second antigenic composition as set forth in any one of items 1 to 46.
49. A vaccine combination comprising:
a first antigenic composition as set forth in any one of items 1 to 46 or a first vaccine composition of item 47; and
a second antigenic composition as set forth in any one of items 1 to 46 or a second vaccine composition of item 48.
50. A kit, preferably for inducing an immune response in a subject; the kit comprising a plurality of separate containers, the contents of at least two containers differing from each other in whole or in part,
the first of such containers containing:
a first antigenic composition as set forth in any one of items 1 to 46 or a first vaccine composition of item 47; and
the second of such containers containing:
a second antigenic composition as set forth in any one of items 1 to 46 or a second vaccine composition of item 48.
51. The kit of item 50, comprising additionally instructions to:
(a) administer to a subject, preferably one in need thereof, at least once an effective amount of the first antigenic composition; and
(b) subsequently administer to the subject at least once an effective amount of the second antigenic composition.
52. A packaged vaccine comprising:
a first antigenic composition as set forth in any one of items 1 to 46 or a first vaccine composition of item 47; and/or
a second antigenic composition as set forth in any one of items 1 to 46 or a second vaccine composition of item 48,
the package comprising additionally instructions to:
(a) administer to a subject, preferably one in need thereof, at least once an effective amount of the first antigenic composition; and
(b) subsequently administer to the subject at least once an effective amount of the second antigenic composition.
53. The first vaccine composition of item 47, the second vaccine composition of item 48, the vaccine combination of item 50, the kit of item 50 or 51 or the packaged vaccine of item 52, for use in a prime-boost vaccination regimen.
54. The kit of item 50, 51 or 53 or the packaged vaccine of item 52 or 54, comprising additional instructions to administer the first and/or second antigenic composition(s) as set forth in any one of items 1 to 46.
55. A method for inducing an immune response in a subject; the method comprising the steps:
(a) administering to a subject in need thereof at least once an effective amount of a first antigenic composition; and
(b) subsequently administering to the subject at least once an effective amount of a second antigenic composition, wherein the first antigenic composition, the second antigenic composition and the administration is as set forth in any one of items 1 to 46.

The invention claimed is:

1. A method for inducing an antigen-specific immune response in a subject, the method comprising the steps:
    (a) administering to a subject in need thereof at least once an effective amount of a first antigenic composition comprising at least one immunogenic polypeptide at least 100 amino acids in length from a tumor antigen or a pathogen antigen; and
    (b) subsequently administering to the subject at least once an effective amount of a second antigenic composition comprising at least one purified mRNA construct that encodes at least one immunogenic polypeptide from the tumor antigen or the pathogen antigen, wherein the at least one immunogenic polypeptide is at least 90% identical to the at least one immunogenic polypeptide comprised in the first antigenic composition,
    wherein neither the first antigenic composition nor the second antigenic composition comprises a self-replicating RNA.

2. The method of claim 1, wherein the at least one immunogenic polypeptide is from a tumor antigen.

3. The method of claim 1, wherein the at least one immunogenic polypeptide is from a pathogen antigen.

4. The method of claim 3, wherein the pathogen antigen is a viral antigen.

5. The method of claim 4, wherein the viral antigen is an influenza hemagglutinin (HA) antigen, an influenza neuraminidase (NA) antigen, a rabies virus glycoprotein (G), a respiratory syncytial virus fusion protein (F) or a coronavirus spike protein (S).

6. The method of claim 1, wherein the purified mRNA is complexed with cationic lipids thereby forms liposomes, lipid nanoparticles and/or lipoplexes.

7. The method of claim 1, wherein the first antigenic composition and the second antigenic composition are administered to the subject in need thereof, respectively, in a prime-boost immunisation regimen.

8. The method of claim 1, wherein the second antigenic composition is subsequently administered within about 28 days of administration of the first antigenic composition.

9. The method of claim 1, wherein:
    the first antigenic composition is administered in two or more doses prior to the administration of the second antigenic composition, or
    the second antigenic composition is administered in two or more doses subsequently to the administration of the first antigenic composition.

10. The method of claim 9, wherein the interval between the administration of one or more pairs of consecutive doses is from about 5 to 120 days.

11. The method of claim 1, wherein the first antigenic composition or the second antigenic composition is administered by subcutaneous, intramuscular, intradermal, or jet injection.

12. The method of claim 1, wherein the G/C content of the region of the mRNA construct encoding at least one epitope of the immunogenic peptide or polypeptide is increased compared with the G/C content of the region of the wild type or reference mRNA that encodes the epitope of the immunogenic peptide or polypeptide.

13. The method of claim 1, wherein the mRNA construct comprises additionally:
    (a) a 5'-CAP structure;
    (b) a poly(A) sequence; and
    (c) optionally a poly (C) sequence.

14. The method of claim 13, wherein the poly(A) sequence comprises a sequence of about 25 to about 400 adenosine nucleotides.

15. The method of claim 1, wherein the mRNA construct comprises additionally at least one histone stem-loop comprising a corresponding RNA sequence to the nucleic acid sequence according to SEQ ID NO. 1.

16. The method of claim 1, wherein the mRNA construct comprises additionally a 3'-UTR element.

17. The method of claim 16, wherein the 3'-UTR element comprises a nucleic acid sequence derived from a 3'-UTR of a gene selected from the group consisting of an albumin gene, an alpha-globin gene, a beta-globin gene, a tyrosine hydroxylase gene, a lipoxygenase gene, and a collagen alpha gene.

18. The method of claim 1, wherein the mRNA construct comprises additionally a 5'-UTR element which comprises a nucleic acid sequence which is derived from the 5'-UTR of a TOP gene, or from a corresponding RNA sequence.

19. The method of claim 18, wherein the 5'-UTR element comprises a nucleic acid sequence which is derived from a 5'-UTR of a TOP gene encoding a ribosomal protein.

20. The method of claim 18, wherein the mRNA construct comprises:
    (a) a 5'-CAP structure;
    (b) a 5'-UTR element which comprises a nucleic acid sequence which is derived from the 5'-UTR of a TOP gene;
    (c) a coding region encoding the at least one immunogenic peptide or polypeptide;
    (d) a 3'-UTR element comprising a nucleic acid sequence which is derived from a gene providing a stable mRNA;
    (e) a poly(A) sequence;
    (f) a poly(C) sequence; and
    (g) a histone-stem-loop.

21. The method of claim 1, wherein the mRNA construct is associated with or complexed with a cationic or polycationic compound or a polymeric carrier.

22. A packaged immunogenic composition comprising:
    a first antigenic composition comprising at least one immunogenic polypeptide at least 100 amino acids in length from a tumor antigen or a pathogen antigen, and
    a second antigenic composition comprising at least one purified mRNA construct that encodes at least one immunogenic polypeptide from the tumor antigen or the pathogen antigen, wherein the at least one immunogenic polypeptide encoded by the mRNA construct is at least 90% identical to the at least one immunogenic polypeptide comprised in the first antigenic composition, and
    the package comprising additionally instructions to:
    (a) administer to a subject in need thereof at least once an effective amount of the first antigenic composition; and (b) subsequently administer to the subject at least once an effective amount of the second antigenic composition.

\* \* \* \* \*